US011633467B2

(12) United States Patent
Blazevic et al.

(10) Patent No.: US 11,633,467 B2
(45) Date of Patent: Apr. 25, 2023

(54) IMMUNOGENIC COMPOSITION AND VACCINE FOR GENERATING AN IMMUNE RESPONSE TO NOROVIRUS

(71) Applicant: Icon Genetics GmbH, Halle (Saale) (DE)

(72) Inventors: Vesna Blazevic, Tampere (FI); Maria Malm, Tampere (FI); Frank Thieme, Seegebiet Mansfelder Land (Ortsteil Lüttchendorf) (DE); Franziska Jarczowski, Röblingen am See (DE); Andre Diessner, Halle (Saale) (DE); Victor Klimyuk, Leipzig (DE)

(73) Assignee: Icon Genetics GmbH, Halle (DE)

( * ) Notice: Subject to any disclaimer, the term of this patent is extended or adjusted under 35 U.S.C. 154(b) by 0 days.

(21) Appl. No.: 16/969,423

(22) PCT Filed: Feb. 14, 2019

(86) PCT No.: PCT/EP2019/053699

§ 371 (c)(1),
(2) Date: Aug. 12, 2020

(87) PCT Pub. No.: WO2019/158653

PCT Pub. Date: Aug. 22, 2019

(65) Prior Publication Data

US 2021/0000941 A1 Jan. 7, 2021

(30) Foreign Application Priority Data

Feb. 15, 2018 (EP) .................................... 18157031
Dec. 21, 2018 (EP) .................................... 18215676

(51) Int. Cl.
*A61K 39/125* (2006.01)
*A61K 39/02* (2006.01)
*A61K 39/39* (2006.01)
*A61K 39/00* (2006.01)

(52) U.S. Cl.
CPC .......... *A61K 39/125* (2013.01); *A61K 39/107* (2013.01); *A61K 39/39* (2013.01); *A61K 2039/5258* (2013.01); *A61K 2039/54* (2013.01); *A61K 2039/55505* (2013.01); *A61K 2039/55544* (2013.01); *A61K 2039/575* (2013.01); *A61K 2039/70* (2013.01); *C12N 2770/16034* (2013.01)

(58) Field of Classification Search
CPC ................ A61K 39/12; A61K 2039/70; A61K 2039/55544; A61K 39/02; A61K 39/125; C07K 14/245; C12N 2770/16034; C12N 1/20; A61P 31/14; C07C 237/10
See application file for complete search history.

(56) References Cited

FOREIGN PATENT DOCUMENTS

| | | |
|---|---|---|
| JP | S58-500998 | 6/1983 |
| JP | 2004-538048 | 12/2004 |
| JP | 2010-539192 | 12/2010 |
| JP | 2016-534070 | 11/2016 |
| JP | 2017-513956 | 6/2017 |
| WO | 2013/009849 A1 | 1/2013 |

OTHER PUBLICATIONS

International Search Report in PCT/EP2019/053699 dated Apr. 28, 2019.
Written Opinion of the International Searching Authority in PCT/EP2019/053699 dated Apr. 28, 2019.
Atul Srivastava et al. (2015) "Mucosal vaccines: a paradigm shift in the development of mucosal adjuvants and delivery vehicles," Apmis, vol. 123, No. 4, pp. 275-288.
Joon Haeng Rhee et al. (2012) "Mucosal vaccine adjuvants update," Clinical and Experimental Vaccine Research, vol. 1, No. 1, pp. 55-56.
J Mattsson et al. (2014) "Cholera toxin adjuvant promates a balanced Th1/Th2/Th17 response independtly of IL-12 and IL-17 by acting on Gs[alpha] in CD11b+ DCs." Mucosal Immunology, vol. 8, No. 4, pp. 815-827.
Yuqi Huo et al. (2015) "Prevailing Sydney like Norovirus Gii.4 VLPs induce systemic and mucosal immune responses in mice," Moleculrar Immunology, vol. 68, No. 2, pp. 367-372.
Periwal S B et al. (2003) "A modified cholera holotoxin CT-E29H enhances systemic and mucosal immune responses to recombinant Norwalk virus-virus like particle vaccine," Vac, Elsevier, Amsterdam, NL, vol. 21, No. 5-6, pp. 376-385.

*Primary Examiner* — Bao Q Li
(74) *Attorney, Agent, or Firm* — Williams Mullen; David M. Saravitz

(57) ABSTRACT

An immunogenic composition comprising at least one Norovirus antigen and at least one adjuvant which is at least one B subunit of an $AB_5$ toxin such as cholera toxin subunit B (CTB) or the B subunit of heat-labile *E. coli* exotoxin LT (LTB).

17 Claims, 16 Drawing Sheets

Specification includes a Sequence Listing.

IMMUNOGENIC COMPOSITION AND VACCINE FOR GENERATING AN IMMUNE RESPONSE TO NOROVIRUS

CROSS-REFERENCE TO RELATED APPLICATIONS

This application is the U.S. National Stage of International Application PCT/EP2019/053699, filed Feb. 14, 2019, which designates the U.S. and was published by the International Bureau in English on Aug. 22, 2019, and which claims the benefit of European Patent Application No. 18 157 031.8, filed Feb. 15, 2018 and European Patent Application No. 18 215 676.0, filed Dec. 21, 2018; all of which are hereby incorporated herein in their entirety by reference.

FIELD OF THE INVENTION

The present invention relates to an immunogenic composition comprising one or more norovirus (NoV) antigen(s) and an adjuvant, in particular to a composition comprising one or more NoV antigen and cholera toxin B (CTB) and/or *E. coli* heat-labile enterotoxin B subunit (LTB) as adjuvant. The present invention also relates to an immunogenic composition comprising one or more norovirus (NoV) antigen(s) and one or more bacterial antigen(s) that is subunit B of a bacterial exotoxin. In addition, the present invention relates to an anti-NoV vaccine comprising the immunogenic composition and to methods of preventing, treating or reducing severity of a NoV infection or for conferring immunity to NoV infections in a human subject. Further, the present invention relates to an immunogenic composition, and an anti-NoV vaccine comprising the immunogenic composition, for use in a method of preventing, treating or reducing severity of gastroenteritis caused by a NoV infection in a subject.

BACKGROUND OF THE INVENTION

Noroviruses are the leading cause of gastroenteritis outbreaks worldwide. They are responsible for 685 million cases annually including 200 million cases among children 5 years old or younger (www.cdc.gov/norovirus/worldwide-.html). Up to date, there is no norovirus vaccine on the market. Also, there are no established protocols for norovirus cultivation, which significantly slows down progress of norovirus vaccine development. In addition, the rapid rate of the genetic changes of circulating noroviruses leads to new norovirus strains emerging every 2-4 years, causing epidemic outbreaks and complicating the development of vaccines and therapies that are required to counter these challenges (de Graaf, M, van Beek, J, & Koopmans, P G, 2016, Nature Rev Microbiol, 14: 421-433). It is evident that genogroup GI and GII representatives have been the main causes of the majority of outbreaks in the last two decades (Matthews et al., 2012, Epidemiol. Infect, 140: 1161-1172) with prevalence of the GII genogroup genotype 4 (GII.4). For example, since 2014, appearance of new GII.17 strains has been described in East Asia as well as re-emergence of old GII.4 strains (Chan et al, 2015, Nat Commun, doi: 10.1038/ncomms10061; Choi et al, 2017, Food Environ Virol, doi: 10.1007/s12560-017-9278-4). This constantly changing landscape adds complexity to defining an efficient vaccine composition, as the most preferred approach is a multivalent vaccine. Current norovirus vaccine development relies on use of virus-like particles (VLPs) subunit vaccines (for most recent reviews please see: Tan, M. & Jiang, X., 2014, Hum. Vaccin Immunother, 10:1449-1456; Debbink, K., Lindesmith, L. & Baric, R. S., 2014, Clin Infect Dis, 58:1746-1752; Ramani, S., Estes, M. K. & Atmar, R. L., 2016, PLoS Pathog, 12:e1005334). There is significant progress in accumulating clinical data on norovirus VLP-based vaccine safety and immunogenicity (Ball et al, 1999, Gastroenterology, 117:40-48; Tacket et al, 2003, Clin Immunol, 108:241-247; Lindesmith et al, 2015, PLoS Med, 12:e1001807). The first VLP bivalent vaccine (GI.2+GII.4 VLPs or strains) has reached phase IIb clinical trials (Reference NCT02669121 in clinical trials database https://clinicaltrials.gov/ct2/show/NCT02669121) and several others are under development in pre-clinical research (Springer, M J, et al., 2016, Vaccine, 34:1452-1458; Ball, J. et al., 2017, PLOS One, 12: e0177310; for review see Cortes-Penfield, N W, et al., 2017, Clin. Ther., pii: S0149-2918(17)30769-5).

A recent publication of the results of a randomized, controlled, double-blind clinical trial in healthy adults demonstrated that some tested adjuvants (MPL, alum) do not have an effect on immunogenicity, do not prevent interference between different Norovirus genotypes in the mixture of different VLPs, but can be used (e.g. alum) to stabilize norovirus VLPs (Leroux-Roels, G (2018), *The Journal of Infectious Diseases,* 217(4), 597-607, doi: 10.1093/infdis/jix572. [Epub ahead of print]). In addition, it is known that alum induces good Th2 responses, but has little capacity to stimulate cellular Th1 immune responses. Also, alum as adjuvant can cause increased IgE production, allergenicity (Gupta et al., 1995, In: Powel M F, Newman M J (eds). Vaccine design: The subunit and adjuvant approach. NY, Plenum Press, 229-248; Goto, N, et al., 1993, Vaccine, 11:914-918; Bergfors E, et al., 2005, Eur J Pediatr., 164: 691-697) and cytotoxicity. Despite the fact that alum-based vaccines are generally well-tolerated, alum has long-lasting biopersistence in the body, ability to migrate in lymphoid organs and accumulate in brain, which is raising concerns. For a review of alum as adjuvant and its side effects, see: Petrovsky, N & Aguilar, J C., 2004, Immunol. &Cell Biol., 82:488-496; Gherardi R K, et al., 2014, Front. Neurol, 6:4; Gherardi R K, et al, 2016, Morphologie, 100:85-94.

Use of VP1 antigens in the form of highly immunogenic VLPs opened opportunities for partially addressing the above problems. However, up to date, the progress with vaccine development is rather slow and more efforts are required to deal with the issue by offering new immunogenic compositions that can provide reliable protection from noroviral infection. Finding a suitable nontoxic adjuvant that can further improve VLP-containing vaccine performance and replace or, at least, reduce the amount of alum in vaccine formulations would help to address this task. It would be an advantage, if an adjuvant of proteinaceous nature, when used at higher doses, can also serve as antigen by triggering an immune response against itself and provide protection or lower severity of gastroenteritis caused by a pathogen other than norovirus, preferably a bacterial pathogen.

Another problem in the prior art is the following dilemma. For providing broad spectrum immunity against norovirus infections, vaccines containing antigen mixtures, such as an antigen from a genogroup I norovirus and an antigen from a genogroup II norovirus were considered. However, interference of the antigen response to one antigen due to the presence of a second antigen is frequently observed. As a consequence, it is difficult to achieve the broad spectrum immunity intended by combining two or more antigens. It would thus be desirable to achieve antigenic compositions and vaccines comprising two or more different antigens, wherein interference of immune response between the antigens is suppressed.

It is therefore an object of the invention to provide antigenic compositions, and vaccines containing them, that are antigenic against norovirus (NoV) antigens and, optionally, also against bacterial pathogens. It is also an object to provide antigenic compositions, and vaccines containing them, that can protect subjects from NoV infection or that can prevent and/or treat NoV infections, or that reduce the severity of a NoV infection. It is also an object to provide antigenic compositions, and vaccines containing them, that can protect subjects from NoV infection by genogroup I and genogroup II NoV or that can prevent and/or treat NoV infections by genogroup I and genogroup II NoV, or that reduce the severity of a NoV infection by genogroup I and genogroup II NoV. It is a further object to provide antigenic compositions, and vaccines containing them, that provide balanced humoral and cellular immune response. It is a further object to provide antigenic compositions, and vaccines containing them, that are sufficiently immunogenic even if they contain a low content of alum as adjuvant or no alum at all, and/or that suppress interference of multiple antigens contained in the composition or vaccine. It is a further object to provide an immunogenic composition and vaccine for increasing the Th1 immune response in a subject against the antigen(s) in the composition or vaccine.

GENERAL DESCRIPTION OF THE INVENTION

Accordingly, the present invention provides the following:

(1) An immunogenic composition comprising at least one norovirus antigen and an adjuvant.

(2) The immunogenic composition according to items (1), wherein said at least one norovirus antigen is or comprises a norovirus VP1 protein.

(3) The immunogenic composition according to any one of items (1) or (2), said immunogenic composition comprising an antigen of a genogroup I norovirus and an antigen of a genogroup II norovirus.

(4) The immunogenic composition according to any one of items (1) to (3), wherein said immunogenic composition comprises norovirus virus-like particles (norovirus VLPs) comprising or consisting of said at least one norovirus antigen.

(5) The immunogenic composition according to any one of items (1) to (4), wherein said immunogenic composition comprises VLPs of a genogroup I norovirus and VLPs of a genogroup II norovirus.

(6) The immunogenic composition according to any one of items (1) to (5), wherein said immunogenic composition comprises VLPs comprising, preferably consisting of, a norovirus genogroup I antigen and VLPs comprising, preferably consisting of, a norovirus genogroup II antigen.

(7) The immunogenic composition according to any one of items (1) to (6), wherein said adjuvant is cholera toxin B (CTB).

(8) The immunogenic composition according to item (7), wherein said composition contains said at least one norovirus antigen and said CTB in a mass ratio range of from 1:0.1 to 1:5, preferably from 1:0.2 to 1:3, more preferably of from 1:0.5 to 1:2.

(9) The immunogenic composition according to any one of items (7) and (8), wherein said CTB is pentameric CTB.

(10) The immunogenic composition according to any one of items (1) to (9), wherein said immunogenic composition comprises a further adjuvant.

(11) The immunogenic composition according to item (10), wherein said further adjuvant is alum.

(12) The immunogenic composition according to any one of items (1) to (10), wherein said composition does not contain added aluminum salt such as alum.

(13) The immunogenic composition according to item (10) or (11), wherein said CTB and said further adjuvant are present in a mass ratio range of from 1:200 to 10:1, preferably of from 1:100 to 5:1, more preferably of from 1:30 to 1:1.

(14) The immunogenic composition according to any one of items (1) to (13), comprising Norovirus VLPs as antigen and CTB as an adjuvant.

(15) The immunogenic composition according to any one of items (1) to (14), comprising VLPs comprising or consisting of a genogroup I noroviral antigen, VLPs comprising or consisting of a genogroup 11 noroviral antigen, and CTB as an adjuvant.

(16) The immunogenic composition according to any one of items (1) to (15), comprising VLPs comprising or consisting of a genotype I.1 or I.4 noroviral antigen, VLPs comprising or consisting of a genotype II.4 noroviral antigen, and CTB as an adjuvant.

(17) The immunogenic composition according to any one of item (15), comprising said genogroup I noroviral antigen and said genogroup II noroviral antigen in a mass ratio range of from 1:1 to 1:6, preferably of from 1:1.5 to 1:5, more preferably of from 1:2 to 1:4.

(18) The immunogenic composition according to item (16), comprising said genotype I.1 or I.4 noroviral antigen and said genotype II.4 noroviral antigen in a mass ratio range of from 1:1 to 1:6, preferably of from 1:1.5 to 1:5, more preferably of from 1:2 to 1:4.

(19) The immunogenic composition according to item (1), wherein said adjuvant is a B subunit of an $AB_5$ toxin, such as the B subunit of cholera toxin (CTB) and/or the B subunit of *E. coli* heat-labile enterotoxin (LTB).

(20) The immunogenic composition according to item (19), wherein said B subunit of an $AB_5$ toxin is a protein defined according to any one or more or all of items (A) to (I) below, and/or wherein said B subunit of an $AB_5$ toxin is a protein as defined according to any one or more or all of items (A') to (I') below.

(21) The immunogenic composition according to any one or more of items (7) to (9), (13) to (16), (20), (22), (24), and (28), wherein said composition is free of the A subunit of said CTB, said LTB, or said $AB_5$ toxin.

(22) An immunogenic composition comprising norovirus virus-like particles (norovirus VLPs), preferably VLPs of a genogroup I norovirus and/or VLPs of a genogroup II norovirus, and at least one B subunit of an $AB_5$ toxin as adjuvant.

(23) The immunogenic composition according to item (22), wherein said VLPs comprise or consist of (a) NoV antigen(s) as defined in items (a) to (k) below.

(24) The immunogenic composition according to item (21) or (22), wherein said B subunit of an $AB_5$ toxin is CTB that is a protein as defined in any one of items (A) to (I) below, or said B subunit of an $AB_5$ toxin is LTB that is a protein as defined in any one of items (A') to (I') below, preferably said B subunit is said CTB.

(25) The immunogenic composition according to any one of items (22) to (24), said immunogenic composition comprising VLPs comprising, preferably consisting of, norovirus genogroup I antigen(s) and VLPs comprising, preferably consisting of, norovirus genogroup II antigen(s).

(26) The immunogenic composition according to item (25), wherein said norovirus genogroup I antigen(s) is/are genotype I.4 antigens and said norovirus genogroup II antigen(s) is/are genotype II.4 antigens.

(27) The immunogenic composition according to any one of items (1) to (26) for use in a method of preventing and/or treating Norovirus infection in a mammal, preferably in a human.

(28) An immunogenic composition for use in a method of preventing and/or treating Norovirus infection and infection by a bacterial pathogen in a mammal, preferably in a human, said immunogenic composition comprising a noroviral antigen as defined in any of items (1) to (26) and a B subunit of a bacterial $AB_5$ toxin capable of generating an immune response against said bacterial pathogen.

(29) The immunogenic composition for the use according to item (27) or (28), wherein the use comprises parenteral administration of the immunogenic composition to a subject.

(30) The immunogenic composition for the use according to item (29), wherein said parenteral administration is intravenous administration.

(31) The immunogenic composition for the use according to item (29), wherein said parenteral administration is intradermal, intramuscular or subcutaneous administration.

(32) The immunogenic composition for the use according to item (31), wherein said immunogenic composition is preferably as defined in any one of items (24), (25) and (26).

(33) The immunogenic composition for the use according to item (27) or (28), wherein the use comprises intranasal, oral, sublingual or buccal administration of the immunogenic composition to a subject.

(34) An anti-norovirus vaccine or a pharmaceutical composition, comprising the immunogenic composition according to any one of items (1) to (33) and preferably a pharmaceutically acceptable carrier.

(35) The anti-norovirus vaccine or a pharmaceutical composition according to item (34), for use in a method of treating or preventing norovirus infection or for reducing severity of norovirus infection in a subject, such as by parenteral administration, notably by intradermal, intramuscular or subcutaneous administration.

(36) The anti-norovirus vaccine or a pharmaceutical composition according to item (34) or (35), for use in a method of treating or preventing or reducing the severity of, preferably preventing, gastroenteritis caused by NoV infection.

(37) The norovirus vaccine or pharmaceutical composition according to item (34), (35) or (36) that is capable of improving the Th1 immune response against the antigen(s) or of increasing the ratio of the Th1 immune response to the The2 immune response against the antigen(s) in a subject.

(38) A single-dose dosage form of an anti-norovirus vaccine comprising the anti-norovirus vaccine according to any one of items (34) to (37) and a pharmaceutically acceptable carrier, said dosage form comprising from 10 to 1000 μg, preferably from 30 to 300 μg, more preferably from 55 to 150 μg of said at least one or more Norovirus antigen(s).

(39) A vaccine for use in preventing or treating norovirus infection and infection by a bacterial pathogen, said vaccine comprising at least one norovirus antigen according to any one of the preceding items and a B subunit of an $AB_5$ toxin capable of generating an immune response against said bacterial pathogen.

(40) The vaccine according to item (39), wherein said bacterial pathogen is selected from the group of *Vibrio cholerae* and *E. choli.*

(41) A method of preventing or treating norovirus infection, comprising administering to a subject the immunogenic composition as defined in any one of items (1) to (33) or a vaccine according to item (34), (35), (36), (37) or (39) or a single dosage form according to (38).

(42) Use of a B subunit of a bacterial $AB_5$ toxin for reducing interference of the immune response in a subject against a noroviral genogroup I antigen by a noroviral genogroup II antigen. These antigens may be present in an immunogenic composition comprising the noroviral genogroup I antigen and the noroviral genogroup II antigen.

(43) The use of item (42), wherein said B subunit of a bacterial $AB_5$ toxin is CTB or LTB, preferably as defined in item (21) and/or (24).

(44) The immunogenic composition according to any one of items (1) to (33), wherein said composition does not contain an A subunit of an $AB_5$ toxin and does not contain an aluminum salt (e.g. aluminum hydroxide, alum).

(45) Use of a B subunit of a bacterial $AB_5$ toxin for improving the Th1 immune response against an immunogenic composition comprising one or more norovirus antigen(s) as defined in any one of items (1) to (33) in a subject, preferably for increasing the ratio of the Th1 immune response to the Th2 immune response in a subject to said one or more norovirus antigen(s).

The immunogenic compositions of the invention comprise, apart from at least one norovirus antigen, at least one B subunit of an $AB_5$ toxin, such as CTB or LTB. The present inventors have found immunogenic compositions, and vaccines containing them, that are immunogenic against norovirus (NoV) antigens and have surprisingly high immunogenic activity, particularly if administered parenterally. In particular, the antigenic compositions and vaccines of the invention have high ability to generate NoV GI-specific serum antibodies that block the binding of NoV VLPs to pig gastric mucin (PGM) as a source of histo-blood group antigens (HBGA). The inventors have also found that use of CTB or LTB as adjuvant allows obtaining a more balanced Th1/Th2 immune response compared to immunogenic compositions not containing it and/or compared to immunogenic compositions containing alum as adjuvant. The B subunit of $AB_5$ toxins, such as CTB or LTB, stimulates much stronger Th1 immune response than alum, particularly if administered parenterally. This is a surprising finding, as according to Estes et al. (J. Inf. Diseases, 18 (2000) S367-S373), use of CT as adjuvant for oral delivery of norovirus VLPs leads to stronger Th2 immune response. Th1 cells generate responses against intracellular parasites such as bacteria and viruses, Th2 cells produce immune responses against extracellular parasites (Mosmann T R et al., 1986, J Immunol., 136:2348-2357; O'Garra A & Arai N, 2000, Trends Cell Biol., 10:542-550). Strong Th1 immune response is an important quality parameter for antiviral vaccines like vaccine against noroviruses.

The inventors have further found that the adjuvant used in the invention reduces and reverses an inhibitory effect (interference) on an immune response to a NoV antigen of a first genogroup or genotype by co-administration of a NoV antigen of a second genogroup or genotype, and can additionally boost the humoral immune response. In particular, the inventors have found that the adjuvant used in the invention reduces and reverses an inhibitory effect on an immune response to a NoV genogroup I antigen by co-administration of a NoV genogroup II antigen.

DETAILED DESCRIPTION OF THE INVENTION

Figure 1:
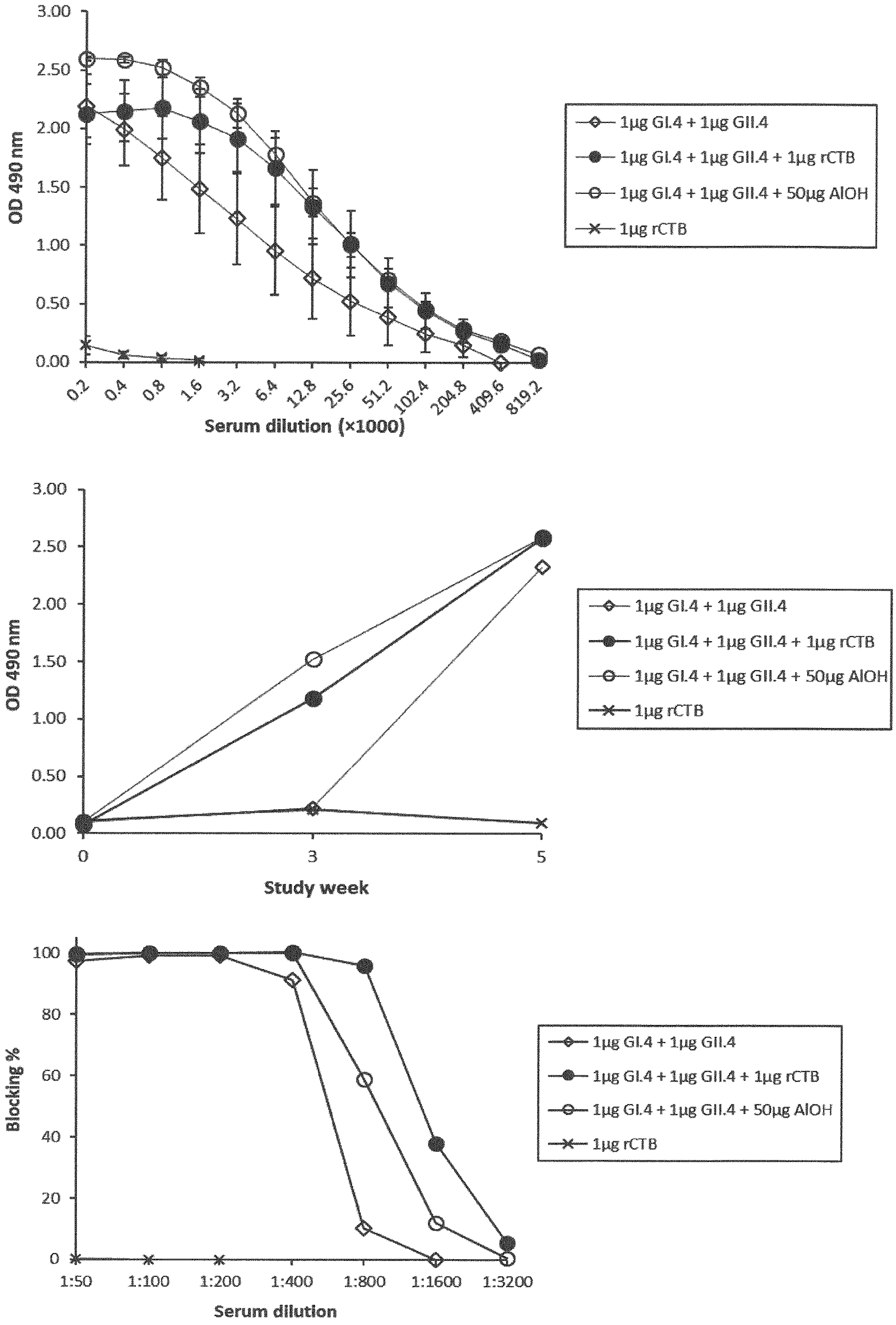
FIG. 1: The upper panel illustrates the result of norovirus (NoV) GI.4-specific serum IgG titers after two (at day 0 and day 21) intramuscular (IM) immunizations of BALB/c mice with a mixture of GI.4 (Chiba) and GII.4 (Aomori) VLPs (1 mkg dose each) alone or formulated with a recombinant CTB (rCTB, 1 mkg (microgram, μg)) or aluminum hydroxide ($Al(OH)_3$, 50 mkg). The mid panel shows kinetics of NoV GI.4-specific IgG immune response development in the pooled sera of mice immunized as described above and measured in ELISA. The lower panel illustrates the ability of NoV GI.4-specific serum antibodies to block the binding of GI.4 VLPs to pig gastric mucin (PGM) as a source of histo-blood group antigens (HBGA). Blocking index (%) was calculated as follows: 100%−(OD[with serum]/OD [without serum]×100%).

Noroviruses are non-enveloped single-stranded positive-sense RNA viruses. They belong to the family Calciviridae. A key structural component of norovirus particles is the VP1 protein. The size of the NoV particle varies between 23 and 40 nm in diameter. Depending on the size, the number of VP1 molecules per viral particle is generally either 60 or 180 molecules (http://viraizone.expasy.org/194). There are five different genogroups of noroviruses (GI, GII, GIII, GIV, and GV) that can be further divided into genotypes. Examples of noroviruses are Norwalk virus (GenBank: AF093797.1), GI.1 strain Aichi/124-89/JP (GenBank: BAA834130), GI.2 strain Funabashi258/96/JP (GenBank: BAC05516), Maryland virus (MV, AY032605), GI.3 strain Shimizu/KK2866/JP (GenBank: A1173765), GII.17 strain C142/1978/GUF (GenBank: AGI17592), GI.4 strain Chiba407/87/JP (GenBank: BAA82106), GI.7 strain TCH-060/USA/2003 (GenBank: AEQ77282), GII.4 strain NU2014/GII.4/Groningen01 (GeneBank: CRL46961), GII.4 strain Aomori2/2006/JP (GenBank: BAG70446), GIV.1 strain Ahrenshoop246/DEU/2012 (GenBank: AFN61315), GII.17 strain JP/2002/Saitama/T87 (GenBank: AII73747), Jena virus (JV, AJ01099), GII.4 strain Sydney/NSW0514/2012/AU (GenBank: AFV08795), GII.3 strain Kashiwa336/00/JP (GenBank: AAZ66774), GII.17 strain JP/2013//Saitama5203 (GenBank: BAR63715), Seto virus (GenBank: AB031013). There are many other norovirus strains the complete genomes of which are annotated in publicly available databases (www.viprbrc.org). Table 1A and B list several NoV strains.

NoV Antigen(s) of the Invention

The immunogenic composition of the invention comprises at least one norovirus (NoV) antigen and at least one adjuvant. A NoV antigen according to the invention is a protein. The NoV antigen is generally a NoV capsid protein or a fragment or derivative thereof. NoV capsid proteins are the VP1 and the VP2 protein, whereby the VP1 protein, fragments and derivatives thereof are preferred for use as an antigen in the present invention, as they may form virus-like particles (VLPs). However, VP2 may also be contained in the immunogenic composition. Table 1B contains the amino acid sequences of VP1 proteins of several NoV strains (SEQ ID NOs 1 to 78). As can be seen, there is considerable variability among VP1 proteins. Thus, the antigen and VP1 protein of the invention are not limited to any specific antigen or VP1 protein of a NoV occurring in nature, but cover fragments, derivatives and fusion proteins of such specific antigen or VP1 protein.

The NoV antigen or the VP1 protein of the invention may be a protein (a) the amino acid sequence of which consists of an amino acid sequence selected from any one of SEQ ID NOs: 1 to 78; or (b) the amino acid sequence of which consists of an amino acid sequence of at least 300, preferably at least 400, more preferably at least 450, even more preferably at least 500 contiguous amino acid residues of an amino acid sequence selected from any one of SEQ ID NOs: 1 to 78; or (c) the amino acid sequence of which comprises an amino acid sequence of at least 300, preferably at least 400, more preferably at least 450, even more preferably at least 500 contiguous amino acid residues of an amino acid sequence selected from any one of SEQ ID NOs: 1 to 78; or (d) the amino acid sequence of which has an amino acid sequence identity of at least 70%, preferably at least 80%, more preferably at least 85%, even more preferably at least 90%, and most preferably at least 95%, to an amino acid sequence selected from any one of SEQ ID NOs: 1 to 78; or (e) the amino acid sequence of which has a length of at least 300 amino acid residues, said amino acid sequence having an amino acid sequence identity of at least 70%, preferably at least 80%, more preferably at least 85%, even more preferably at least 90%, and most preferably at least 95%, to at least a segment of at least 300 contiguous amino acid residues of an amino acid sequence selected from any one of SEQ ID NOs: 1 to 78; or (f) the amino acid sequence of which has a length of at least 400, preferably at least 450, amino acid residues, said amino acid sequence having an amino acid sequence identity of at least 70%, preferably at least 80%, more preferably at least 85%, even more preferably at least 90%, and most preferably at least 95%, to at least a segment of at least 400, preferably at least 450, respectively, contiguous amino acid residues of an amino acid sequence selected from any one of SEQ ID NOs: 1 to 78; or (g) the amino acid sequence of which has a length of at least 500 amino acid residues, said amino acid sequence having an amino acid sequence identity of at least 70%, preferably at least 80%, more preferably at least 85%, even more preferably at least 90%, and most preferably at least 95%, to at least a segment of at least 500 contiguous amino acid residues of an amino acid sequence selected from any one of SEQ ID NOs: 1 to 78; or (h) the amino acid sequence of which has from 1 to 100, preferably from 1 to 80, more preferably from 1 to 60, more preferably from 1 to 40, more preferably from 1 to 30, more preferably from 1 to 20, even more preferably from 1 to 10, amino acid residue deletions, substitutions, additions or insertions compared to an amino acid sequence selected from any one of SEQ ID NOs: 1 to 78; or (i) the amino acid sequence of which has a length of at least 300 amino acid residues and has from 1 to 100, preferably from 1 to 80, more preferably from 1 to 60, more preferably from 1 to 40, more preferably from 1 to 30, more preferably from 1 to 20, even more preferably from 1 to 10, amino acid deletions, substitutions, additions or insertions compared to a segment of at least 300 contiguous amino acid residues of an amino acid sequence selected from any one of SEQ ID NOs: 1 to 78; or (j) the amino acid sequence of which has a length of at least 400, preferably at least 450, amino acid residues and has from 1 to 100, preferably from 1 to 80, more preferably from 1 to 60, more preferably from 1 to 40, more preferably from 1 to 30, more preferably from 1 to 20, even more preferably from 1 to 10, amino acid deletions, substitutions, additions or insertions compared to a segment of at least 400, preferably at least 450, respectively, contiguous amino acid residues of an amino acid sequence selected from any one of SEQ ID NOs: 1 to 78; or (k) the amino acid sequence of which has a length of at least 500 amino acid residues and has from 1 to 100, preferably from 1 to 80, more preferably from 1 to 60, more preferably from 1 to 40, more preferably from 1 to 30, more preferably from 1 to 20, even more preferably from 1 to 10, amino acid deletions, substitutions, additions or insertions compared to a segment of at least 500 contiguous amino acid residues of an amino acid sequence selected from any one of SEQ ID NOs: 1 to 78.

The antigen or protein defined above may have a maximum length in terms of number of amino acid residues of 550 amino acid residues, preferably 520 amino acid residues.

SEQ ID NOs: 1 to 78 are also referred to herein as "reference sequences". A definition following the wording "protein the amino acid sequence of which . . . " defines the entire amino acid sequence of the protein (not just a part thereof). The expression "an amino acid sequence selected from any one of SEQ ID NOs: 1 to 78" means the entire amino acid sequence of any one of SEQ ID NOs: 1 to 78, respectively, unless explicit reference is made to a "segment" or "portion". A "segment" or "portion" of an amino acid sequence is a partial sequence (or fragment) of contiguous amino acid residues of any given number of amino acid residues of the amino acid sequence which is referred to. The length of an amino acid sequence is measured by the number of amino acid residues it consists of. Amino acid sequence identities may be determined by protein sequence search and alignment programs freely accessible from internet, for example PROTEIN BLAST (https://blast.ncbi.nlm.nih.gov/Blast.cgi?PAGE=Proteins) and ExPASy (http://web.expasy.org/sim/). A comprehensive list of sequence alignment tools can be found at http://molbiol-tools.ca/Alignments.htm.

The NoV antigen may be a NoV VP1 protein of any NoV genogroup, a fragment of such protein, a derivative of the protein or the fragment, or a protein comprising an amino acid sequence of a NoV VP1 protein or derivative, as defined above in items (a) to (k). Preferably, the antigen is an antigen of genogroups I, II or IV, especially a VP1 protein of genogroups I, II or IV.

The antigen or protein may have amino acid deletions, substitutions, additions or insertions compared to the reference sequences indicated above. Among these, deletions, substitutions, and additions are preferred. The number(s) of such alterations indicated above refer to the sum of all deletions, substitutions, additions and insertions. The term "insertion" relates to insertions within the amino acid sequence of a reference sequence, i.e. excluding additions at the C- or N-terminal end. The term additions means additions at the C- or N-terminal end of the amino acid sequence of a reference sequence. A deletion may be a deletion of a terminal or an internal amino acid residue of a reference sequence.

A fragment of a protein antigen such as of the NoV VP1 protein may be any protein fragment having a length of at least 300, preferably at least 400, more preferably at least 450, and even more preferably at least 500 contiguous amino acid residues of a VP1 protein of any NoV found in nature or those given in Table 1B. A fragment may be as defined in item (b) above, but having less amino acid residues than the reference sequence. If, as is preferred, the composition contains VLPs as an antigen, the antigen forming the VLPs must have a sufficient length to form VLPs. Whether VLPs are formed can be determined by established methods such as by electron microscopy (Laue M & Banned N., 2010, J Applied Microbiol., 109:1159-1168; Harris J R, 1999, Methods Mol Biol., 117:13-30; Pogan R et al., 2018, J Phys.: Condens. Matter, 30: 064006) or by size exclusion chromatography (Effio C L et al., 2016, Vaccine, 34:1259-1267).

A derivative or derivative of a fragment of a VP1 protein may be as defined above in any one of items (d) to (k). A protein comprising a NoV antigen or VP1 protein, or a fragment or derivative thereof may be a fusion protein comprising the antigen or VP1 protein, fragment or derivative, respectively, and an added domain or sequence stretch such as a signal sequence or a purification tag. Such added domain or sequence stretch may be added at the N- or C-terminus of the VP1 protein, fragment or derivative, and may consist of not more than 30, preferably not more than 20, more preferably not more than 10 amino acid residues. It is also possible that the antigen contains a covalently bound non-proteinaceous covalent modification, such as a PEGylation.

A NoV antigen for use in the invention, such as the VP1 protein or a fragment or derivative thereof, may be from any NoV found in nature, preferably an antigen is an antigen of NoV genogroups I, II or IV. The antigen may be of any NoV genogroup and/or any genotype, such as those listed in Table 1A or B. In one embodiment, the NoV antigen is from a genogroup I NoV. In another embodiment, the NoV antigen is from a genogroup II NoV. Among these genogroups, the composition of the invention may contain at least an antigen of a NoV of genogroup II. A given NoV antigen of any one of the above items (a) to (k) is considered a NoV antigen of the genogroup and/or genotype indicated in Table 1A or 1B for the SEQ ID NO for which the definition of items (a) to (k) applies. Where a given NoV antigen may, according to the definition of items (a) to (k), belong to more than one genogroup or genotype, it is an antigen of the genogroup or genotype to which it has a higher sequence identity, e.g. over the entire length of the respective reference sequence.

A NoV antigen of genogroup I may be a protein (a') the amino acid sequence of which comprises or consists of an amino acid sequence selected from any one of SEQ ID NOs: 1 to 22; or (b') the amino acid sequence of which consists of an amino acid sequence of at least 300, preferably at least 400, more preferably at least 500 contiguous amino acid residues of an amino acid sequence selected from any one of SEQ ID NOs: 1 to 22; or (c') the amino acid sequence of which comprises an amino acid sequence of at least 300, preferably at least 400, more preferably at least 500 contiguous amino acid residues of an amino acid sequence selected from any one of SEQ ID NOs: 1 to 22; or (d') the amino acid sequence of which has an amino acid sequence identity of at least 70%, preferably at least 80%, more preferably at least 85%, even more preferably at least 90%, and most preferably at least 95% to an amino acid sequence selected from any one of SEQ ID NOs: 1 to 22; or (e') the amino acid sequence of which has a length of at least 300 amino acid residues, said amino acid sequence having an amino acid sequence identity of at least 70%, preferably at least 80%, more preferably at least 85%, even more preferably at least 90%, and most preferably at least 95%, to at least a segment of at least 300 contiguous amino acid residues of an amino acid sequence selected from any one of SEQ ID NOs: 1 to 22; or (f') the amino acid sequence of which has a length of at least 400, preferably at least 450, amino acid residues, said amino acid sequence having an amino acid sequence identity of at least 70%, preferably at least 80%, more preferably at least 85%, even more preferably at least 90%, and most preferably at least 95%, to at least a segment of at least 400, preferably at least 450, respectively, contiguous amino acid residues of an amino acid sequence selected from any one of SEQ ID NOs: 1 to 22; or (g') the amino acid sequence of which has a length of at least 500 amino acid residues, said amino acid sequence having an amino acid sequence identity of at least 70%, preferably at least 80%, more preferably at least 85%, even more preferably at least 90%, and most preferably at least 95%, to at least a segment of at least 500 contiguous amino acid residues of an amino acid sequence selected from any one of SEQ ID NOs: 1 to 22; or (h') the amino acid sequence of which has from 1 to 100, preferably from 1 to 80, more preferably from 1 to 60, more preferably from 1 to 40, more preferably from 1 to 30, more preferably from 1 to 20, even more preferably from 1 to 10, amino acid deletions, substitutions, additions or insertions compared to an amino acid sequence selected from any one of SEQ ID NOs: 1 to 22; or (i') the amino acid sequence of which has a length of at least 300 amino acid residues and having from 1 to 100, preferably from 1 to 80, more preferably from 1 to 60, more preferably from 1 to 40, more preferably from 1 to 30, more preferably from 1 to 20, even more preferably from 1 to 10, amino acid deletions, substitutions, additions or insertions compared to a segment of at least 300 contiguous amino acid residues of an amino acid sequence selected from any one of SEQ ID NOs: 1 to 22; or (j') the amino acid sequence of which has a length of at least 400, preferably at least 450, amino acid residues and has from 1 to 100, preferably from 1 to 80, more preferably from 1 to 60, more preferably from 1 to 40, more preferably from 1 to 30, more preferably from 1 to 20, even more preferably from 1 to 10, amino acid deletions, substitutions, additions or insertions compared to a segment of at least 400, preferably at least 450, respectively, contiguous amino acid residues of an amino acid sequence selected from any one of SEQ ID NOs: 1 to 22; or (k') the amino acid sequence of which has a length of at least 500 amino acid residues and has from 1 to 100, preferably from 1 to 80, more preferably from 1 to 60, more preferably from 1 to 40, more preferably from 1 to 30, more preferably from 1 to 20, even more preferably from 1 to 10, amino acid deletions, substitutions, additions or insertions compared to a segment of at least 500 contiguous amino acid residues of an amino acid sequence selected from any one of SEQ ID NOs: 1 to 22.

A NoV antigen of genogroup II may be a protein as defined in above items (a') to (k') except that the wording "an amino acid sequence selected from any one of SEQ ID NOs: 1 to 22" is replaced by "an amino acid sequence selected from any one of SEQ ID NOs: 23 to 75". A NoV antigen of genogroup IV may be a protein as defined in above items (a') to (k') except that the wording "an amino acid sequence selected from any one of SEQ ID NOs: 1 to 22" is replaced by "an amino acid sequence selected from any one of SEQ ID NOs: 76 to 78".

An antigen of genogroup I may be of any one or more of the following genotypes: I.1, I.2, I.3, I.4, I.5, I.6, I.7, I.8, or I.9. An antigen of genogroup II may be an antigen of any one or more of the following genotypes: II.1, II.2, II.3, II.4, II.5, II.6, II.7, II.8, II.12, II.13, II.14, II.17, II.21, II.22, II.24, or II.25. An antigen of genogroup IV may be an antigen of any one or more of the following genotypes: IV.1 or IV.3.

A NoV antigen of genotype I.1 (GI.1) may be a protein as defined in above items (a') to (k') except that the wording "an amino acid sequence selected from any one of SEQ ID NOs: 1 to 22" is replaced by "an amino acid sequence selected from any one of SEQ ID NOs: 5 or 6". A NoV antigen of any other genotype listed in Table 1B is defined accordingly by substituting the SEQ ID NO of the previous sentence by those given in Table 1A or 1B for the respective genotype. For example, a NoV antigen of genotype I.4 (GI.4) may be a protein as defined in above items (a') to (k') for the amino acid sequence of SEQ ID NO: 13 or 14. A NoV antigen of genotype II.4 may be a protein as defined in above items (a') to (k') for the amino acid sequence selected from any one of SEQ ID NOs: 40-54. A NoV antigen of genotype II.6 may be a protein as defined in above items (a') to (k') for the amino acid sequence selected from any one of SEQ ID NOs: 56-58.

Among NoV antigens of genogroup I, those of genotype I.1 and I.4 are preferred, those of genotype I.4 are more preferred. Among NoV antigens of genogroup II, those of genotypes II.1 (GII.1), II.4 (GII.4), II.6 (GII.6), and II.17 (GII.17) are preferred, those of genotypes II.1 (GII.1), II.4 (GII.4), and II.6 (GII.6) are more preferred, and those of genotype II.4 are even more preferred in the present invention.

Adjuvant Used in the Invention

The immunogenic composition of the invention comprises, apart from the at least one NoV antigen, at least one adjuvant (also referred to as "vaccine adjuvant"). Adjuvants are pharmacological or immunological agents that boost the immune response after administration to a subject, which generally leads to higher titer of antibodies and longer-lasting immune protection. Adjuvants may also modulate the immune response, for example may affect the balance between cellular and humoral immune responses. Vaccine adjuvants are described in numerous research publications as well as in review articles (Lee S. & Nguen M T., 2015, Immune Netw., 15:51-57; Di Pasquale A et al., 2015, Vaccines, 3:320-343; Cimica, V, & Galarza, J M., 2017, Clin. Immunol., 183:99-108; McKee A S & Marrack P., 2017, Curr. Opin. Immunol., 47:44-51). However, only few adjuvants are currently used in vaccines that are approved for use in humans. These adjuvants include aluminum salts, oil-in water emulsions (MF59 and AS03), and a few more have been tested in clinical trials (CpG, Flagellin, PolyI:C, AS1, AS2, ISCOS and ISCOMMATRIX (Lee S. & Nguen M T., 2015, Immune Netw., 15:51-57). Adjuvants are frequently classified by their mode of action and/or preferred route of application. Following their mode of action, some of the adjuvants belong to the group of Toll-like Receptor (TLR) agonists. Examples of adjuvants or adjuvant classes are: TLR (toll-like receptor) agonists such as CpG (TLR9 agonist), poly (U) (TLR7/8 agonist), bacterial endotoxin derivatives like monophosphoryl lipid A or MPLA (TLR4 agonist), etc.

Bacterial exotoxins and their fusions can also act as adjuvants in a vaccine composition. Some bacterial exotoxins have been used in immunogenicity studies. These include Cholera toxin (CT) that is produced by the bacterium *Vibrio cholerae* and consists of two subunits: the toxic subunit A (CTA) and the non-toxic subunit B (CTB) that forms a homopentameric structure (Lemcer, W I & Tsai, B. 2003, Trends Biochem. Sci., 28:639-645; Chinnapen, D J, et al., 2007, FEMS Microbiol. Le., 266:129-137; Wernick, N L, et al., 2010, Toxins 2:310-325). Another bacterial exotoxin that is identical or very similar in terms of tertiary and quaternary structure to CT is heat-labile enterotoxin of *E. coli* (LT). CT and LT are highly homologous and show about 80% of homology. For review of CT-like enterotoxins, please refer to Basset, C et al., 2010, Toxins, 2:1774-17795. Like CT, LT also consists of two subunits the toxic subunit A (LTA) and the non-toxic subunit B (LTB) that forms a pentameric structure. Non-toxic LT mutants and derivatives thereof can serve as adjuvants (for review, please refer to Ma, Y, 2016, Expert Rev. Vaccines, 15:1361-1371). The LT and CT can be structurally classified and are known in the art as $AB_5$ multimeric proteins or $AB_5$ toxins and consist of single catalytic A subunit and pentameric B oligomer (Burnett, W N, 1994, Structure, 2:151-158). For a review on $AB_5$ toxins, reference is made to Merritt, E A & Hol, W G., 1995, Curr. Opin. Struct. Biol., 5:165-171; Beddoe T, et al., 2010 Trends Biochem. Sci. 35:411-418.

LTB, like CTB, was successfully used in animal studies as mucosal adjuvant and for parenteral administration, as fusion with antigen of interest (Zhang, J, et al., 2016, Vaccine, 34:622-629; Marchioro, S B, et al., 2014, Vaccine, 32:4689-4694). Clinical trials to evaluate safety and immunogenicity of orally delivered vaccine against enterotoxigenic *Escherichia coli* (ETEC), composed of inactivated recombinant *E. coli* expressing increased levels of ETEC colonization factors and LTB/CTB hybrid protein showed that presence of hybrid LTB/CTB protein does not change the safety profile, but increases the strength and quality of the immune responses (Lundgren, A, et al., 2013, Vaccine, 31:1163-1170). Use of bacterial exotoxins as mucosal adjuvants in combination with norovirus antigens was described in the past, for heat-labile *E. coli* toxin LT and its non-toxic mutant R192G (Nicollier-Jamot, B, et al., 2004, Vaccine, 22:1079-86; Clements, J D & Norton, E B, 2018, mSphere, 3:e00215-18). U.S. Pat. No. 7,527,801 describes the use of the non-toxic LT mutants LTK63 or LTR72. In this invention, preference is given not to mutant versions of exotoxins, but to their B subunits of, preferably, recombinant origin and to parenteral delivery route of administration of the vaccine in the absence of the A subunit.

In one embodiment of the invention, the adjuvant (or co-antigen) used is a CTB. The CTB usable in the invention may be a protein (A) the amino acid sequence of which comprises or consists of an amino acid sequence selected from any one of SEQ ID NOs: 79 to 96; or (B) the amino acid sequence of which consists of an amino acid sequence of at least 90, preferably at least 100 amino acid residues of an amino acid sequence selected from any one of SEQ ID NOs: 79 to 96; or (C) the amino acid sequence of which comprises an amino acid sequence of at least 90, preferably at least 100 contiguous amino acid residues of an amino acid sequence selected from any one of SEQ ID NOs: 79 to 96; or (D) the amino acid sequence of which has an amino acid sequence identity of at least 85%, preferably at least 90%, more preferably at least 95%, to an amino acid sequence selected from any one of SEQ ID NOs: 79 to 96; or (E) the amino acid sequence of which has a length of at least 90 amino acid residues, said amino acid sequence having an amino acid sequence identity of at least 85%, preferably at least 90%, more preferably at least 95%, to at least a segment of at least 90 contiguous amino acid residues of an amino acid sequence selected from any one of SEQ ID NOs: 79 to 96; or (F) the amino acid sequence of which has a length of at least 100 amino acid residues, said amino acid sequence having an amino acid sequence identity of at least 85%, preferably at least 90%, more preferably at least 95%, to at least a segment of at least 100 contiguous amino acid residues of an amino acid sequence selected from any one of SEQ ID NOs: 79 to 96; or (G) the amino acid sequence of which has from 1 to 15, preferably from 1 to 10, more preferably from 1 to 5, and even more preferably from 1 to 3, amino acid residue deletions, substitutions, additions or insertions compared to an amino acid sequence selected from any one of SEQ ID NOs: 79 to 96; or (H) the amino acid sequence of which has a length of at least 90 amino acid residues and has from 1 to 15, preferably from 1 to 10, more preferably from 1 to 5, and even more preferably from 1 to 3, amino acid deletions, substitutions, additions or insertions compared to a segment of at least 90 contiguous amino acid residues of an amino acid sequence selected from any one of SEQ ID NOs: 79 to 96; or (I) the amino acid sequence of which has a length of at least 100 amino acid residues and having from 1 to 15, preferably from 1 to 10, more preferably from 1 to 5, and even more preferably from 1 to 3, amino acid deletions, substitutions, additions or insertions compared to a segment of at least 100 contiguous amino acid residues of an amino acid sequence selected from any one of SEQ ID NOs: 79 to 96.

In another embodiment of the invention, the adjuvant (or co-antigen) used is an LTB. The LTB usable in the invention may be a protein (A') the amino acid sequence of which comprises or consists of an amino acid sequence selected from any one of SEQ ID NOs: 97 to 100; or (B') the amino acid sequence of which consists of an amino acid sequence of at least 90, preferably at least 100 amino acid residues of an amino acid sequence selected from any one of SEQ ID NOs: 97 to 100; or (C') the amino acid sequence of which comprises an amino acid sequence of at least 90, preferably at least 100 contiguous amino acid residues of an amino acid sequence selected from any one of SEQ ID NOs: 97 to 100; or (D') the amino acid sequence of which has an amino acid sequence identity of at least 85%, preferably at least 90%, more preferably at least 95%, to an amino acid sequence selected from any one of SEQ ID NOs: 97 to 100; or (E') the amino acid sequence of which has a length of at least 90 amino acid residues, said amino acid sequence having an amino acid sequence identity of at least 85%, preferably at least 90%, more preferably at least 95%, to at least a segment of at least 90 contiguous amino acid residues of an amino acid sequence selected from any one of SEQ ID NOs: 97 to 100; or (F') the amino acid sequence of which has a length of at least 100 amino acid residues, said amino acid sequence having an amino acid sequence identity of at least 85%, preferably at least 90%, more preferably at least 95%, to at least a segment of at least 100 contiguous amino acid residues of an amino acid sequence selected from any one of SEQ ID NOs: 97 to 100; or (G') the amino acid sequence of which has from 1 to 15, preferably from 1 to 10, more preferably from 1 to 5, and even more preferably from 1 to 3, amino acid residue deletions, substitutions, additions or insertions compared to an amino acid sequence selected from any one of SEQ ID NOs: 97 to 100; or (H') the amino acid sequence of which has a length of at least 90 amino acid residues and has from 1 to 15, preferably from 1 to 10, more preferably from 1 to 5, and even more preferably from 1 to 3, amino acid deletions, substitutions, additions or insertions compared to a segment of at least 90 contiguous amino acid residues of an amino acid sequence selected from any one of SEQ ID NOs: 97 to 100; or (I') the amino acid sequence of which has a length of at least 100 amino acid residues and having from 1 to 15, preferably from 1 to 10, more preferably from 1 to 5, and even more preferably from 1 to 3, amino acid deletions, substitutions, additions or insertions compared to a segment of at least 100 contiguous amino acid residues of an amino acid sequence selected from any one of SEQ ID NOs: 97 to 100.

The definitions given above with regard to the wording of items (a) to (k) also apply to the above items (A) to (I) and (A') to (I'). As above, a "segment" or "portion" of an amino acid sequence is a partial sequence (or fragment) of contiguous amino acid residues of any given number of amino acid residues of the amino acid sequence of a reference sequence. The length of an amino acid sequence is measured by the number of amino acid residues it consists of. Amino acid sequence identities may be determined as described above in the context of the antigen of the invention. Similarly, sequence identities are determined as defined above. Also, the above definitions regarding amino acid deletions, substitutions, additions or insertions as defined above apply analogously.

Preferably, the CTB used in the invention such as those defined in items (A) to (I) above has a pentameric quaternary structure, e.g. as CTB does in CT. Whether CTB forms a pentameric quaternary structure, as opposed to being monomeric, can be determined using MALDI mass spectroscopy, non-denaturing gel chromatography or by size-exclusion chromatography. These methods are known to the skilled person. In another embodiment, the CTB is monomeric CTB.

Two or more variants of the CTB as defined above may be combined in an immunogenic composition of the invention. In such case, any amounts or mixing ratios disclosed herein refer to the sum of all CTB variants according to the invention.

Similarly, the LTB used in the invention such as those defined in items (A') to (I') above has a pentameric quaternary structure, e.g. as LTB does in LT. Whether LTB forms a pentameric quaternary structure, as opposed to being monomeric, can be determined using MALDI mass spectroscopy, non-denaturing gel chromatography or by size-exclusion chromatography. These methods are known to the skilled person. In another embodiment, the LTB is monomeric LTB.

Two or more variants of the LTB as defined above may be combined in an immunogenic composition of the invention. In such case, any amounts or mixing ratios disclosed herein refer to the sum of all LTB variants according to the invention.

In a further alternative, one or more CTB as defined above may be combined with one or more LTB as defined above in an immunogenic composition of the invention. In such case, any amounts or mixing ratios disclosed herein refer to the sum of all LTB and all CTB variants.

Examples of amino acid sequences of the CTB for use in the invention are provided in Table 2. Examples of amino acid sequences of the LTB for use in the invention are provided in Table 3. Modifications such as mutations may be made to alter some properties of the CTB or LTB, such as expression yield, or to express it in a desired compartment of the cell or plant where it is expressed. Further or alternatively, a purification tag may be added.

Figure 5:
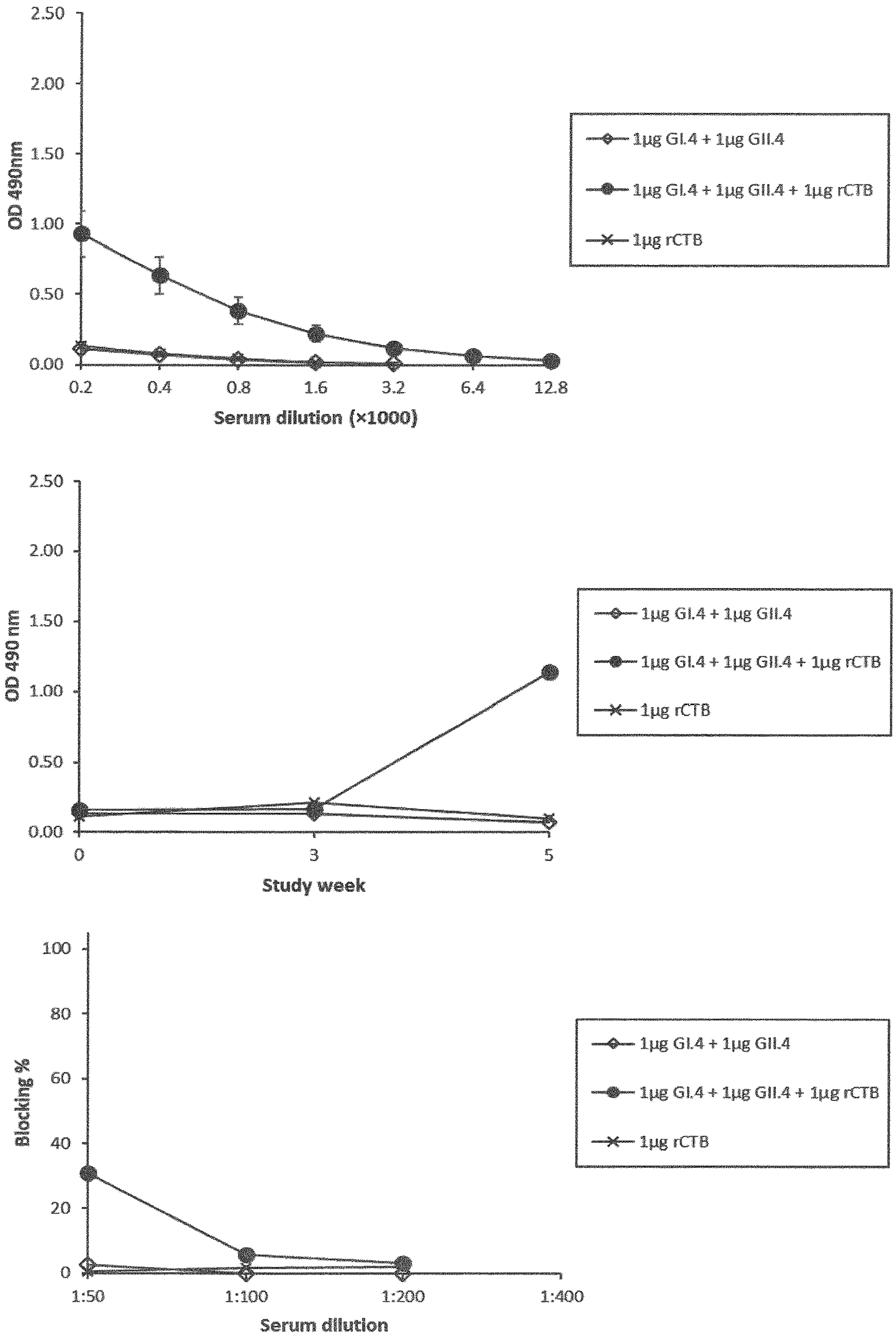
FIG. 5: Upper panel illustrates the result of norovirus (NoV) GI.4-specific serum IgG titers after two (at day 0 and day 21) intranasal (IN) immunizations of BALB/c mice with a mixture of GI.4 (Chiba) and GII.4 (Aomori) VLPs (1 mkg dose each) alone or formulated with a recombinant CTB (rCTB, 1 mkg). Mid panel shows kinetics of NoV GI.4-specific IgG immune response development in the pooled sera of mice immunized as described above and measured in ELISA. Lower panel illustrates the ability of NoV GI.4-specific serum antibodies to block the binding of GI.4 VLPs to pig gastric mucin (PGM) as a source of histo-blood group antigens (HBGA). Blocking index (%) was calculated as follows: 100%−(OD[with serum]/OD[without serum]× 100%).
Figure 6:
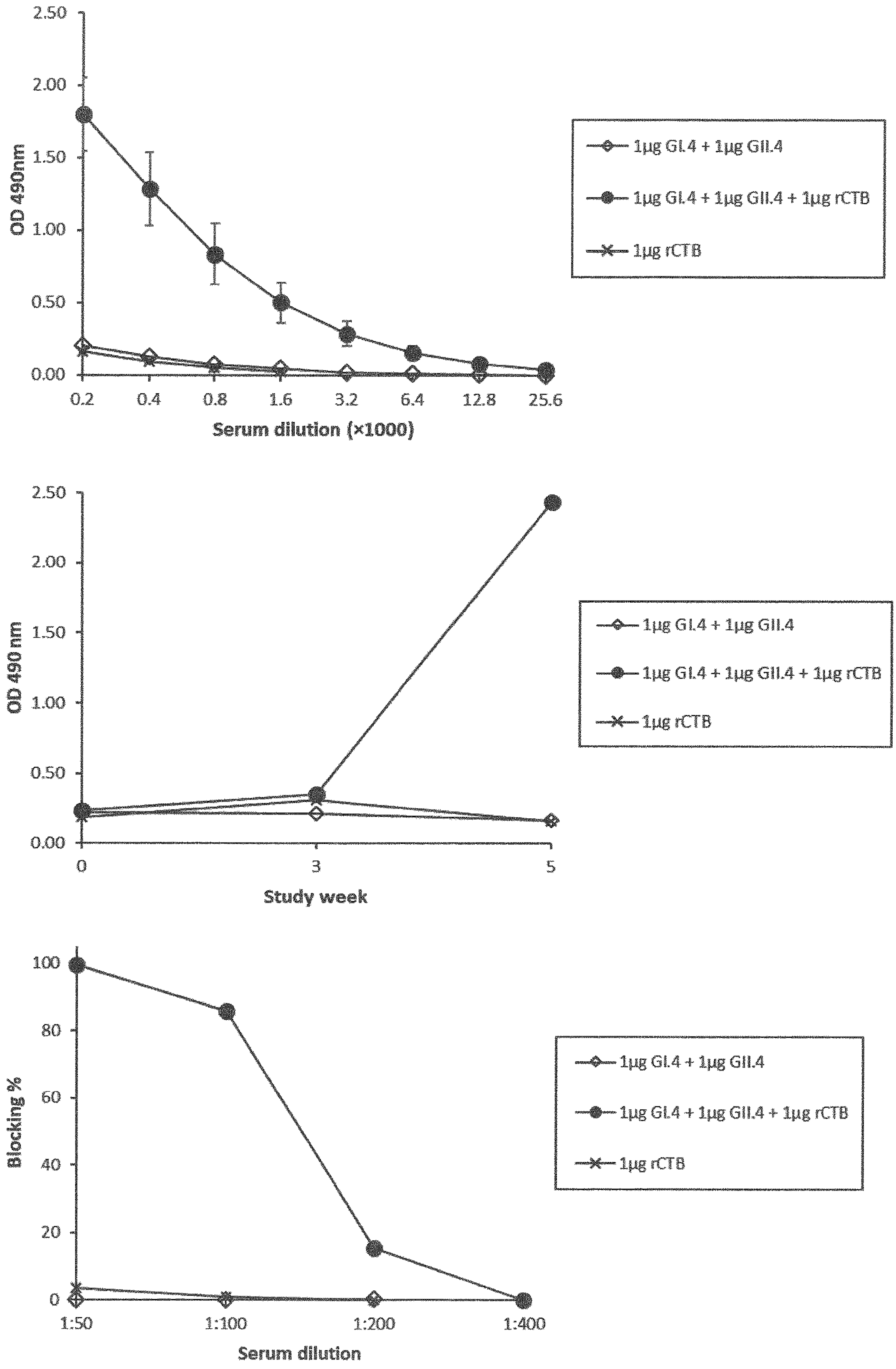
FIG. 6: Upper panel illustrates the result of norovirus (NoV) GII.4-specific serum IgG titers after two (at day 0 and day 21) intranasal (IN) immunizations of BALB/c mice with a mixture of GI.4 (Chiba) and GII.4 (Aomori) VLPs (1 mkg dose each) alone or formulated with a recombinant CTB (rCTB, 1 mkg). Mid panel shows kinetics of NoV GII.4-specific IgG immune response development in the pooled sera of mice immunized as described above and measured in ELISA. Lower panel illustrates the ability of NoV GII.4-specific serum antibodies to block the binding of GII.4 VLPs to pig gastric mucin (PGM) as a source of histo-blood group antigens (HBGA). Blocking index (%) was calculated as follows: 100%−(OD[with serum]/OD[without serum]× 100%).

Use of CTB as vaccine adjuvant or as antigen as well as antigen fusion is described in review articles (Holgren, J, et al., 1994, Am. J. Trop. Med. Hyg., 50:42-54; Lebens, M. & Holmgren, J. 1994, Dev. Biol. Stand., 82:215-227; Sun, J B., et al., 2010, Scand. J. Immunol., 71:1-11; Baldauf K J, et al., 2015, Toxins, 7:974-996; Stratmann, T., 2015, Vaccines, 3, 579-596). CTB is usually used in vaccines for mucosal (predominantly oral or intranasal) route of delivery. CTB is known to trigger humoral immune responses in vaccines administered via the mucosal route (Holmgren et al., 2005, Immunol. Lett., 97:181-188; Holgren et al., 2003, Expert Rev. Vaccines, 2:205-217). A similar effect of Cholera Toxin applied as mucosal adjuvant with plant-made Norwalk virus VLPs was shown (Velaskuez et al., 2010, Clinical & Vaccine Immunol., 17:1850-1858). However, use of CTB as adjuvant in combination with baculovirus-produced noroviral VLPs does not seem to increase mucosal immune responses when delivered orally (Huo, Y et al., 2015, Mol. Immunol., 68:367-72). Similar data were obtained for intranasal delivery of plant-made VLPs in combination with recombinant CTB (Flarebio Biotech LLC, USA) (please refer to Example 4, FIGS. 5 and 6).

Surprisingly, as found in the present invention, NoV antigens such as NoV VLPs with CTB showed much better results when delivered parenterally (such as intramuscular (IM), subcutaneous (SC) or intradermal (ID)). The immune responses were comparable to and sometimes higher than the immune responses produced by formulations with much higher content (in terms of mass) of aluminum hydroxide (see Examples 1 and 2, FIGS. 1-4). Similar vaccines and dosages applied by the mucosal route of delivery produced much weaker immune responses. The inventors have found that use of the B subunit of an $AB_5$ toxin, such as CTB, as adjuvant with norovirus antigens, notably VLPs, for parenteral delivery (intradermal, subcutaneous or intramuscular) increases the strength and quality of immune response in comparison with norovirus VLPs alone or in combination with $Al(OH)_3$. The invention therefore also provides antigenic compositions and vaccines that do not contain alum or contain alum in lower amounts than in the prior art (Leroux-Roels et al. (2018), The Journal of Infectious Diseases, 217(4), 597-607).

Accordingly, the B subunit of a bacterial $AB_5$ toxin such as CTB or LTB can be used for reducing interference of the immune response in a subject against a noroviral genogroup I antigen by a noroviral genogroup II antigen. These antigens may be present in an immunogenic composition comprising the noroviral genogroup I antigen and the noroviral genogroup II antigen.

Accordingly, the B subunit of a bacterial $AB_5$ toxin can also be used, as component of an immunogenic composition comprising one or more NoV antigens as described therein, for preventing and/or treating Norovirus infection and infection by a bacterial pathogen in a mammal, preferably in a human. Further, the B subunit of a bacterial $AB_5$ toxin can be used for improving the Th1 immune response to an immunogenic composition comprising one or more norovirus antigen(s) as defined herein in a subject. Preferably, the B subunit of a bacterial $AB_5$ toxin can be used for increasing the ratio of the Th1 immune response to the Th2 immune response, in a subject, to the one or more norovirus antigen(s) described herein. In these uses, CTB or LTB are the preferred B subunits of the $AB_5$ toxin.

CTB for use in the invention can be obtained from commercial sources. CTB can be expressed as wild-type or mutated versions with enhanced properties, e.g. yield, stability, post-translational modifications, or in the form of fusions to antigens in a variety of organisms, including prokaryotes like *E. coli* or eukaryots like green plants (Miata, T., et al., 2012, Vaccine; 30(28):4225-32; Hamorsky, K T., et al., 2013, PLoS Negl Trop Dis., 7(3):e2046; Hamorsky, K T., et al., 2015, Sci Rep. 2015 Jan. 23; 5:8003; Stratmann, T., 2015, Vaccines, 3, 579-596). Further, CTB may be expressed in plants analogously as described below for the antigen and in EXAMPLE 6. This allows any modification or mutation desired to be made such as those given in Table 2. In an important embodiment of the invention, the immunogenic composition or vaccine does not contain alum (aluminum hydroxide).

LTB for use in the invention can be obtained from commercial sources (for example, supplied by Merck recombinant LTB produced in *Pichia pastoris*, Cat. No. E8656). LTB can be expressed as wild-type or mutated versions with enhanced properties, e.g. yield, stability, post-translational modifications, or in the form of fusions to antigens in a variety of organisms, including prokaryotes like *E. coli* or eukaryotes like yeasts and green plants (Pillai, D, et al., 1996, FEBS Lett., 387:23-26; Lim, J G, et al., 2009, J. Microbiol. Biotechnol., 19:502-510; Wagner, B, et al., 2004, J. Immunol. Methods, 287:203-215; Sim, J S, et al., 2009, Plant Mol. Biol. Rep., 27:388-399; Soh, H S, et al., 2015, SpringerPlus, 4:148). Further, LTB may be expressed in plants analogously as described below for the antigen and in EXAMPLE 6. This allows any modification or mutation desired to be made such as those given in Table 3.

Immunogenic Composition of the Invention

The immunogenic composition of the invention comprises at least one NoV antigen and an adjuvant. It may comprise two or more different NoV antigens, such as two or more VP1 proteins, in order to generate immune responses in a mammal against multiple NoV antigens at the same time, such as three different NoV antigens. The NoV antigen(s) used in the composition of the invention depend on the NoV or NoVs against which immunization in a mammal should be achieved using the vaccine of the invention. As NoVs that cause infections in mammals evolve, the antigen(s) used in the composition may be changed or adapted so as to cause immune response in a subject against the NoVs considered a health risk. As mentioned above, composition of the invention may contain a NoV antigen from any NoV genogroup such as GI, GII or GIV. The composition may contain one NoV antigen from any of these genogroups. However, if it contains only one antigen, this antigen may be from genogroup II, since NoV of this genogroup has more frequently caused health risks in past years. Preferably, the composition of the invention comprises two or more different NoV antigens that may be antigens of two or more different NoV genogroups. In preferred embodiments, the immunogenic composition of the invention comprises at least two NoV antigens from two different NoV genogroups, preferably an antigen from a NoV genogroup I and an antigen of a NoV genogroup II. In a further embodiment, the immunogenic composition comprises two or more antigens from one NoV genogroup, preferably of genogroup II. An antigen from any genogroup I NoV listed in Table 1A or 1B may be combined with an antigen from any genogroup II NoV listed in Table 1A or 1B in the composition (and vaccine) of the invention. It is of course possible to add a further antigen from a genogroup I, genogroup II or another genogroup (e.g. those of Table 1A or B) to the composition of the invention.

Regarding genotypes of the antigens to be used in the composition of the invention, there are no particular limitations. Preferred genotypes of genogroup I are genotypes I.1 and I.4. Preferred genotype of genogroup II are genotypes II.4 and II.17. A more preferred genotype of genogroup II is genotype II.4. If the composition of the invention contains antigens from both genogroups I and II, an antigen from genotype I.4 and an antigen of genotype II.4 may be combined. As above, the antigens are preferably VP1 proteins. If the composition of the invention contains two or more NoV antigens or VP1 proteins, each may be as defined in items (a) to (k) above.

With regard to embodiments wherein an antigen from NoV genogroup I is combined with an antigen from NoV genogroup II, the following examples of immunogenic compositions may be mentioned:

a composition comprising an antigen of genotype I.1 and an antigen of genotype II.1;

a composition comprising an antigen of genotype I.1 and an antigen of genotype II.4;

a composition comprising an antigen of genotype I.1 and an antigen of genotype II.6;

a composition comprising an antigen of genotype I.4 and an antigen of genotype II.1;

a composition comprising an antigen of genotype I.4 and an antigen of genotype II.4;

a composition comprising an antigen of genotype I.4 and an antigen of genotype II.17;

a composition comprising an antigen of genotype I.4 and an antigen of genotype II.2;

a composition comprising an antigen of genotype I.1 and an antigen of genotype II.17;

a composition comprising an antigen of genotype I.1 and an antigen of genotype II.2;

and a composition comprising an antigen of genotype I.4 and an antigen of genotype II.6.

Preferred is an embodiment, wherein the immunogenic composition contains an antigen of genotype I.1 or I.4 (GI.4) and an antigen of genotype II.4 (GII.4) or II.17. More preferred is an embodiment, wherein the immunogenic composition contains an antigen of genotype I.1 or I.4 (GI.4) and an antigen of genotype II.4 (GII.4). In all these embodiments, the immunogenic compositions further contain one or more adjuvants as described herein.

As mentioned above, the immunogenic composition may, in a further embodiment, comprises two or more antigens from one NoV genogroup, preferably of genogroup II. The immunogenic composition may comprise two different antigens of genogroup II noroviruses, such as an antigen of a first genotype of a genogroup II norovirus and an antigen of a second genotype of a genogroup II norovirus. For example, the composition may comprise an antigen (e.g. VP1 protein) of a genotype II.1 NoV and an antigen (e.g. VP1 protein) of a genotype II.4 NoV. Alternatively, the composition may comprise an antigen (e.g. VP1 protein) of a genotype II.1 NoV and an antigen (e.g. VP1 protein) of a genotype II.17 NoV. Alternatively, the composition may comprise an antigen (e.g. VP1 protein) of a genotype II.4 NoV and an antigen (e.g. VP1 protein) of a genotype II.17 NoV. A NoV antigen of genogroup II may be a protein as defined in above items (a') to (k') except that the wording "an amino acid sequence selected from any one of SEQ ID NOs: 1 to 22" is replaced by "an amino acid sequence selected from any one of SEQ ID NOs: 23 to 75". Antigens of genotypes II.1, II.4 and II.17 may be selected from these SEQ ID NOs.

Derivatives of an antigen as defined above (e.g. in items (b) to (k)) are considered antigens of the genogroup and/or genotype to which the native antigen (e.g. of SEQ ID NOs 1 to 78) belongs. If an antigen such as a VP1 protein may, using this rule, belong to two different genogroups or genotypes, the antigen or derivative belongs to the genogroup or genotype to which the antigen or derivative is most similar in terms of amino acid sequence identity over the entire length of an amino acid sequence of a native VP1 protein such as of any one of SEQ ID NOs 1 to 78.

The immunogenic composition of the invention preferably contains NoV virus-like particles (norovirus VLPs or NoV VLPs) as the antigen(s). VLPs are viral particles consisting of virus structural protein(s), but do not contain viral nucleic acid. In the case of norovirus, VLPs consist of structural protein(s) VP1 or of VP1 and VP2 proteins (or any fragments or derivatives as described herein). The VLPs used in the invention comprise or consist of NoV capsid proteins as antigens, notably VP1 as defined herein. The VLPs may comprise or consists of a protein as defined in any one of items (a) to (k) above. Thus, the proteins of items (a) to (k) above are preferably capable of forming VLPs. Herein, a VLP comprises generally at least 60 VP1 molecules, preferably at least 80 VP1 molecules, more preferably at least 100 VP1 molecules. In a more preferred embodiment, a VLP comprises at least 60 protein molecules as defined in any one of items (a) to (k), preferably at least 80 protein molecules as defined in any one of items (a) to (k), more preferably at least 100 protein molecules as defined in any one of items (a) to (k).

The immunogenic composition of the invention may comprise the genogroup I noroviral antigen and the genogroup II noroviral antigen in a mass ratio range of from 1:1 to 1:6, preferably of from 1:1.5 to 1:5, more preferably of from 1:2 to 1:4. In another embodiment, the immunogenic composition of the invention comprises the genogroup I noroviral antigen and the genogroup II noroviral antigen in a mass ratio range of from 3:1 to 1:3, preferably of from 2:1 to 1:2, and more preferably of from 1.5:1 to 1:1.5, and even more preferably of from 1.2:1 to 1:1.2.

VLPs may comprise a protein as defined in any one of items (a) to (k) above and a further component. The further component may be a NoV VP2 protein or another (i.e. a different) NoV antigen as defined in any one of items (a) to (k). It is possible that a VLP contains two different antigens as defined in any one of items (a) to (k). However, if two or more different antigens are to be included in the composition as VLPs, it is preferred that VLPs of the first antigen are combined with VLPs of a second antigen, since this allows better control of the content of the two antigens in the immunogenic composition.

As described above, the immunogenic composition of the invention preferably contains antigens from two or more (or three or more) different NoV genogroups, such as an antigen from genogroup I and an antigen of genogroup II. The composition of the invention may contain VLPs comprising or consisting of each of these antigen(s). Preferably, the composition contains VLPs comprising or consisting of a NoV antigen of a first genogroup (e.g. genogroup I) and VLPs comprising or consisting of a NoV antigen of a second genogroup (e.g. genogroup II). With regard to embodiments wherein VLPs of a NoV antigen from genogroup I is combined with VLPs of an antigen from genogroup II, the following immunogenic compositions may be mentioned as examples:

a composition comprising VLPs consisting of or comprising an antigen of genotype I.1 and VLPs consisting of or comprising an antigen of genotype II.1;

a composition comprising VLPs consisting of or comprising an antigen of genotype I.1 and VLPs consisting of or comprising an antigen of genotype II.4;

a composition comprising VLPs consisting of or comprising an antigen of genotype I.1 and VLPs consisting of or comprising an antigen of genotype II.6;

a composition comprising VLPs consisting of or comprising an antigen of genotype I.1 and VLPs consisting of or comprising an antigen of genotype II.2;

a composition comprising VLPs consisting of or comprising an antigen of genotype I.1 and VLPs consisting of or comprising an antigen of genotype II.17;

a composition comprising VLPs consisting of or comprising an antigen of genotype I.4 and VLPs consisting of or comprising an antigen of genotype II.1;

a composition comprising VLPs consisting of or comprising an antigen of genotype I.4 and VLPs consisting of or comprising an antigen of genotype II.4; and a composition comprising VLPs consisting of or comprising an antigen of genotype I.4 and VLPs consisting of or comprising an antigen of genotype II.6.

a composition comprising VLPs consisting of or comprising an antigen of genotype I.4 and VLPs consisting of or comprising an antigen of genotype II.2;

a composition comprising VLPs consisting of or comprising an antigen of genotype I.4 and VLPs consisting of or comprising an antigen of genotype II.17;

In a preferred embodiment, the immunogenic composition of the invention contains VLPs of a genotype I.4 antigen and VLPs of a genotype II.4 antigen, whereby each of the antigens may be VP1 proteins. In another embodiment, the immunogenic composition of the invention contains VLPs of a genotype I.1 antigen and VLPs of a genotype II.4 antigen, whereby each of the antigens may be VP1 proteins. In all these embodiments, each antigen may be as defined in items (a) to (k) above (but from the indicated genotype).

The immunogenic composition of the invention may comprise the genogroup I VLPs and the genogroup II VLPs in a mass ratio range of from 1:1 to 1:6, preferably of from 1:1.5 to 1:5, more preferably of from 1:2 to 1:4. In another embodiment, the immunogenic composition of the invention comprises the genogroup I VLPs and the genogroup II VLPs in a mass ratio range of from 3:1 to 1:3, preferably of from 2:1 to 1:2, and more preferably of from 1.5:1 to 1:1.5, and even more preferably of from 1.2:1 to 1:1.2.

As described above, the invention also provides immunogenic compositions that comprise two or more antigens from one NoV genogroup, preferably of genogroup II. Accordingly, the immunogenic composition of the invention may comprise VLPs consisting of or comprising an antigen of a first genotype of genogroup II NoV and VLPs consisting of or comprising an antigen of a second genotype of genogroup II NoV. In more detail, the immunogenic composition of the invention may comprise VLPs consisting of or comprising an antigen of genotype II.1 and VLPs consisting of or comprising an antigen of genotype II.4. Alternatively, the immunogenic composition may comprise VLPs consisting of or comprising an antigen of genotype II.1 and VLPs consisting of or comprising an antigen of genotype II.17. Alternatively, the immunogenic composition may comprise VLPs consisting of or comprising an antigen of genotype II.4 and VLPs consisting of or comprising an antigen of genotype II.17.

The invention also provides an immunogenic composition for use in a method of preventing and/or treating Norovirus infection and infection by a bacterial pathogen in a mammal, preferably in a human, said immunogenic composition comprising a noroviral antigen as defined above, preferably NoV VLPs as defined above, and a B subunit of a bacterial $AB_5$ toxin capable of generating an immune response against said bacterial pathogen. The B subunit of a bacterial $AB_5$ toxin may be CTB or LTB, preferably CTB, as defined above. Such immunogenic composition may be or may be used as a combination vaccine for preventing and/or treating Norovirus infection and infection by the bacterial pathogen. The amounts of NoV antigen, said B subunit and ratios thereof may be as mentioned herein.

For all embodiments mentioned above, the immunogenic composition of the invention does preferably not contain a nucleic acid encoding a NoV antigen(s).

The immunogenic composition of the invention comprises at least one NoV antigen as described above and at least one adjuvant as described above as components. The compositions are immunogenic in that they generate an immune response against the antigen(s) of the invention if the composition is administered to a mammal, such as a human. Further, a suitable carrier or excipient may be present in said compositions. The composition may be obtained by simply mixing the components, optionally in a suitably carrier, in desired amounts and mixing ratios. A suitable carrier may be water or an aqueous solution that should be at an appropriate pH such as from 6 to 8, preferably from 6.7 to 7.5. The aqueous solution may contain, apart from water, a buffer, a tonicity agent and/or a preservative as required.

The immunogenic composition may contain the at least one NoV antigen and the B subunit of the $AB_5$ toxin (such as CTB) in a mass ratio range of from 1:0.1 to 1:5, preferably from 1:0.2 to 1:3, more preferably of from 1:0.5 to 1:2. The CTB may be one as defined in items (A) to (I) above. If more than one NoV antigen is present, these values apply to the sum of all NoV antigens. If more than one CTB is present, these values apply to the sum of all CTBs or CTB variants. Where the composition contains LTB, these ratio ranges apply analogously to the LTB.

The composition may contain further desired components, such as an additional adjuvant. An example of an additional adjuvant is aluminum hydroxide (alum) that is a generally know adjuvant for vaccines or other aluminum salts. The composition may contain the CTB and the further adjuvant in a mass ratio range of from 1:200 to 10:1, preferably of from 1:100 to 5:1, more preferably of from 1:30 to 1:1. If more than one additional adjuvant is contained, these values relate to the sum of all adjuvants other than the B subunit of the $AB_5$ toxin (such as CTB).

Where the composition contains both a B subunit of the $AB_5$ toxin (such as CTB) and an aluminum salt such as aluminum hydroxide (alum) as the further adjuvant, the composition may contain the B subunit of the $AB_5$ toxin and the aluminum salt in a mass ratio range of from 1:50 to 20:1, preferably of from 1:20 to 10:1, more preferably of from 1:5 to 5:1, and even more preferably from 1:1 to 5:1. In one embodiment, the immunogenic composition (and the vaccine) does not contain an aluminum salt such as aluminum hydroxide (alum).

Where the composition contains both CTB and an aluminum salt such as aluminum hydroxide (alum) as the further adjuvant, the composition may contain the CTB and the aluminum salt in a mass ratio range of from 1:50 to 20:1, preferably of from 1:20 to 10:1, more preferably of from 1:5 to 5:1, and even more preferably from 1:1 to 5:1. In one embodiment, the immunogenic composition (and the vaccine) does not contain an aluminum salt such as aluminum hydroxide (alum).

The composition may be liquid or solid. If it is liquid, it may be a solution in water or an aqueous buffer. If it is solid, it may be a mixture of the NoV antigen(s), preferably the NoV VLPs of the invention, and the adjuvant (such as CTB) used in the invention. A preferred solid form is a lyophilized form.

For preparing the immunogenic composition of the invention, the one or more antigens, preferably in the form of VLPs, may be mixed with the adjuvant(s) preferably in or with a suitable carrier or medium. Preferably, VLPs comprising or consisting of antigens from a first genogroup or genotype may be mixed with VLPs comprising or consisting of antigens from a second genogroup or genotype with a suitable carrier or medium, followed by addition of the adjuvant(s). The carrier or medium may be water or an aqueous medium such as a solution. The aqueous medium may contain a buffer to control the pH and may contain physiologic saline and/or other additives. The additives can be, but are not limited to, sucrose, glycerol, trehalose. The antigen may be stored in an aqueous medium until the immunogenic composition or the vaccine of the invention are produced. For longer storage times, it may be frozen or lyophilized. After production of the immunogenic composition, it may be sterilized, e.g. by sterile filtration and stored. Storage may be in liquid form or frozen. It may also be stored after lyophilization as a dry powder.

The lyophilization of immunogenic composition and vaccines is well known in the art. Typically the composition is freeze dried in the presence of agents to protect the antigen and/or adjuvant of the invention during the lyophilization process and to yield powders with desirable characteristics. Sugars such as sucrose, mannitol, trehalose, or lactose (present at an initial concentration of 10-200 mg/mL) are commonly used for cryoprotection and lyoprotection of protein antigens and to yield lyophilized cake or powders with desirable characteristics. Lyophilized compositions may be more stable. Other drying technologies, such as spray drying or spray freeze drying may also be used.

The immunogenic composition of the invention does preferably not contain the A subunit of the $AB_5$ toxin and/or does not contain an aluminum salt (e.g. aluminum hydroxide, alum).

Vaccine of the Invention

The vaccine of the invention comprises the immunogenic composition of the invention in a form suitable for administration to a subject or in a form that can, prior to administration, be easily brought in a form suitable for administration to a subject. For example, the vaccine may be a solid formulation that can be reconstituted prior to administration by addition of a predetermined amount of water or aqueous solution, suspension or emulsion. In general, the vaccine comprises, apart from the immunogenic composition, one or more pharmaceutical excipients or carriers. Excipients may be liquid or solid. Liquid excipients include, without limitation, water, alcohol, saline, and buffered solutions. Other possible excipients include, without limitation, preservatives and other additives such as antimicrobials, anti-oxidants, chelating agents, buffer substances. The immunogenic composition of the invention may itself be a vaccine in the sense of the invention.

The vaccine is an anti-NoV vaccine. It is at the same time a pharmaceutical composition. The vaccine is generally used for preventing or treating NoV infection in a subject, or for suppressing the severity of a NoV infection. The invention also provides a method of preventing or treating norovirus infection, or for suppressing the severity of a NoV infection, generally comprising administering to a subject the immunogenic composition or vaccine of the invention. Subjects in which NoV may be prevented or treated or in which the severity of a NoV infection may be suppressed are mammals, preferably humans. Among humans, both children and adults may be subjects for preventing or treating NoV infection. Among humans, children are preferred for achieving immunization early in life. Human subjects are considered children up to the age of 16. Preferably, the NoV vaccine is used in children of age between 1 and 16, preferably 2 to 14, and more preferably from 3 to 12 years of age.

As the vaccine is generally administered to subjects by injection, the norovirus vaccine is generally a liquid aqueous formulation. However, the norovirus vaccine may also be in solid form such as in a lyophilized form to be reconstituted with water or an aqueous medium before administration.

The vaccine of the invention is preferably administered to a subject parenterally. The parenteral administration may be intravenous, intradermal, intramuscular or subcutaneous administration. Preferred are intradermal, intramuscular or subcutaneous administration, more preferably intradermal and intramuscular administration. In one embodiment, the vaccine is administered intradermally. In another embodiment, the vaccine is administered intramuscularly.

When the vaccine is administered to a human subject, or in the method of the invention, the NoV antigen(s) is (are) administered in an amount of from 10 to 1000 μg, preferably from 30 to 300 μg, more preferably from 55 to 150 μg of NoV antigen. If the vaccine contains more than one NoV antigen, these amounts relate to the sum of the amounts of the individual antigens. If the vaccine contains antigens of genogroup I and antigens of genogroup II, the amount of the genogroup II antigen may be the same or higher than that of the genogroup I antigen. The amount of the genogroup II antigen(s) may be from 1.5 to 6 times, preferably from 2.0 to 5 times, more preferably from 2.5 to 4.5 times, and even more preferably from 3.0 to 4.0 times the amount of the genogroup I antigen(s) in terms of mass.

The vaccine may be packaged in a single-dose or multiple dose form in a container that contains the desired amount of the vaccine. Preferred are single-dose forms, where the single dose contains the administration amount of NoV antigen as given above. The single-dose form may comprise from 10 to 1000 μg, preferably from 30 to 300 μg, more preferably from 55 to 150 μg of NoV antigen(s). If the vaccine contains antigens of genotype I and antigens of genotype II, the ratios of these antigens may be as defined in the previous paragraph.

The vaccine may be administered once or twice to a subject for improving the immunity against NoV infection. If the vaccine to be administered twice, the second administration may be made within 2 to 8 weeks, preferably within 3 to 5 weeks after the first administration of the vaccine.

The vaccine of the invention may also contain antigens against other infectious diseases for generating immune protection not only against NoV, but also against other viruses. It may, for example, be considered to include into the vaccine rotavirus antigens to generate protection against NoV and rotavirus.

The inventors have found that the adjuvant of the invention itself acts as an antigen and can generate an immune response in a mammal, preferably a human, against it. The adjuvant of the invention is a B subunit of an $AB_5$ toxin, such as CTB or LTB. CTB and LTB are proteins that are expressed or can be derived from *Vibrio cholerae* and *E. choli*, respectively. This finding opens up the possibility for providing a combination vaccine for preventing and/or treating Norovirus infection and infection by a bacterial pathogen in a mammal, preferably in a human, said vaccine comprising a noroviral antigen as defined in any preceding claims and a B subunit of a bacterial $AB_5$ toxin capable of generating an immune response against these bacterial pathogens. Regarding excipients, routes of administration, amounts of NoV antigens to be administered, amounts of B subunits to be administered, etc. the conditions mentioned above on the immunogenic composition and vaccine apply also to this embodiment.

In one embodiment, the vaccine does not contain an aluminum salt such as aluminum hydroxide (alum). In another embodiment, the vaccine does not contain the A subunit of the bacterial $AB_5$ toxin, i.e. is free of the A subunit. In a further embodiment, the vaccine does not contain an aluminum salt such as aluminum hydroxide (alum) and does also not contain the A subunit of the bacterial $AB_5$ toxin. These preferred embodiments can be combined with other preferred embodiments described herein, e.g. preferred embodiments of the antigens and antigen combinations used.

Herein, the immunogenic composition, vaccine or pharmaceutical composition is considered not to contain the A subunit of the $AB_5$ toxin (such as CT or LT) or to be free of the A subunit, if the content of the $AB_5$ protein (toxin) (that contains the A subunit) is at most 1% of the content of the B protein (generally the $B_5$ pentamer that is composed of only B subunit). The content of the $AB_5$ protein relative to that of the B protein (or the $B_5$ pentamer) may be determined by separating the proteins of the B subunit-containing sample, the proteins of the immunogenic composition, or the proteins of the vaccines using non-reducing SDS gel electrophoresis (Laemmli, U. K., 1970, Nature, 227: 680-685), detecting separated B subunit-containing proteins on the Coomassie-stained gel by employing a ChemiDoc™ Imaging System (Bio-Rad) equipped with Image Lab 6.0.1software, and determining the area under the curve for the bands of the $AB_5$ protein and B protein (e.g. the $B_5$ pentamer). The content of the $AB_5$ protein is considered to be at most 1% of the content of the B protein (e.g. the $B_5$ pentamer) (i.e. the B subunit-containing sample is free of the A subunit) if the area under the curve of the $AB_5$ protein is at most 1% of the area under the curve of the B protein(s) (e.g. the $B_5$ pentamer). The position of the bands of the $AB_5$ protein and the B protein (e.g. the $B_5$ protein) on the gel can be determined by the skilled person based on the known molecular weight of these proteins and the position on the gel, optionally with the help of suitable molecular weight markers.

If the composition or vaccine (or a sample) contains two or more different B subunits of $AB_5$ toxins, the above test may be conducted for each B subunit-containing sample separately or on the same gel. The composition, vaccine or sample is free of the A subunit if the sum of the areas under the curve(s) of the $AB_5$ proteins is at most 1% of the sum of the areas under the curve(s) of the B proteins.

Production of NoV Antigens

NoV antigens as described above can be expressed in and purified from different production hosts including mammalian cells, insect cells and plants (for review: Herbst-Kralovetz, M., Mason, H. S. & Chen, Q. 2010, Exp. Rev. Vaccines, 9:299-307). Reliable NoV antigen and NoV VLP purification protocols and modifications thereof have been described for insect cells using baculoviral expression system (Jiang, X. et al., 1992, J. Virol., 66:6527-6532; Prasad B W, Hardy D, Estes M. 2000, J. Infect. Dis., 181:S317S321; Huhti, L., et al., 2010, Arch. Virol., 155:1855-1858; Koho, T., et al., 2012, J. Virol. Methods, 181:6-11; Huhti, L., et al., 2013, Arch. Virol., 158:933-942; WO2013192604) and for plants (Santi L. et al., 2008, Vaccine, 26:1846-1854; Lai, H. & Chen, Q. 2012, Plant Cell Rep., 31:573-584). EP2601970 may also be considered regarding the production of NoV VLPs. Although there is no difference observed in the structure and immunogenic properties of VLPs isolated from insect and plant cells, a preferred system for VLP production is plant-based, as this allows avoiding baculoviral impurities in the antigen or VLPs isolated from plant tissues. In addition, plant-based transient expression systems, unlike the baculoviral one, are easily scalable. Successful expression of many NoV antigen genes in plants using plant virus-based expression system called magnICON® (Gleba et al., 2005, Vaccine, 23:17-18; Marillonnet et al., 2005, Nat. Biotechnol., 23:718-723; Gleba et al., Curr. Opin. Biotechnol., 2007, 18:134-141; Klimyuk, V., et al., 2014, Curr. Top. Microbiol. Immunol., 375:127-154) that allows to easily express viral VLPs in *Nicotiana benthamiana* plants (Zahin, M. et al., 2016, PLoS One, 11(8):e0160995). A list of NoV antigens (VP1 proteins) of various genotypes, expression of was done in plants and VLPs formation was confirmed is given Table 1B.

In more detail, the antigen of the invention may be produced by known methods of protein expression in a standard expression system. For producing the antigen, a nucleotide sequence encoding it may be expressed in a suitable host organism. Methods usable for producing and purifying a protein of interest have been described in the prior art and any such methods may be used. If a eukaryotic expression system is used, one or more introns may be inserted in the coding sequence of the antigen.

Particularly efficient expression methods are plant expression systems that are also known in the prior art. A possible way of achieving expression of a nucleotide sequence of interest encoding an antigen according to the invention in plants is the use of self-replicating (viral) replicons containing the nucleotide sequence encoding the antigen. Plant viral expression systems have been described in many publications, such as in WO2012019660, WO2008028661, WO2006003018, WO2005071090, WO2005049839, WO2006012906, WO02101006, WO2007137788 or WO02068664 and many more publications are cited in these documents. Various methods for introducing a nucleic acid molecule, such as a DNA molecule, into a plant or plant part for transient expression are known. Agrobacteria may be used for transfecting plants with the nucleic acid molecule (vector) or nucleic acid construct e.g. by agroinfiltration or spraying with agrobacterial suspensions. For references, see WO 2012019660, WO 2014187571, or WO 2013149726.

In embodiments wherein strong expression of the antigen is desired, a nucleic acid construct containing a nucleotide sequence encoding the antigen may encode a viral vector that can replicate in plant cells to form replicons of the viral vector. In order to be replicating, the viral vector and the replicons may contain an origin of replication that can be recognized by a nucleic acid polymerase present in plant cells, such as by the viral polymerase expressed from the replicon. In case of RNA viral vectors (referred to as "RNA replicons"), the replicons may be formed by transcription under the control of a promoter active in plant cells, from the DNA construct after the latter has been introduced into plant cell nuclei. In case of DNA replicons, the replicons may be formed by recombination between two recombination sites flanking the sequence encoding the viral replicon in the DNA construct, e.g. as described in WO00/17365 and WO 99/22003. If the replicon is encoded by the DNA construct, RNA replicons are preferred. Use of DNA and RNA viral vectors (DNA or RNA replicons) has been extensively described in the literature over the years. Some examples are the following patent publications: WO2008028661, WO2007137788, WO 2006003018, WO2005071090, WO2005049839, WO02097080, WO02088369, WO02068664. Examples of DNA viral vectors are those based on geminiviruses. For the present invention, viral vectors or replicons based on plant RNA viruses, notably those based on plus-sense single-stranded RNA viruses may be preferably used. Accordingly, the viral replicon may be a plus-sense single-stranded RNA replicon. Examples of such viral vectors are those based on tobacco mosaic virus (TMV) and potexvirus X (PVX). "Based on" means that the viral vector uses the replication system such as the replicase and/or other proteins involved in replication of these viruses. Potexvirus-based viral vectors and expression systems are described in EP2061890 or WO2008/028661.

The antigen may be expressed in a multi-cellular plant or a part thereof, notably a higher plant or parts thereof. Both monocot and dicot (crop) plants can be used. Common plants usable for expressing proteins include *Nicotiana tabacum* and *Nicotiana benthamiana*. However, many others can be employed as well.

Generally, the antigen may be expressed in the cytosol of cells of the plants or plant parts. In this case, no signal peptide directing the protein of interest into a particular compartment is added to the enzyme. Alternatively, the antigen or VP1 protein can be expressed in or targeted into chloroplasts of the plants or be secreted into the extracellular space; in these cases, an N-terminal pre-sequence, such as a plastid transit peptide or a signal sequence for targeting to the extracellular space, is added to the N-terminal or C-terminal end, preferably the C-terminal end, of the antigen as the protein of interest.

In the next step, plant material containing expressed antigen from a plant having expressed the antigen is harvested. Plant material may e.g. be leaves, roots, tubers, or seeds, or a crushed, milled or comminuted product of leaves, roots, tubers, or seeds. The antigen may then be extracted from the plant material using an aqueous buffer. This may include that the plant material is homogenized and insoluble material may be removed by centrifugation or filtration. Soluble components including the antigen will be extracted into the aqueous buffer to produce an antigen solution in the aqueous buffer. The aqueous buffer may contain an inorganic or organic acid or salts thereof and may have a pH as defined below for the aqueous solution as a composition of the invention. Further, the aqueous buffer may contain salt and/or a sulfhydryl compound. The antigen in the obtained antigen preparation may then be further purified using standard methods of protein purification, such as chromatographic methods.

Antigen being VP1 protein or derivative can form VLPs. These VLPs generally form spontaneously in the aqueous buffer used in extraction and purification. Formation of VLPs can be verified e.g. using electron microscopy.

If the immunogenic composition of the invention contains two or more NoV antigens, the two or more antigens may be expressed and purified separately and then mixed desired ratios when preparing the composition. It is also possible to co-express two or more antigens in the same plant cells or plants and purifying the together as a mixture.

Production of B Subunit of an $AB_5$ Toxin

The B subunit of an $AB_5$ toxin such as CTB or LTB may be obtained commercially as indicated above. Alternatively, they may be expressed and be purified from different production hosts including mammalian cells, insect cells and plants, similarly as described above for the NoV antigens. Expressed CTB and LTB generally assemble spontaneously to $B_5$ pentamers. Section "Adjuvant used in the invention" above gives multiple references to $AB_5$ toxins such as CTB and LTB.

EXAMPLES

Example 1

Norovirus VLPs Purification from Plant Material

Norovirus VP1 VLPs have been purified as described below for GII.4 Aomori strain. The five weeks old *Nicotiana benthamiana* plants were vacuum-infiltrated (80-100 mbar for 3-4 minutes) with diluted *Agrobacterium tumefaciens* cultures carrying TMV-based assembled magnICON® vectors (Gleba et al., 2005, Vaccine, 23:17-18; Marillonnet et al., 2005, Nat. Biotechnol., 23:718-723; Gleba et al., Curr. Opin. Biotechnol., 2007, 18:134-141; Klimyuk, V., et al., 2014, Curr. Top. Microbiol. Immunol., 375:127-154) that allows to easily express viral VLPs in *Nicotiana benthamiana* plants (Zahin, M. et al., 2016, PLoS One, 11(8): e0160995). Plant material was harvested 6-14 days post infiltration. A harvesting time point 7-8 days post infiltration results in the highest expression level for GII.4 strain.

The green biomass was homogenized in the presence of two volumes neutral buffer (i.e. 15 g biomass and 30 mL 100 mM Tris, 5 mM $Na_2S_2O_5$ pH 7.5). For clarification the plant homogenate was centrifuge 20 min. at 15.000×g. The resulting extract was further clarified by filtration using a Millipore® glass fiber filter (AP25).

High molecular weight components were sedimented by ultracentrifugation (150.000×g for 90 min.). The pellet was suspended in 1 mL of 20 mM histidine, 137 mM NaCl pH 6.0 and clarified by 15.000×g centrifugation for 20 minutes. The VLP containing supernatant was placed on the top of a 30% sucrose cushion (in 20 mM histidine, 137 mM NaCl pH 6.5). Ultracentrifugation was performed for 90 min. at 150.000×g. The resulting pellet was resuspended in 20 mM histidine, 137 mM NaCl pH 6.5. VLP formation was confirmed by SEC-HPLC with light scattering analysis.

Example 2

Immunogenicity of Purified VP1 VLPs in Mice Using Intramuscular (IM) Route of Delivery Study Animals BALB/c Ola/Hsd female mice (Envigo, Netherlands) were shipped at ambient temperature to animal facility. Animals were acclimatized 1-2 weeks prior to immunizations and immunized at 7 weeks of age. Health monitoring data summary form was provided with the shipment of the mice. Animal health (clinical signs of illness) and welfare were monitored daily by the staff of the animal facility. All procedures were authorized and performed according to the guidelines of the Finnish National Animal Experiment Board.

Immunization Procedures

The mice were anesthetized with inhalation of isoflurane (Attane® vet) for the time of immunization and related procedures. Animals were weighted at the beginning of the study and marked with a group tattoo and individually by ear piercing. Fecal samples were collected at the beginning of the study (week (wk) 0) and at the day of termination (wk 5). Tail blood sample (5 mkl volume diluted 1:100 in PBS) was collected at wk 0 and wk 3 prior to immunization. Test article was administered IM in the caudal tight muscle (50 mkl volume) with 0.3 ml insulin syringe (29G×1/2"-0.33×12 mm).

Termination Procedures and Sample Collection

Animal weights were recorded at the time of termination. Fecal samples were collected, pooled and 10% suspensions were prepared before storing at −80° C. until use. The mice were terminated by anesthetizing mice with 1 mg/kg medetomidine (Dorbene® 1 mg/ml, Laboratorios Syva) and 75 mg/kg ketamine (Ketalar® 50 mg/ml, Pfizer) and collecting the terminal whole blood from axillary (armpit) area. Serum was separated of individually collected whole blood samples and stored at −20° C. until used. Spleens were collected and single cell suspensions were prepared. Groupwise pooled cells were aliquoted and stored frozen in liquid nitrogen until used.

We have determined the immunogenicity of the purified, plant-produced form of the norovirus (NoV) GI.4 Chiba and GII.4 Aomori virus-like particles (VLPs) and the effect of Cholera toxin B (CTB, Flarebio Biotech LLC, USA) adjuvant via intramuscular (IM) route. Additionally, as control, the adjuvant effect of aluminum hydroxide [$Al(OH)_3$, alum] was evaluated. Completely purified recombinant NoV VLPs were administered two times IM to BALB/c mice at weeks 0 and 3 in PBS (pH 7.3). The dose of 1 mkg (microgram or μg) of each Nov VLP was given either alone or combined with 1 mkg of CTB adjuvant, or with 50 mkg alum adjuvant. Mice receiving 1 mkg CTB only were used as negative controls in addition to carrier only (PBS) immunized mice samples of previous study. All mice were terminated at study week 5. Humoral (antibody) immune responses were analyzed by ELISA-based assays and cell-mediated (T cells) immune responses by ELISPOT assays. NoV GI.4 Chiba and GII.4 Aomori VLPs used for immunizations were produced in plants and completely purified at Icon Genetics GmbH laboratory using standard purification technologies. Protein concentration and purity was determined and particles are examined under electron microscopy. VLPs stocks (ca. 1 mg/ml of VLPs in PBS—(10 mM NaH2PO4, 137 mM NaCl pH 6.5) were kept at +4° C. until the use. NoV VLP protein stocks were diluted in PBS pH 7.3 (Lonza BioWhittaker, Cat. BE17-516F) prior to the first immunization at desirable concentration and stored at +4° C. until use.

As a control antigen used in immunological assays, mock preparation magnICON/*N. benthamiana*, batch #T1070-pICH56122 SmSc1, with the date of manufacture (DOM) Apr. 20, 2016 was used. NoV GI.1, GI.3, GII.4-1999, GII.4 New Orleans (NO), GII.4 Sydney (SYD), and GII.12 VLPs used to detect NoV specific cross-reactive immune responses were produced in a baculovirus-insect cells expression system by VRC laboratory as previously described (Huhti et al. 2010). GII.17 VLPs used for cross-reactivity analysis were produced in plants and purified by ICON Genetics GmbH.

Adjuvants

Cholera Toxin B (CTB) subunit from recombinant *Vibrio cholerae* serotype O1 was manufactured by Flarebio (batch #03285; Seq ID No. 83 shown in Table 2) and was provided as a lyophilized protein. Reconstituted by dissolving into 1 mg/ml with sterile Aqua Sterilisata (Fresenius Kabi) according to manufacturer's instructions and stored at −20° C. in aliquots prior to use. This adjuvant is referred to as "rCTB" in these Examples. It was added to vaccine antigen preparations 1 day prior to immunizations and mixtures stored overnight at +4° C.

Aluminum hydroxide gel adjuvant, (Alhydrogel® adjuvant 2%, InvivoGen, #vac-alu-250) was provided as a ready-to-use gel suspension. Alum was added to vaccine antigen preparations 1 day prior to immunizations and mixtures stored overnight at +4° C.

Study Assays

Humoral Immune Response Assays

Titers of antigen-specific (Nov GI.4 Chiba, GII.4 Aomori) IgG, IgG1 and IgG2a in serum were tested by enzyme-linked immunosorbent assay (ELISA) as previously described (Blazevic et al., 2011, Vaccine, 29:81268133; Tamminen et al., 2012, Immunology, 135:89-99). The serum IgG mock responses (antimagnICON/*N. benthamiana*) were tested by ELISA at 1:200 dilution.

Kinetics were analyzed from tail blood samples collected from individual mice at week (wk) 0 and 3. The cross-reactivity of serum IgG antibodies to NoV VLP genotypes not included in the administered antigen preparation was determined by ELISA. Pooled fecal suspensions were analysed for homotypic NoV IgG antibodies.

Pig gastric mucin (PGM)-based homologous blocking assay (Lindesmith et al., 2012, J. Virol., 86:873-883) and human type A saliva-based cross-blocking assay was used to determine the ability of immune sera to block the binding of NoV VLPs to the putative NoV receptors, human histo-blood group antigens (HBGA) as previously described (Uusi-Kerttula et al., 2014, Microbes Infect., 16:472-480).

Figure 2:
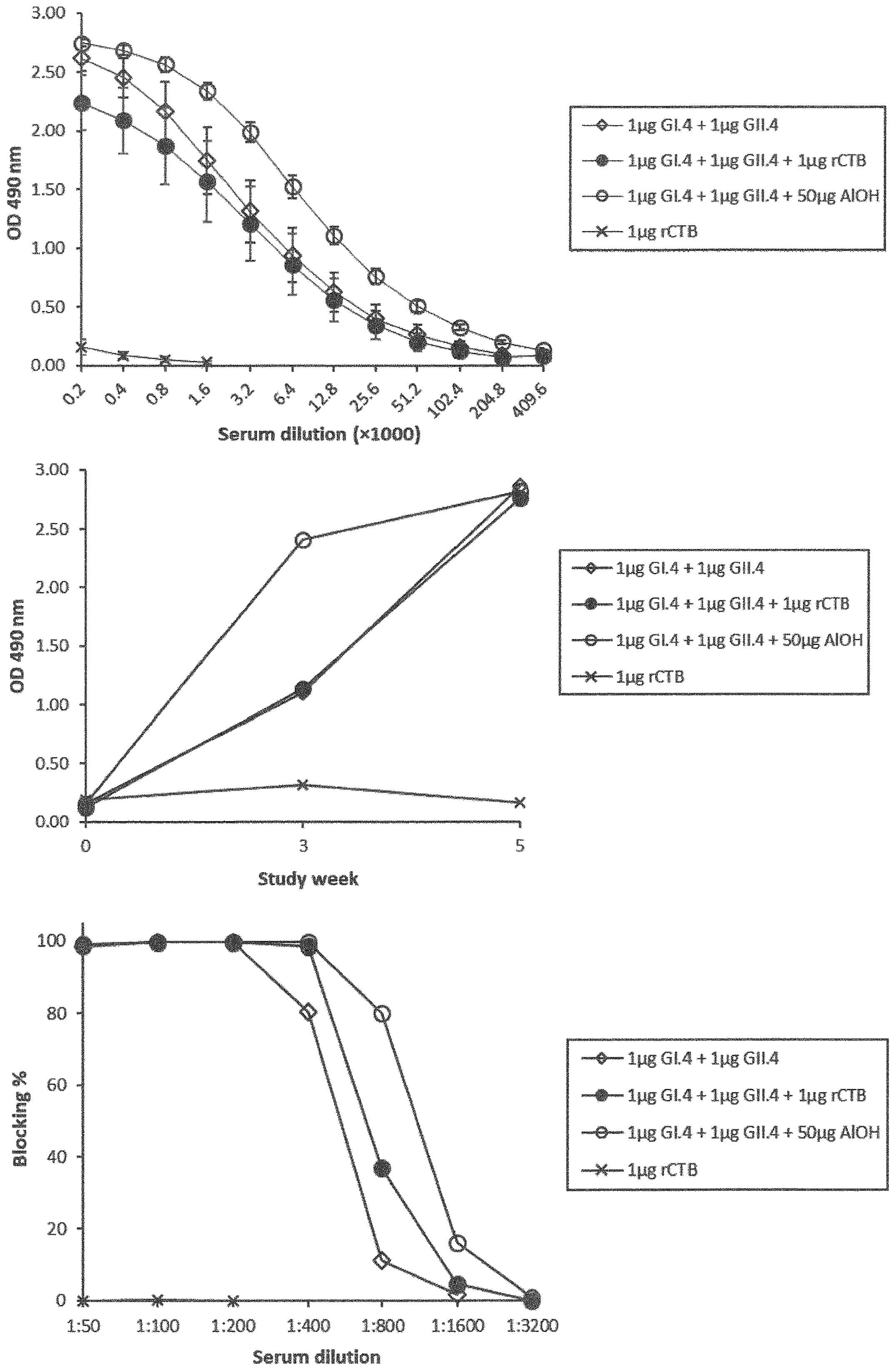
FIG. 2: Upper panel illustrates the result of norovirus (NoV) GII.4-specific serum IgG titers after two (at day 0 and day 21) intramuscular (IM) immunizations of BALB/c mice with a mixture of GI.4 (Chiba) and GII.4 (Aomori) VLPs (1 mkg dose each) alone or formulated with a recombinant CTB (rCTB, 1 mkg) or aluminum hydroxide ($Al(OH)_3$, 50 mkg). Mid panel shows kinetics of NoV GII.4-specific IgG immune response development in the pooled sera of mice immunized as described above and measured in ELISA. Lower panel illustrates the ability of NoV GII.4-specific serum antibodies to block the binding of GII.4 VLPs to pig gastric mucin (PGM) as a source of histo-blood group antigens (HBGA). Blocking index (%) was calculated as follows: 100%−(OD[with serum]/OD[without serum]× 100%).
Figure 3:
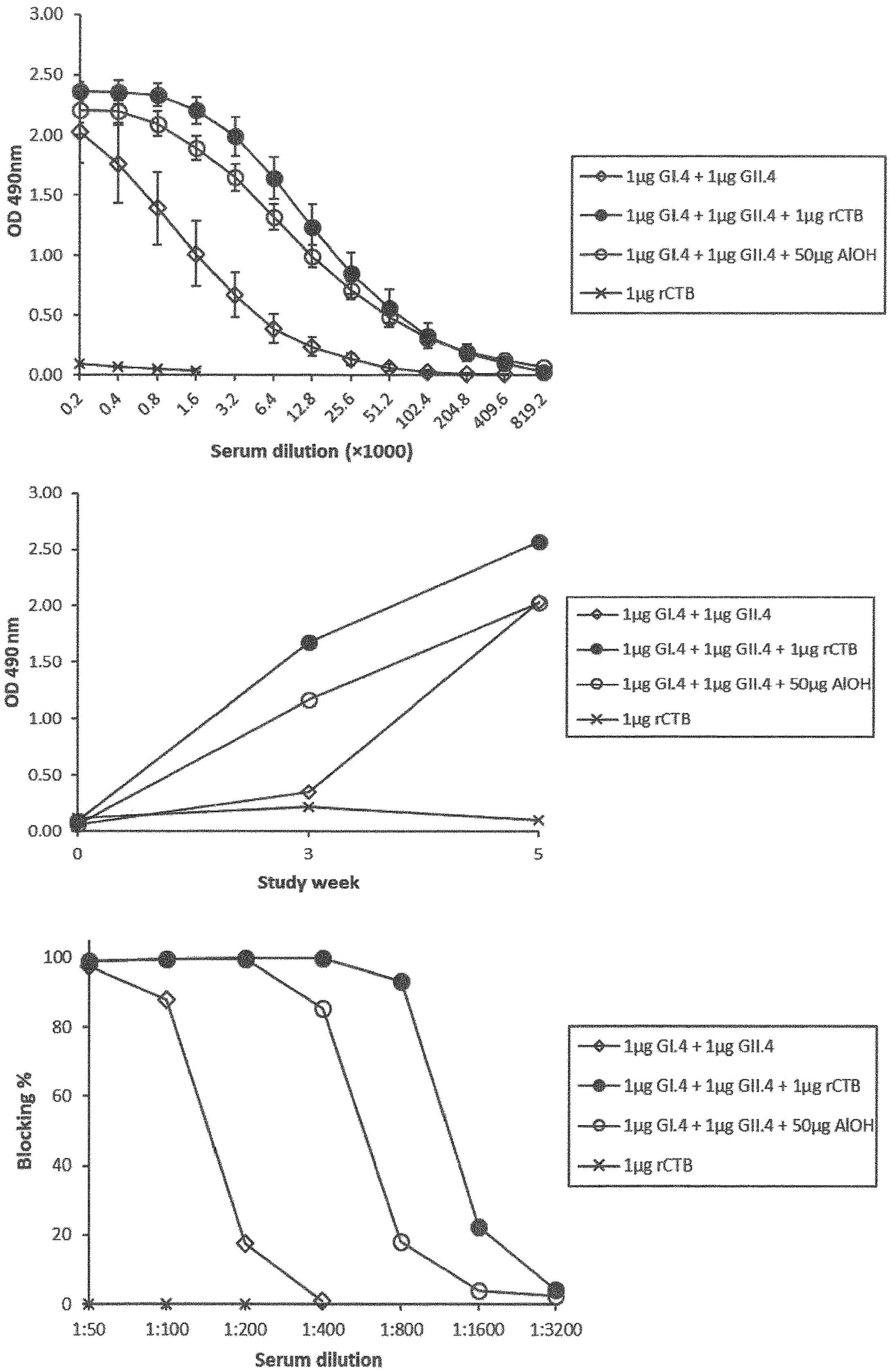
FIG. 3: Upper panel illustrates the result of norovirus (NoV) GI.4-specific serum IgG titers after two (at day 0 and day 21) intradermal (ID) immunizations of BALB/c mice with a mixture of GI.4 (Chiba) and GII.4 (Aomori) VLPs (1 mkg dose each) alone or formulated with a recombinant CTB (rCTB, 1 mkg) or aluminum hydroxide ($Al(OH)_3$, 50 mkg). Mid panel shows kinetics of NoV GII.4-specific IgG immune response development in the pooled sera of mice immunized as described above and measured in ELISA. Lower panel illustrates the ability of NoV GII.4-specific serum antibodies to block the binding of GII.4 VLPs to pig gastric mucin (PGM) as a source of histo-blood group antigens (HBGA). Blocking index (%) was calculated as follows: 100%−(OD[with serum]/OD[without serum]× 100%).
Figure 4:
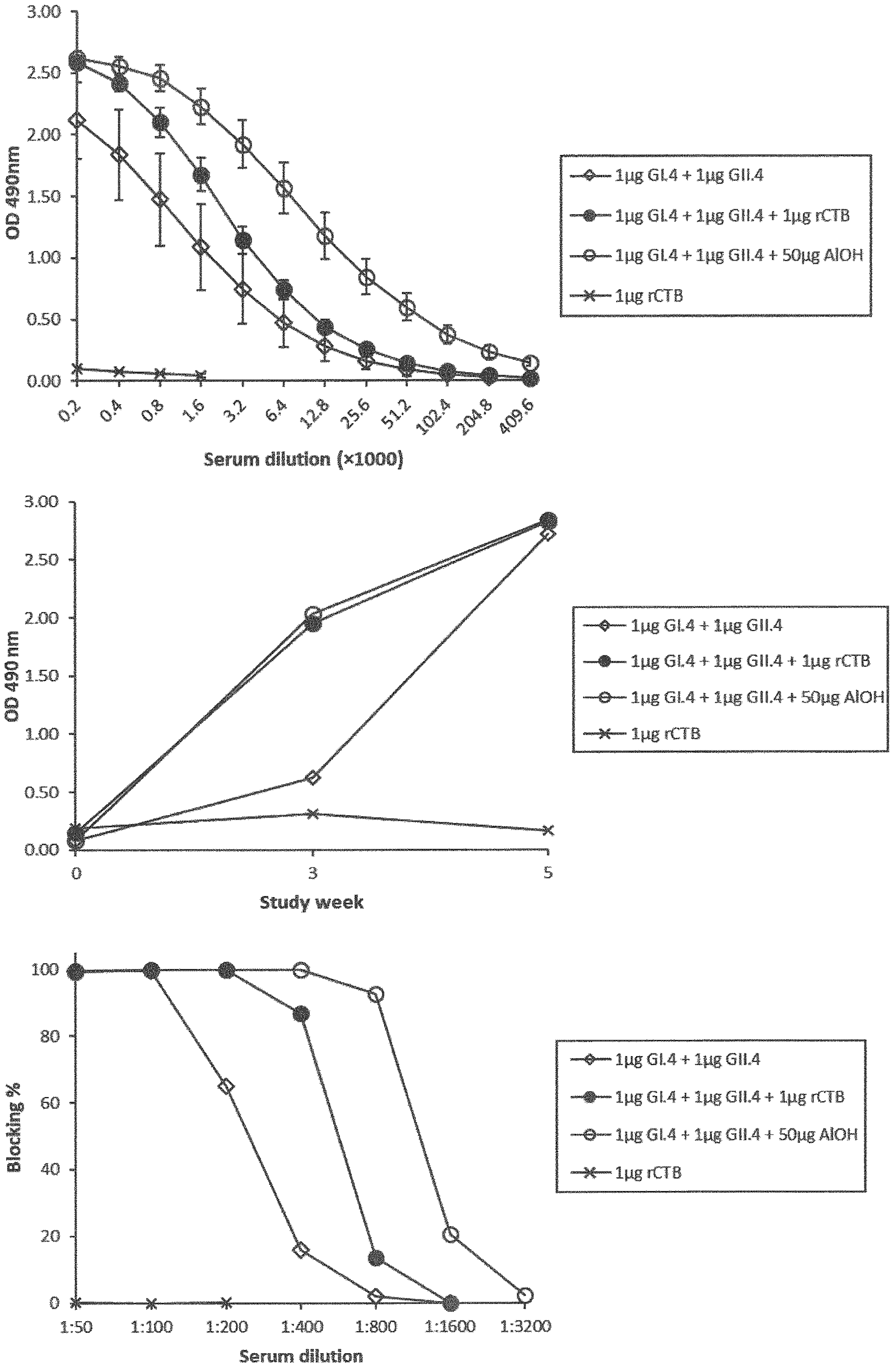
FIG. 4: Upper panel illustrates the result of norovirus (NoV) GII.4-specific serum IgG titers after two (at day 0 and day 21) intradermal (ID) immunizations of BALB/c mice with a mixture of GI.4 (Chiba) and GII.4 (Aomori) VLPs (1 mkg dose each) alone or formulated with a recombinant CTB (rCTB, 1 mkg) or aluminum hydroxide ($Al(OH)_3$, 50 mkg). Mid panel shows kinetics of NoV GII.4-specific IgG immune response development in the pooled sera of mice immunized as described above and measured in ELISA. Lower panel illustrates the ability of NoV GII.4-specific serum antibodies to block the binding of GII.4 VLPs to pig gastric mucin (PGM) as a source of histo-blood group antigens (HBGA). Blocking index (%) was calculated as follows: 100%−(OD[with serum]/OD[without serum]× 100%).

The results of experiments for immune responses against IM delivered GI.4 and GII.4 antigens are shown in the FIGS. 1 and 2, respectively. In both figures, upper panel shows serum IgG titers; middle panel shows kinetics of norovirus-specific IgG immune responses developed in pooled sera and lower panel shows blocking efficiency of NoV-specific sera. For more details, reference is made to the figures legends.

Example 3

Immunogenicity of Purified VP1 VLPs in Mice Using Intradermal (ID) Route of Delivery The mice, antigens formulations and measurements for testing immunogenicity of intradermally delivered vaccine were prepared and carried out as described in Example 2. The results of experiments for immune responses against ID delivered GI.4 and GII.4 antigens are shown in the FIGS. 3 and 4, respectively. In both figures, the upper panel shows serum IgG titers; the middle panel shows kinetics of norovirus-specific IgG immune responses developed in pooled sera and lower panel shows blocking efficiency of NoV-specific sera. For more details, reference is made to the figures legends.

Example 4

Immunogenicity of Purified VP1 VLPs in Mice Using Intranasal (IN) Route of Delivery The mice, antigens formulations and measurements for testing immunogenicity of intranasally delivered vaccine were prepared and carried out as described in Example 2. The results of experiments for immune responses against IN delivered GI.4 and GII.4 antigens are shown in the FIGS. 5 and 6, correspondingly. In both figures upper panel shows serum IgG titers; middle panel shows kinetics of norovirus-specific IgG immune responses developed in pooled sera and lower panel shows blocking efficiency of NoV-specific sera. For more details, reference is made to the figures legends.

Example 5

Figure 9:
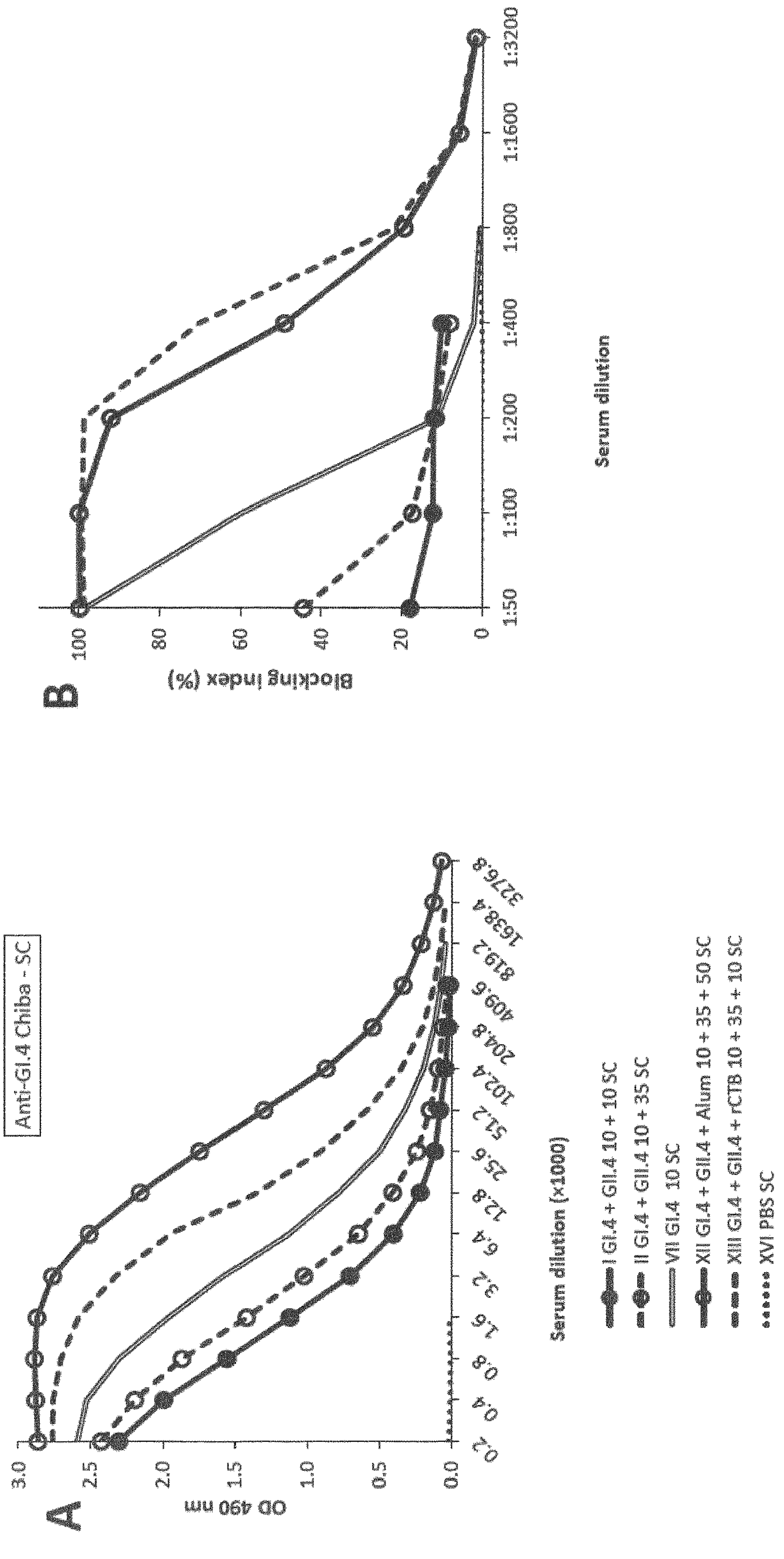
FIG. 9: Homologous norovirus (NoV) VP1 antigen-specific serum IgG and blocking activity in subcutaneously (SC) immunized mice. Individual, serially diluted serum samples were analysed for antibody levels at week 5 in ELISA against GI.4 (A) and GII.4 Aomori (C). Group-wise pooled and two-fold titrated serum samples were tested for genotype-specific blocking (neutralizing) activity against GI.4 (B) and GII.4 (D) VLPs using pig gastric mucin (PGM)-based blocking assay. The blocking index (%) was calculated as 100%−[(OD wells with VLP and serum/OD wells without serum, "maximum binding")×100%]. Immunizations of BALB/c mice with a mixture of GI.4 (Chiba) and GII.4 (Aomori) VLPs (10 mkg dose each or 10 mkg GI.4 and 35 mkg of GII.4) alone or formulated with a recombinant CTB (rCTB, 10 mkg). As positive control mixture of VLPs with 50 mkg of $Al(OH)_3$ was used.
Figure 9:
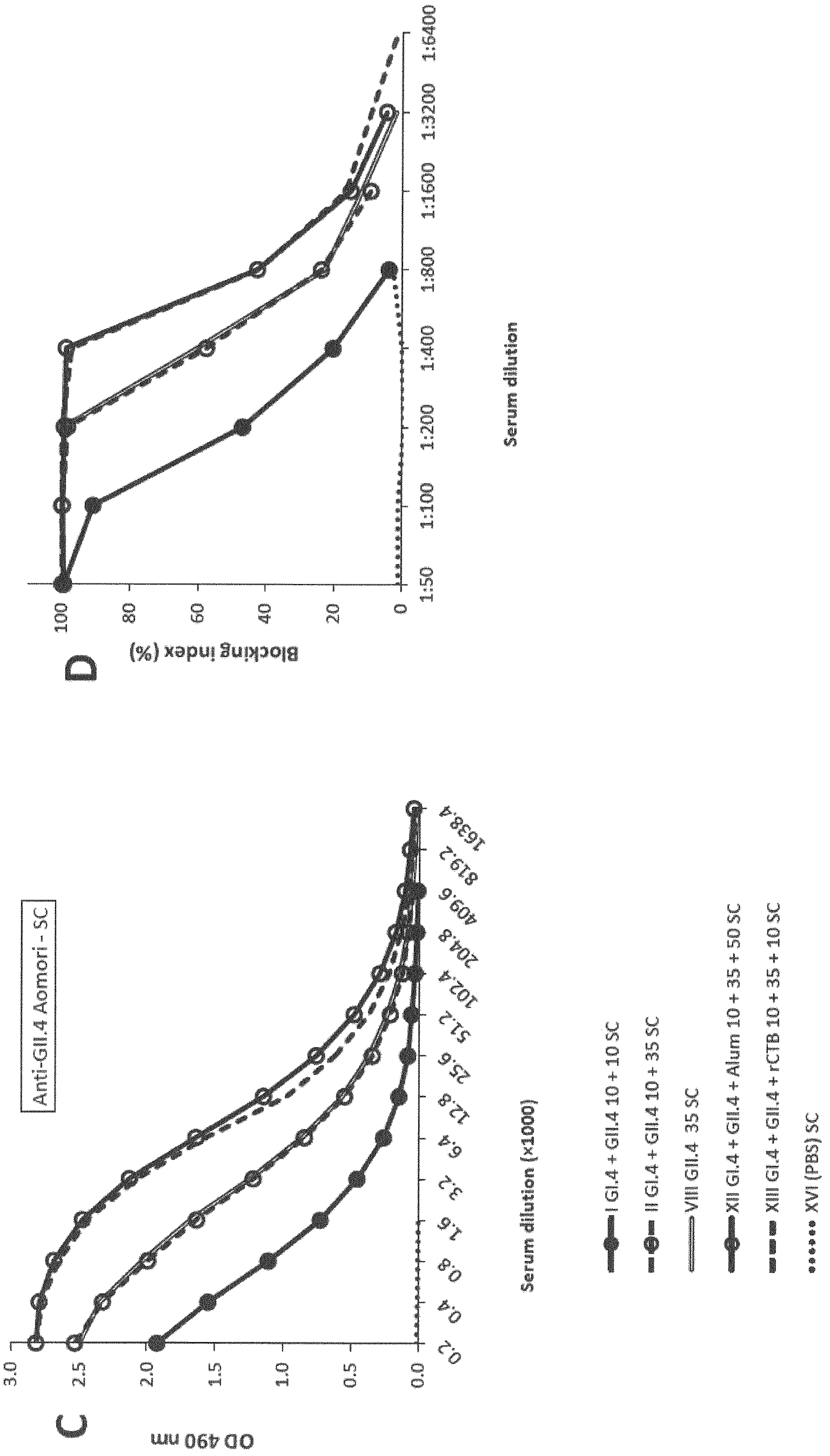
Figure 10:
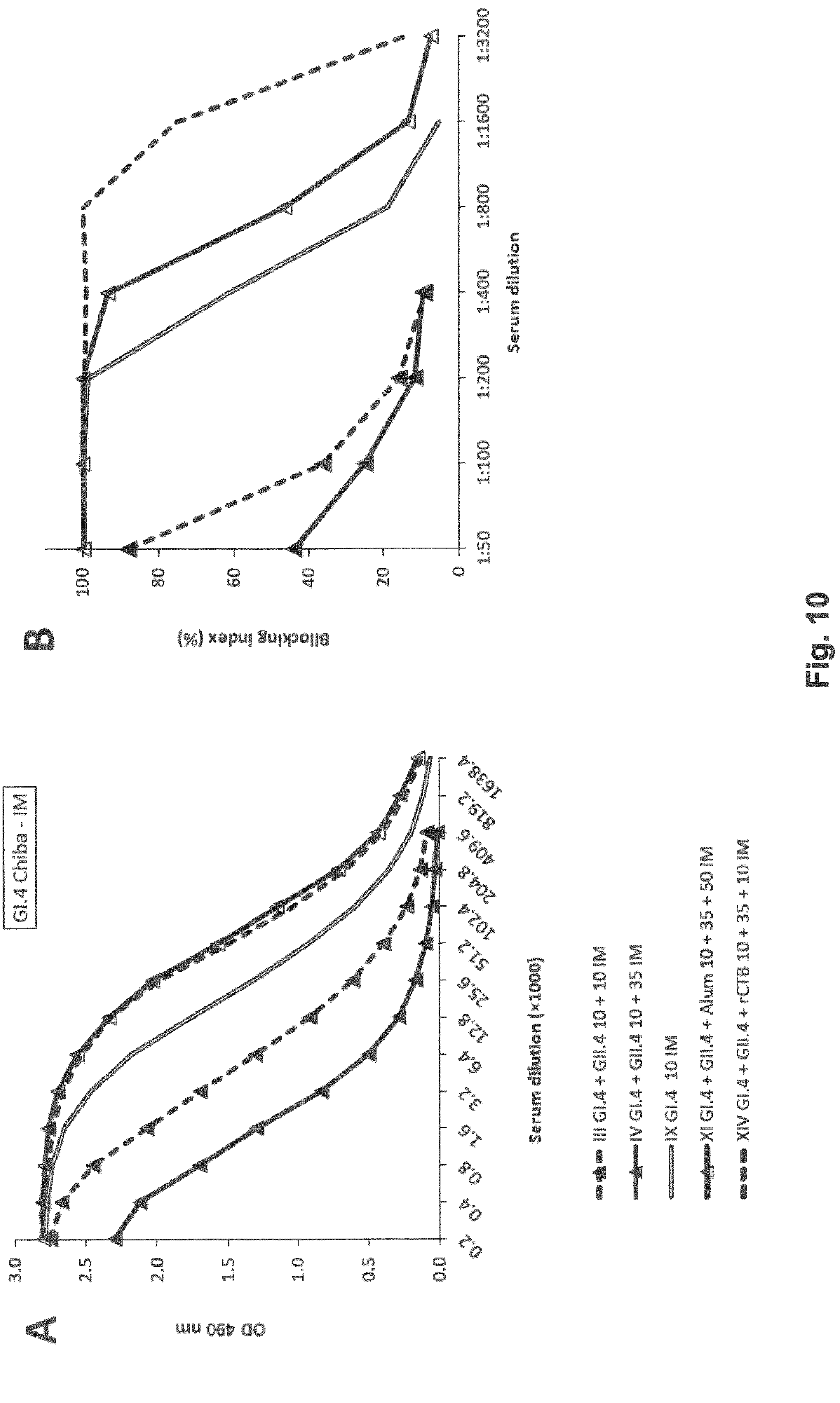
FIG. 10: Homologous norovirus (NoV) VP1 antigen-specific serum IgG and blocking activity in intramuscularly (IM) immunized mice. Individual, serially diluted serum samples were analysed for antibody levels at week 5 in ELISA against GI.4 (A) and GII.4 Aomori (C). Group-wise pooled and two-fold titrated serum samples were tested for genotype-specific blocking (neutralizing) activity against GI.4 (B) and GII.4 (D) VLPs using pig gastric mucin (PGM)-based blocking assay. The blocking index (%) was calculated as 100%−[(OD wells with VLP and serum/OD wells without serum, "maximum binding")×100%]. Immunizations of BALB/c mice with a mixture of GI.4 (Chiba) and GII.4 (Aomori) VLPs (10 mkg dose each or 10 mkg GI.4 and 35 mkg of GII.4) alone or formulated with a recombinant CTB (rCTB, 10 mkg). As positive control mixture of VLPs with 50 mkg of $Al(OH)_3$ was used.
Figure 10:
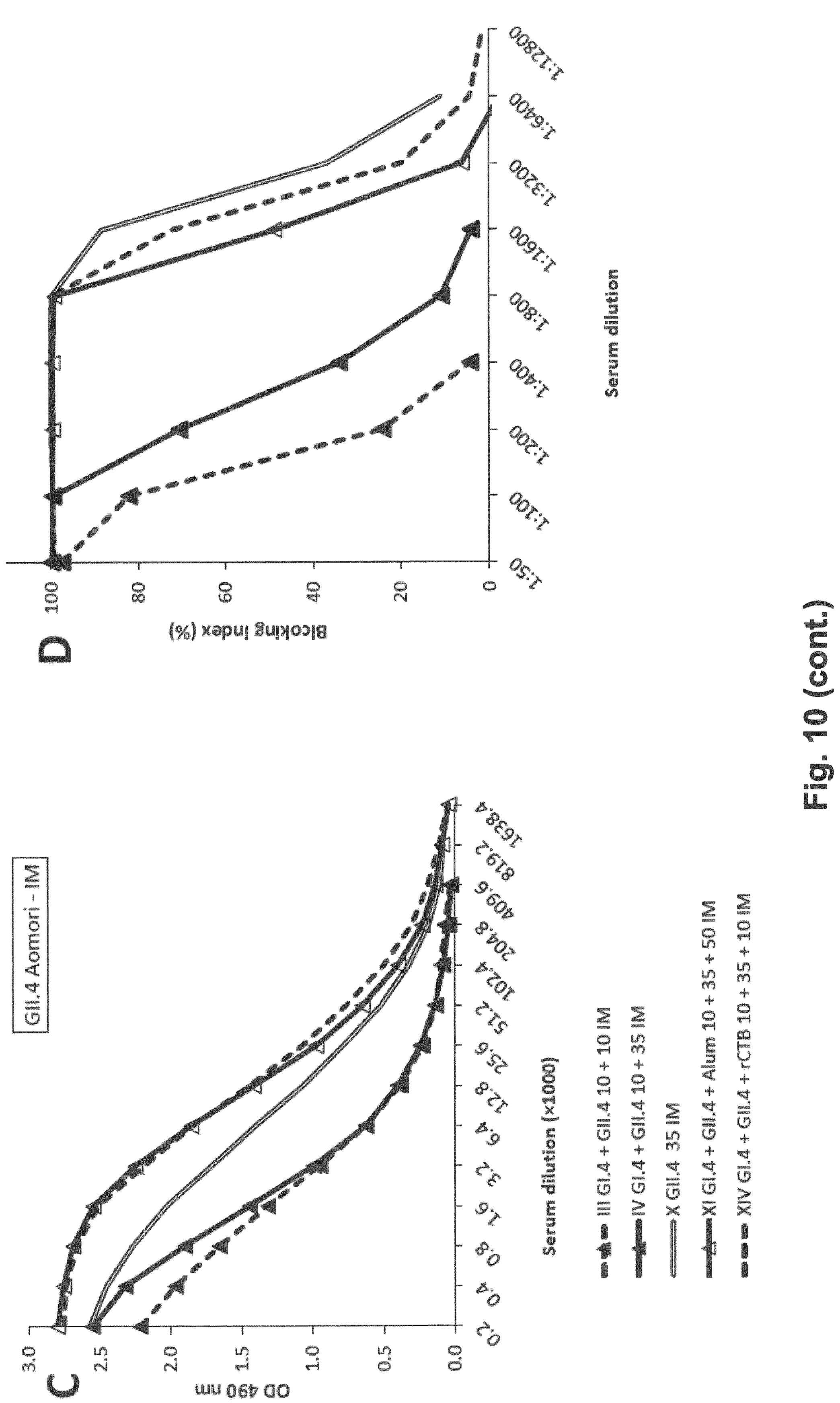
Figure 11:
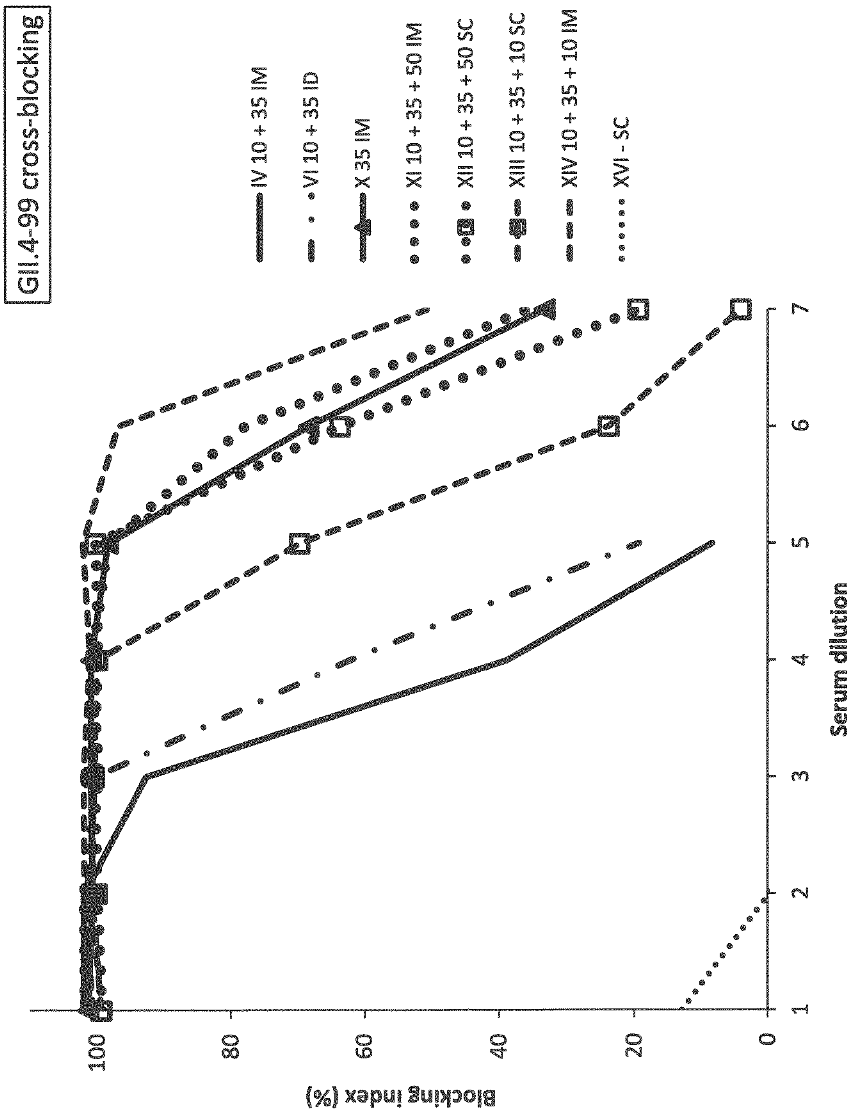
FIG. 11: Cross-blocking of GII.4-99 NoV VLP binding in saliva HBGA-based assay. Pooled serum of immunized groups was analyzed for the ability to block binding of GII.4-1999 VLP to saliva HBGAs. The blocking index (%) was calculated as 100%−[(OD wells with VLP and serum/OD wells without serum, "maximum binding")×100%]. All vaccine doses (except X−35 mkg of GII.4 only, and XVI-PBS) contain 10 mkg of GI.4+35 mkg of GII.4 VLPs. XI and XII, in addition to VLPs contain 50 mkl of $Al(OH)_3$; XIII and XIV contain 10 mkg of CTB.

Immunogenicity of Purified VP1 VLPs in Mice Using Subcutaneous (SC) Route of Delivery The mice, antigens formulations and measurements for testing immunogenicity of subcutaneously delivered vaccine were prepared and carried out as described in Example 2. The results of experiments for immune responses against SC delivered GI.4 and GII.4 antigens are shown in the FIG. 9. For more details, reference is made to the figure legend.

Example 6

Production of Recombinant Exotoxin B Subunits in Plants

B subunits of bacterial type I exotoxins (Cholera toxin and *E. coli* heat-labile toxin) have been purified as described below. Five weeks old *Nicotiana benthamiana* plants were vacuum-infiltrated (80-100 mbar for 3-4 minutes) with diluted *Agrobacterium tumefaciens* cultures carrying TMV-based assembled magnICON® vectors (Gleba et al., 2005, Vaccine, 23:17-18; Marillonnet et al., 2005, Nat. Biotechnol., 23:718-723; Gleba et al., Curr. Opin. Biotechnol., 2007, 18:134-141; Klimyuk, V., et al., 2014, Curr. Top. Microbiol. Immunol., 375:127-154) which allow easy expression of B subunits of bacterial type I exotoxins in *Nicotiana benthamiana* plants (Hamorsky et al., 2013, PLoS Negl Trop Dis. 7(3):e2046; Hamorsky et al., 2015, Sci Rep. 5:8003). Plant material was harvested 6-14 days post infiltration. The green biomass was homogenized in the presence of two volumes neutral buffer (i.e. 15 g biomass and 30 mL 100 mM Tris, 60 mM Ascorbic acid, 0.5M NaCl pH 7.5). For clarification the plant homogenate was centrifuge 20 min. at 15.000×g. The resulting extract was further clarified by filtration using a Millipore® glass fiber filter (AP25). The recombinant exotoxin B subunits were purified by affinity chromatography on a lyso-GM1 ganglioside-Spherosil® column using the procedure described by J. L. Tayot et al, 1981, Eur J Biochem 113:249-258. Formation of subunit B pentamers was confirmed by size exclusion chromatography.

Example 7

Use of Recombinant Exotoxin B Subunits in Vaccine Formulations

Figure 7A:
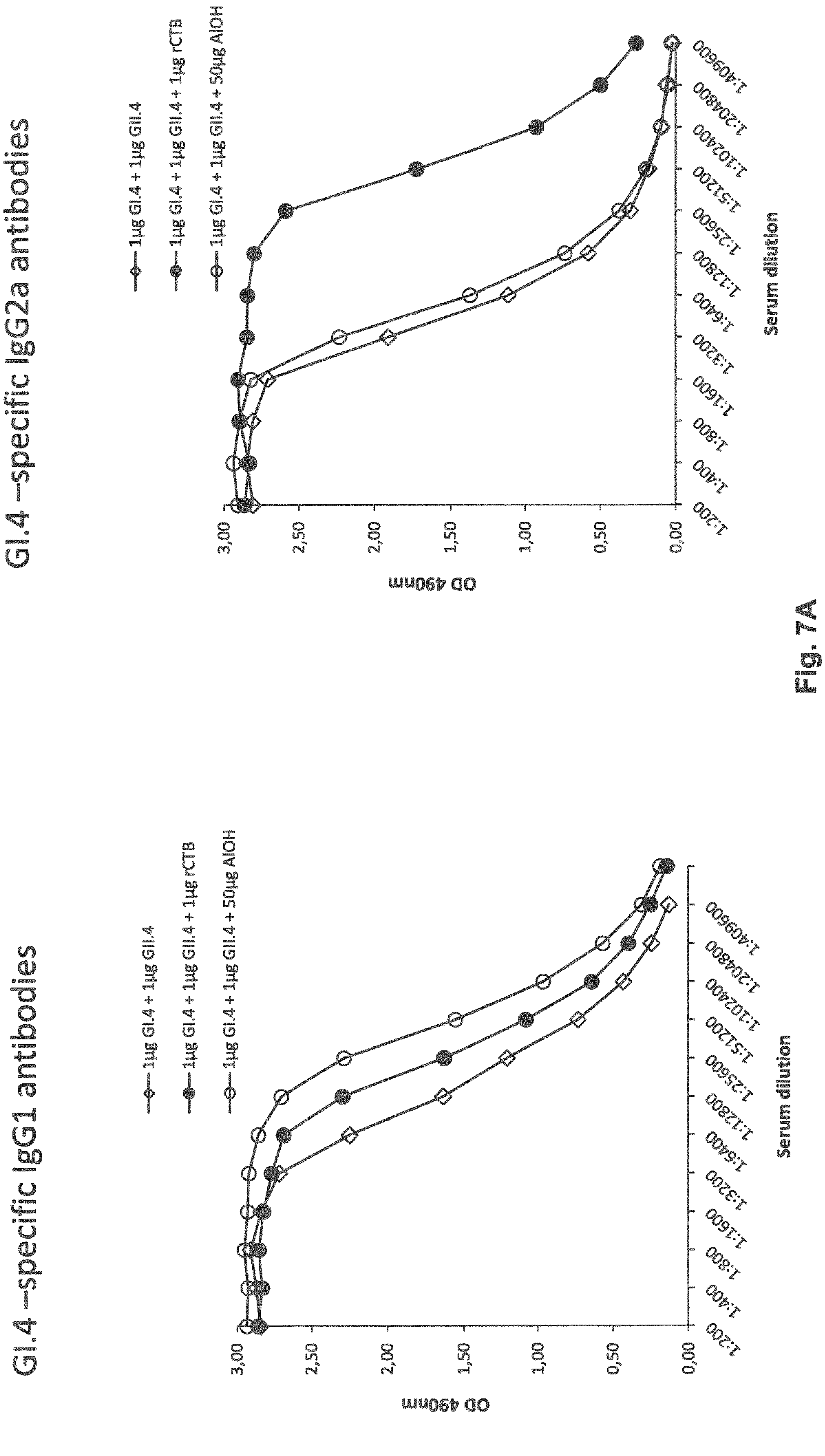
FIG. 7: Figure illustrates the result of norovirus (NoV) GI.4-specific (FIG. 7A) and GII.4-specific (FIG. 7B) serum IgG1 and IgG2a titers after two (at day 0 and day 21) intramuscular (IM) immunizations of BALB/c mice with a mixture of GI.4 (Chiba) and GII.4 (Aomori) VLPs (1 mkg dose each) alone or formulated with a recombinant CTB (rCTB, 1 mkg). As positive control mixture of VLPs with 50 mkg of $Al(OH)_3$ was used.
Figure 7B:
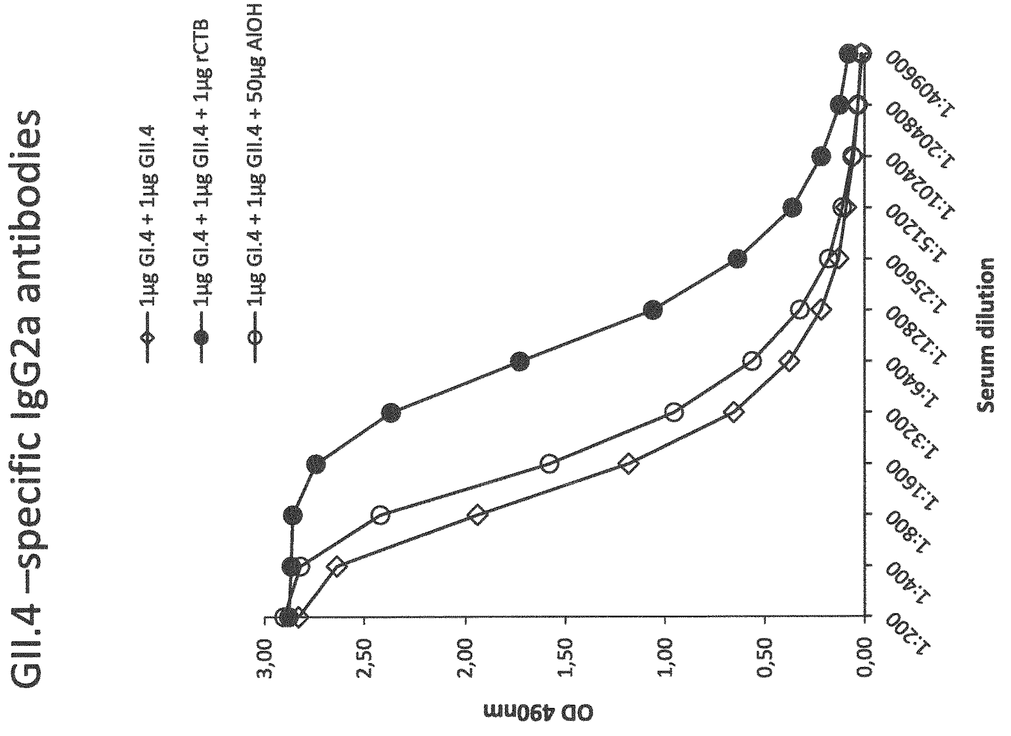
Figure 7B:
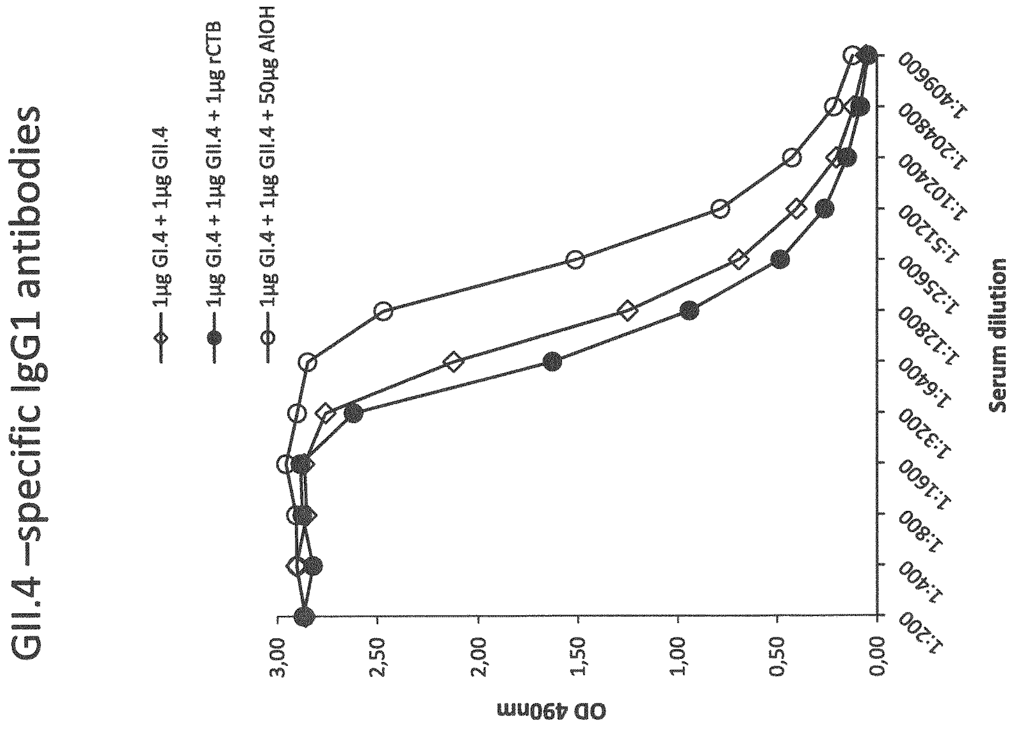
Figure 8:
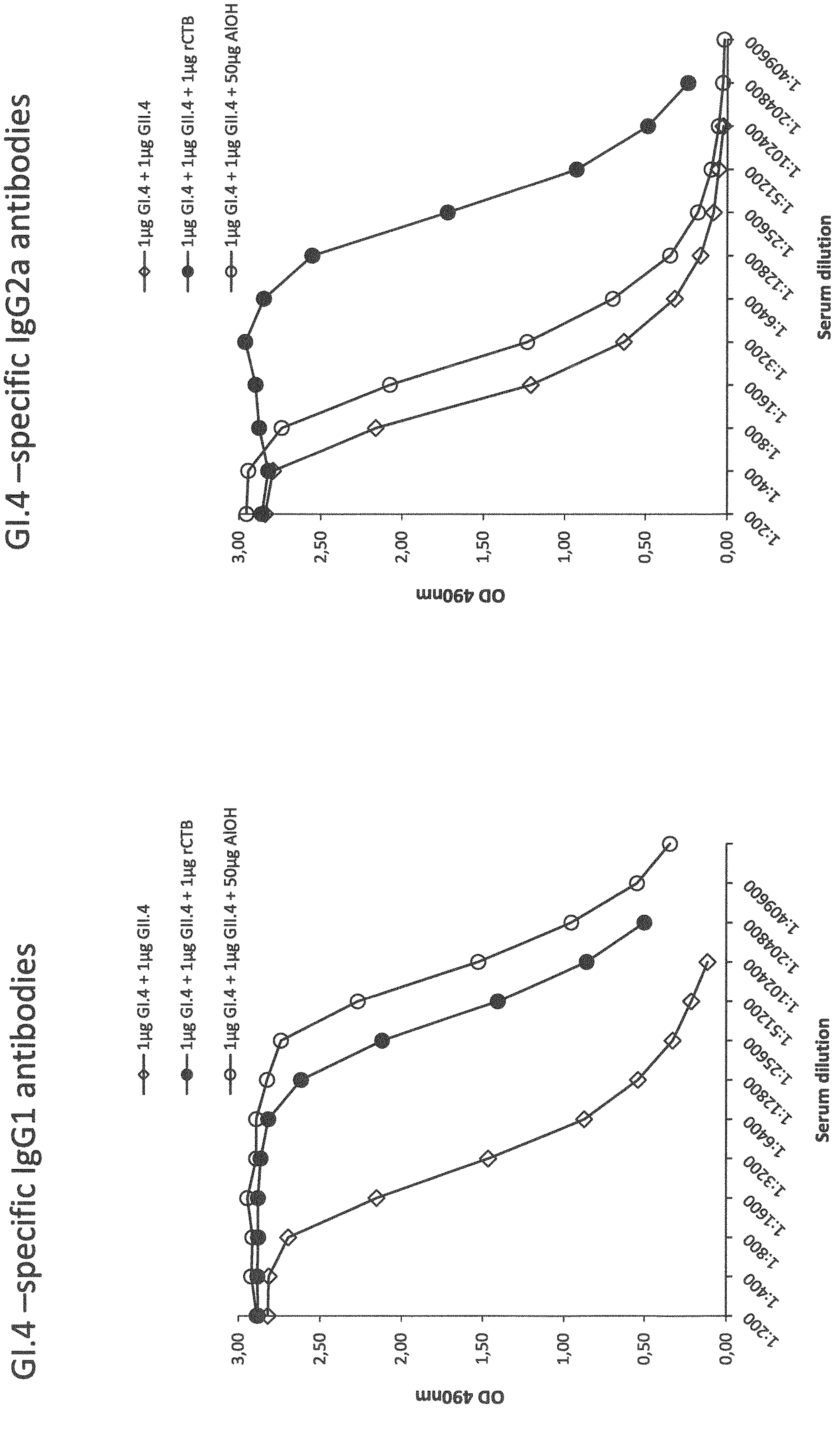
FIG. 8: Figure illustrates the result of norovirus (NoV) GI.4-specific (FIG. 8A) and GII.4-specific (FIG. 8B) serum IgG1 and IgG2a titers after two (at day 0 and day 21) intradermal (ID) immunizations of BALB/c mice with a mixture of GI.4 (Chiba) and GII.4 (Aomori) VLPs (1 mkg dose each) alone or formulated with a recombinant CTB (rCTB, 1 mkg). As positive control mixture of VLPs with 50 mkg of $Al(OH)_3$ was used.
Figure 8:
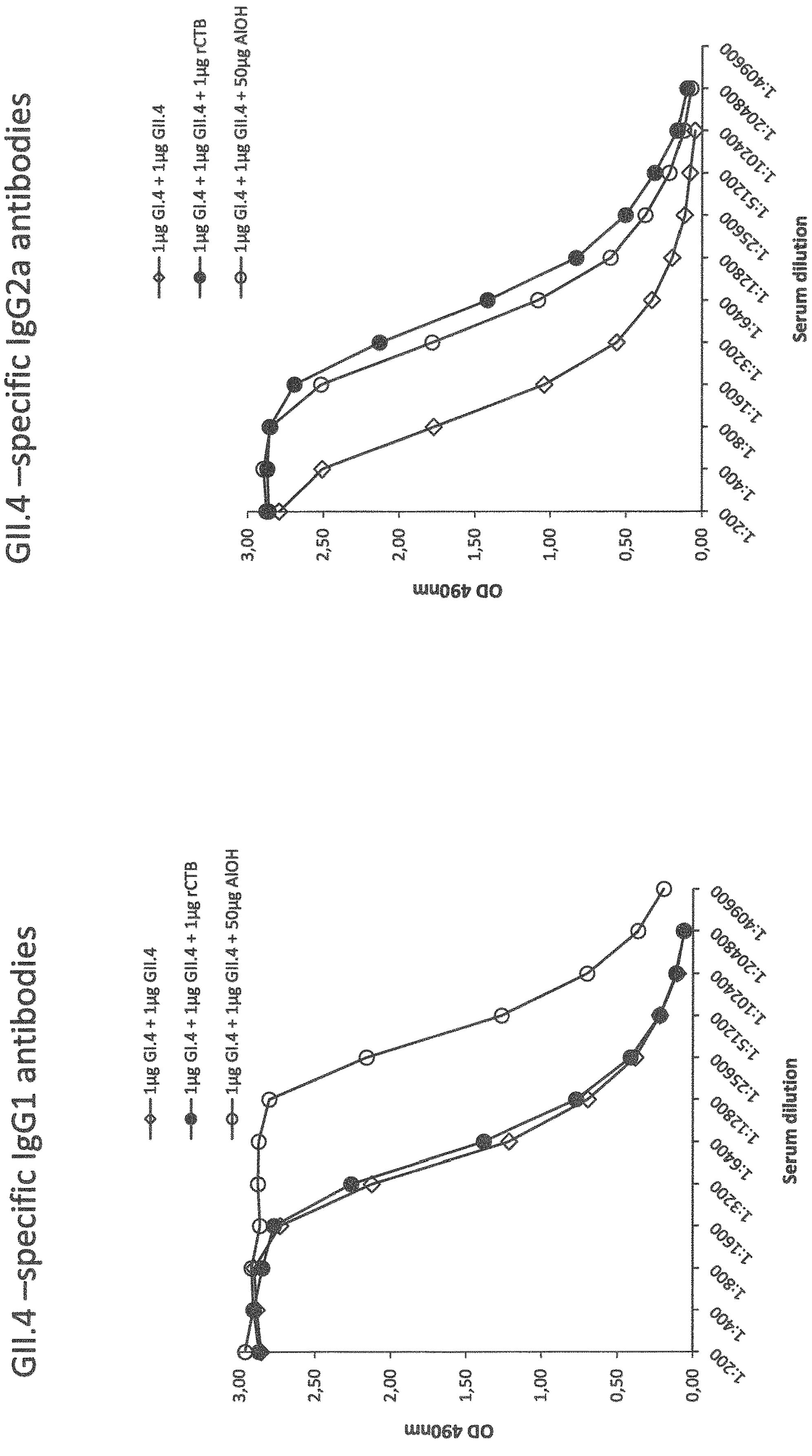
Figure 12:
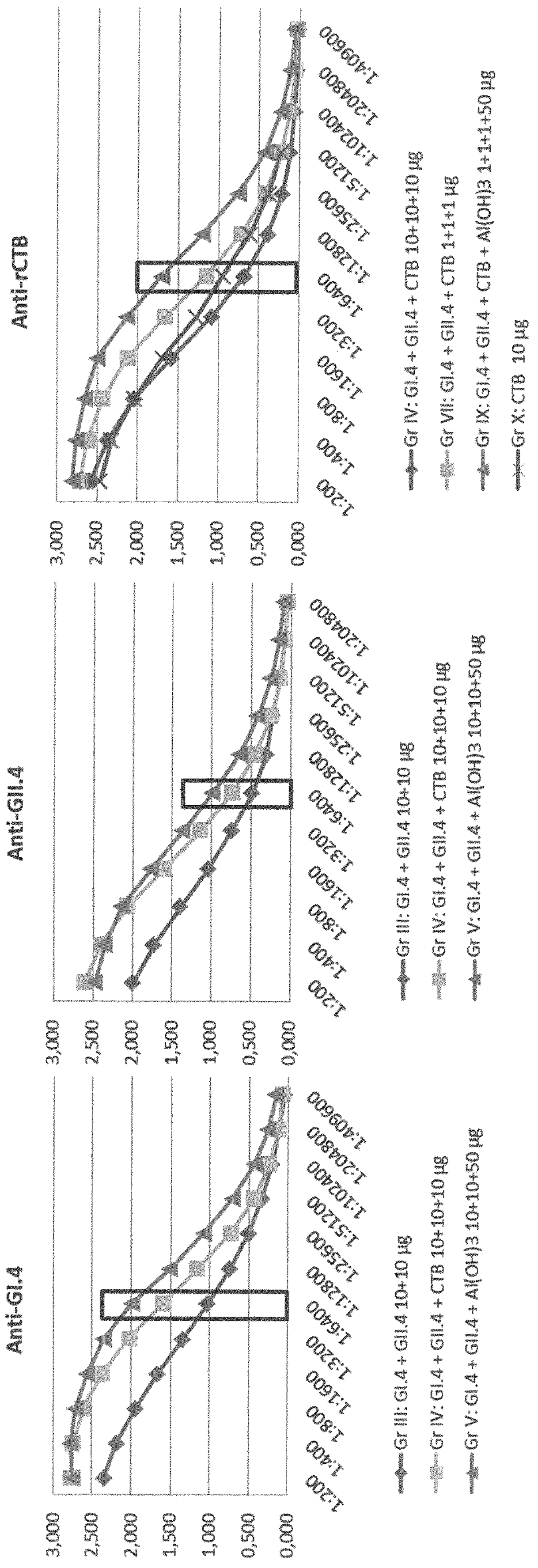
FIG. 12: Serum IgG titers after two (at day 0 and day 21) intramuscular (IM) immunizations of BALB/c mice with a mixture of GI.4 (Chiba) and GII.4 (Aomori) VLPs (1 or 10 mkg dose each) alone or formulated with plant-made recombinant CTB (CTB, 1 or 10 mkg) alone or in combination with aluminum hydroxide ($Al(OH)_3$, 50 mkg). Left panel shows NoV GI.4-specific IgG immune responses, middle panel shows NoV GII.4-specific IgG immune responses, right panel CTB-specific IgG immune responses.

CTB or LTB of any origin, preferably recombinant CTB or LTB produced in plants, can be used for the immunogenic and vaccine formulation of the invention. Depending on the dose of exotoxin B subunit and norovirus VLPs, LTB or CTB fulfill the function of an adjuvant (please refer to FIGS. 7-8), but also show antigenic properties by causing immune response to itself (see FIG. 12, right panel).

TABLE 1A

Norovirus capsid protein sequences cloned in this invention.

| No. | Genotype | Strain | GenBank acc. | UniProt acc. | Vector designation |
|---|---|---|---|---|---|
| 1 | GI. 1 | Aichi/124-89/JP | BAA83413 | Q9QT39 | pICH99711 |
| 2 | GI. 2 | Funabashi258/96/JP | BAC05516 | Q8JW44 | pICH99723 |
| 3 | GI. 3 | Shimizu/KK2866/JP | AII73765 | A0A076JEQ3 | pICH99735 |
| 4 | GI. 4 | Chiba407/87/JP | BAA82106 | Q9QTE7 | pICH96101 |
| 5 | GI. 6 | WUG1/00/JP | BAC11840 | Q8JVV5 | pICH99744 |
| 6 | GI. 7 | TCH-060/USA/2003 | AEQ77282 | G8FL04 | pICH99758 |
| 7 | GII. 1 | Noda485/00/JP | AAZ66776 | Q20K66 | pICH99766 |
| 8 | GII. 2 | MK04/2004/JP | ABE41641 | A4K7J2 | pICH99770 |
| 9 | GII. 2 | Ina NG1/JP/2002 | BAD72797 | Q5TKU0 | pICK00111 |
| 10 | GII. 2 | OC08154/JP/2008 | BAL60769 | H3JZF7 | pICK00123 |
| 11 | GII. 3 | SaitamaU201/98/JP | BAB84155 | Q8V768 | pICH96113 |
| 12 | GII. 3 | Texas/TCH04-577/2004/US | BAG30939 | B2DD27 | pICH99781 |
| 13 | GII. 3 | Kashiwa336/00/JP | AAZ66774 | Q20K68 | pICH99798 |
| 14 | GII. 3 | HKG/2014/CUHK-NS-232 | AHZ12739 | A0A024B5V5 | pICH99803 |
| 15 | GII. 4 | Aomori2/2006/JP | BAG70446 | B5BTJ5 | pICH96125 |
| 16 | GII. 4 | Sydney/NSW0514/2012/AU | AFV08795 | K4LM89 | pICH96137 |
| 17 | GII. 4 | NIHIC35/2013/USA | AGX85919 | U5N472 | pICH99812 |
| 18 | GII. 4 | NL/2014/GII.4/Groningen01 | CRL46961 | A0A0G4PZF4 | pICH99829 |
| 19 | GII. 4 | Sequence 1 from US 2016 0168543 | n.a. | n.a. | pICK02813 |
| 20 | GII. 6 | Ueno7k/94/JP | BAC05518 | Q8JW42 | pICH99834 |
| 21 | GII. 6 | Sanbu445/00/JP | AAZ66775 | Q20K67 | pICH99848 |
| 22 | GII. 7 | Osaka10-25/99/JP | BD011881 | n.a. | pICH99850 |
| 23 | GII. 13 | Kashiwa47/97/JP | BAC05515 | Q8JW45 | pICH99861 |
| 24 | GII. 14 | JP/2007/Fukuoka/KK282 | AII73780 | A0A076JER8 | pICH99872 |
| 25 | GII. 17 | C142/1978/GUF | AGI17592 | M4WL70 | pICH99887 |
| 26 | GII. 17 | JP/2013//Saitama5203 | BAR63715 | A0A0E3VY34 | pICH99890 |
| 27 | GII. 17 | JP/2015/Kawasaki308 | BAR42289 | A0A0E4B1P1 | pICH99909 |
| 28 | GII. 17 | JP/2002/Saitama/T87 | AII73747 | A0A076JB57 | pICH99912 |
| 29 | GIV. 1 | Ahrenshoop246/DEU/2012 | AFN61315 | I6Y0E0 | pICH99924 |

TABLE 1B

Norovirus capsid proteins with SEQ ID NOs and amino acid sequences.

| SEQ ID No. | Geno-type | Strain | GenBank acc. | Amino Acid Sequence | magnICON ® vector designation | magnICON ® expression confirmed | VLP formation confirmed* |
|---|---|---|---|---|---|---|---|
| 1 | GI | HuzhouN11/ 2008/CHN | AGJ52175 | MMASKDAPTSPDGASGAGQLVPEANTAEQISMDPVAGASTAVATAGQVNMIDPWIFNNF<br>VQAPQGEFTISPNNTPGDILFDLQLGPHLNPFLAHLSQMYNGWVGNMRVRILLAGNAFT<br>AGKIIICCVPPGFDARILTIAQATLFPHLIADVRTLEPVELPLEDVRNVLYHNSSQPQP<br>TMRLVAMLYTPLRTGGGSGGTDAFVVAGRVLTCPAPDFSFLFLVPPSVEQKTRVFSVPN<br>IPLKDLSNSRVPVPIQGMFMSPDVNQSVQFQNGRCQIDGQLQGTTPVSLSQLCKIRGKT<br>SSNARVLNLSEVDGTPFIPLESPAPVGFPDLGGCDWHVNFSFQTQDRDPSQSVTFATND<br>ASFVPYLGSVSPHNGEGFQAGDIIGSLGWISAPSDNSQFNVWAIPKYGSSLQMSPILLL<br>LCSPRLWEVILYFYSTFPGSGQPSQLQVPCLLPQEFITHFCNEQAPIAGEAALLHYVDP<br>DTGRNLGEFKLYPDGFMTCVPNSVSSGPQTLPINGVFVFVSWVSRFYQLKPVGTASAAR<br>RLGLRRI | n.a. | n.a. | n.a. |
| 2 | GI | ETH/ 2016/P15 | AUF81820 | MMMASKDAPTNMDGTSGAGQLVPEANTAEPISMEPVAGAATAAATAGQVNMIDPWIMNN<br>YVQAPQGEFTISPNNTPGDILFDLQLGPHLNPFLSHLAQMYNGWVGNMKVKVLLAGNAF<br>TAGKIIISCIPPGFAAQNISIAQATMFPHVIADVRVLEPIEIPLEDVRNVLFHNNDNTP<br>TMRLVCMLYTPLRASGSSSGTDPFVIAGRVLTCPSPDFSFLFLVPPNVEQKTKPFSVPN<br>LPLNILSSSRVPSLIKSMMISRDHGQMVQFQNGRVTLDGQLQGTTPTSASQLCKIRGSV<br>FHANGGNGYNLTELDGSPYHAFESPAPIGFPDLGECDWHMEASPTIQFDTGDVIKQINV<br>KQESAFAPHLGTVQADGLDGVSANTNMIAKLGWVSPVSDGHRRDVDPWVIPRYGSTLTE<br>AAQLAPPIYPPGFGEAIVFFMSDFPIAHGTNGLSVPCTIPQEFVTHFVNEQAPTRGEAA<br>LLHYLDPDTHRNLGEFKLYPDGFMTCVPNSSGSGPQTLPINGVFVFVSWVSRFYQLKPV<br>GTAGPARRLGIRRS | n.a. | n.a. | n.a. |
| 3 | GI | E8/UG/ 1976 | AFN06736 | MMMASKDAPTNMDGTSGAGQLVPEANTAEPISMDPVAGAATAVATAGQINMIDPWIMSN<br>FVQAPQGEFTVSPNNTPGDVLFDLQLGPQLNPFLAHLAQMYNGWVGNMRVKVLLAGNAF<br>TAGKIIISCIPPGFTSQNISIAQMTMFPHVIADVRVLEPIEIPLEDVRNVLFHTNDNRP<br>TMRLVCMLYTPLRANGSSSGTDPFVIAGRVLTCPDSNFSFLFLVPPNVEQKTRPFSVPN<br>IPLNTLSNSRVPSLIKSMTISRDQNQIIQFQNGRVTLDGQLQGTTPTSVSQLCKIRGTT<br>YHATGGNGINLTELNGEPYHAFESPAPIGFPDLGGCDWHLTATPTQAFNDGAKVVRLSV<br>TQGAAFAPHLGTIHYTTTDHDYDPNTSIICTLDWLSQTTGQNNVDPWQIPTYGSTLTEA<br>AQLAPPIFPPGFGETLVFFLSDFPISNGKNGLSVPCTLPQEFVTHFVNEQAPIRGEAAL<br>LHYVDPDTHRNLGEFKLYPEGFMTCVPNTSGGGPQTLPINGVFVFVSWVSRFYQLKPVG<br>TAGAARRLGIRRS | n.a. | n.a. | n.a. |
| 4 | GI | 46-2/ Tokyo/ 1977/ JPN | BAV21674 | MASKDAPSNMDGTSGAGQLVPEANTAEPINMESVVGAATATATAGQVNLIDPWIMNNYV<br>QAPQGEFTISPNNTPGDVLFDLQLGPHLNPFLSHLSRMYNGWVGNMKVRVMLAGNAFSA<br>GKIIICCIPPGFTSQSISIAQATMFPHVIADVRVLEPIDVPLDDVRNVLFHNNDNAQTM<br>RLLCMLYTPLRTGASSSGSDPFVIAGRVLTCPTQDFNFLFLVPPDVEQKTKPFSVPNIP<br>LNLMSNSRVPALIDGMTVSSDQNQVVQFQNGRVTLDGQLQGTTAVSASCVAKIRGRIFS<br>NASHYGINLTEVDGTQYHAFDSPAPLGFPDFGNCDWHVTGTKASQGDLQTDNPTISGTI<br>KSYESSFAPHLGTVRIEGDDNELARFNGKDVLLNLTWFSQRNGSQLNLWTIPSYGSNLT<br>EASQLAPPIYPPGFGEAIVYFTSTFPAISRPSVPCTMPQEFVSHFVNEQAPTRGEAALL<br>HYLDPDTHRNLGEFKMYPEGFFTCVPNAGGSGPQTLPINGVFVFVSWVSRYYQLKPVGT<br>VGMTRRLGLMKQ | n.a. | n.a. | n.a. |

TABLE 1B-continued

Norovirus capsid proteins with SEQ ID NOs and amino acid sequences.

| SEQ ID No. | Geno-type | Strain | GenBank acc. | Amino Acid Sequence | magnICON® vector designation | magnICON® expression confirmed | VLP formation confirmed* |
|---|---|---|---|---|---|---|---|
| 5 | GI.1 | Aichi/ 124- 89/JP | BAA83413 | MMMASKDATSSVDGASGAGQLVPEVNASDPLAMDPVAGSSTAVATAGQVNPIDPWIINN FVQAPQGEFTISPNNTPGGVLFDLSLGPHLNPFLLHLSQMYNGWVGNMRVRIMLAGNAF TAGKIIVSCIPPGFGSHNLTIAQATLFPHVIADVRTLDPIEVPLEDVRNVLFHNNDRNQ PLSSLSNSRAPLPISGMGISPDNVQSVQFQNGRCTLDGRLVGTTPVSLSHVAKIRGTSN GTVINLTELDGTPFHPFEGPAPIGFPDLGGCDWHINMTQFGHSSQTQYDVDTTPDTFVP HLGSIQANGIGSGNYIGVLSWVSPPSHPSGSQVDLWKIPNYGSSITEATHLAPSVYPPG FGEVLVFFMSKIPGPGAYSLPCLLPQEYISHLASEQAPTVGEAALLHYVDPDTGRTLGE FKAYPDGFLTCVPNGASSGPQQLPINGVFVFVSWVSRFYQLKPVGTASSARGRLGLRR | pICH99711 | Yes | n.t. |
| 6 | GI.1 | United States/ Norwalk/ 1968 | NP_056821 | MMMASKDATSSVDGASGAGQLVPEVNASDPLAMDPVAGSSTAVATAGQVNPIDPWIINN FVQAPQGEFTISPNNTPGDVLFDLSLGPHLNPFLLHLSQMYNGWVGNMRVRIMLAGNAF TAGKIIVSCIPPGFGSHNLTIAQATLFPHVIADVRTLDPIEVPLEDVRNVLFHNNDRNQ QTMRLVCMLYTPLRTGGGTGDSFVVAGRVMTCPSPDFNFLFLVPPTVEQKTRPFTLPNL PLSSLSNSRAPLPISSMGISPDNVQSVQFQNGRCTLDGRLVGTTPVSLSHVAKIRGTSN GTVINLTELDGTPFHPFEGPAPIGFPDLGGCDWHINMTQFGHSSQTQYDVDTTPDTFVP HLGSIQANGIGSGNYVGVLSWISPPSHPSGSQVDLWKIPNYGSSITEATHLAPSVYPPG FGEVLVFFMSKMPGPGAYNLPCLLPQEYISHLASEQAPTVGEAALLHYVDPDTGRNLGE FKAYPDGFLTCVPNGASSGPQQLPINGVFVFVSWVSRFYQLKPVGTASSARGRLGLRR | n.a. | n.a. | n.a. |
| 7 | GI.2 | Funabashi258/ 96/JP | BAC05516 | MMMASKDAPQSADGASGAGQLVPEVNTADPLPMEPVAGPTTAVATAGQVNMIDPWIVNN FVQSPQGEFTISPNNTPGDILFDLQLGPHLNPFLSHLSQMYNGWVGNMRVRILLAGNAF SAGKIIVCCVPPGFTSSSLTIAQATLFPHVIADVRTLEPIEMPLEDVRNVLYHTNDNQP TMRLVCMLYTPLRTGGGSGNSDSFVVAGRVLTAPSSDFSFLFLVPPTIEQKTRAFTVPN IPLQTLSNSRFPSLIQGMILSPDASQVVQFQNGRCLIDGQLLGTTPATSGQLFRVRGKI NQGARTLNLTEVDGKPFMAFDSPAPVGFPDFGKCDWHMRISKTPNNTSSGDPMRSVSVQ TNVQGFVPHLGSIQFDEVFNHPTGDYIGTIEWISQPSTPPGTDINLWEIPDYGSSLSQA ANLAPPVFPPGFGEALVYFVSAFPGPNNRSAPNDVPCLLPQEYITHFVSEQAPTMGDAA LLHYVDPDTNRNLGEFKLYPGGYLTCVPNGVGAGPQQLPLNGVFLFVSWVSRFYQLKPV GTASTARSRLGVRRI | pICH99723 | Yes | n.t. |
| 8 | GI | Kaohsiung/ 16-AF-2/ 2016/TW | ARC53064 | MMMASKDAPQSADGASGAGQLVPEVNTADPLPMEPVAGPTTAVATAGQVNMIDPWIVNN FVQSPQGEFTISPNNTPGDILFDLQLGPHLNPFLSHLSQMYNGWVGNMRVRILLAGNAF SAGKIIVCCVPPGFTSSSLTIAQATLFPHVIADVRTLEPIEMPLEDVRNVLYHTNDNQP TMRLVCMLYTPLRTGGGSGSSDSFVVAGRVLTAPSSDFSFLFLVPPTIEQKTRAFTVPN IPLQTLSNSRFPSLIQGMILSPDASQVVQFQNGRCLIDGQLLGTTPATSGQLFRVRGKI NQGARTLNLTEVDGKPFMAFDSPAPVGFPDFGKCDWHMRISKTPNNTSSGDPMRSVSVQ TNVQGFVPHLGSIQFDEVFNHPTGDYIGTIEWISQPSTPPGTDINLWEIPDYGSSLSQA ANLAPPVFPPGFGEALVYFVSAFPGPNNRSAPNDVPCLLPQEYITHFVSEQAPTMGDAA LLHYVDPDTNRNLGEFKLYPGGYLTCVPNGVGAGPQQLPLNGVFLFVSWVSRFYQLKPV GTASTARGRLGVRRI | n.a. | n.a. | n.a. |
| 9 | GI.3 | Shimizu/ KK2866/ JP | AII73765 | MMMASKDAPTNMDGTSGAGQLVPEANTAEPISMEPVAGAATAAATAGQVNMIDPWIMNN YVQAPQGEFTISPNNTPGDILFDLQLGPHLNPFLSHLAQMYNGWVGNMKVKVLLAGNAF TAGKIIISCIPPGFVAQNVSIAQATMFPHVIADVRVLEPIEVPLEDVRNVLFHNNDNTP TMRLVCMLYTPLRASGSSSGTDPFVIAGRVLTCPSPDFSFLFLVPPNVEQKTKPFSVPN LPLNTLSNSRVPSLIKSMMVSRDHGQMVQFQNGRVTLDGQLQGTTPTSASQLCKIRGSV FHANGGNGYNLTELDGSPYHAFESPAPIGFPDLGECDWHMEASPTTQFNTGDVIKQINV | pICH99735 | Yes | n.t. |

TABLE 1B-continued

Norovirus capsid proteins with SEQ ID NOs and amino acid sequences.

| SEQ ID No. | Geno-type | Strain | GenBank acc. | Amino Acid Sequence | magnICON ® vector designation | magnICON ® expression confirmed | VLP formation confirmed* |
|---|---|---|---|---|---|---|---|
| | | | | KQESAFAPHLGTIQADGLSDVSVNTNMIAKLGWVSPVSDGHKGDVDPWVIPRYGSTLTE<br>AAQLAPPIYPPGFGEAIVFFMSDFPIAHGTNGLSVPCTIPQEFVTHFVNEQAPTRGEAA<br>LLHYLDPDTHRNLGEFKLYPDGFMTCVPNSSGTGPQTLPINGVFVFVSWVSRFYQLKPV<br>GTAGPARRLGIRRS | | | |
| 10 | GI.3 | 0304-19. | ARI71147 | MMMASKDAPTNMDGTSGAGQLVPEANTAEPISMEPVAGAATAAATAGQVNMIDPWDANN<br>YVQAPQGEFTISPNNTPGDILFDLQLGPHLNPFLSHLAQMYNGWVGNMKVKVLLAGNAF<br>TAGKIIISCIPPGFAAQNISIAQATMFPHVIADVRVLEPIEVPLEDVRNVLFHNNDNTP<br>TMRLVCMLYTPLRASGSSSGTDPFVIAGRVLTCPSPDFSFLFLVPPNVEQKTKPFSVPN<br>LPLNTLSNSRVPSLIKSMMVSRDHGQMVQFQNGRVTLDGQLQGTTPTSASQLCKIRGSV<br>FHANGGNGYNLTELDGSPYHAFESPAPIGFPDLGECDWHMEASPTTQFNTGDVIKQINV<br>KQESAFAPHLGTIQADGLSDVSVNTNMIAKLGWVSPVSDGHKRDVDPWVIPRYGSTLTE<br>AAQLAPPIYPPGFGEAIVFFMSDFPIAHGTNGLSVPCTIPQEFVTHFVNEQAPTRGEAA<br>LLHYLDPDTHRNLGEFKLYPDGFMTCVPNSSGTGPQTLPINGVFVFVSWVSRFYQLKPV<br>GTAGPARRLGIRRS | n.a. | n.a. | n.a. |
| 11 | GI.3 | B8/CF/ 1977 | AFN06739 | MMMASKDAPTNMDGTSGAGQLVPEANTAEPISMEPVAGAATAAATAGQVNMIDPWINNN<br>YVQAPQGEFTISPNNTPGDILFDLQLGPHLNPFLSHLAQMYNGWVGNMKVKVLLAGNAF<br>TAGKIIISCIPPGFASQNISIAQATMFPHVIADVRVLEPIEVPLEDVRNVLFHNNDNTP<br>TMRLVCMLYTPLRASGSSSGTDPFVIAGRVLTCPSPDFSFLFLVPPNVEQKTKPFSVPN<br>LPLNVLSNSRVPSLIKSMMVSQDHGQMVQFQNGRVTLDGQLQGTTPTSASQLCKMRGTV<br>YHASGGQGLNLTEIDGTPYHAFESPAPIGFPDIGDSDWHINASPATTFDSGESIKRLDM<br>EQGSSFAPHLGTVHYTNADYPANTDLICSLEWLSPPSGGTPNKVNPWTIPRYGSTLTEA<br>AQLAPPIYPPGFGEAIVFFMSDFPIANGQDGLKVPCTIPQEFVTHFVNEQAPTRGEAAL<br>LHYVDPDTHRNLGEFKLYPEGFMTCVPNSSGSGPQTLPINGVFTFVSWVSRFYQLKPVG<br>TTGPVRRLGIRRS | n.a. | n.a. | n.a. |
| 12 | GI.3 | 15-EN- 3/2015 | AOO95034 | MMMASKDAPTNMDGTSGAGQLVPEANTAEPISMEPVAGAATAAATAGQVNMIDPWIMNN<br>YVQAPQGEFTISPNNTPGDILFDLQLGPHLNPFLSHLAQMYNGWVGNMKVKVLLAGNAF<br>TAGKIIISCIPPGFASQNISIAQATMFPHVIADVRVLEPIEVPLEDVRNVLFHNNDNSP<br>TMRLVCMLYTPLRASGSSSGTDPFVIAGRVLTCPSPDFSFLFLVPPNVEQKTKPFSVPN<br>LPLNTLSNSRVPSLINAMMISRDHGQMVQFQNGRVTLDGQLQGTTPTSLSQLCKIRGKV<br>FLASGGNGLNLTELDGSAYHAFESPAPIGFPDIGDCDWHMNATATSNFTGSNDEHQILV<br>KQESTFAPHLGHVQADHLPEVANTDLMVSLSWISPVSDQHRRDVDPWVIPRYGSTLTEA<br>AQLAPPIYPPGFGEAIVFFMSDFPVVSGVNGMRIPCTLPQEYVAHFVNEQAPTRGEAAL<br>LHYVDPDTHRNLGEFKIYPEGFMTCVPNSSGTGPQTLPINGVFTFVSWVSRFYQLKPVG<br>TAGPARRLGIRRS | n.a. | n.a. | n.a. |
| 13 | GI.4 | Chiba407/ 87/JP | BAA82106 | MMMASKDATPSADGATGAGQLVPEVNTADPIPIDPVAGSSTALATAGQVNLIDPWIINN<br>FVQAPQGEFTISPNNTPGDVLFDLQLGPHLNPFLSHLSQMYNGWVGNMRVRVVLAGNAF<br>TAGKVIICCVPPGFQSRTLSIAQATLFPHVIADVRTLDPVEVPLEDVRNVLYHNNDTQP<br>TMRLLCMLYTPLRTGGASGGTDSFVVAGRVLTCPGPDFNFLFLVPPTVEQKTRPFTVPN<br>IPLKYLSNSRIPNPIEGMSLSPDQTQNVQFQNGRCTIDGQPLGTTPVSVSQLCKFRGRI<br>TSGQRVLNLTELDGSPFMGFGAPAPAGFPDLGSCDWHIEMSKIPNSSTQNNPIVTNSVK | pICH96101 | Yes | Yes |

TABLE 1B-continued

| SEQ ID No. | Geno-type | Strain | GenBank acc. | Amino Acid Sequence | magnICON ® vector designation | magnICON ® expression confirmed | VLP formation confirmed* |
|---|---|---|---|---|---|---|---|
| Norovirus capsid proteins with SEQ ID NOs and amino acid sequences. | | | | | | | |
| | | | | PNSQQFVPHLSSITLDENVSSGGDYIGTIQWTSPPSDSGGANTNFWKIPDYGSSLAEAS<br>QLAPAVYPPGFNEVIVYFMASIPGPNQSGSPNLVPCLLPQEYITHFISEQAPIQGEAAL<br>LHYVDPDTNRNLGEFKLYPGGYLTCVPNSSSTGPQQLPLDGVFVFASWVSRFYQLKPVG<br>TAGPARGRLGVRR | | | |
| 14 | GI.4 | S14/2008/ Lilla Edet/ Sweden | AEY77031 | MMMASKDATPSADGATGAGQLVPEVNTADPIPIDPVAGSSTALATAGQVNLIDPWIINN<br>FVQAPQGEFTISPNNTPGDVLFDLQLGPHLNPFLSHLSQMYNGWVGNMRVRVVLAGNAF<br>TAGKVIICCVPPGFQSRTLSIAQATLFPHVIADVRTLDPVEVPLEDVRNVLYHNNDTQP<br>TMRLLCMLYTPLRTGGASGGTDSFVVAGRVLTCPGPDFNFLFLVPPTVEQKTRPFTVPN<br>IPLKYLSNSRIPNPIEGMSLSPDQTQNVQFQNGRCTIDGQPLGTTPVSVSQLCKFRGRI<br>TSGQRVLNLTELDGSPFMAFAAPAPAGFPDLGSCDWHIEMSKIPNSSTQNNPIVVNSVK<br>PNSQQFVPHLSSITLDDNVSSGGDYIGTIQWTSPPSDSGGANTNFWKIPDYGSSLAEAS<br>QLAPAVYPPGFNEVIVYFMASIPGPNQSGSPNLVPCLLPQEYITHFISEQAPIQGEAAL<br>LHYVDPDTNRNLGEFKLYPGGYLTCVPNSSSTGPQQLPLDGVFVFASWVSRFYQLKPVG<br>TA | n.a. | n.a. | n.a. |
| 15 | GI.5 | 15-EN-8/2015 | AOO95019 | MMMASKDATPSADGANGAGQLVPEVNNAEPLPLDPVAGASTALATAGQVNMIDPWIFNN<br>FVQAPQGEFTISPNNTPGDILFDLQLGPHLNPFLAHLSQMYNGWVGNMRVRVILAGNAF<br>TAGKVIICCVPPGFQSRTLSIAQATLFPHIIADVRTLEPIEIPLEDVRNTLYHTNDNQP<br>TMRLLCMLYTPLRTGGGSGGTDAFVVAGRVLTSPSPDFNFLFLVPPTVEQKTRPFSVPN<br>IPLQLLSNSRVPNLIQSMVPSPDQAQNVQFQNGRCTTDGQLLGTTPVSVSQILKFRGKV<br>SAGSKVINLTELDGSPFLAFEAPAPTGFPDLGTSDWHIEMSLNSNSQSSGNPILLRDIQ<br>PNSSDFVPHLGSVAVTTAIDTAGDYTGTIQWTSQPSNVTPVPDVNFWTIPQYGSNLAEA<br>SQLAPVVYPPGFGEAIVYFMSPIPGPNTAHKPNLVPCLLPQEFVTHFVSEQAPSMGEAA<br>LVHYVDPDTNRNLGEFKLYPEGFITCVPNGTGPQQLPLNGVFVFASWVSRFYQLKPVGT<br>ANSARGRLGVRR | n.a. | n.a. | n.a. |
| 16 | GI.5 | Jp/2002/ OC020180 | BAU16307 | MMMASKDATPSADGANGAGQLVPEVNNAEPLPLDPVAGASTALATAGQVNMIDPWIFNN<br>FVQAPQGEFTISPNNTPGDILFDLQLGPHLNPFLAHLSQMYNGWVGNMRVRVILAGNAF<br>TAGKVIICCVPPGFQSRTLSIAQATLFPHVIADVRTLEPLEIPLEDVRNTLYHNNDSQP<br>TMRLLCMLYTPLRTGGGSGGTDAFVVAGRVLTCPSPDFNFLFLVPPTVEQKTRPFSVPN<br>IPLQNLSNSRVPSLIQSMVLSSDHAQTVQFQNGRCTTDGHLLGTTPVSSGQLNKFRGKV<br>TPGSKVLNLTELDGSPFLAFEPPAPAGFPDLGKCDWHIEMSLYQVNNQDNPIVLRAIEP<br>NSSSFVPHLGSVSFNQNVDAAGDYVCTIQYTSPPSNSHDADVDFWSIPDYGSNLAEASQ<br>LAPVVYPPGFGEAIVYFMSRVPGWNRTNRLNLVPCLLPQEFIGHFVSEQAPAIGEAALL<br>HYVDPDTNRNLGEFKLYPEGFITCVPNGTGPQQLPLNGVFVFSSWVSRFYQLKPVGTAS<br>SARGRLGIRR | n.a. | n.a. | n.a. |
| 17 | GI.6 | 6WUG1/ 00/JP | BAC11840 | MMMASKDAPTSPDGASGAGQLVPEANTAEQISMDPVAGASTAVATAGQVNMIDPWIFNN<br>FVQAPQGEFTISPNNTPGDILFDLQLGPHLNPFLAHLSQMYNGWVGNMRVRILLAGNAF<br>TAGKIIICCVPPGFDARILTIAQATLFPHLIADVRTLEPVELPLEDVRNVLYHNSSQPQ<br>PTMRLVAMLYTPLRTGGGSGGTDAFVVAGRVLTCPAPDFSFLFLVPPSVEQKTRVFSVP<br>NIPLKDLSNSRVPVPIQGMFMSPDVNQSVQFQNGRCQIDGQLQGTTPVSLSQLCKIRGK<br>TSSNARVLNLSEVDGTPFIPLESPAPVGFPDLGGCDWHVNFTFQAQNQDPSQSVTFATN | pICH99744 | Yes | n.t. |

TABLE 1B-continued

Norovirus capsid proteins with SEQ ID NOs and amino acid sequences.

| SEQ ID No. | Geno-type | Strain | GenBank acc. | Amino Acid Sequence | magnICON ® vector designation | magnICON ® expression confirmed | VLP formation confirmed* |
|---|---|---|---|---|---|---|---|
| | | | | DASFVPYLGSISPHNGGDFHAGDIIGSLGWISAPSDNTQLNVWTIPKYGSSLQMSLTLH<br>LLCSPRLWEVILYFYSTFPGSGQPSQLQVPCLLPQEFITHFCNEQAPIAGEAALLHYVD<br>PDTGRNLGEFKLYPDGFMTCVPNSVSSGPQTLPINGVFVFVSWVSRFYQLKPVGTASAA<br>RRLGLRRI | | | |
| 18 | GI.6 | Jp/2013/<br>s130147 | BAU16303 | MMMASKDVPTSPDGASGAGQLVPEVNTADQISMDPVAGASTAVATAGQVNMIDPWIFNN<br>FVQAPQGEFTISPNNTPGDILFDLQLGPHLNPFLAHLSQMYNGWVGNMRVRILLAGNAF<br>TAGKIIICCVPPGFDARILTIAQATLFPHLIADVRTLEPVELPLEDVRNVLYHNSSQPQ<br>PTMRLVAMLYTPLRTGGGSGGTDAFVVAGRVLTCPAPDFSFLFLVPPSVEQKTRVFSVP<br>NIPLKDLSNSRVPTLIQGMFVSPDVNQSVQFQNGRCQIDGQLQGTTPVSLSQLCKIRGK<br>TSSNTRVLNLSEVDGTPFVPLESPAPVGFPDIGGCDWHVGFTFEARDQGPSQNVTFATN<br>DSSFVPYLGSISPHNGDGFHSGDIIGSLDWISAPSDGSALDVWSIPKYGSSLPDVTHLA<br>PAVFPPGFGEVILYFHSKFPGSGPTDKLRVPCLMPQEFITHFCDEQAPIAGEAALLHYV<br>DPDAGRNLGEFKLYPDGFMTCVPNSISSGPQTLPINGVFVFVSWVSRFYQLKPVGTASM<br>ARRLGLRRI | n.a. | n.a. | n.a. |
| 19 | GI.7 | TCH-<br>060/USA/<br>2003 | AEQ77282 | MMMASKDAPSNMDGTSGAGQLVPEVNAAEPLPLEPVVGAATAAATAGQVNLIDPWIMNN<br>FVQAPEGEFTISPNNTPGDILFDLHLGPHLNPFLQHLSQMYNGWVGNMRVRVMLAGNAF<br>TAGKIIICCVPPGFASQNISIGQATMFPHVIADVRVLEPIEIPLDDVRNVLFHTNENRP<br>TMRLLCMLYTPLRAGGASSGTDPFVIAGRVLTCPSPDFNFLFLVPPSVEQKTRQLTVPN<br>IPLNNLANSRVPAMINKMTVSTDQNQVVQFQNGRCTLEGQLLGTTPVSASQVARIRGKV<br>FSTASGKGLNLTELDGTPYHAFESPAPLGFPDIGACDWHVSTFKVDQNLSGDPMSRLDV<br>KQNAPFAPHLGSIEFTSDQDPTGDQLGTLAWVSPSTSGARVDPWKIPSYGSTVTESTHL<br>APPIFPPGFGEAIVYFMSDFPIVSGNTAQVPCTLPQEFVSHFVEQQAPVRGEAALLHYV<br>DPDTHRNLGEFKLYPDGFITCVPNTGGGPQNLPTNGVFVFSSWVSRYYQLKPVGTAGPA<br>RRLGVRRV | pICH99758 | Yes | n.t. |
| 20 | GI.7 | USA/2011/<br>GI.P7_<br>GI.7/<br>CS5567 | APA31976 | MMMASKDAPSNMDGTSGAGQLVPEVNAAEPLPLEPVVGAATAVATAGQVNLIDPWIMNN<br>FVQAPEGEFTISPNNTPGDILFDLQLGPHLNPFLQHLSQMYNGWVGNMRVRVMLAGNAF<br>TAGKIIICCVPPGFASQNISIGQATMFPHVIADVRVLEPIETPLDDVRNVLFHTNESRP<br>TMRLLCMLYTPLRAGGASSGTDPFVIAGRVLTCPSPDFNFLFLVPPSVEQKTRQLTVPN<br>IPLNNLANSRVPAMINKMTVSTDQSQVVQFQNGRCTLEGQLLGTTPVSASQVARIRGKV<br>FSTASGKGLNLTELDGTPYHAFESPAPLGFPDIGACDWHVSTFKVDQNLSGDPMSRLDI<br>KQNAPFAPHLGSIEFTSDQEPTGDQLGTLAWVSPSTSGARVDPWKIPSYGSTVTESTHL<br>APPIFPPGFGEAIVYFMSDFPIVSGNTAQVPCTLPQEFVSHFVEQQAPIRGEAALLHYV<br>DPDTHRNLGEFKLYPDGFITCVPNTGGGPQNLPINGVFVFSSWVSRYYQLKPVGTAGPA<br>RRLGVRRV | n.a. | n.a. | n.a. |
| 21 | GI.8 | CHN/2008/<br>GI.P8_<br>GI.8/<br>Huzhou/<br>N10 | AKM20815 | MMMASKDAPTNMDGTSGAGQLVPEANTAEPLPIKPVAGAATAVATAGQVNMIDPWIMNN<br>FVQAPQGEFTISPNNTPGDILFDLQLGPHLNPFLAHLSRMYNGWVGNMQVRIMLAGNAF<br>SAGKIIVCCIPPGFSSQSISIAQATMFPHVIADVRVLEPIDVPLDDVRNVLFHNNDNPQ<br>TMRLLCMLYTPLRSGGTSSGTDPFVIAGRVLTCPTPDFSFLFLVPPDIEQRTKPFSVPN<br>IPMNLMSNSRVSMLIDGMMVSNDQNQVPQFQNGRVTLDGQLQGTTTVSAACVARMRGRI<br>FNNNGNYGVNLTELDGNPYHAFDSPAPLGFPDFGNCDLHMTFVKINPNELSSGDPSGKV | n.a. | n.a. | n.a. |

TABLE 1B-continued

| Norovirus capsid proteins with SEQ ID NOs and amino acid sequences. | | | | | | | |
|---|---|---|---|---|---|---|---|
| SEQ ID No. | Geno-type | Strain | GenBank acc. | Amino Acid Sequence | magnICON ® vector designation | magnICON ® expression confirmed | VLP formation confirmed* |
| | | | | VIRSYDATFAPHLGTVKLENDDELARFVGKEVVLELTWVSNREGATLNLWAVPNYGSSL<br>TQASQLAPPIYPPGFGEAIVYFTSTFPTVSNPKVPCTLPQEFVSHFVNEQAPTRGDAAL<br>LHYVDPDTHRNLGEFKMYPEGYMTCVPNAGGGPQTLPINGVFVFISWVSRYYQLKPVGT<br>AGAARRLGLRRS | | | |
| 22 | GI.9 | USA/2016/<br>GI.P9_<br>GI.9/<br>SC6350 | APA31982 | MMMASKDATSNMDGTSGAGQLVPENNNTSEPINMEPVAGAVTAAATAGQVNMIDPWIMN<br>NYVQAPQGEFTISPNNTPGDILFDLQLGPHLNPFLAHLSQMYNGWVGNMKVRVVLAGNA<br>FSAGKIIVCCIPPGFSAPNISIAQATMFPHVIADVRVLEPIDIPLDDVRNVLFHNNDNG<br>NQTMRLLCMLYTPLRSGGTSSGTDPFVIAGRVLTCPTPDFNFLFLVPPTVEQKTKQFSV<br>PNLPLNVMSNSRVPSLLNAMVVSPDQAQVVQFQNGRCTLDGQMLGTTTVSASCVARFRG<br>KTFQAPDNRLGINLAEISGEPYHAFESPAPLGFPDFGDGDWHVTATKVTPSQLEANDPV<br>VMGNVQPYNPQFAPHLGTLVVENPTPDNVTTGTDLLFNITWLSNRANNRFNPWVIPNYG<br>STLTEAAQLAPSIFPPGFGETIVYFNSTFPAVGATTHAAIPCLLPQEFVAHFVNEQAPI<br>RGEAALLHYIDPDTHRNLGEFKIYPEGFVTCVPNVGGTGPQSLPTNGIFVFVSWVSRYY<br>QLKPVGTAGQARRLGFRRV | n.a. | n.a. | n.a. |
| 23 | GII | PE/2012/<br>GII.P<br>NA1-<br>GII.NA1/<br>Loreto1041 | AUD54969 | MKMASNDAAPSNDGAAGLVPEINNETMALEPVAGGAIAAPLTGQTNFIDPWIRNNYVQA<br>PNGEFTVSPRNSPGEILLNLELGPELNPFLAHLSRMYNGYAGGIDVQVIMAGNAFTAGK<br>IIFAAVPPHFPIDNISPPQITMFPHIIIDVRTLEPVNIPLPDVRNSFFHYSQNNEPRMR<br>LLAMLYTPLRSNGSADDVFTVSCRVLTKPSADFEFNYLVPPTVESRTKPFTIPILTIGE<br>MTNSRFPVAIDMLHTSPTDNFIVQPQNGRCTLDGELQGTTQLVTSNICAFRGSISGHEN<br>NGDQHQWHFSITNPNGTPFDPTEDVPAPLGTPDFKGQLYGVISQRNREGSPGNGNQKAN<br>RSHEGVISTVAPRFTPKLGSVMIGTWTTDDIQDQPSRFTPVGLNDDDNYKQWELPNYSG<br>ALTLNMGLAPSVFPTYPGEQLLFFRSYIPMKGGYGSPYIDCLIPQEWISHFYQESAPSQ<br>TDVALIRYVNPDTGRVLFEAKLHRQGYITVAKTGDSPINVPANGYFRFDSWVSQFYSLA<br>PMGTGNGRRRIQ | n.a. | n.a. | n.a. |
| 24 | GII | 768/2002/<br>TUN | AUO28670 | MRMASSDAPVSGTDGAAGLVPESQQEVLPLEPVAGVQLAAPVAGQSNIIDPWIRMNFVQ<br>APAGEFTVSPRNAPGEVLIDLELGPELNPYLNHLARMYNGYVGGMEVEVVLAGNAFTAG<br>KILFAAVPPSFPTHGISAAQATMLPHVIVDVRQLEPVRLPLPDVRNVMFHFCQENKEPR<br>MRIVAILYTPLRANGAGDDVFTVSCRVLTRPSPDFDFIFLVPPSVESKLKQFTLPNLQP<br>NEMTNSRFPTGITQLYTSPNTNLVVQFQNGRCLLDGTLLGTTPVRAADICSFRGVTSTE<br>VDATDSPRVAGSHRIMVQLKEPDGEEFSPTGPNPAPVGTPDFQAAIFGTLSQRNTGGTG<br>QNSNRAHFAYFYTRNPTFAPGIGTVVFSFDTTDFQNRQPTKFSPSGVFDDDSSEPFNQF<br>SLPYYNGSLGAVDAGKLAPPVAPNYPGEQILYFRGNIPFKGGYGEGEIDSLLPQEWITH<br>FYAEQAPTQGDAALLRYYNPDTGRVLFECKLHREGFITINYTGSNALAVPVNGVFRFEG<br>WVNKFYTLTPMGNGNGRRGRRREL | n.a. | n.a. | n.a. |
| 25 | GII | JP/2011/<br>Yuzawa/<br>Gira2HS | AII73762 | MKMASKDASPSTDGTANLVPESQQEVLALQPVAGAQIAAPVAGQFNVIDPWIYQNFVQA<br>PEGEFTVSPRNSTGEILMNLELGPQLNPYLAHLARMYNAYAGGFEVQVLLAGNAFTAGK<br>IIVCAVPPNFPLQNISAAQATQLPHVVVDVRQLEPVVLPLPDVRAGFYHYNQVEESRMR<br>LVAILYTPLRTNSAGDDAFTVSCRILTRPAPDFSFFFLIPPTIESKTTPFTLPRLPISE<br>MTNSRFPLVIKGMVVDPNLPLQANFQNGRITLDGELQGTTLPTSTSIGRISGTHMSSTP<br>SRIIQHEDSGDSTQPRVFNPVWMDLTENNWTEFQPFNDQPAPLGCPDFKAKILGTLIRQ | n.a. | n.a. | n.a. |

TABLE 1B-continued

Norovirus capsid proteins with SEQ ID NOs and amino acid sequences.

| SEQ ID No. | Geno-type | Strain | GenBank acc. | Amino Acid Sequence | magnICON ® vector designation | magnICON ® expression confirmed | VLP formation confirmed* |
|---|---|---|---|---|---|---|---|
| | | | | PNNGSYYFDAYLDTRQHGTFAPYTGHAAVHSDQQAGHLAQGYKIQFSPTGIESDQNTDL<br>NQLPDYGGAMTVSKGLAPAAAPDFPGEMILYFVSDMPVRNPNGERRDTEILCLLPQEMV<br>THFYEQQAPSQGDVALVRYINAETGRVMFEGKLHRNGFFTVSATARTLIVPDGYFRFDS<br>WVNRFYTLSPMGTGNGRRRARMLE | | | |
| 26 | GII | OC07118/<br>2007/JP | BAJ25074 | MKMASNDANPSSDGSANLVPEISNEVMALEPVAGAAIAAPVAGQQNIIDPWIRNNFVQA<br>PGGEFTVSPRNAPGEVLLNLPLSPDINPYLAHLSRMYNGYAGGVEVEVVLAGNAFTAGK<br>IIFAAVPPNFPPENLSPSQITMLPHIIVDVRQLEPVRIPLPDVRNNFYHYSRENDSTLR<br>LIAMLYTPLRANNAGDDVFTVSCRVLTRPSPDFDFIFLVPPTVESKSKPFTIPMLTIEE<br>MTNSRFPAPLELMTTGPSHDIVVQPQNGRCTIDGVLLGTTQLSPVNICSLRGVPTKRTN<br>GNDNCFVQLENPNGSAYDPTEDIPAVLGSPDFVGELYGTITQRSSDNSTRAHPFTLNTG<br>SPRYTPKIGSVDIRVTDVSDLQDHDPVKLTPVGLSGDRGSIHQWQLPNYSGVATHNMHL<br>APSVAPLFPGEQILFFRSTVPGCGGYPNSNIDCLIPQEWVQHFYQEGAPARTDVALLRF<br>INPDTGRVLFECKLHKHGFITVAYSGNHDLVMPPNGYFRFESWVNQFHTLAPMGTGSGR<br>RRIQ | n.a. | n.a. | n.a. |
| 27 | GII | PE/2013/<br>GII.P<br>NA2-<br>GII.NA2/<br>Loreto1257 | AUD54972 | MKMASNDAAPSNDGAAGLVPEINNETMALEPVAGGAIAAPLTGQTNFIDPWIRGNYVQA<br>PNGEFTVSPRNSPGEILLNLELGPELNPFLAHLSRMYNGYAGGIDVQVIMAGNAFTAGK<br>IIFAAVPPHFPVENISPPQITMFPHIIVDVRTLEPINIPVPDVRNNFFHYNQDRDSRMR<br>LVAMLYTPLRSNGSTDDVFTVSCRVLTKPSADFEFNYLVPPTVESRTKPFSIPILTIGE<br>MTNSRFPLPIDMLYTSPTENLVVQPQNGRCTTEGELLGTTQLVTPSICSLRGAITGHEG<br>NDDDHKWHMTVTSPNGAAFDPTEDVPAPLGTPDFTGDIYGVLSQRDRNINPGQTAPANR<br>AHEAVVSTRSNKFTPKLGSVMIATWETTDVLQQPTKFTPVGLESPNHYNQWQLPNYSGA<br>LTLNMGLAPSVFPTYPGEQILFFRSFIPLKGGYGNSAIDCLVPQEWIQHFYQESAPSQT<br>DVALIRYVNPETGRVLFEAKLHRQGFITVAKTGDSPINVPANGYFRFDSWVNPFYSLAP<br>MGTGNGRRRNQ | n.a. | n.a. | n.a. |
| 28 | GII | T091/TN/<br>1976 | AGL98416 | MKMASNDANPSDGSAANLVPEVNNEVMALEPVVGAAIAAPVAGQQNVIDPWIRNNFVQA<br>PGGEFTVSPRNAPGEILWSMPLSPELNPYLSHLSRMYNGYAGGFEVQVILAGNAFTAGK<br>IIFAAIPPNFPTDGLSPSQVTMFPHIIVDVRQLEPVLIPLPDVRNNFYHYNQANDSTLK<br>MTNSRFPTPLEKLHTGPNNSIVVQPQNGRCTIDGVLLGTTQLSTVNICNFRGSTTRAGQ<br>SHAYTMNLVSQNWNNYDPTEEIPAPLGTPDFVGKIVGMLSQTTRENSSTRAHKATVSTG<br>DAHFTPKSGSVLFTTDTDDLQNGQNTRFTPVGVAQDGEPHQNEPQQWRLPNYSGTPGHN<br>VHLAPPVAPTFPGEQLLFFRSTMPGCGGYPNMDLDCLLPQEWVRHFYQEAAPAQSDVAL<br>LRFVNPDTGRVLFECKLHKAGYITVSHTGPYDLVIPPNGYFRFDSWVNQFYALAPMGTG<br>TGRRRAL | n.a. | n.a. | n.a. |
| 29 | GII.1 | Noda485/<br>00/JP | AAZ66776 | MKMASNDAAPSNDGAAGLVPEVNNEMMALEPVAGASIAAPLTGQNNVIDPWIRMNFVQA<br>PNGEFTVSPRNSPGEILLNLELGPELNPFLAHLSRMYNGYAGGVEVQVLLAGNAFTAGK<br>LVFAAIPPRFPIENLSPGQITMFPHVIIDVRTLEPVLLPLPDVRNNFFHYNQEPEPRMR<br>LVAMLYTPLRSNGSGDDVFTVSCRVLTRPSPDFDFNYLVPPTVESKTKPFTLPILTIGE<br>LSNSRFPAPIDELYTSPNEGLVVQPQNGRSTLDGELLGTTQLVPSNICSLRGRINAHLP<br>DNQHRWNMQVTNANGTPFDPTEDVPAPLGTPDFLANIYGVTSQRNPDNTCRAHDGILAT<br>WSPKFTPKLGSVVLGTWEDRDFDINQPTRFTPVGLYDTDHFNQWALPNYSGALTLNMNL<br>APSVAPLFPGEQLLFFRSHIPLKGGTSNGAIDCLLPQEWVQHFYQESAPSSTDVALIRY<br>TNPDTGRVLFEAKLHRQGFITVANSGSRPIVVPPNGYFRFDSWVNQFYSLAPMGTGNGR<br>RRVQ | pICH99766 | Yes | Yes |

TABLE 1B-continued

| Norovirus capsid proteins with SEQ ID NOs and amino acid sequences. | | | | | | | |
|---|---|---|---|---|---|---|---|
| SEQ ID No. | Geno-type | Strain | GenBank acc. | Amino Acid Sequence | magnICON ® vector designation | magnICON ® expression confirmed | VLP formation confirmed* |
| 30 | GII.1 | IDN/IT D11-3/ 2015/ GII.Pg/ GII.1 | ASW22508 | MKMASNDVAPSNDGAAGLVPEVSNETMALEPVAGASIAAPLTGQNNVIDPWIRMNFVQA<br>PNGEFTVSPRNSPGEVLLNLELGPELNPFLAHLARMYNGYAGGVEVQVLLAGNAFTAGK<br>LVFAAIPPHFPLENLSPGQITMFPHVIIDVRTLEPVLLPLPDVRNNFFHYNQQPEPRMR<br>LVAMLYTPLRSNGSGDDVFTVSCRVLTRPSPDFDFNYLVPPTVESKTKPFTLPILTIGE<br>LSNSRFPVPIDELYTSPNEGVVVQPQNGRSTLDGELLGTTQLVPSNICALRGRINAQVP<br>DDHHQWNLQVTNANGTSFDPTEDVPAPLGTPDFLANIYGVTSQRNPDNTCRAHDGVLAT<br>WSPKFTPKLGSVVLGTWEESDLDLNQPTRFTPVGLYDTNHFDQWILPNYSGRLTLNMNL<br>APSVAPLFPGEQILFFRSHIPLKGGTSNGAIDCLLPQEWIQHFYQESAPSPTDVALIRY<br>TNPDTGRVLFEAKLHRQGFITVANSGSRPIVVPPNGYFRFDSWVNQFYSLAPMGTGNGR<br>RRVQ | n.a. | n.a. | n.a. |
| 31 | GII.2 | MK04/2004/ JP | ABE41641 | MKMASNDAAPSTDGAAGLVPESNNEVMALEPVAGAALAAPVTGQTNIIDPWIRANFVQA<br>PNGEFTVSPRNAPGEVLLNLELGPELNPYLAHLARMYNGYAGGMEVQVMLAGNAFTAGK<br>LVFAAVPPHFPVENLSPQQITMFPHVIIDVRTLEPVLLPLPDVRNNFFHYNQKDDPKMR<br>IVAMLYTPLRSNGSGDDVFTVSCRVLTRPSPDFDFTYLVPPTVESKTKPFTLPILTLGE<br>LSNSRFPVSIDQMYTSPNEVISVQCQNGRCTLDGELQGTTQLQVSGICAFKGEVTAHLH<br>DNDHLYNVTITNLNGSPFDPSEDIPAPLGVPDFQGRVFGVISQRDKHNSPGHNEPANRG<br>HDAVVPTYTSQYTPKLGQIQIGTWQTDDLTVNQPVKFTPVGLNDTEHFNQWVVPRYAGA<br>LNLNTNLAPSVAPVFPGERLLFFRSYIPLKGGYGNPAIDCLLPQEWVQHFYQEAAPSMS<br>EVALVRYINPDTGRALFEAKLHRAGFMTVSSNTSAPVVVPANGYFRFDSWVNQFYSLAP<br>MGTGNGRRRVQ | pICH99770 | Yes | Yes |
| 32 | GII.2 | Ina NG1/JP/ 2002 | BAD72797 | MKMASNDAAPSTDGAAGLVPESNNEVMALEPVAGAALAAPVTGQTNIIDPWIRANFVQA<br>PNGEFTVSPRNAPGEVLLSLELGPELNPYLAHLARMYNGYAGGMEVQVMLAGNAFTAGK<br>LVFAAVPPHFPVENLSPQQITMFPHVIIDVRTLEPVLLPLPDVRNNFFHYNQKDDPKMR<br>IVAMLYTPLRSNGSGDDVFTVSCRVLTRPSPDFDFTYLVPPTVESKTKPFTLPILTLGE<br>LSNSRFPVSIDQMYTSPNEVISVQCQNGRCTLDGELQGTTQLQVSGICAFKGEVTAHLH<br>DNDHLYNVTITNLNGPPFDPSEDIPAPLGVPDFQGRVFGVISQRDKQNAAGHSEPANRG<br>HDAVVPTYTAQYTPKLGQVQIGTWQTDDLQVNQPVKFTPVGLNDTEHFNQWVVPRYAGA<br>LNLNTNLAPSVAPVFPGERLLFFRSYIPLKGGYGNPAIDCLLPQEWVQHFYQEAAPSMS<br>EVALVRYINPDTGRALFEAKLHRAGFVTVSSNTSAPVVVPANGYFRFDSWVNQFYSLAP<br>MGAGNGRRRVQ | pICK00111 | Yes | n.t. |
| 33 | GII.2 | OC08154/ JP/2008 | BAL60769 | MKMASNDAVPSTDGAAGLVPESNNEVMALEPVAGAALAAPVTGQTNIIDPWIRANFVQA<br>PNGEFTVSPRNSPGEVLLNLELGPELNPYLAHLARMYNGYAGGMEVQVMLAGNAFTAGK<br>LVFAAVPPHFPVENLSPQQITMFPHVIIDVRTLEPVLLPLPDVRNNFFHYNQKDDPKMR<br>IVAMLYTPLRSNGSGDDVFTVSCRVLTRPSPDFDFTYLVPPTVESKTKPFTLPILTLGE<br>LSNSRFPVSIDQMYTSPNEVISVQCQNGRCTLDGELQGTTQLQVSGICAFKGEVTAHLH<br>DNEHLYNVTITNLNGSPFDPSEDIPAPLGVPDFQGRVFGVISQRDKHNTPGHNEPANRA<br>HDAVVPTYTAQYTPKLGQVQIGTWQTDDLTDNQPVKFTPVGLNDTEHFNQWVVPRYAGA<br>LNLNTNLAPSVAPVFPGERLLFFRSYIPLKGGYGTPAIDCLLPQEWVQHFYQEAAPSMS<br>EVALVRYINPDTGRALFEAKLHRAGFMTVSSNTSAPVVVPANGYFRFDSWVNQFYSLAP<br>MGTGNGRRRIQ | pICK00123 | Yes | n.t. |
| 34 | GII.2 | JP/2004/ GII.P2_ | BBB86933 | MKMASIDAAPSTDGAAGLVPESNNEVMALEPVAGAALAAPVTGQTNIIDPWIRANFVQA<br>PNGEFTVSPRNAPGEVLLNLELGPELNPYLAHLARMYNGYAGGMEVQVMLAGNAFTAGK | n.a. | n.a. | n.a. |

TABLE 1B-continued

Norovirus capsid proteins with SEQ ID NOs and amino acid sequences.

| SEQ ID No. | Geno-type | Strain | GenBank acc. | Amino Acid Sequence | magnICON ® vector designation | magnICON ® expression confirmed | VLP formation confirmed* |
|---|---|---|---|---|---|---|---|
| | | GII.2/ Tochigi-86 | | LVFAAVPPHFPVENLSPQQITMFPHVIIDVRTLEPVLLPLPDVRNNFFHYNQKDDPKMR<br>IVAMLYTPLRSNGSGDDVFTVSCRVLTRPSPDFDFTYLVPPTVESKTKPFTLPILTLGE<br>LSNSRFPVSIDQMYTSPNEVISVQCQNGRCTLDGELQGTTQLQVSGICAFKGEVTAHLH<br>DNDHLYNVTITNLNGSPFDPSEDIPAPLGVPDFQGRVFGVISQRDKHNSPGHNEPANRG<br>HDAVVPTYTSQYTPKLGQIQIGTWQTDDLTVNQPVKFTPVGLNDTEHFNQWVVPRYAGA<br>LNLNTNLAPSVAPVFPGERLLFFRSYIPLKGGYGNPAIDCLLPQEWVQHFYQEAAPSMS<br>EVALVRYINPDTGRALFEAKLHRAGFMTVSSNTSAPVVVPANGYFRFDSWVNQFYSLAP<br>MGTGNGRRRVQ | | | |
| 35 | GII.3 | SaitamaU201/ 98/JP | BAB84155 | MKMASNDAAPSNDGAAGLVPEINNEAMALEPVAGAAIAAPLTGQQNIIDPWIMNNFVQA<br>PGGEFTVSPRNSPGEVLLNLELGPEINPYLAHLARMYNGYAGGFEVQVVLAGNAFTAGK<br>VIFAAIPPNFPIDNLSAAQITMCPHVIVDVRQLEPINLPMPDVRNNFFHYNQGSDSRLR<br>LIAMLYTPLRANNSGDDVFTVSCRVLTRPSPDFSFNFLVPPTVESKTKLFTLPILTISE<br>MSNSRFPVPIDSLHTSPTENIVVQCQNGRVTLDGELMGTTQLLPSQICAFRGTLTRSTS<br>RASDQADTPTPRLFNHRWHIQLDNLNGTPYDPAEDIPAPLGTPDFRGKVFGVASQRNPD<br>STTRAHEAKVDTTSGRFTPKLGSLEITTESDDFDTNQSTKFTPVGIGVDNEAEFQQWSL<br>PNYSGQFTHNMNLAPAVAPNFPGEQLLFFRSQLPSSGGRSNGVLDCLVPQEWVQHFYQE<br>SAPAQTQVALVRYVNPDTGRVLFEAKLHKLGFMTIAKNGDSPITVPPNGYFRFESWVNP<br>FYTLAPMGTGNGRRRIQ | pICH96113 | Yes | Yes |
| 36 | GII.3 | Texas/ TCH04-577/2004/ US | BAG30939 | MKMASNDATPSNDGAAGLVPEINNEAMALDPVAGAAIAAPLTGQQNIIDPWIMNNFVQA<br>PGGEFTVSPRNSPGEVLLNLELGPEINPYLAHLARMYNGYAGGFEVQVVLAGNAFTAGK<br>IIFAAIPPNFPIDNLSARQITMCPHVIVDVRQLEPVNLPMPDVRNNFFHYNQGSDSRLR<br>LIAMLYTPLRANNSGDDVFTVSCRVLTRPSPDFSFNFLVPPTVESKTKPFTLPILTISE<br>MSNSRFPVPIDSLHTSPTENIVVQCQNGRVTLDGELMGTTQLLPSQICAFMGVLTRSTS<br>RASDQADTATPRLFNYYWHIQLDNPNGTPYDPAEDIPGPLGTPDFRGKVFGVASQRNPD<br>STTRAHEAKVDTTAGRFTPKLGSLEISTESDDFHQNQPTRFTPVGIGVDNEADFQQWSL<br>PDYSGQFTHNMNLAPAVAPNFPGEQLLFFRSQLPSSGGRSNGILDCLVPQEWVQHFYQE<br>SAPSQTQVALVRYVNPDTGRVLFEAKLHKLGFMTIAKNGDSPITVPPNGYFRFESWVNP<br>FYTLAPMGTGNGRRRIQ | pICH99781 | Yes | n.t. |
| 37 | GII.3 | Kashiwa336/ 00/JP | AAZ66774 | MKMASNDAAPSNDGAAGLVPEINNEAMALDPVAGAAIAAPLTGQQNIIDPWIMNNFVQA<br>PGGEFTVSPRNSPGEVLLNLELGPEINPYLAHLARMYNGYAGGFEVQVVLAGNAFTAGK<br>VIFAAIPPNFPIDNLSAAQITMCPHVIVDVRQLEPINLPMPDVRNNFFHYNQGSDSRLR<br>LIAMLYTPLRANNSGDDVFTVSCRVLTRPSPDFSFNFLVPPTVESKTKPFTLPILTISE<br>MSNSRFPVPIDSLHTSPTESVVVQCQNGRVTLDGELMGTTQLLPSQICAFRGTLTRPTN<br>RASDQADTATPRLFNHQWHIQLDNLNGTPYDPAEDIPAPLGTPDFRGKVFGVASQRDPD<br>GTTRAHEAKVDTTSGRFTPKLGSLEITTESDDFNQNKPTRFTPVGIGVDNEADFQQWIL<br>PDYSGQFTHNMNLAPAVAPNFPGEQLLFFRSQLPSSGGRSNGILDCLVPQEWVQHFYQE<br>SAPAQTQVALVRYVNPDTGRVLFEAKLHKMGFMTIAKNGDSPITVPPNGYFRFESWVNP<br>FYTLAPMGTGKGRRRIQ | pICH99798 | Yes | n.t. |
| 38 | GII.3 | HKG/2014/ CUHK-NS-232 | AHZ12739 | MKMASNDATPSNDGAAGLVPEINNEAMALDPVAGAAIAAPLTGQQNIIDPWIMNNFVQA<br>PGGEFTVSPRNSPGEVLLNLELGPEINPYLAHLARMYNGYAGGFEVQVVLAGNAFTAGK<br>IIFAAIPPNFPIDNLSAAQITMCPHVIVDVRQLEPVNLPMPDVRNNFFHYNQGSDSRLR<br>LVAMLYTPLRANNSGDDVFTVSCRVLTRPSPEFSFNFLVPPTVESKTKPFTLPILTISE<br>MSNSRFPVPIDSLHTSPTENIVVQCQNGRVTLDGELMGTTQLLPSQICAFRGVLTRSTS | pICH99803 | Yes | n.t. |

TABLE 1B-continued

| SEQ ID No. | Geno-type | Strain | GenBank acc. | Amino Acid Sequence | magnICON ® vector designation | magnICON ® expression confirmed | VLP formation confirmed* |
|---|---|---|---|---|---|---|---|
| Norovirus capsid proteins with SEQ ID NOs and amino acid sequences. | | | | | | | |
| | | | | RTSDQADTATPRLFNYYWHIQLDNLNGTPYDPAEDIPGPLGTPDFRGKVFGVASQRNPD<br>STTRAHEAKVDTTAGRFTPKLGSLEISTESGDFDQNQPTRFTPVGIGVDHEADFQQWSL<br>PDYSGQFTHNMNLAPAVAPNFPGEQLLFFRSQLPSSGGRSNGILDCLVPQEWVQHFYQE<br>SAPAQTQVALVRYVNPDTGRVLFEAKLHKLGFMTIAKNGDSPITVPPNGYFRFESWVNP<br>FYTLAPMGTGNGRRRVQ | | | |
| 39 | GII.3 | Tokyo/<br>10-<br>1105/2010/<br>JPN | BAK43275 | MKMASNDAAPSNDGAAGLVPEINNEAMALEPVAGAAIAAPLTGQQNIIDPWIMNNFVQA<br>PGGEFTVSPRNSPGEVLLNLELGPEINPYLAHLARMYNGYAGGFEVQVVLAGNAFTAGK<br>IIFAAIPPNFPIDNLSAAQITMCPHVIVDVRQLEPVNLPMPDVRNNFFHYNQGSDSRLR<br>LVAMLYTPLRANNSGDDVFTVSCRVLTRPSPDFSFNFLVPPTVESKTKPFTLPILTISE<br>MSNSRFPVPIDSLHTSPTENIVVQCQNGRVTLDGELMGTTQLLPSQICAFRGVLTRSTS<br>RASDQADTATPRLFNYYWHIQLANLNGTPYDPAEDIPGPLGTPDFRGKVFGVACQRNPD<br>CTTRAHEAKVDTTAGRFTPKLGSLEISTESGDFDQNQPTRFTPVGIGVDHEADFQQWSL<br>PDYSGQFTHNMNLAPAVAPNFPGEQLLFFRSQLPSSGGRSNGILDCLVPQEWVQHFYQE<br>SAPAQTQVALVRYVNPDTGRVLFEAKLHKLGFMTIAKNGDSPITVPPNGYFRFESWVNP<br>FYTLAPMGTGNGRRRIQ | n.a. | n.a. | n.a. |
| 40 | GII.4 | Aomori2/<br>2006/JP | BAG70446 | MKMASSDANPSDGSTANLVPEVNNEVMALEPVVGAAIAAPVAGQQNVIDPWIRNNFVQA<br>PGGEFTVSPRNAPGEILWSAPLGPDLNPYLSHLARMYNSYAGGFEVQVILAGNAFTAGK<br>IIFAAVPPNFPTEGLSPSQVTMFPHIIVDVRQLEPVLIPLPDVRNNFYHYNQSNDPTIK<br>LIAMLYTPLRANNAGDDVFTVSCRVLTRPSPDFDFIFLVPPTVESRTKPFSVPILTVEE<br>MTNSRFPIPLEKLFTGPSSAFVVQPQNGRCTTDGVLLGTTQLSPVNICTFRGDVTHIAG<br>TQEYTMNLASQNWNNYDPTEEIPAPLGTPDFVGKIQGVLTQTTRRDGSTRGHKATVSTG<br>SVHFTPKLGRIQFSTDTSNDFETGQNTRFTPVGVVQDGSTTHQNEPQQWVLPNYSGRDS<br>HNVHLAPAVAPSFPGEQLLFFRSTMPGCSGYPNMNLDCLLPQEWVQHFYQEAAPAQSDV<br>ALLRFVNPDTGRVLFECKLHKSGYVTVAHTGQHDLVIPPNGYFRFDSWVNQFYTLAPMG<br>NGTGRRRAL | pICH96125 | Yes | Yes |
| 41 | GII.4 | Sydney/<br>NSW0514/<br>2012/<br>AU | AFV08795 | MKMASSDANPSDGSAANLVPEVNNEVMALEPVVGAAIAAPVAGQQNVIDPWIRNNFVQA<br>PGGEFTVSPRNAPGEILWSAPLGPDLNPYLSHLARMYNGYAGGFEVQVILAGNAFTAGK<br>VIFAAVPPNFPTEGLSPSQVTMFPHIVVDVRQLEPVLIPLPDVRNNFYHYNQSNDPTIK<br>LIAMLYTPLRANNAGDDVFTVSCRVLTRPSPDFDFIFLVPPTVESRTKPFSVPVLTVEE<br>MTNSRFPIPLEKLFTGPSSAFVVQPQNGRCTTDGVLLGTTQLSPVNICTFRGDVTHITG<br>SRNYTNNLASQNWNDYDPTEEIPAPLGTPDFVGKIQGVLTQTTRTDGSTRGHKATVYTG<br>SADFAPKLGRVQFETDTDRDFEANQNTKFTPVGVIQDGGTTHRNEPQQWVLPSYSGRNT<br>HNVHLAPAVAPTFPGEQLLFFRSTMPGCSGYPNMDLDCLLPQEWVQYFYQEAAPAQSDV<br>ALLRFVNPDTGRVLFECKLHKSGYVTVAHTGQHDLVIPPNGYFRFDSWVNQFYTLAPMG<br>NGTGRRRAV | pICH96137 | Yes | Yes |
| 42 | GII.4 | NIHIC35/<br>2013/<br>USA | AGX85919 | MKMASNDANPSDGSAANLVPEVNNEVMALEPVVGAAIAAPVAGQQNVIDPWIRNNFVQA<br>PGGEFTVSPRNAPGEILWSAPLGPDLNPYLSHLARMYNGYAGGFEVQVILAGNAFTAGK<br>IIFAAVPPNFPTEGLSPSQVTMFPHIIVDVRQLEPVLIPLPDVRNNFYHYNQSNDSTIK<br>LIAMLYTPLRANNAGDDVFTVSCRVLTRPSPDFDFIFLVPPTVESRTKPFSVPILTVEE<br>MTNSRFPIPLEKLFTGPSSTFVVQPQNGRCTTDGVLLGTTQLSPVNICTFRGDVTHIAG<br>SRNYTMNLASQNWNSYDPTEEIPAPLGTPDFVGKIQGVLTQTTRTDGSTRGHKATVYTG<br>SADFSPKLGRVQFATDTENDFVTNQNTKFTPVGVIQDGGTTHRNEPQQWVLPSYSGRNT<br>HNVHLAPAVAPTFPGEQLLFFRSTMPGCSGYPDMDLDCLLPQEWIQYFYQEAAPAQSDV | pICH99812 | Yes | n.t. |

TABLE 1B-continued

Norovirus capsid proteins with SEQ ID NOs and amino acid sequences.

| SEQ ID No. | Geno-type | Strain | GenBank acc. | Amino Acid Sequence | magnICON ® vector designation | magnICON ® expression confirmed | VLP formation confirmed* |
|---|---|---|---|---|---|---|---|
| | | | | ALLRFVNPDTGRVLFECKLHKSGYVTVAHTGQHDLVIPPNGYFRFDSWVNQFYTLAPMG<br>NGTGRRRAL | | | |
| 43 | GII.4 | NL/2014/<br>GII.4/<br>Gronin<br>gen01 | CRL46961 | MKMASSDANPSDGSAANLVPEVNNEVMALEPVVGAAIAAPVAGQQNVIDPWIRNNFVQA<br>PGGEFTVSPRNAPGEILWSAPLGPDLNPYLSHLARMYNGYAGGFEVQVILAGNAFTACK<br>IIFAAVPPNFPTEGLSPSQVTMFPHIIVDVRQLEPVLIPLPDVRNNFYHYNQSNDSTIK<br>LIAMLYTPLRANNAGDDVFTVSCRVLTRPSPDFDFIFLVPPTVESRTKPFSVPVLTVEE<br>MTNSRFPIPLEKLFTGPSSAFVVQPQNGRCTTDGVLLGTTQLSPVNICTFRGDVSHITG<br>SRNYTMNLASQNWNNYDPTEEIPAPLGTPDFVGKIQGMLTQTTRADGSTRGHKATVYTG<br>SADFAPKLGRVQFETDTDHDFEANQNTKFTPVGVIQDGSTTHRNEPQQWVLPSYSGRNT<br>HNVHLAPAVAPTFPGEQLLFFRSTMPGCSGYPNMDLDCLLPQEWVQYFYQEAAPAQSDV<br>ALLRFVNPDTGRVLFECKLHKSGYVTVAHTGQHDLVIPPNGYFRFDSWVNQFYTLAPMG<br>NGTGRRRAV | pICH99829 | Yes | n.t. |
| 44 | GII.4 | Sequence<br>1<br>from<br>US20160168543 | n.a. | MKMASNDANPSDGSTANLVPEVNNEVMALEPVVGAAIAAPVAGQQNVIDPWIRNNFVQA<br>PGGEFTVSPRNAPGEILWSAPLGPDLNPYLSHLARMYNGYAGGFEVQVILAGNAFTAGK<br>IIFAAVPPNFPTEGLSPSQVTMFPHIIVDVRQLEPVLIPLPDVRNNFYHYNQSNDSTIK<br>LIAMLYTPLRANNAGDDVFTVSCRVLTRPSPDFDFIFLVPPTVESRTKPFTVPILTVEE<br>MSNSRFPIPLEKLYTGPSSAFVVQPQNGRCTTDGVLLGTTQLSAVNICTFRGDVTHIAG<br>SHDYTMNLASQNWNNYDPTEEIPAPLGTPDFVGKIQGLLTQTTREDGSTRAHKATVSTG<br>SVHFTPKLGSVQYTTDTNNDFQTGQNTKFTPVGVIQDGNNHQNEPQQWVLPNYSGRTGH<br>NVHLAPAVAPTFPGEQLLFFRSTMPGCSGYPNMNLDCLLPQEWVQHFYQEAAPAQSDVA<br>LLRFVNPDTGRVLFECKLHKSGYVTVAHTGPHDLVIPPNGYFRFDSWVNQFYTLAPMGN<br>GAGRRRAL | pICK02813 | Yes | Yes |
| 45 | GII.4 | Hong<br>Kong/<br>CUB001/<br>2010/CHN | AEG79288 | MKMASNDANPSDGSAANLVPEVNNEVMALEPVAGAALAAPVAGQQNVIDPWIRNNFVQA<br>PGGEFTVSPRNAPGEILWSAPLSPDLNPYLSHLARMYNSYAGGFEVQVILAGNAFTAGK<br>IIFAAVPPNFPIEGLSPSQVTMFPHIIVDVRQLEPVLIPLPDVRNNFYHYNQTNEPTIK<br>LIAMLYTPLRANNAGEDVFTVSCRVLTRPSPDFDFIFLVPPTVESRTKPFTVPILTVEE<br>MTNSRFPIPLEKLFTGPSSSFVVQPQNGRCTTDGVLLGTTQLSPVNICTFRGDVTHIAG<br>SRNYTMNLASINWNNYDPTEEIPAPLGTPDFVGKIQGMLTQTTRGEGSTRAHRATVYTG<br>SAPFTPKLGSVQFTTDTDNDFDANQNTKFTPVGVIQDGDTAHRNEPQQWVLPSYSGRNV<br>QNVHLAPAVAPTFPGEQLLFFRSTMPGCSGYPNMDLDCLLPQEWVQHFYQEAAPAQSDV<br>ALLRFVNPDTGRVLFECKLHKSGYVTVAHTGQHDLVIPPNGYFRFDSWVNQFYTLAPMG<br>NGAGRRRAL | n.a. | n.a. | n.a. |
| 46 | GII.4 | 3.10 | AQU14484 | MKMASNDANPSDGSAANLVPEVNNEVMALEPVVGAAIAAPVAGQQNVIDPWIRNNFVQA<br>PGGEFTVSPRNAPGEILWSAPLGPDLNPYLSHLARMYNGYAGGFEVQVILAGNAFTAGK<br>IIFAAVPPNFPTEGLSPSQVTMFPHIIVDVRQLEPVLIPLPDVRNNFYHYNQSNDSTIK<br>LIAMLYTPLRANNAGDDVFTVSCRVLTRPSPDFDFIFLVPPTVESRSKPFSVPVLTVEE<br>MTNSRFPATLDKLFTGPSSTFVVQPQNGRCMIDGVLLGTTQLSPVNICTFRGDVTHLRD<br>SPIYTNNLASPNWNNYDSTEEIPAPLGTPDFVGKIQGVLTQTTKGEGSTRGHRATVYVG<br>SANYTPKLGKVQFETNTTNDLYAHQNTKFTPVGVVQGGESAHRSEPQQWVLPGYSGRDT<br>PNVHLAPAVAPTFPGEQLLFFRSTIPGCGGHPNMDLDCLLPQEWVQHFYQEAAPAQSDV<br>ALLRFVNPDTSRVLFECKLHKSGYVTVAHTGQHDLVIPPNGYFRFDSWVNQFYTLAPMG<br>NGTGRKRAI | n.a. | n.a. | n.a. |

TABLE 1B-continued

Norovirus capsid proteins with SEQ ID NOs and amino acid sequences.

| SEQ ID No. | Geno-type | Strain | GenBank acc. | Amino Acid Sequence | magnICON ® vector designation | magnICON ® expression confirmed | VLP formation confirmed* |
|---|---|---|---|---|---|---|---|
| 47 | GII.4 | 2.8b | AQU14462 | MKMASSDANPSDGSAANLVPEVNNEVMALEPVVGAAIAAPVAGQQNVIDPWIRNNFVQA PGGEFTVSPRNAPGEILWSAPLGPDLNPYLSHLARMYNGYAGGFEVQVILAGNAFTAGK IIFAAVPPTFPTEGLSPSQVTMFPHIIVDVRQLEPVLIPLPDVRNNFYHYNQSNDSTIK LIAMLYTPLRANNPGDDVFTVSCRVLTRPSPDFDFIFLVPPTVESRTKPFSVPILTVGE MTNSRFPINLERLFTGPSSANVVQPQNGRCTIDGELLGTTQLSSVNICTFRGDVTHIGS THHWTNNLASPNWNNYDPTEETPAPLGTPDFVGKIHGMLTQTTQGNGSTRGHRATVYVG SAEFTPKLGKVQFKTETDHDLAIRQNTKFTPVGVIQESDHHRDEPQQWRLPNYSGANTF NVHLAPAVAPNFPGEQLLFFRSTLPGCGGHPNMDLDCLLPQEWVQHFYQEAAPAQSDVA LLRFVNPDTSRVLFECKLHKSGYVTVAHTGQYDLVLPSNGYFRFDSWVNQFYTLAPMGN GTGRRRAL | n.a. | n.a. | n.a. |
| 48 | GII.4 | patient_C/ 2010/ USA | AHH44895 | MKMASNDASPSDGSAANLVPEVNNEVMALEPVVGAAIAAPVAGQQNVIDPWIRNNFVQA PGGEFTVSPRNAPGEILWSAPLGPDLNPYLSHLARMYNGYAGGFEVQVILAGNAFTAGK IIFAAVPPNFPTEGLSPSQVTMFPHIVVDVRQLEPVLIPLPDVRNNFYHYNQSKDPTIK LIAMLYTPLRANNAGEDVFTVSCRVLTRPSPDFDFIFLVPPTVESRSKPFTVPILTVEE MTNSRFPIPLEKLFTGPSGAFVVQPQNGRCTTDGVLLGTTQLSPVNICTFRGDLTHFTG TSEYAMNLASQNWDNYDPTEEIPAPLGAPDFVGKIRGMLTQTTRRDGSTRGHRATLSTG SAHFTPKLGNIRFSTDTNNDFEAGQNTKFTPVGVFQEGDNHQNEPQQWVLPNYSGATAH NVHLAPAVAPAFPGEQLLFFRSTMPGCGGYPNMNLDCLLPQEWVQHFYQEAAPAQSDVA LLRFVNPDTSRVLFECKLHKSGYVTVAHTGQHDLVIPPNGYFRFDSWVNQFYTLAPMGN GTGRRRAL | n.a. | n.a. | n.a. |
| 49 | GII.4 | NIHIC1.8/ 2012/ USA | AGX85889 | MKMASSDANPSDGSTANLVPEANNEVMALEPVVGAAIAAPVAGQQNVIDPWIRNNFVQA PGGEFTVSPRNAPGEILWSAPLGPDLNPYLSHLSRMYNGYAGGFEVQVILAGNAFAAGK IIFAAVPPNFPTEGLSPSQVTMFPHLIVDVRQLEPVMIPLPDIRNNFYHYNQSNDPTIK LIAMLYTPLRANNVGDDVFTVSCRVLTRPSPDFDFIFLVPPTVESKTNPFSVPILTIEE MTNSRFPIPLEKLFTGPSSALVVQPQNGRCTTDGVLLGTTQLSPVNICTFRGDVTHTTK THTYQMNLAAQNWNSYDPTEEIPAPLGTPDFVGKIQGVLTQTTKGNGSTRAHKATVYTG SAEFTPKLGRIQLFTDTDNDLEANQNTKFTPVGVIQDGDTHQNEPQQWVLPSYSGRNNH NVHLAPAVAPTFPGEQLLFFRSTMPGCSGYPNMNLDCLLPQEWVQYFYQEAAPAQSDVA LLRFVNPDTGRVLFECKLHKSGYVTVAHTGHHDLFIPPNGYFRFDSWVSPFYTLAPMGN GTGRRRAL | n.a. | n.a. | n.a. |
| 50 | GII.4 | patient_A/ 2010/ USA | AHH44878 | MKMASSDANPSDGSAANLVPEVNNEVMALEPVVGAAIAAPVAGQQNVIDPWIRNNFVQA PGGEFTISPRNAPGEILWSAPLGPDLNPYLSHLARMYNGYAGGFEVQVVLAGNAFTAGK IIFAAVPPNFPTEGLSPSQVTMFPHIIVDVRQLEPVLIPLPDVRNNFYHYNQSKDSTIK LIAMLYTPLRANNAGDDVFTVSCRVLTRPSPDFDFIFLVPPTVESRTKPFSVPVLTVEE MTNSRFPIPLEKLFTGPSSAFVVQPQNGRCTTDGVLLGTTQLSAVNICTFRGDVTHVAG DTFAMNLASLNWNNYDPTEETPAPLGTPDFVGRIHGMLTQTTRSDGATRAHKATVSTGG ADFTPKLGSVRYSTDTSSDLEVRENTKFTPIGVLHSSGGHRAEPDQWRLPEYSGRNVHN VHLAPAVAPTFPGEQLLFFRSTMPGCGGYPNMDLDCLLPQEWVQHFYQEAAPAQSDVAL LRFVNPDTGRVLFECKLHKSGYVTVAHTGPHDLVIPPNGYFRFDSWVNQFYTLAPMGNG TGRRRAL | n.a. | n.a. | n.a. |
| 51 | GII.4 | 3-157/Tokyo/ 1994/JPN | BAW33648 | MKMASSDANPSDGSAANLVPEVNNEVMALEPVVGAAIAAPVAGQQNIIDPWIRNNFVQA PGGEFTVSPRNAPGEILWSAPLGPDLNPYLSHLSRMYNGYAGGFEVQVILAGNAFTAGK VIFAAVPPNFPTEGLSPSQVTMFPHIIVDVRQLEPVLIPLPDVRNNFYHYNQSHDSTLK | n.a. | n.a. | n.a. |

TABLE 1B-continued

Norovirus capsid proteins with SEQ ID NOs and amino acid sequences.

| SEQ ID No. | Geno-type | Strain | GenBank acc. | Amino Acid Sequence | magnICON ® vector designation | magnICON ® expression confirmed | VLP formation confirmed* |
|---|---|---|---|---|---|---|---|
| | | | | LIAVLYTPLRTNNAGDDVFTVSCRVLTRPSPDFDFIFLVPPTVESRTKPFTVPILTVEE<br>MSNSRFPIPLEKLYTGPSSAFVVQPQNGRCTTDGVLLGTTQLSAVNICNFRGDVTHIVG<br>SHETTMNLASQNWSNYDPTQKIPAPLGTPHFVGKIQGLLTQTTRAHGSTRAHKATVSTG<br>SVHFTPKLGSVQFTTDTNNDFQTGQNTKFTPVGVIQDGDHHQNEPQQWVLPNYSGRTGH<br>NVHLAPAVAPTFPGEQLLFFRSTMPGCSGYPNMNLDCLLPHEWVLHFYQEAAPAQSDVA<br>LLRFVNPDTGRVLFECKLHKSGYITVAHTGPFDLGIPPNGYFRFDSWVNQFYTLAPMGN<br>GTGRRRAL | | | |
| 52 | GII.4 | Beijing/<br>CR2905/<br>2004/CHN | ABD77588 | MKMASNDASPSDGSTANLVPEVNNEVMALEPVVGAAIAAPVAGQQNVIDPWIRNSSVQA<br>PGGEFTVSPRDAPGEILWSAPLGPDLNPYLSHLARMYNGYAGGFEVQVILAGNAFTAGK<br>IIFAAAPPNFPTEGLSPSQVTMFPHIIVGVRQLEPVLIPLPDVRNNFYHYNQSNDSTIK<br>LIANLYTPLRANNAGDDVFTVSCRVLTRPSPDFDFIFLVPPTVESRTKPFTVPILTVEE<br>MTNSRFPIPLENCSRVPAVPLSSNHKMQCTTDGVLLGTTQLSPVNICTFRGDVTHIPGT<br>RTYRMNLASQNWNNYDPTEEIPAPLGTPDFVGKIQGMLTQTTKGDGSTRGHKATVSTGS<br>VDFTPKLGSVQFATDTDNDFETGQNTRFTPVGVIQDGSSTHRNEPQQWVLPDYSGRTVH<br>NVHLAPAVAPTFPGEQLLFFRSTMPGCSGYPNMDLDCLLPQEWVQHFYQEAAPSQSDVA<br>LLRFVNPDTGRVLFECKLHKAGYVTVAHTGQHDLVIPPNGYFRFDSWVNQFYTLAPMGN<br>GAGRRRAL | n.a. | n.a. | n.a. |
| 53 | GII.4 | KL45/1978/<br>MYS | AGE99612 | MKMASSDANPSDGSSANLVPEVNNEVMALEPVVGAAIAAPVAGQQNIIDPWIRNNFVQA<br>PGGEFTVSPRNAPGEILWSAPLSPDLNPYLSHLSRMYNGYAGGFEVQVILAGNAFTAGK<br>IVFAAVPPNFPTEGLSPSQVTMFPHIIVDVRQLEPVLIPLPDVRNNFYHYNQANDSTLK<br>LIAMLYTPLRANNAGDDVFTVSCRVLTRPSPDFDFIFLVPPTVESRTKPFTVPVLTVEE<br>MTNSRFPIPLERLFTGPSTAFVVQPQNGRCTTDGVLLGTTQLSAVNICNFRGEVNHIAG<br>THDYTMRLTSQNWNNYDPTEEIPAPLGTPDFVGRIQGVLTQTTRSDGSTRSHKATVSTG<br>SVHFTPKLGSVQFTTDTTNDLNAGQNTKFTPVGVEQTSGDHQSEPQQWTLPNYSGTPNH<br>NVHLAPAVAPTFPGEQLLFFRSTLPGCGGYPNMNLDCLLPQEWVLHFYQEAAPAQSDVA<br>LLRFVNPDTGRVLFECKLHRSGFITVAHSGSHDLVIPPNGYFRFDSWVNQFYTLAPMGN<br>GSGRRRVV | n.a. | n.a. | n.a. |
| 54 | GII.4 | 32-15 | AND99841 | MKMASSDANPSDGSTASLVPEVNNEVMALEPVVGAAIAAPVAGQQNVIDPWIRNNFVQA<br>PGGEFTVSPRNAPGEILWSAPLGPDLNPYLSHLARMYNGYAGGFEVQVILAGNAFTAGK<br>IIFAAVPPNFPTEGLSPSQVTMFPHIIVDVRQLEPVLIPLPDVRNNFYHYNQSNDSTIK<br>LIAMLYTPLRANNAGDDVFTVSCRVLTRPSPDFDFIFLVPPTVESRTKPFSVPILTVEE<br>MTNSRFPIPLEKLFTGPSSTFVVQPQNGRCTTDGVLLGTTQLSPVNICTFRGGITRIGQ<br>SESYKNNLASQNWNNYDPTEEIPAPLGTPDFKGRIRGLLTQTTKGAGSTRGHKATVLTG<br>GSDFTPKLGTVRFDTKSIDFENNQNTKFTPVGVVQDGNNHDEPTQWVLPNYSGPDTHNV<br>HLAPAVAPTFPGEQLLFFRSTMPGCSGYPKMELDCLLPQEWVQHFYQEAAPAQTDVALL<br>RFVNPDTGRVLFECKLHKSGYVTVAHTGDHDLVIPPNGYFRFDSWVNQFYTLAPMGNGT<br>GRRRAL | n.a. | n.a. | n.a. |
| 55 | GII.5 | JP/2002/<br>GII.P5_<br>GII.5/<br>Saitama/<br>T52 | AII73753 | MKMASNDATPSNDGAAGLVPESNNEAMALEPVVGASLAAPVTGQTNIIDPWIRTNFVQA<br>PNGEFTVSPRNSPGEILVNLELGPELNPYLAHLARMYNGYAGGMEVQVNLAGNAFTAGK<br>IIFAAVPPYFPVENLSPSQITMFPHVIIDVRTLEPVLLPMPDVRSTLFHFNQKDEPKMR<br>LVAMLYTPLRSNGSGDDVFTVSCRILTRPSPEFDFTYLVPPTVESKTKPFTLPVLTLGE<br>LSNSRFPLSIDEMVTSPNESIVVQPQNGRVTLDGELLGTTQLQACNICSIRGKVTGQVP<br>NEQHMWNLQITNLNGTQFDPTDDVPAPLGVPDFAGEVFGVLSQRNRGESNPANRAHDAV | n.a. | n.a. | n.a. |

TABLE 1B-continued

Norovirus capsid proteins with SEQ ID NOs and amino acid sequences.

| SEQ ID No. | Geno-type | Strain | GenBank acc. | Amino Acid Sequence | magnICON ® vector designation | magnICON ® expression confirmed | VLP formation confirmed* |
|---|---|---|---|---|---|---|---|
| | | | | VATYSDKYTPKLGLVQIGTWNTNDVENQPTKFTPIGLNEVANGHRFEQWTLPRYSGALT LNNNLAPAVAPLFPGERLLFFRSYVPLKGGFGNPAIDCLVPQEWVQHFYQESAPSLGDV ALVRYVNPDTGRVLFEAKLHKGGFLTVSSTSTGPVVVPANGYFRFDSWVNQFYSLAPMG TGNGRRRFQ | | | |
| 56 | GII.6 | Ueno7k/ 94/JP | BAC05518 | MKMASNDAAPSNDGAANLVPEANDEVMALEPVVGASIAAPVVGQQNIIDPWIRENFVQA PQGEFTVSPRNSPGEMLLNLELGPELNPYLSHLSRMYNGYAGGMQVQVVLAGNAFTAGK IIFAAVPPHFPVENISAAQITMCPHVIVDVRQLEPVLLPLPDIRNRFFHYNQENTPRMR LVAMLYTPLRANSGEDVFTVSCRVLTRPAPDFEFTFLVPPTVESKTKPFTLPILTLGEL SNSRFPAAIDMLYTDPNESIVVQPQNGRCTLDGTLQGTTQLVPTQICAFRGTLISQTAR AADSTDSPQRARNHPLHVQVKNLDGTQYDPTDDIPAVLGAIDFKGTVFGVASQRDVSGQ QEQGHYATRAHEAHIDTTDPKYAPKLGTILIKSGSDDFNTNQPIRFTPVGMGDNNWRQW ELPDYSGRLTLNMNLAPAVSPSFPGERILFFRSIVPSAGGYGSGYIDCLIPQEWVQHFY QEAAPSQSAVALVRYVNPDTGRNIFEAKLHREGFLTVANCGNNPIVVPPNGYFRFEAWG NQFYTLAPMGSGQGRRRAQ | pICH99834 | Yes | Yes |
| 57 | GII.6 | Sanbu445/ 00/JP | AAZ66775 | MKMASNDAAPSNDGAANLVPEANNEVMALEPVVGASIAAPVVGQQNIIDPWIRENFVQA PQGEFTVSPRNSPGEMLLNLELGPELNPYLSHLSRMYNGYAGGMQVQVVLAGNAFTAGK IIFAAVPPHFPVDNISAAQITMCPHVIVDVRQLEPVLLPLPDIRNRFFHYNQENTPRMR LVAMLYTPLRANSGEDVFTVSCRVLTRPAPDFEFTFLVPPTVESKTKPFTLPILTLGEL SNSRFPAAIDMLYADPNESIVVQPQNGRCTLDGTLQGTTQLVPTQICAFRGTLISQTAR ATDSTDSPQRARDHPLHVQVKNLDGTQYDPTDDIPAVLGAIDFKGTVFGVASQRDVSGP QEQGHYATRAHEAHIDTTDPKYAPKLGTILIKSESNDFITNQPIRFTPVGMGDNNWRQW ELPDYSGRLTLNMNLAPAVSPSFPGERILFFRSIVPSAGGYGSGYIDCLIPQEWGQHFY QEAAPSQSAVALVRYVNPDTGRNIFEAKLHREGFLTVANSGNNPIVVPPNGYFRFEAWV NQFYTLAPMGSGQGRRRAQ | pICH99848 | Yes | n.t. |
| 58 | GII.6 | Ehime090549/ 2009/JP | BAN16287 | MKMASNDAAPSNDGAANLVPEANNEVMALEPVAGASIAAPVVGQQNIIDPWIRENFVQA PQGEFTVSPRNSPGEMLLNLELGPELNPYLSHLSRMYNGYAGGMQVQVVLAGNAFTAGK IIFAAVPPHFPVKNISAAQITMCPHVIVDVRQLEPVLLPLPDIRNRFFHYNQENTPRMR LVAMLYTPLRANSGEDVFTVSCRVLTRPAPDFEFTFLVPPTVESKTKPFTLPILTLGEL SNSRFPAPIDMLYTDPNEGIVVQPQNGRCTLDGTLQGTTQLVPTQICAFRGTLIGQTSR SSDSTDSAPRRRDHPLHVQLKNLDGTQYDPTDEVPAVLGAIDFKGTVFGVASQRDVSGQ QVGATRAHEVHINTTDPRYTPKLGSILIHSESDDFVTGQPVRFTPIGMGDNDWHQWELP DYSGHLTLNMNLAPAVAPAFPGERILFFRSMVPSAGGYGSGQIDCLIPQEWVQHFYQEA APSQSAVALIRYVNPDTGRNIFEAKLHREGFITVANSGNNPIVVPHNGYFRFEAWVNQF YTLTPMGTGQGRRRNQ | n.a. | n.a. | n.a. |
| 59 | GII.7 | Osaka10- 25/99/JP | BD011881 | MKMASNDAAPSSDGAAGLVPEINNEVMPLEPVAGASLATPVVGQQNIIDPWIRNNFVQA PAGEFTVSPRNSPGEILLDLELGPDLNPYLAHLARMYNGHAGGMEVQIVLAGNAFTAGK IIFAAIPPGFPYENLSPSQITMCPHVIIDVRQLEPFLLPMPDIWNNFFHYNQGNDPKLR LVAMLYTPLRANNSGDDVFTVSCRVLTKPSPDFEFTFLVPPTVESKTKQFALPILKISE MTNSRFPVPVDVMYTARNENQVVQPQNGRVTLDGELLGTTPLLAVNICKFKGEVIAKNG DVRSYRMDMEITNTDGTPIDPTEDTPGPIGSPDFQGILFGVASQRNKNEQNPATRAHEA IINTGGDHLCPQISSSEIYLTSPNILRCTNPQPLPQSGLRGTILIRSDNGHCHDMVGTS | pICH99850 | Yes | n.t. |

TABLE 1B-continued

Norovirus capsid proteins with SEQ ID NOs and amino acid sequences.

| SEQ ID No. | Geno-type | Strain | GenBank acc. | Amino Acid Sequence | magnICON ® vector designation | magnICON ® expression confirmed | VLP formation confirmed* |
|---|---|---|---|---|---|---|---|
| | | | | PTTPTWPQQWRRCSRGSNCCSSGHRYPVPVVMNRVTWIVLSHKSGFSTSTRKLPQLNLRWPLIRFINPDTGRVLFEARLHKQGFITVAHTGDNPIVMPPNGYFRFEAWVNQFYSLAPVGTGKGRRRVQ | | | |
| 60 | GII.7 | JP/2010/ GII.P7_ GII.7/ Musashi murayama/ TAKAsan Kimchi | AII73774 | MKMASNDAAPSNDGAAGLVPEINNEVMPLEPVAGASLATPVVGQQNIIDPWIRNNFVQAPAGEFTVSPRNSPGEILLDLELGPELNPYLAHLARMYNGHAGGMEVQIVLAGNAFTAGKIIFAAIPPGFPYENLSPSQITMCPHVIIDVRQLEPVLLPMPDIRNNFFHYNQGNDPKLRLIAMLYTPLRANNSGDDVFTVSCRVLTKPSPDFEFTFLVPPTVESKTKQFTLPILKISEMTNSRFPVPVEMMYTARNENQVVQPQNGRVTLDGELLGTTPLLAVNICKFKGEVIAKNGDVRSYRMDMEITNTDGTPIDPTEDTPGPIGSPDFQGILFGVASQRNKNEQNPATRAHEANINTGGDQYAPKLAQVKFFSESQDFEVHQPTVFTPVGVAGDTSHPFRQWVLPRYGGHLTNNTHLAPAVAPLFPGEQILFFRSQIPSSGGHELGYMDCLVPQEWVQHFYQEAATAQSEVALIRFINPDTGRVLFEAKLHKQGFITVAHTGDNPIVMPPNGYFRFEAWVNQFYSLAPVGTGNGRRRIQ | n.a. | n.a. | n.a. |
| 61 | GII.8 | JC231/ ZS/GD/ CHN/2016 | ATI15126 | MKMASNDAAPSNDGAAGLVPEINHEVMAIEPVAGASLAAPVVGQLNIIDPWIRNNFVQAPAGEFTVSPRNAPGEFLLDLELGPELNPYLAHLARMYNGHAGGMEVQIVLAGNAFTAGKILFAVIPPGFPYENLSPAQLTMCPHVVVDVRQLEPILLPMPDIRNTFFHYNQSNGPKLRLVAMLYTPLRANNAGDDVFTVSCRVLTRPSPDFEFNFLVPPSVESKTKAFTLPILKISEMTNSRFPIPVDQMYTSRNENVVVQPQNGRVTLDGELQGTTTLQPVSICGFRGTLQTRLADQPNYTYQVHLENLDGSPVDPTDEVPAPLGTPDFQAQLFGVVSQRSSDNATRAHEARVNTNDPTFAPQIAQVRFKSPSHDFFDNEPIKFTPVGISVDSENSYNQWLLPRYGGHLTNNTHLAPSVSPMFPGEQILFFRSFMPGASGHTDGAIDCLLPQEWVAHFYQEAATAQTDVALIRFVNPDTGRVLFEGKLHKQGFITISNSGDHPIVMPANGYFRFEAWVNQFYSLAPVGTGSGRRRIQ | n.a. | n.a. | n.a. |
| 62 | GII.12 | Hu/GII.12/ CGMH39/ 2010/TW | AGT39194 | MKMASNDAAPSNDGAAGLVPEVNNETMALEPVAGASIAAPLTGQNNVIDPWIRLNFVQAPNGEFTVSPRNSPGEVLLNLELGPELNPYLAHLSRMYNGYAGGVEVQVLLAGNAFTAGKLVFAAVPPHFPLENISPGQITMFPHVIIDVRTLEPVLLPLPDVRNNFFHYNQQNEPRMRLVANLYTPLRSNGSGDDVFTVSCRVLTRPSPDFDFNYLVPPTVESKTKPFTLPILTIGELTNSRFPVPIDELYTSPNESLVVQPQNGRCALDGELQGTTQLLPTAICSFRGRINQKVSGENHVWNMQITNINGTPFDPTEDVPAPLGTPDFSGKLFGVLSQRDHDNACRSHDAVIATNSAKFTPKLGAIQIGTWEQDDVHINQPTKFTPVGLFESEGFNQWTLPNYSGALTLNMGLAPPVAPTFPGEQILFFRSHIPLKGGVADPVIDCLLPQEWIQHLYQESAPSQTDVALIRFTNPDTGRVLFEAKLHRSGYITVANTGSRPIVVPANGYFRFDSWVNQFYSLAPMGTGNGRRRVQ | n.a. | n.a. | n.a. |
| 63 | GII.13 | Kashiwa47/ 97/JP | BAC05515 | MKMASNDAAPSNDGAASLVPEGINETMPLEPVAGASIAAPVAGQTNIIDPWIRTNFVQAPNGEFTVSPRNSPGEILLNLELGPDLNPYLAHLSRMYNGYAGGVEVQVLLAGNAFTAGKILFAAIPPNFLVDMISPAQITIMPHLIVDVRTLEPIMTPLPDVRNVFYHFNNQPQPRNRLVAMLYTPLRSNGSGDDVFTVSCRVLTRPTPDFEFIYLVPPSVESKTKPFTLPILTISELTNSRFPIPIEQLYTAPNETNVVQCQNGRCTLDGELQGTTQLLSSAVCFLQGRTVADNGDNWDQNLLQLTYPNGASYDPTDEVPAPLGTQDFSGMLYGVLTQDNVNVSTGEAKNAKGIYISTTSGKFTPKIGSIGLHSITEHVHPNQQSRFTPVGVAVDENTPFQQWVLPHYAGSLALNTNLAPAVAPTFPGEQLLFFRSRVPCVQGLQGQDAFIDCLLPQEWVNHFYQEAAPSQADVALIRYVNPDTGRTLFEAKLHRSGFITVSHTGAYPLVVPPNGHFRFDSWVNQFYSLAPMGTGNGRRRIQ | pICH99861 | Yes | n.t. |

TABLE 1B-continued

Norovirus capsid proteins with SEQ ID NOs and amino acid sequences.

| SEQ ID No. | Geno-type | Strain | GenBank acc. | Amino Acid Sequence | magnICON ® vector designation | magnICON ® expression confirmed | VLP formation confirmed* |
|---|---|---|---|---|---|---|---|
| 64 | GII.13 | Hu/GII.13/ 10N4555/ 2010/NP | BAQ94581 | MKMASNDAAPSNDGAASLVPEAINETMPLEPVAGASIAAPVAGQTNIIDPWIRTNFVQA PNGEFTVSPRNSPGEILLNLELGPDLNPYLAHLSRMYNGYAGGVEVQVLLAGNAFTAGK ILFAAIPPNFPVDMISPAQITMLPHLIVDVRTLEPIMIPLPDVRNVFYHFNNQPQPRMR LVAMLYTPLRSNGSGDDVFTVSCRVLTRPTPDFEFIYLVPPSVESKTKPFTLPILTISE LTNSRFPIPIEQLYTAPNENNVVQCQNGRCTLDGELQGTTQLLSSAVCSYRGRTVANRG DNWDQNLLQLTYPSGASYDPTDEVPAPLGTQDFSGILYGVLTQDNVSEGTGEAKNAKGV YISTTSGKFTPKIGSIGLHSITENVHPNQQSRFTPVGVAQNENTPFQQWVLPHYAGALA LNTNLAPAVAPTFPGEQLLFFRSRVPCVQGLRGQDAFIDCLLPQEWVNHFYQEAAPSQA DVALIRYVNPDTGRTLFEAKLHRSGFITVSHTGAYPLVVPPNGHFRFDSWVNQFYS | n.a. | n.a. | n.a. |
| 65 | GII.14 | JP/2007/ Fukuoka/ KK282 | AII73780 | MKMASNDATPSDDGAAGLVPEINSEVMALEPVAGASIAAPVVGQQNIIDPWIRNNFVQA PAGEFTVSPRNSPGELLLDLELGPELNPYLAHLARMYNGHAGGMEVQIVLAGNAFTAGK ILFAAIPPSFPYENLSPAQLTMCPHVIVDVRQLEPVLLPMPDIRNVFYHYNQNNSPKLR LVAMLYTPLRANNSGDDVFTVSCRVLTRPSPDFQFTFLVPPTVESKTKNFTLPVLRVSE MTNSRFPVVLDQMYTSRNENTIVQPQNGRCTTDGELLGTTILQSVSICNFKGTMQAKLN EEPRYQLQLTNLDGSPIDPTDDMPAPLGTPDFQAVLYGVASQRSSRDNATRAHDAQIDT AGDTFAPKIGQVRFKSSSNDFDLHDPTKFTPIGVNVDDQHPFRQWSLPNYGGHLALNNH LAPAVTPLFPGEQILFFRSYIPSAGGHTDGAMDCLLPQEWVEHFYQEAAPSQSDIALVR FINPDTGRVLFEAKLHKQGFLTIAASGDHPIVMPTNGYFRFEAWVNPFYTLAPVGTGSG RRRIQ | pICH99872 | Yes | Yes |
| 66 | GII.14 | NLV/M7/ 1999/US | AAN05735 | MKMASNDATPSDDGAAGLVPEINNEVMALEPVAGASIAAPVVGQQNIIDPWIRNNFVQA PAGEFTVSPRNSPGELLLDLELGPELNPYLAHLARMYNGHAGGMEVQIVLAGNAFTAGK ILFAAIPPSFPYENLSPAQLTMCPHVIVDVRQLEPVLLPMPDIRNVFYHYNQNNSPKLR LVAMLYTPLRANNSGDDVFTVSCRVLTRPSPDFQFTFLVPPTVESKTKNFTLPVLRVSE MTNSRFPVVLDQMYTSRNENIIVQPQNGRCTTDGELLGTTTLQSVSICNFRGTMQAKLN EQPRYQLQLTNLDGSPIDPTDDMPAPLGTPDFQAMLYGVASQRSSRDNATRAHDAQIDT AGDTFAPKIGQVRFKSSSDDFDLHDPTKFTPIGVNVDDQHPFRQWSLPNYGGHLALNNH LAPAVTPLFPGEQILFFRSHIPSAGGHTDGAIDCLLPQEWIEHFYQEAAPSQSDIALVR FINPDTGRVLLEAKLHKQGFLTVAASGDHPIVMPTNGYFRFEAWVNPFYTLAPVGTGSG RRRIQ | n.a. | n.a. | n.a. |
| 67 | GII.17 | C142/1978/ GUF | AGI17592 | MMMASNDAAPSNDGATGLVPEINHETLPLEPVAGAAIAAPVTGQNNIIDPWIRTNFVQA PNGEFTVSPRNSPGEILLNLELGPDLNPYLAHLSRMYNGYAGGVEVQVLLAGNAFTAGK ILFAAVPPNFPVEFLSPAQITMLPHLIVDVRTLEPIMIPLPDVRNTFFHYNNQPANRMR LVAMLYTPLRSNGSGDDVFTVSCRVLTRPTPDFEFTYLVPPSVESKTKPFSLPILTISE LTNSRFPAPIDSLYTAQNNNLNVQCQNGRCTLDGELQGTTQLLPSGICAFRGKLTADVH QSHDDRWHMQLTNLNGTPFDPTEDVPAPLGTPDFTGLLFGVASQRNVVSNPNTTRAHEA VISTTSSQFVPKLGSINFGSTSDDFQLQQPTKFTPVGIKVESGHDFDQWALPRYSGHLT LNMNLAPPVAPNFPGEQLLFFRSNVPCAGGVSDGVIDCLLPQEWIQYFYQESAPSQSDV ALIRYVNPDTGRTLFEAKLHRTGYITVAHSGDYPLVVPSNGYFRFDSWVNQFYSLAPMG TGNGRRRVQ | pICH99887 | Yes | n.t. |
| 68 | GII.17 | JP/2013/ Saitama5203 | BAR63715 | MKMASNDAAPSNDGAAGLVPEGNNETLPLEPVAGAAIAAPVTGQNNIIDPWIRTNFVQA PNGEFTVSPRNSPGEILLNLELGPDLNPYLAHLSRMYNGYAGGVEVQVLLAGNAFTAGK ILFAAVPPNFPVEFLSPAQITMLPHLIVDVRTLEPIMIPLPDVRNTFFHYNNQPNSRMR | pICH99890 | Yes | Yes |

TABLE 1B-continued

Norovirus capsid proteins with SEQ ID NOs and amino acid sequences.

| SEQ ID No. | Geno-type | Strain | GenBank acc. | Amino Acid Sequence | magnICON ® vector designation | magnICON ® expression confirmed | VLP formation confirmed* |
|---|---|---|---|---|---|---|---|
| | | | | LVAMLYTPLRSNGSGDDVFTVSCRVLTRPTPDFEFTYLVPPSVESKTKPFSLPILTLSE<br>LTNSRFPVPIDSLFTAQNNVLQVQCQNGRCTLDGELQGTTQLLPSGICAFRGRVTAETD<br>HRDKWHNQLQNLNGTTYDPTDDVPAPLGTPDFKGVVFGVASQRNVGNDAPGSTRAHEAV<br>ISTYSPQFVPKLGSVNFRSNDNDFQLQPTKFTPVGINDDGDHPFRQWELPDYSGLLTLN<br>NNLAPPVAPNFPGEQLLFFRSFVPCSGGYNQGIVDCLIPQEWIQHFYQESAPSQSDVAL<br>IRYVNPDTGRTLFEAKLHRSGYITVAHSGDYPLVVPANGYFRFDSWVNQFYSLAPMGTG<br>NGRRRAQ | | | |
| 69 | GII.17 | JP/2015/ Kawasaki308 | BAR42289 | MKMASNDAAPSNDGAAGLVPEGNNETLPLEPVAGAAIAAPVTGQNNIIDPWIRTNFVQA<br>PNGEFTVSPRNSPGEILLNLELGPDLNPYLAHLSRMYNGYAGGVEVQVLLAGNAFTAGK<br>ILFAAVPPNFPVEFLSPAQITMLPHLIVDVRTLEPIMIPLPDVRNTFFHYSNQPNSRMR<br>LVANLYTPLRSNGSGDDVFTVSCRVLTRPTPDFEFTYLVPPSVESKTKPFSLPILTLSE<br>LTNSRFPVPIDSLFTAQNNVLQVQCQNGRCTLDGELQGTTQLLPTGICAFRGRVTAQIN<br>QRDRWHMQLQNLNGTTYDPTDDVPAPLGTPDFKGVVFGMVSQRNVGNDAPGSTRAQQAW<br>VSTYSPQFVPKLGSVNLRISDNDDFQFQPTKFTPVGVNDDDDGHPFRQWELPNYSGELT<br>LNMNLAPPVAPNFPGEQLLFFRSFVPCSGGYNQGIIDCLIPQEWIQHFYQESAPSQSDV<br>ALIRYVNPDTGRTLFEAKLHRSGYITVAHSGDYPLVVPANGHFRFDSWVNQFYSLAPMG<br>TGNGRRRAQ | pICH99909 | Yes | Yes |
| 70 | GII.17 | JP/2002/ Saitama/ T87 | AII73747 | MKMASNDAAPSNDGATGLVPEINNETLPLEPVAGAAIAAPVTGQNNIIDPWIRTNFVQA<br>PNGEFTVSPRNSPGEILLNLELGPDLNPYLAHLSRMYNGYAGGVEVQVLLAGNAFTAGK<br>ILFAAVPPNFPVEFLSPAQITMLPHLIVDVRTLEPIMIPLPDVRNTFFHYNNQPANRMR<br>LVAMLYTPLRSNGSGDDVFTVSCRVLTRPTPDFEFTYLVPPSVESKTKPFSLPILTISE<br>LTNSRFPAPIDSLFTAQNNNLNVQCQNGRCTLDGELQGTTQLLPSGICAFRGRLTADVD<br>GSHDDRWHMQLTNLNGTPFDPTEDVPAPLGTPDFTGLLFGVASQRNVGSNPNTTRAHEA<br>VISTTSSQFVPKLGSVNFGSTSTDFQLQQPTKFTPVGIKIESGHEFDQWALPRYSGHLT<br>LNMNLAPPIAPNFPGEQLLFFRSNVPCAGGVSDGVIDCLLPQEWIQHFYQESAPSQSDV<br>ALIRYVNPDTGRTLFEAKLHRTGYITVAHSGDYPLVVPSNGYFRFDSWVNQFYSLAPMG<br>TGNGRRRVQ | pICH99912 | Yes | Yes |
| 71 | GII.17 | E11161 | AOQ30449 | MKMASNDAAPSNDGAAGLVPEGNNETLPLEPVAGAAIAAPVTGQNNIIDPWIRTNFVQA<br>PNGEFTVSPRNSPGEILLNLELGPDLNPYLAHLSRMYNGYAGGVEVQVLLAGNAFTAGK<br>ILFAAVPPNFPVEFLSPAQITMLPHIIVDVRTLEPIMIPLPDVRNTFFHYNNQPNSRMR<br>LVAMLYTPLRSNGSGDDVFTVSCRVLTRPTPDFEFTYLVPPSVESKTKPFSLPILTLSE<br>LTNSRFPVPIDSLFTAQNNVLQVQCQNGRCTLDGELQGTTQLLPSGICAFRGRVTAETD<br>NPDKWHMQLQNLNGTTYDPTDDVPAPLGTPDFKGVVFGVASQRNVGNDAPGSTRAHEAV<br>ISTYSPKFVPKLGSVNFRSNDDDFQLQPTRFTPVGINDDGNHPFRQWELPDYSGVLTLN<br>MNLAPPVAPNFPGEQLLLFRSFVPCSGGYNQGIIDCLIPQEWIQHFYQESAPSQSDVAL<br>IRYVNPDTGRTLFEAKLHRSGYITVAHSGDYPLVVPANGYFRFDSWVNQFYSLAPMGTG<br>NGRRRAQ | n.a. | n.a. | n.a. |
| 72 | GII.21 | Hu/GII.21/ CUHK-NS-290/HKG/ 2014 | ALP48670 | MKMASNDAAPSNDGAAGLVPEINTETLPLEPVAGAAIAAPVTGQNNIIDPWIRNNFVQA<br>PNGEFTVSPRNSPGEILMNLELGPDLNPYLAHLSRMYNGYAGGVEVQVLLAGNAFTAGK<br>ILFAAVPPNFPVDMLSPAQITMLPHLIVDVRTLEPIMIPLPDVRNVFYHFNNQPAPRMR<br>LVAMLYTPLRSNGSGDDVFTVSCRVLTRPTPDFEFTYLVPPSVESKTKPFTLPILTIGE<br>LTNSRFPAPIDQLYTSPNADVVVQPQNGRCTLDGELQGTTQLLTTAICSYRGTTSNPTS<br>DYWDDHLLHLVHPNGATYDPTEDVPAPFGTQDFRGILYGVLTQNTQNPRDEVSNSRGIY | n.a. | n.a. | n.a. |

TABLE 1B-continued

Norovirus capsid proteins with SEQ ID NOs and amino acid sequences.

| SEQ ID No. | Geno-type | Strain | GenBank acc. | Amino Acid Sequence | magnICON ® vector designation | magnICON ® expression confirmed | VLP formation confirmed* |
|---|---|---|---|---|---|---|---|
| | | | | ISSTSDKFTPKLGTIGLHQVQGDTASNQQSKFTPVGIAVNQNTPFKQWELPNYSGALTL<br>NTNLAPAVGPNFPGEQILFFRSNVPSVQGNHPTQEIDCLIPQEWISHFYQESAPSQSDV<br>ALVRYVNPDTGRTIFEAKLHRQGFITIAATGSNPVVVPPNGYFRFDSWVNQFYALAPMG<br>TGNGRRRAQ | | | |
| 73 | GII.22 | BD/2012/<br>GII.P22-<br>GII.22/<br>Dhaka1940 | AUD54981 | MKMASNDAAPSNDGAAGLVPEINTEVMALEPVAGGAIAAPLTGQTNIIDPWIRNNFVQA<br>PNGEFTISPRNSPGEILLNMELGPELNPFLAHLSRMYNGFAGGMEVQVLMAGNAFTAGK<br>VIFAAIPPHFPVENLSPPQITMFPHIIIDVRTLEPVLLPMPDVRNQFFHYNQVNEPRMR<br>LVAMLYTPLRSNGSTEDVFTVSCRVLTRPSPDFEFNYLVPPTVESRTKPFTLPILTIGE<br>MTNSRFPAPIDNLYTSPNDNVVVQPQNGRCTLDGELQGSTQLVPANVCAFKGKITARIV<br>DQAAHQWHMQIDNPNGTLFDPTEDVPAPLGTPDFKAKIFGVISQRNDYNDGSQGPANRA<br>HDAVVPTTSAKFTPKLGSILVGTWENNDIETQPSKFTPVGLLEMNDFNQWSLPNYSGAL<br>TLNMGLAPAVFPTFPGEQILFFRSFIPLKGGHGNPAIDCLLPQEWIQHFYQESAPSQTS<br>VALIRYVNPDTGRVLFEGKLHRQGFITIAKSGDGPIVVPPNGYFRFDSWVNQFYSLAPM<br>GNGNGRRRIQ | n.a. | n.a. | n.a. |
| 74 | GII.24 | PE/2014/<br>GII.P24-<br>GII.24/<br>Loreto6424 | AUD54978 | MKMASNDAAPSNDGAANLVPEANKEVMALEPVAGGAIAAPLTGQTNIIDPWIMNNFVQA<br>PNGEFTISPRNSPGEVLLNLELGPDLNPFLAHLSRMYNGYAGGVEVQVIMAGNAFTAGK<br>VIFAAVPPHFPVDNLSPPQVTMFPHVIVDVRTFEPILLPLPDVRNSFYHYNQVNDSRMR<br>LIAMLYTPLRSNGSSDDVFTVSCRVLTRPTPDFEFNYLVPPTVESRTKPFSVPILTIGE<br>MTNSRFPLPIDMLYTSPTENIVVQPQNGRCTLEGELLGTTQLVTPNICALRGEIRGHEG<br>SGDNHKWHFMVRSPNGAAFDPTEDVPAPLGTPDFIGDVFGVLSQRNRNTDSGQSGPANR<br>SHDAVVSTRDSRFTPKLGSVMIATWETSDIQDQPTRFTPVGLENPDHYNQWQLPNYSGA<br>LTLNMGLAPSVFPTYPGEQILFFRSYIPLKGGYGDSHIDCLVPQEWIQHFYQESAPSQT<br>DVALIRYVNPETGRVLFEAKLHRQGYITVARSGSSPINVPANGYFRFDSWVNQFYSLAP<br>MGTGNGRRRIQ | n.a. | n.a. | n.a. |
| 75 | GII.25 | BD/2012/<br>GII.P22-<br>GII.25/<br>Dhaka1928 | AUD54984 | MKMASNDAAPSNDGAAGLVPEINNEVMALEPVAGGAIAAPLTGQTNVIDPWIRTNFVQA<br>PNGEFTISPRNSPGEVLLNMELGPELNPFLGHLSRMYNGYAGGIEVQVLMAGNAFTAGK<br>VIFAAVPPHFPVENLSPPQVTMFPHIIVDVRTLEPILLPLPDVRNQFFHYSQVDEPKMR<br>LVAMLYTPLRSNGSAEDVFTVSCRVLTRPSPDFEFNYLVPPTVESRTKPFTVPILTIGE<br>MSNSRFPAPIDMLYTSPNDNQNVQPQNGRCTLDGELQGTTQLVPSGVCAFRGRITGHEG<br>SEQNQWHMQLTNLNGTPFDPTEDIPAPLGTPDFKGEIFGFISQRNAQNDPGQSQPANRA<br>HDAVVSTRAPKFTPKLGSVMIGTWVNSDIENQPSKFTPVGLNSNENFRQWELPDYSGVL<br>TLNMGLAPVVHPTYPGEQILFFRSYIPLKGGHGNPAIDCLLPQEWIQHFYQESAPSQTD<br>VALLRYVNPDTGRVLFEAKLHRQGYITIAKSGDGPIVVPPNGYFRFDSWVNQFYSLAPM<br>GNGNGRRRVQ | n.a. | n.a. | n.a. |
| 76 | GIV.1 | Ahrenshoop246/<br>DEU/2012 | AFN61315 | MKMASSDAAPSADGAGNLVPESQQEVLPLAPVAGAALAAPVVGQTNIIDPWIKENFVQA<br>PQGEFTVSPKNSPGEILVNLELGPKLNPYLDHLSRMYNSYAGGIDVMVVLAGNAFTAGK<br>VLIAAIPPNFPVEGVSASQATQFPHVIIDVRTLDPVRLPLPDVRSTFFHYTNDTEPKMR<br>LVIWLYTPLRTNGSGDDSFTVSGRILTRPSQDFEFAFLIPPTVETKTTPFSVPGFSVQE<br>MSNSRWPAAISAMVVRGNEPQVVQFQNGRAHLDGMLLGTTPVSPNYIASYRGISTGNSR<br>SASSEADERAVGSFDVWIRLQEPDGQPYDIFGKQPAPIGTPDFKAVIVGFAARPLTSGS<br>YANEAYVNTTASDYAPATGNMRFTVRNGGTGHISANKYWEFRSFGVEGERHTDVQYQEY | pICH99924 | Yes | Yes |

TABLE 1B-continued

Norovirus capsid proteins with SEQ ID NOs and amino acid sequences.

| SEQ ID No. | Geno-type | Strain | GenBank acc. | Amino Acid Sequence | magnICON ® vector designation | magnICON ® expression confirmed | VLP formation confirmed* |
|---|---|---|---|---|---|---|---|
| | | | | ELPDYSGQVASNHNLAPPVAPRMPGESLLLFQSNMPVWDDGRGESTPKKIHCLLPQEFI GHFFDKQAPSLGDAALLRYVNQETNRVLFECKLYRDGYITVAAASGLLDFPLDGFFRFD SWVSSFYILSPVGSGQGRRGRVRFQ | | | |
| 77 | GIV.1 | Lake Macquarie/ NSW2680/ 2010/AU | YP_ 009237904 | MKMASSDAAPSTDGAGNLVPESQQEVLPLAPVAGAALAAPVVGQTNIIDPWIKENFVQA PQGEFTVSPKNSPGEILVNLELGPKLNPYLDHLSRMYNSYAGGIDVMVVLAGNAFTAGK VLIAAIPPNFPVEGVSASQATQFPHVIIDVRTLDPVRLPLPDVRSTFFHYTNDTEPKMR LVIWLYTPLRTNGSGDDSFTVSGRILTRPSQDFEFAFLIPPTVETKTTPFSVPGFSVQE MSNSRWPAAISAMVVRGNEPQVVQFQNGRAHLDGMLLGTTPVSPNYIASYRGISTGNSR SASSEADERAVGSFDVWVRLQEPDGQPYDIFGKQPAPIGTPDFKAVIVGFAARPLTSGS YANEAYVNTTASDYAPATGNMRFTVRNGGTGHISANKYWEFKSFGVEGERHTDIQYQEY ELPDYSGQVASNHNLAPPVAPRMPGESLLLFQSNMPVWDDGHGESTPKKIHCLLPQEFI GHFFDRQAPSLGDAALLRYVNQETNRVLFECKLYRDGYITVAASSGLLDFPLDGFFRFD SWVSSFYILSPVGSGQGRRGRVRFQ | n.a. | n.a. | n.a. |
| 78 | GIV.3 | USA/2016/ WI7002 | APA31973 | MKMASNDAPPSSDGAGNLVPESHQEVLPLAPVAGAELAAPVVGQTNIIDPWIKENFVQA PQGEFTVSPKNAPGEILVNLELGPNLNPYLEHLSRMYNAYAGGIEVEIILAGNAFTAGK ILIAAVPPNFPVESVSASQATQFPHAIVDVRTLEPVRLPLPDVRSNFFHYTTKDEPKMR LVIWLYTPLRTNGSGDDSFTVSGRLLTRPSMDFQFSFLVPPTVETKTVLFTVPGLTPQE MSNSRWPAQISGMVVRGNEPQVVQFQNGRCHTDGTLLGTTTVSEQCIAGFVGTSTNTRS ATGSTTETRTGDTDLWLRLEEPNGQPYDIFGDQPAPLGTPDFRAVIVGFASRPQTQGSY MNEAYVNTVDSHFAPATGNTKIILRRGGTGHVGGGHLWKFRPFGVEGGEGRVSYQEYVL PNYSGATASNHNLAPPVAPRMPGELLLLFESDMPVWDDGHGAAPAQKIHCLLPQQFITH FEDSQAPALAEAALLRYVHPDSSRVLFETKLYREGFMVVSAPTGREDFPLDGYFREDSW VNSFYVLSPVGSGQGRRGRSKVV | n.a. | n.a. | n.a. |

*Presence of Virus-like particles confirmed by transmission electron microscopy; n.a.: not applicable; n.t.: not tested

TABLE 2

Cholera enterotoxin subunit B sequences.

| SEQ ID No. | Description | Sequence | Expression host | Reference |
|---|---|---|---|---|
| 79 | Cholera enterotoxin subunit B sequence from Vibrio cholerae O1 biovar El Tor str. N16961, mature protein | TPQNITDLCA YHNTQIHTL NDKIFSYTES AGKREMAII TFKNGATFQV VPGSQHIDS QKKAIERMKD LRIAYLTEA KVEKLCVWNN TPHAIAAIS MAN | Prokaryotic Eukaryotic | Acc. no.: P01556 |
| 80 | T1C/T92C mutations for generation of inter-subunit disulfide crosslinks | **C**PQNITDLCA YHNTQIHTL NDKIFSYTES AGKREMAII TFKNGATFQV VPGSQHIDS QKKAIERMKD LRIAYLTEA KVEKLCVWNN **C**PHAIAAIS MAN | Prokaryotic Eukaryotic | 1 |
| 81 | S100T mutation for improved yield | TPQNITDLCA YHNTQIHTL NDKIFSYTES AGKREMAII TFKNGATFQV VPGSQHIDS QKKAIERMKD LRIAYLTEA KVEKLCVWNN TPHAIAAI**T** MAN | Prokaryotic Eukaryotic | 2 |
| 82 | T1C/T92C mutations for generation of inter-subunit disulfide crosslinks and S100T mutation for improved yield | **C**PQNITDLCA YHNTQIHTL NDKIFSYTES AGKREMAII TFKNGATFQV VPGSQHIDS QKKAIERMKD LRIAYLTEA KVEKLCVWNN **C**PHAIAAI**T** MAN | Prokaryotic Eukaryotic | 1, 2 |
| 83 | N-terminal tag 6xHis-tag and 17-tag with thrombin cleavage sites | **MGSSHSEHBH SGLVPRGSH MASMTGGQQM GRGSEFRT** TPQNITDLCA YHNTQIHTL NDKIFSYTES AGKREMAII TFKNGATFQV VPGSQHIDS QKKAIERMKD LRIAYLTEA KVEKLCVWNN TPHAIAAIS MAN | Prokaryotic | |
| 84 | N-terminal tag 6xHis-tag and enterokinase cleavage site | **MHEIHMHSSG DDDDRG** TPQNITDLCA YHNTQIHTL NDKIFSYTES AGKREMAII TFKNGATFQV VPGSQHIDS QKKAIERMKD LRIAYLTEA KVEKLCVWNN TPHAIAAIS MAN | Prokaryotic Eukaryotic | |

TABLE 2 -continued

Cholera enterotoxin subunit B sequences.

| SEQ ID No. | Description | Sequence | Expression host | Reference |
|---|---|---|---|---|
| 85 | N4S mutation to remove a N-glycosylation site | TPQ**S**ITDLCA YHNTQIHTL NDKIFSYTES AGKREMAII TFKNGATFQV VPGSQHIDS QKKAIERMKD LRIAYLTEA KVEKLCVWNN TPHAIAAIS MAN | Eukaryotic | 3, 4, 5 |
| 86 | N4S mutation to remove a N-glycosylation site and C-terminal ER-retention signal | TPQ**S**ITDLCA YHNTQIHTL NDKIFSYTES AGKREMAII TFKNGATFQV VPGSQHIDS QKKAIERMKD LRIAYLTEA KVEKLCVWNN TPHAIAAIS MAN**SEKDEL** | Eukaryotic | 4, 5 |
| 87 | C-terminal ER-retention signal | TPQNITDLCA YHNTQIHTL NDKIFSYTES AGKREMAII TFKNGATFQV VPGSQHIDS QKKAIERMKD LRIAYLTEA KVEKLCVWNN TPHAIAAIS MAN**SEKDEL** | Eukaryotic | 3, 5 |
| 88 | N4S mutation to remove a N-glycosylation site and T1C/T92C mutations for generation of inter-subunit disulfide crosslinks | **C**PQ**S**ITDLCA YHNTQIHTL NDKIFSYTES AGKREMAII TFKNGATFQV VPGSQHIDS QKKAIERMKD LRIAYLTEA KVEKLCVWNN **C**PHAIAAIS MAN | Eukaryotic | 1, 3, 5 |
| 89 | N4S mutation to remove a N-glycosylation site and S100T mutation for improved yield | TPQ**S**ITDLCA YHNTQIHTL NDKIFSYTES AGKREMAII TFKNGATFQV VPGSQHIDS QKKAIERMKD LRIAYLTEA KVEKLCVWNN TPHAIAAI**T** MAN | Eukaryotic | 2, 3, 5 |
| 90 | N4S mutation to remove a N-glycosylation site, T1C/T92C mutations for generation of inter-subunit disulfide crosslinks and S100T mutation for improved yield | **C**PQ**S**ITDLCA YHNTQIHTL NDKIFSYTES AGKREMAII TFKNGATFQV VPGSQHIDS QKKAIERMKD LRIAYLTEA KVEKLCVWNN **C**PHAIAAI**T** MAN | Eukaryotic | 1, 2, 3, 5 |

TABLE 2 -continued

Cholera enterotoxin subunit B sequences.

| SEQ ID No. | Description | Sequence | Expression host | Reference |
|---|---|---|---|---|
| 91 | T1C/T.92C mutations for generation of inter-subunit disulfide crosslinks and C-terminal ER-retention signal | **C**PQNITDLCA YHNTQIHTL NDKIFSYTES AGKREMAII TFKNGATFQV VPGSQHIDS QKKAIERMKD LRIAYLTEA KVEKLCVWNN **C**PHAIAAIS MAN**SEKDEL** | Eukaryotic | 1, 3, 4, 5 |
| 92 | S100T mutation for improved yield and C-terminal ER-retention signal | TPQNITDLCA YHNTQIHTL NDKIFSYTES AGKREMAII TFKNGATFQV VPGSQHIDS QKKAIERMKD LRIAYLTEA KVEKLCVWNN TPHAIAAI**T** MAN**SEKDEL** | Eukaryotic | 2-5 |
| 93 | T1C/T92C mutations for generation of inter-subunit disulfide crosslinks and S100T mutation for improved yield and C-terminal ER-retention signal | **C**PQNITDLCA YHNTQIHTL NDKIFSYTES AGKREMAII TFKNGATFQV VPGSQHIDS QKKAIERMKD LRIAYLTEA KVEKLCVWNN **C**PHAIAAI**T** MAN**SEKDEL** | Eukaryotic | 1-5 |
| 94 | N4S mutation to remove a N-glycosylation site, T1C/T92C mutations for generation of inter-subunit disulfide crosslinks and C-terminal ER-retention signal | **C**PQ**S**ITDLCA YHNTQIHTL NDKIFSYTES AGKREMAII TFKNGATFQV VPGSQHIDS QKKAIERMKD LRIAYLTEA KVEKLCVWNN **C**PHAIAAIS MAN**SEKDEL** | Eukaryotic | 1, 4, 5 |
| 95 | N4S mutation to remove a N-glycosylation site, S100T mutation for improved yield and C-terminal ER-retention signal | TPQ**S**ITDLCA YHNTQIHTL NDKIFSYTES AGKREMAII TFKNGATFQV VPGSQHIDS QKKAIERMKD LRIAYLTEA KVEKLCVWNN TPHAIAAI**T** MAN**SEKDEL** | Eukaryotic | 2-5 |
| 96 | N4S mutation to remove a N-glycosylation site, T1C/T92C mutations for generation of inter-subunit disulfide crosslinks and S100T mutation for improved yield and C-terminal ER-retention signal | **C**PQ**S**ITDLCA YHNTQIHTL NDKIFSYTES AGKREMAII TFKNGATFQV VPGSQHIDS QKKAIERMKD LRIAYLTEA KVEKLCVWNN **C**PHAIAAI**T** MAN**SEKDEL** | Eukaryotic | 1-5 |

Mutations and modifications are indicated in the amino acid sequences in bold.

1: Miyata T, Oshiro S, Harakuni T, Taira T, Matsuzaki G, Arakawa T. Physicochemically stable cholera toxin B subunit pentamer created by peripheral molecular constraints imposed by de novo-introduced intersubunit disulfide crosslinks. Vaccine. 2012 Jun. 13; 30(28):4225-32.

2: Bakhshi B, Boustanshenas M, Ghorbani M. A single point mutation within the coding sequence of cholera toxin B subunit will increase its expression yield. Iran Biomed J. 2014 July; 18(3):130-5. PubMed PMID: 24842138; PubMed Central PMCID: PMC4048476.

3: Hamorsky K T, Kouokam J C, Bennett L J, Baldauf K J, Kajiura H, Fujiyama K, Matoba N. Rapid and scalable plant-based production of a cholera toxin B subunit variant to aid in mass vaccination against cholera outbreaks. PLoS Negl Trop Dis. 2013; 7(3):e2046.

4: Hamorsky K T, Kouokam J C, Jurkiewicz J M, Nelson B, Moore L J, Husk A S, Kajiura H, Fujiyama K, Matoba N. N-glycosylation of cholera toxin B subunit in *Nicotiana benthamiana*: impacts on host stress response, production yield and vaccine potential. Sci Rep. 2015 Jan. 23; 5:8003.

5: US20140286986, Title: Polypeptides having immunoactivating activity and methods of producing the same, Published: 25. Sep. 2014, Applicant: University Of Louisville Research Foundation, Inc.

TABLE 3

Escherichia con Heat-labile enterotoxin subunit B sequences.

| SEQ ID No. | Description | Sequence | Reference |
|---|---|---|---|
| 97 | *Escherichia coli* Heat-labile enterotoxin B chain, porcine | APQTITELCS EYRNTQIYTI NDKILSYTES MAGKREMVII TFKSGETFQV EVPGSQHIDS QKKAIERMKD TLRITYLTET KIDKLCVWNN KTPNSIAAIS MKN | Acc. no.: P32890 |

TABLE 3 -continued

Escherichia con Heat-labile enterotoxin subunit B sequences.

| SEQ ID No. | Description | Sequence | Reference |
|---|---|---|---|
| 98 | *Escherichia coli* 078:H11 (strain H10407/ETEC) Heat-labile enterotoxin B chain | APQSITELCS EYRNTQIYTI NDKILSYTES MAGKREMVII TFKSGATFQV EVPGSQHIDS QKKAIERMKD TLRITYLTET KIDKLCVWNN KTPNSIAAIS MEN | Acc. no.: D0Z6T1 |
| 99 | *Escherichia coli* 078:H11 (strain H10407/ETEC) Heat-labile enterotoxin B chain with C-terminal ER-retention signal | APQSITELCS EYRNTQIYTI NDKILSYTES MAGKREMVII TFKSGATFQV EVPGSQHIDS QKKAIERMKD TLRITYLTET KIDKLCVWNN KTPNSIAAIS MEN**SEKDEL** | Derived from acc. no.: D0Z6T1 |
| 100 | *Escherichia coli* Heat-labile enterotoxin B chain, human | APQSITELCS EYHNTQIYTI NDKILSYTES MAGKREMVII TFKSGATFQV EVPGSQHIDS QKKAIERMKD TLRITYLTET KIDKLCVWNN KTPNSIAAIS MEN | Acc. no.: P0CK94 |

Mutations and modifications are indicated in the amino acid sequences in bold.

The content of European patent applications No. 18 157 031.8 and No. 18 215 676.0, filed on Feb. 15, 2018 and Dec. 21, 2018, respectively, is incorporated herein including entire descriptions, claims and figures.

The invention claimed is:

1. A combination vaccine for preventing and/or treating Norovirus infection and infection by a bacterial pathogen in a mammal, said vaccine comprising at least one noroviral antigen and a B subunit of a bacterial ABs toxin capable of generating an immune response against said bacterial pathogen, and a pharmaceutically acceptable carrier, wherein said bacterial pathogen is *E. coli* and wherein said B subunit of bacterial $AB_5$ toxin is a B subunit of *E. coli* heat-labile enterotoxin (LTB).

2. A method of preventing and/or treating norovirus infection and/or for reducing the severity of norovirus infection, comprising administering an immunogenic composition comprising at least one norovirus antigen and at least one B subunit of an $AB_5$ toxin to a subject by parenteral administration of the immunogenic composition selected from intradermal, intramuscular and subcutaneous administration, wherein said B subunit is a B subunit of *E. coli* heat-labile enterotoxin (LTB).

3. The method according to claim 2, wherein said composition is free of the A subunit of said toxin.

4. The method according to claim 2, wherein said B subunit is an antigen, and said at least one norovirus antigen and said B subunit are components of a combination vaccine.

5. The method according to claim 2, wherein said at least one norovirus antigen is or comprises a norovirus VP1 protein.

6. The method according to claim 2, said immunogenic composition comprising an antigen of a genogroup I norovirus and an antigen of a genogroup II norovirus.

7. The method according to claim 2, wherein said immunogenic composition comprises norovirus virus-like particles (norovirus VLPs) comprising or consisting of said at least one norovirus antigen.

8. The method according to claim 2, wherein said immunogenic composition comprises VLPs of a genogroup I norovirus and VLPs of a genogroup II norovirus.

9. The method according to claim 2, wherein said LTB is pentameric LTB.

10. A method of preventing and/or treating Norovirus infection and infection by a bacterial pathogen in a mammal, comprising administering to a subject an immunogenic composition comprising at least one noroviral antigen and a B subunit of a bacterial ABs toxin capable of generating an immune response against said bacterial pathogen, wherein said bacterial pathogen is *E Coli* and wherein said B subunit of bacterial AB5 toxin is a B subunit of *E. coli* heat-labile enterotoxin (LTB).

11. The method according to claim 2, said immunogenic composition comprising a genotype II.4 noroviral antigen and a genotype II.17 noroviral antigen.

12. The method according to claim 2, said immunogenic composition comprising VLPs comprising or consisting of a genogroup I noroviral antigen, VLPs comprising or consisting of a genogroup II noroviral antigen, and LTB as an adjuvant.

13. The method according to claim 6, said immunogenic composition comprising said genogroup I noroviral antigen and said genogroup II noroviral antigen in a mass ratio range of from 1:1 to 1:6.

14. The method according to claim 2, said composition not comprising an aluminum salt.

15. The method according to claim 2, said method being for preventing and/or treating and/or for reducing the severity of norovirus infection in a mammal.

16. An anti-norovirus vaccine or a pharmaceutical composition, comprising the immunogenic composition as defined in claim 2 and a pharmaceutically acceptable carrier.

17. A method of preventing and/or treating Norovirus infection and infection by a bacterial pathogen in a mammal, comprising administering to a subject an immunogenic composition comprising at least one norovirus antigen and a B subunit of a bacterial $AB_5$ toxin capable of generating an immune response against said bacterial pathogen, wherein said bacterial pathogen is *E. coli* and wherein said B subunit of bacterial $AB_5$ toxin is a B subunit of *E. coli* heat-labile enterotoxin (LTB).

* * * * *

SEQUENCE LISTING

```
<160> NUMBER OF SEQ ID NOS: 100

<210> SEQ ID NO 1
<211> LENGTH: 538
<212> TYPE: PRT
<213> ORGANISM: Norovirus

<400> SEQUENCE: 1

Met Met Ala Ser Lys Asp Ala Pro Thr Ser Pro Asp Gly Ala Ser Gly
1               5                   10                  15

Ala Gly Gln Leu Val Pro Glu Ala Asn Thr Ala Glu Gln Ile Ser Met
            20                  25                  30

Asp Pro Val Ala Gly Ala Ser Thr Ala Val Ala Thr Ala Gly Gln Val
        35                  40                  45

Asn Met Ile Asp Pro Trp Ile Phe Asn Asn Phe Val Gln Ala Pro Gln
    50                  55                  60

Gly Glu Phe Thr Ile Ser Pro Asn Asn Thr Pro Gly Asp Ile Leu Phe
65                  70                  75                  80
```

-continued

```
Asp Leu Gln Leu Gly Pro His Leu Asn Pro Phe Leu Ala His Leu Ser
                85                  90                  95

Gln Met Tyr Asn Gly Trp Val Gly Asn Met Arg Val Arg Ile Leu Leu
            100                 105                 110

Ala Gly Asn Ala Phe Thr Ala Gly Lys Ile Ile Ile Cys Cys Val Pro
        115                 120                 125

Pro Gly Phe Asp Ala Arg Ile Leu Thr Ile Ala Gln Ala Thr Leu Phe
    130                 135                 140

Pro His Leu Ile Ala Asp Val Arg Thr Leu Glu Pro Val Glu Leu Pro
145                 150                 155                 160

Leu Glu Asp Val Arg Asn Val Leu Tyr His Asn Ser Ser Gln Pro Gln
                165                 170                 175

Pro Thr Met Arg Leu Val Ala Met Leu Tyr Thr Pro Leu Arg Thr Gly
            180                 185                 190

Gly Gly Ser Gly Gly Thr Asp Ala Phe Val Val Ala Gly Arg Val Leu
        195                 200                 205

Thr Cys Pro Ala Pro Asp Phe Ser Phe Leu Phe Leu Val Pro Pro Ser
    210                 215                 220

Val Glu Gln Lys Thr Arg Val Phe Ser Val Pro Asn Ile Pro Leu Lys
225                 230                 235                 240

Asp Leu Ser Asn Ser Arg Val Pro Val Pro Ile Gln Gly Met Phe Met
                245                 250                 255

Ser Pro Asp Val Asn Gln Ser Val Gln Phe Gln Asn Gly Arg Cys Gln
            260                 265                 270

Ile Asp Gly Gln Leu Gln Gly Thr Thr Pro Val Ser Leu Ser Gln Leu
        275                 280                 285

Cys Lys Ile Arg Gly Lys Thr Ser Ser Asn Ala Arg Val Leu Asn Leu
    290                 295                 300

Ser Glu Val Asp Gly Thr Pro Phe Ile Pro Leu Glu Ser Pro Ala Pro
305                 310                 315                 320

Val Gly Phe Pro Asp Leu Gly Gly Cys Asp Trp His Val Asn Phe Ser
                325                 330                 335

Phe Gln Thr Gln Asp Arg Asp Pro Ser Gln Ser Val Thr Phe Ala Thr
            340                 345                 350

Asn Asp Ala Ser Phe Val Pro Tyr Leu Gly Ser Val Ser Pro His Asn
        355                 360                 365

Gly Glu Gly Phe Gln Ala Gly Asp Ile Ile Gly Ser Leu Gly Trp Ile
    370                 375                 380

Ser Ala Pro Ser Asp Asn Ser Gln Phe Asn Val Trp Ala Ile Pro Lys
385                 390                 395                 400

Tyr Gly Ser Ser Leu Gln Met Ser Pro Ile Leu Leu Leu Leu Cys Ser
                405                 410                 415

Pro Arg Leu Trp Glu Val Ile Leu Tyr Phe Tyr Ser Thr Phe Pro Gly
            420                 425                 430

Ser Gly Gln Pro Ser Gln Leu Gln Val Pro Cys Leu Leu Pro Gln Glu
        435                 440                 445

Phe Ile Thr His Phe Cys Asn Glu Gln Ala Pro Ile Ala Gly Glu Ala
    450                 455                 460

Ala Leu Leu His Tyr Val Asp Pro Asp Thr Gly Arg Asn Leu Gly Glu
465                 470                 475                 480

Phe Lys Leu Tyr Pro Asp Gly Phe Met Thr Cys Val Pro Asn Ser Val
                485                 490                 495
```

```
Ser Ser Gly Pro Gln Thr Leu Pro Ile Asn Gly Val Phe Val Phe Val
            500                 505                 510

Ser Trp Val Ser Arg Phe Tyr Gln Leu Lys Pro Val Gly Thr Ala Ser
        515                 520                 525

Ala Ala Arg Arg Leu Gly Leu Arg Arg Ile
    530                 535


<210> SEQ ID NO 2
<211> LENGTH: 545
<212> TYPE: PRT
<213> ORGANISM: Norovirus

<400> SEQUENCE: 2

Met Met Met Ala Ser Lys Asp Ala Pro Thr Asn Met Asp Gly Thr Ser
1               5                   10                  15

Gly Ala Gly Gln Leu Val Pro Glu Ala Asn Thr Ala Glu Pro Ile Ser
            20                  25                  30

Met Glu Pro Val Ala Gly Ala Ala Thr Ala Ala Ala Thr Ala Gly Gln
        35                  40                  45

Val Asn Met Ile Asp Pro Trp Ile Met Asn Asn Tyr Val Gln Ala Pro
    50                  55                  60

Gln Gly Glu Phe Thr Ile Ser Pro Asn Asn Thr Pro Gly Asp Ile Leu
65                  70                  75                  80

Phe Asp Leu Gln Leu Gly Pro His Leu Asn Pro Phe Leu Ser His Leu
                85                  90                  95

Ala Gln Met Tyr Asn Gly Trp Val Gly Asn Met Lys Val Lys Val Leu
            100                 105                 110

Leu Ala Gly Asn Ala Phe Thr Ala Gly Lys Ile Ile Ile Ser Cys Ile
        115                 120                 125

Pro Pro Gly Phe Ala Ala Gln Asn Ile Ser Ile Ala Gln Ala Thr Met
    130                 135                 140

Phe Pro His Val Ile Ala Asp Val Arg Val Leu Glu Pro Ile Glu Ile
145                 150                 155                 160

Pro Leu Glu Asp Val Arg Asn Val Leu Phe His Asn Asn Asp Asn Thr
                165                 170                 175

Pro Thr Met Arg Leu Val Cys Met Leu Tyr Thr Pro Leu Arg Ala Ser
            180                 185                 190

Gly Ser Ser Ser Gly Thr Asp Pro Phe Val Ile Ala Gly Arg Val Leu
        195                 200                 205

Thr Cys Pro Ser Pro Asp Phe Ser Phe Leu Phe Leu Val Pro Pro Asn
    210                 215                 220

Val Glu Gln Lys Thr Lys Pro Phe Ser Val Pro Asn Leu Pro Leu Asn
225                 230                 235                 240

Ile Leu Ser Ser Ser Arg Val Pro Ser Leu Ile Lys Ser Met Met Ile
                245                 250                 255

Ser Arg Asp His Gly Gln Met Val Gln Phe Gln Asn Gly Arg Val Thr
            260                 265                 270

Leu Asp Gly Gln Leu Gln Gly Thr Thr Pro Thr Ser Ala Ser Gln Leu
        275                 280                 285

Cys Lys Ile Arg Gly Ser Val Phe His Ala Asn Gly Gly Asn Gly Tyr
    290                 295                 300

Asn Leu Thr Glu Leu Asp Gly Ser Pro Tyr His Ala Phe Glu Ser Pro
305                 310                 315                 320

Ala Pro Ile Gly Phe Pro Asp Leu Gly Glu Cys Asp Trp His Met Glu
                325                 330                 335
```

```
Ala Ser Pro Thr Ile Gln Phe Asp Thr Gly Asp Val Ile Lys Gln Ile
            340                 345                 350

Asn Val Lys Gln Glu Ser Ala Phe Ala Pro His Leu Gly Thr Val Gln
        355                 360                 365

Ala Asp Gly Leu Asp Gly Val Ser Ala Asn Thr Asn Met Ile Ala Lys
    370                 375                 380

Leu Gly Trp Val Ser Pro Val Ser Asp Gly His Arg Arg Asp Val Asp
385                 390                 395                 400

Pro Trp Val Ile Pro Arg Tyr Gly Ser Thr Leu Thr Glu Ala Ala Gln
                405                 410                 415

Leu Ala Pro Pro Ile Tyr Pro Pro Gly Phe Gly Glu Ala Ile Val Phe
            420                 425                 430

Phe Met Ser Asp Phe Pro Ile Ala His Gly Thr Asn Gly Leu Ser Val
        435                 440                 445

Pro Cys Thr Ile Pro Gln Glu Phe Val Thr His Phe Val Asn Glu Gln
    450                 455                 460

Ala Pro Thr Arg Gly Glu Ala Ala Leu Leu His Tyr Leu Asp Pro Asp
465                 470                 475                 480

Thr His Arg Asn Leu Gly Glu Phe Lys Leu Tyr Pro Asp Gly Phe Met
                485                 490                 495

Thr Cys Val Pro Asn Ser Ser Gly Ser Gly Pro Gln Thr Leu Pro Ile
            500                 505                 510

Asn Gly Val Phe Val Phe Val Ser Trp Val Ser Arg Phe Tyr Gln Leu
        515                 520                 525

Lys Pro Val Gly Thr Ala Gly Pro Ala Arg Arg Leu Gly Ile Arg Arg
    530                 535                 540

Ser
545


<210> SEQ ID NO 3
<211> LENGTH: 544
<212> TYPE: PRT
<213> ORGANISM: Norovirus

<400> SEQUENCE: 3

Met Met Met Ala Ser Lys Asp Ala Pro Thr Asn Met Asp Gly Thr Ser
1               5                   10                  15

Gly Ala Gly Gln Leu Val Pro Glu Ala Asn Thr Ala Glu Pro Ile Ser
            20                  25                  30

Met Asp Pro Val Ala Gly Ala Ala Thr Ala Val Ala Thr Ala Gly Gln
        35                  40                  45

Ile Asn Met Ile Asp Pro Trp Ile Met Ser Asn Phe Val Gln Ala Pro
    50                  55                  60

Gln Gly Glu Phe Thr Val Ser Pro Asn Asn Thr Pro Gly Asp Val Leu
65                  70                  75                  80

Phe Asp Leu Gln Leu Gly Pro Gln Leu Asn Pro Phe Leu Ala His Leu
                85                  90                  95

Ala Gln Met Tyr Asn Gly Trp Val Gly Asn Met Arg Val Lys Val Leu
            100                 105                 110

Leu Ala Gly Asn Ala Phe Thr Ala Gly Lys Ile Ile Ile Ser Cys Ile
        115                 120                 125

Pro Pro Gly Phe Thr Ser Gln Asn Ile Ser Ile Ala Gln Met Thr Met
    130                 135                 140

Phe Pro His Val Ile Ala Asp Val Arg Val Leu Glu Pro Ile Glu Ile
```

```
145                 150                 155                 160

Pro Leu Glu Asp Val Arg Asn Val Leu Phe His Thr Asn Asp Asn Arg
                165                 170                 175

Pro Thr Met Arg Leu Val Cys Met Leu Tyr Thr Pro Leu Arg Ala Asn
            180                 185                 190

Gly Ser Ser Ser Gly Thr Asp Pro Phe Val Ile Ala Gly Arg Val Leu
        195                 200                 205

Thr Cys Pro Asp Ser Asn Phe Ser Phe Leu Phe Leu Val Pro Pro Asn
    210                 215                 220

Val Glu Gln Lys Thr Arg Pro Phe Ser Val Pro Asn Ile Pro Leu Asn
225                 230                 235                 240

Thr Leu Ser Asn Ser Arg Val Pro Ser Leu Ile Lys Ser Met Thr Ile
                245                 250                 255

Ser Arg Asp Gln Asn Gln Ile Ile Gln Phe Gln Asn Gly Arg Val Thr
            260                 265                 270

Leu Asp Gly Gln Leu Gln Gly Thr Thr Pro Thr Ser Val Ser Gln Leu
        275                 280                 285

Cys Lys Ile Arg Gly Thr Thr Tyr His Ala Thr Gly Gly Asn Gly Ile
    290                 295                 300

Asn Leu Thr Glu Leu Asn Gly Glu Pro Tyr His Ala Phe Glu Ser Pro
305                 310                 315                 320

Ala Pro Ile Gly Phe Pro Asp Leu Gly Gly Cys Asp Trp His Leu Thr
                325                 330                 335

Ala Thr Pro Thr Gln Ala Phe Asn Asp Gly Ala Lys Val Val Arg Leu
            340                 345                 350

Ser Val Thr Gln Gly Ala Ala Phe Ala Pro His Leu Gly Thr Ile His
        355                 360                 365

Tyr Thr Thr Thr Asp His Asp Tyr Asp Pro Asn Thr Ser Ile Ile Cys
    370                 375                 380

Thr Leu Asp Trp Leu Ser Gln Thr Thr Gly Gln Asn Asn Val Asp Pro
385                 390                 395                 400

Trp Gln Ile Pro Thr Tyr Gly Ser Thr Leu Thr Glu Ala Ala Gln Leu
                405                 410                 415

Ala Pro Pro Ile Phe Pro Pro Gly Phe Gly Glu Thr Leu Val Phe Phe
            420                 425                 430

Leu Ser Asp Phe Pro Ile Ser Asn Gly Lys Asn Gly Leu Ser Val Pro
        435                 440                 445

Cys Thr Leu Pro Gln Glu Phe Val Thr His Phe Val Asn Glu Gln Ala
    450                 455                 460

Pro Ile Arg Gly Glu Ala Ala Leu Leu His Tyr Val Asp Pro Asp Thr
465                 470                 475                 480

His Arg Asn Leu Gly Glu Phe Lys Leu Tyr Pro Glu Gly Phe Met Thr
                485                 490                 495

Cys Val Pro Asn Thr Ser Gly Gly Gly Pro Gln Thr Leu Pro Ile Asn
            500                 505                 510

Gly Val Phe Val Phe Val Ser Trp Val Ser Arg Phe Tyr Gln Leu Lys
        515                 520                 525

Pro Val Gly Thr Ala Gly Ala Ala Arg Arg Leu Gly Ile Arg Arg Ser
    530                 535                 540
```

<210> SEQ ID NO 4
<211> LENGTH: 543
<212> TYPE: PRT
<213> ORGANISM: Norovirus

<400> SEQUENCE: 4

Met Ala Ser Lys Asp Ala Pro Ser Asn Met Asp Gly Thr Ser Gly Ala
1 5 10 15

Gly Gln Leu Val Pro Glu Ala Asn Thr Ala Glu Pro Ile Asn Met Glu
20 25 30

Ser Val Val Gly Ala Ala Thr Ala Thr Ala Thr Ala Gly Gln Val Asn
35 40 45

Leu Ile Asp Pro Trp Ile Met Asn Asn Tyr Val Gln Ala Pro Gln Gly
50 55 60

Glu Phe Thr Ile Ser Pro Asn Asn Thr Pro Gly Asp Val Leu Phe Asp
65 70 75 80

Leu Gln Leu Gly Pro His Leu Asn Pro Phe Leu Ser His Leu Ser Arg
85 90 95

Met Tyr Asn Gly Trp Val Gly Asn Met Lys Val Arg Val Met Leu Ala
100 105 110

Gly Asn Ala Phe Ser Ala Gly Lys Ile Ile Ile Cys Cys Ile Pro Pro
115 120 125

Gly Phe Thr Ser Gln Ser Ile Ser Ile Ala Gln Ala Thr Met Phe Pro
130 135 140

His Val Ile Ala Asp Val Arg Val Leu Glu Pro Ile Asp Val Pro Leu
145 150 155 160

Asp Asp Val Arg Asn Val Leu Phe His Asn Asn Asp Asn Ala Gln Thr
165 170 175

Met Arg Leu Leu Cys Met Leu Tyr Thr Pro Leu Arg Thr Gly Ala Ser
180 185 190

Ser Ser Gly Ser Asp Pro Phe Val Ile Ala Gly Arg Val Leu Thr Cys
195 200 205

Pro Thr Gln Asp Phe Asn Phe Leu Phe Leu Val Pro Pro Asp Val Glu
210 215 220

Gln Lys Thr Lys Pro Phe Ser Val Pro Asn Ile Pro Leu Asn Leu Met
225 230 235 240

Ser Asn Ser Arg Val Pro Ala Leu Ile Asp Gly Met Thr Val Ser Ser
245 250 255

Asp Gln Asn Gln Val Val Gln Phe Gln Asn Gly Arg Val Thr Leu Asp
260 265 270

Gly Gln Leu Gln Gly Thr Thr Ala Val Ser Ala Ser Cys Val Ala Lys
275 280 285

Ile Arg Gly Arg Ile Phe Ser Asn Ala Ser His Tyr Gly Ile Asn Leu
290 295 300

Thr Glu Val Asp Gly Thr Gln Tyr His Ala Phe Asp Ser Pro Ala Pro
305 310 315 320

Leu Gly Phe Pro Asp Phe Gly Asn Cys Asp Trp His Val Thr Gly Thr
325 330 335

Lys Ala Ser Gln Gly Asp Leu Gln Thr Asp Asn Pro Thr Ile Ser Gly
340 345 350

Thr Ile Lys Ser Tyr Glu Ser Ser Phe Ala Pro His Leu Gly Thr Val
355 360 365

Arg Ile Glu Gly Asp Asp Asn Glu Leu Ala Arg Phe Asn Gly Lys Asp
370 375 380

Val Leu Leu Asn Leu Thr Trp Phe Ser Gln Arg Asn Gly Ser Gln Leu
385 390 395 400

Asn Leu Trp Thr Ile Pro Ser Tyr Gly Ser Asn Leu Thr Glu Ala Ser

```
                405                 410                 415

Gln Leu Ala Pro Pro Ile Tyr Pro Pro Gly Phe Gly Glu Ala Ile Val
            420                 425                 430

Tyr Phe Thr Ser Thr Phe Pro Ala Ile Ser Arg Pro Ser Val Pro Cys
        435                 440                 445

Thr Met Pro Gln Glu Phe Val Ser His Phe Val Asn Glu Gln Ala Pro
    450                 455                 460

Thr Arg Gly Glu Ala Ala Leu Leu His Tyr Leu Asp Pro Asp Thr His
465                 470                 475                 480

Arg Asn Leu Gly Glu Phe Lys Met Tyr Pro Glu Gly Phe Phe Thr Cys
                485                 490                 495

Val Pro Asn Ala Gly Gly Ser Gly Pro Gln Thr Leu Pro Ile Asn Gly
            500                 505                 510

Val Phe Val Phe Val Ser Trp Val Ser Arg Tyr Tyr Gln Leu Lys Pro
        515                 520                 525

Val Gly Thr Val Gly Met Thr Arg Arg Leu Gly Leu Met Lys Gln
    530                 535                 540


<210> SEQ ID NO 5
<211> LENGTH: 530
<212> TYPE: PRT
<213> ORGANISM: Norovirus

<400> SEQUENCE: 5

Met Met Met Ala Ser Lys Asp Ala Thr Ser Ser Val Asp Gly Ala Ser
1               5                   10                  15

Gly Ala Gly Gln Leu Val Pro Glu Val Asn Ala Ser Asp Pro Leu Ala
            20                  25                  30

Met Asp Pro Val Ala Gly Ser Ser Thr Ala Val Ala Thr Ala Gly Gln
        35                  40                  45

Val Asn Pro Ile Asp Pro Trp Ile Ile Asn Asn Phe Val Gln Ala Pro
    50                  55                  60

Gln Gly Glu Phe Thr Ile Ser Pro Asn Asn Thr Pro Gly Gly Val Leu
65                  70                  75                  80

Phe Asp Leu Ser Leu Gly Pro His Leu Asn Pro Phe Leu Leu His Leu
                85                  90                  95

Ser Gln Met Tyr Asn Gly Trp Val Gly Asn Met Arg Val Arg Ile Met
            100                 105                 110

Leu Ala Gly Asn Ala Phe Thr Ala Gly Lys Ile Ile Val Ser Cys Ile
        115                 120                 125

Pro Pro Gly Phe Gly Ser His Asn Leu Thr Ile Ala Gln Ala Thr Leu
    130                 135                 140

Phe Pro His Val Ile Ala Asp Val Arg Thr Leu Asp Pro Ile Glu Val
145                 150                 155                 160

Pro Leu Glu Asp Val Arg Asn Val Leu Phe His Asn Asn Asp Arg Asn
                165                 170                 175

Gln Gln Thr Met Arg Leu Val Cys Met Leu Tyr Thr Pro Leu Arg Thr
            180                 185                 190

Gly Gly Gly Thr Gly Asp Ser Phe Val Val Ala Gly Arg Val Met Thr
        195                 200                 205

Cys Pro Ser Pro Asp Phe Asn Phe Leu Phe Leu Val Pro Pro Thr Val
    210                 215                 220

Glu Gln Lys Thr Arg Pro Phe Thr Leu Pro Asn Leu Pro Leu Ser Ser
225                 230                 235                 240
```

-continued

```
Leu Ser Asn Ser Arg Ala Pro Leu Pro Ile Ser Gly Met Gly Ile Ser
                245                 250                 255

Pro Asp Asn Val Gln Ser Val Gln Phe Gln Asn Gly Arg Cys Thr Leu
            260                 265                 270

Asp Gly Arg Leu Val Gly Thr Thr Pro Val Ser Leu Ser His Val Ala
        275                 280                 285

Lys Ile Arg Gly Thr Ser Asn Gly Thr Val Ile Asn Leu Thr Glu Leu
    290                 295                 300

Asp Gly Thr Pro Phe His Pro Phe Glu Gly Pro Ala Pro Ile Gly Phe
305                 310                 315                 320

Pro Asp Leu Gly Gly Cys Asp Trp His Ile Asn Met Thr Gln Phe Gly
                325                 330                 335

His Ser Ser Gln Thr Gln Tyr Asp Val Asp Thr Thr Pro Asp Thr Phe
            340                 345                 350

Val Pro His Leu Gly Ser Ile Gln Ala Asn Gly Ile Gly Ser Gly Asn
        355                 360                 365

Tyr Ile Gly Val Leu Ser Trp Val Ser Pro Pro Ser His Pro Ser Gly
    370                 375                 380

Ser Gln Val Asp Leu Trp Lys Ile Pro Asn Tyr Gly Ser Ser Ile Thr
385                 390                 395                 400

Glu Ala Thr His Leu Ala Pro Ser Val Tyr Pro Pro Gly Phe Gly Glu
                405                 410                 415

Val Leu Val Phe Phe Met Ser Lys Ile Pro Gly Pro Gly Ala Tyr Ser
            420                 425                 430

Leu Pro Cys Leu Leu Pro Gln Glu Tyr Ile Ser His Leu Ala Ser Glu
        435                 440                 445

Gln Ala Pro Thr Val Gly Glu Ala Ala Leu Leu His Tyr Val Asp Pro
    450                 455                 460

Asp Thr Gly Arg Thr Leu Gly Glu Phe Lys Ala Tyr Pro Asp Gly Phe
465                 470                 475                 480

Leu Thr Cys Val Pro Asn Gly Ala Ser Ser Gly Pro Gln Gln Leu Pro
                485                 490                 495

Ile Asn Gly Val Phe Val Phe Val Ser Trp Val Ser Arg Phe Tyr Gln
            500                 505                 510

Leu Lys Pro Val Gly Thr Ala Ser Ser Ala Arg Gly Arg Leu Gly Leu
        515                 520                 525

Arg Arg
    530


<210> SEQ ID NO 6
<211> LENGTH: 530
<212> TYPE: PRT
<213> ORGANISM: Norovirus

<400> SEQUENCE: 6

Met Met Met Ala Ser Lys Asp Ala Thr Ser Ser Val Asp Gly Ala Ser
1               5                   10                  15

Gly Ala Gly Gln Leu Val Pro Glu Val Asn Ala Ser Asp Pro Leu Ala
            20                  25                  30

Met Asp Pro Val Ala Gly Ser Ser Thr Ala Val Ala Thr Ala Gly Gln
        35                  40                  45

Val Asn Pro Ile Asp Pro Trp Ile Ile Asn Asn Phe Val Gln Ala Pro
    50                  55                  60

Gln Gly Glu Phe Thr Ile Ser Pro Asn Asn Thr Pro Gly Asp Val Leu
65                  70                  75                  80
```

-continued

```
Phe Asp Leu Ser Leu Gly Pro His Leu Asn Pro Phe Leu Leu His Leu
                85                  90                  95

Ser Gln Met Tyr Asn Gly Trp Val Gly Asn Met Arg Val Arg Ile Met
            100                 105                 110

Leu Ala Gly Asn Ala Phe Thr Ala Gly Lys Ile Ile Val Ser Cys Ile
        115                 120                 125

Pro Pro Gly Phe Gly Ser His Asn Leu Thr Ile Ala Gln Ala Thr Leu
    130                 135                 140

Phe Pro His Val Ile Ala Asp Val Arg Thr Leu Asp Pro Ile Glu Val
145                 150                 155                 160

Pro Leu Glu Asp Val Arg Asn Val Leu Phe His Asn Asn Asp Arg Asn
                165                 170                 175

Gln Gln Thr Met Arg Leu Val Cys Met Leu Tyr Thr Pro Leu Arg Thr
            180                 185                 190

Gly Gly Gly Thr Gly Asp Ser Phe Val Val Ala Gly Arg Val Met Thr
        195                 200                 205

Cys Pro Ser Pro Asp Phe Asn Phe Leu Phe Leu Val Pro Pro Thr Val
    210                 215                 220

Glu Gln Lys Thr Arg Pro Phe Thr Leu Pro Asn Leu Pro Leu Ser Ser
225                 230                 235                 240

Leu Ser Asn Ser Arg Ala Pro Leu Pro Ile Ser Ser Met Gly Ile Ser
                245                 250                 255

Pro Asp Asn Val Gln Ser Val Gln Phe Gln Asn Gly Arg Cys Thr Leu
            260                 265                 270

Asp Gly Arg Leu Val Gly Thr Thr Pro Val Ser Leu Ser His Val Ala
        275                 280                 285

Lys Ile Arg Gly Thr Ser Asn Gly Thr Val Ile Asn Leu Thr Glu Leu
    290                 295                 300

Asp Gly Thr Pro Phe His Pro Phe Glu Gly Pro Ala Pro Ile Gly Phe
305                 310                 315                 320

Pro Asp Leu Gly Gly Cys Asp Trp His Ile Asn Met Thr Gln Phe Gly
                325                 330                 335

His Ser Ser Gln Thr Gln Tyr Asp Val Asp Thr Thr Pro Asp Thr Phe
            340                 345                 350

Val Pro His Leu Gly Ser Ile Gln Ala Asn Gly Ile Gly Ser Gly Asn
        355                 360                 365

Tyr Val Gly Val Leu Ser Trp Ile Ser Pro Pro Ser His Pro Ser Gly
    370                 375                 380

Ser Gln Val Asp Leu Trp Lys Ile Pro Asn Tyr Gly Ser Ser Ile Thr
385                 390                 395                 400

Glu Ala Thr His Leu Ala Pro Ser Val Tyr Pro Pro Gly Phe Gly Glu
                405                 410                 415

Val Leu Val Phe Phe Met Ser Lys Met Pro Gly Pro Gly Ala Tyr Asn
            420                 425                 430

Leu Pro Cys Leu Leu Pro Gln Glu Tyr Ile Ser His Leu Ala Ser Glu
        435                 440                 445

Gln Ala Pro Thr Val Gly Glu Ala Ala Leu Leu His Tyr Val Asp Pro
    450                 455                 460

Asp Thr Gly Arg Asn Leu Gly Glu Phe Lys Ala Tyr Pro Asp Gly Phe
465                 470                 475                 480

Leu Thr Cys Val Pro Asn Gly Ala Ser Ser Gly Pro Gln Gln Leu Pro
                485                 490                 495
```

```
Ile Asn Gly Val Phe Val Phe Val Ser Trp Val Ser Arg Phe Tyr Gln
            500                 505                 510

Leu Lys Pro Val Gly Thr Ala Ser Ser Ala Arg Gly Arg Leu Gly Leu
        515                 520                 525

Arg Arg
    530


<210> SEQ ID NO 7
<211> LENGTH: 546
<212> TYPE: PRT
<213> ORGANISM: Norovirus

<400> SEQUENCE: 7

Met Met Met Ala Ser Lys Asp Ala Pro Gln Ser Ala Asp Gly Ala Ser
1               5                   10                  15

Gly Ala Gly Gln Leu Val Pro Glu Val Asn Thr Ala Asp Pro Leu Pro
            20                  25                  30

Met Glu Pro Val Ala Gly Pro Thr Thr Ala Val Ala Thr Ala Gly Gln
        35                  40                  45

Val Asn Met Ile Asp Pro Trp Ile Val Asn Asn Phe Val Gln Ser Pro
    50                  55                  60

Gln Gly Glu Phe Thr Ile Ser Pro Asn Asn Thr Pro Gly Asp Ile Leu
65                  70                  75                  80

Phe Asp Leu Gln Leu Gly Pro His Leu Asn Pro Phe Leu Ser His Leu
                85                  90                  95

Ser Gln Met Tyr Asn Gly Trp Val Gly Asn Met Arg Val Arg Ile Leu
            100                 105                 110

Leu Ala Gly Asn Ala Phe Ser Ala Gly Lys Ile Ile Val Cys Cys Val
        115                 120                 125

Pro Pro Gly Phe Thr Ser Ser Ser Leu Thr Ile Ala Gln Ala Thr Leu
    130                 135                 140

Phe Pro His Val Ile Ala Asp Val Arg Thr Leu Glu Pro Ile Glu Met
145                 150                 155                 160

Pro Leu Glu Asp Val Arg Asn Val Leu Tyr His Thr Asn Asp Asn Gln
                165                 170                 175

Pro Thr Met Arg Leu Val Cys Met Leu Tyr Thr Pro Leu Arg Thr Gly
            180                 185                 190

Gly Gly Ser Gly Asn Ser Asp Ser Phe Val Val Ala Gly Arg Val Leu
        195                 200                 205

Thr Ala Pro Ser Ser Asp Phe Ser Phe Leu Phe Leu Val Pro Pro Thr
    210                 215                 220

Ile Glu Gln Lys Thr Arg Ala Phe Thr Val Pro Asn Ile Pro Leu Gln
225                 230                 235                 240

Thr Leu Ser Asn Ser Arg Phe Pro Ser Leu Ile Gln Gly Met Ile Leu
                245                 250                 255

Ser Pro Asp Ala Ser Gln Val Val Gln Phe Gln Asn Gly Arg Cys Leu
            260                 265                 270

Ile Asp Gly Gln Leu Leu Gly Thr Thr Pro Ala Thr Ser Gly Gln Leu
        275                 280                 285

Phe Arg Val Arg Gly Lys Ile Asn Gln Gly Ala Arg Thr Leu Asn Leu
    290                 295                 300

Thr Glu Val Asp Gly Lys Pro Phe Met Ala Phe Asp Ser Pro Ala Pro
305                 310                 315                 320

Val Gly Phe Pro Asp Phe Gly Lys Cys Asp Trp His Met Arg Ile Ser
                325                 330                 335
```

```
Lys Thr Pro Asn Asn Thr Ser Ser Gly Asp Pro Met Arg Ser Val Ser
            340                 345                 350

Val Gln Thr Asn Val Gln Gly Phe Val Pro His Leu Gly Ser Ile Gln
        355                 360                 365

Phe Asp Glu Val Phe Asn His Pro Thr Gly Asp Tyr Ile Gly Thr Ile
    370                 375                 380

Glu Trp Ile Ser Gln Pro Ser Thr Pro Pro Gly Thr Asp Ile Asn Leu
385                 390                 395                 400

Trp Glu Ile Pro Asp Tyr Gly Ser Ser Leu Ser Gln Ala Ala Asn Leu
                405                 410                 415

Ala Pro Pro Val Phe Pro Pro Gly Phe Gly Glu Ala Leu Val Tyr Phe
            420                 425                 430

Val Ser Ala Phe Pro Gly Pro Asn Asn Arg Ser Ala Pro Asn Asp Val
        435                 440                 445

Pro Cys Leu Leu Pro Gln Glu Tyr Ile Thr His Phe Val Ser Glu Gln
    450                 455                 460

Ala Pro Thr Met Gly Asp Ala Ala Leu Leu His Tyr Val Asp Pro Asp
465                 470                 475                 480

Thr Asn Arg Asn Leu Gly Glu Phe Lys Leu Tyr Pro Gly Gly Tyr Leu
                485                 490                 495

Thr Cys Val Pro Asn Gly Val Gly Ala Gly Pro Gln Gln Leu Pro Leu
            500                 505                 510

Asn Gly Val Phe Leu Phe Val Ser Trp Val Ser Arg Phe Tyr Gln Leu
        515                 520                 525

Lys Pro Val Gly Thr Ala Ser Thr Ala Arg Ser Arg Leu Gly Val Arg
    530                 535                 540

Arg Ile
545


<210> SEQ ID NO 8
<211> LENGTH: 546
<212> TYPE: PRT
<213> ORGANISM: Norovirus

<400> SEQUENCE: 8

Met Met Met Ala Ser Lys Asp Ala Pro Gln Ser Ala Asp Gly Ala Ser
1               5                   10                  15

Gly Ala Gly Gln Leu Val Pro Glu Val Asn Thr Ala Asp Pro Leu Pro
            20                  25                  30

Met Glu Pro Val Ala Gly Pro Thr Thr Ala Val Ala Thr Ala Gly Gln
        35                  40                  45

Val Asn Met Ile Asp Pro Trp Ile Val Asn Asn Phe Val Gln Ser Pro
    50                  55                  60

Gln Gly Glu Phe Thr Ile Ser Pro Asn Asn Thr Pro Gly Asp Ile Leu
65                  70                  75                  80

Phe Asp Leu Gln Leu Gly Pro His Leu Asn Pro Phe Leu Ser His Leu
                85                  90                  95

Ser Gln Met Tyr Asn Gly Trp Val Gly Asn Met Arg Val Arg Ile Leu
            100                 105                 110

Leu Ala Gly Asn Ala Phe Ser Ala Gly Lys Ile Ile Val Cys Cys Val
        115                 120                 125

Pro Pro Gly Phe Thr Ser Ser Ser Leu Thr Ile Ala Gln Ala Thr Leu
    130                 135                 140

Phe Pro His Val Ile Ala Asp Val Arg Thr Leu Glu Pro Ile Glu Met
```

```
145                 150                 155                 160

Pro Leu Glu Asp Val Arg Asn Val Leu Tyr His Thr Asn Asp Asn Gln
                165                 170                 175

Pro Thr Met Arg Leu Val Cys Met Leu Tyr Thr Pro Leu Arg Thr Gly
            180                 185                 190

Gly Gly Ser Gly Ser Ser Asp Ser Phe Val Val Ala Gly Arg Val Leu
        195                 200                 205

Thr Ala Pro Ser Ser Asp Phe Ser Phe Leu Phe Leu Val Pro Pro Thr
    210                 215                 220

Ile Glu Gln Lys Thr Arg Ala Phe Thr Val Pro Asn Ile Pro Leu Gln
225                 230                 235                 240

Thr Leu Ser Asn Ser Arg Phe Pro Ser Leu Ile Gln Gly Met Ile Leu
                245                 250                 255

Ser Pro Asp Ala Ser Gln Val Val Gln Phe Gln Asn Gly Arg Cys Leu
            260                 265                 270

Ile Asp Gly Gln Leu Leu Gly Thr Thr Pro Ala Thr Ser Gly Gln Leu
        275                 280                 285

Phe Arg Val Arg Gly Lys Ile Asn Gln Gly Ala Arg Thr Leu Asn Leu
    290                 295                 300

Thr Glu Val Asp Gly Lys Pro Phe Met Ala Phe Asp Ser Pro Ala Pro
305                 310                 315                 320

Val Gly Phe Pro Asp Phe Gly Lys Cys Asp Trp His Met Arg Ile Ser
                325                 330                 335

Lys Thr Pro Asn Asn Thr Ser Ser Gly Asp Pro Met Arg Ser Val Ser
            340                 345                 350

Val Gln Thr Asn Val Gln Gly Phe Val Pro His Leu Gly Ser Ile Gln
        355                 360                 365

Phe Asp Glu Val Phe Asn His Pro Thr Gly Asp Tyr Ile Gly Thr Ile
    370                 375                 380

Glu Trp Ile Ser Gln Pro Ser Thr Pro Pro Gly Thr Asp Ile Asn Leu
385                 390                 395                 400

Trp Glu Ile Pro Asp Tyr Gly Ser Ser Leu Ser Gln Ala Ala Asn Leu
                405                 410                 415

Ala Pro Pro Val Phe Pro Pro Gly Phe Gly Glu Ala Leu Val Tyr Phe
            420                 425                 430

Val Ser Ala Phe Pro Gly Pro Asn Asn Arg Ser Ala Pro Asn Asp Val
        435                 440                 445

Pro Cys Leu Leu Pro Gln Glu Tyr Ile Thr His Phe Val Ser Glu Gln
    450                 455                 460

Ala Pro Thr Met Gly Asp Ala Ala Leu Leu His Tyr Val Asp Pro Asp
465                 470                 475                 480

Thr Asn Arg Asn Leu Gly Glu Phe Lys Leu Tyr Pro Gly Gly Tyr Leu
                485                 490                 495

Thr Cys Val Pro Asn Gly Val Gly Ala Gly Pro Gln Gln Leu Pro Leu
            500                 505                 510

Asn Gly Val Phe Leu Phe Val Ser Trp Val Ser Arg Phe Tyr Gln Leu
        515                 520                 525

Lys Pro Val Gly Thr Ala Ser Thr Ala Arg Gly Arg Leu Gly Val Arg
    530                 535                 540

Arg Ile
545
```

<210> SEQ ID NO 9

<211> LENGTH: 545
<212> TYPE: PRT
<213> ORGANISM: Norovirus

<400> SEQUENCE: 9

```
Met Met Met Ala Ser Lys Asp Ala Pro Thr Asn Met Asp Gly Thr Ser
1               5                   10                  15

Gly Ala Gly Gln Leu Val Pro Glu Ala Asn Thr Ala Glu Pro Ile Ser
            20                  25                  30

Met Glu Pro Val Ala Gly Ala Ala Thr Ala Ala Ala Thr Ala Gly Gln
        35                  40                  45

Val Asn Met Ile Asp Pro Trp Ile Met Asn Asn Tyr Val Gln Ala Pro
    50                  55                  60

Gln Gly Glu Phe Thr Ile Ser Pro Asn Asn Thr Pro Gly Asp Ile Leu
65                  70                  75                  80

Phe Asp Leu Gln Leu Gly Pro His Leu Asn Pro Phe Leu Ser His Leu
                85                  90                  95

Ala Gln Met Tyr Asn Gly Trp Val Gly Asn Met Lys Val Lys Val Leu
            100                 105                 110

Leu Ala Gly Asn Ala Phe Thr Ala Gly Lys Ile Ile Ile Ser Cys Ile
        115                 120                 125

Pro Pro Gly Phe Val Ala Gln Asn Val Ser Ile Ala Gln Ala Thr Met
    130                 135                 140

Phe Pro His Val Ile Ala Asp Val Arg Val Leu Glu Pro Ile Glu Val
145                 150                 155                 160

Pro Leu Glu Asp Val Arg Asn Val Leu Phe His Asn Asn Asp Asn Thr
                165                 170                 175

Pro Thr Met Arg Leu Val Cys Met Leu Tyr Thr Pro Leu Arg Ala Ser
            180                 185                 190

Gly Ser Ser Ser Gly Thr Asp Pro Phe Val Ile Ala Gly Arg Val Leu
        195                 200                 205

Thr Cys Pro Ser Pro Asp Phe Ser Phe Leu Phe Leu Val Pro Pro Asn
    210                 215                 220

Val Glu Gln Lys Thr Lys Pro Phe Ser Val Pro Asn Leu Pro Leu Asn
225                 230                 235                 240

Thr Leu Ser Asn Ser Arg Val Pro Ser Leu Ile Lys Ser Met Met Val
                245                 250                 255

Ser Arg Asp His Gly Gln Met Val Gln Phe Gln Asn Gly Arg Val Thr
            260                 265                 270

Leu Asp Gly Gln Leu Gln Gly Thr Thr Pro Thr Ser Ala Ser Gln Leu
        275                 280                 285

Cys Lys Ile Arg Gly Ser Val Phe His Ala Asn Gly Gly Asn Gly Tyr
    290                 295                 300

Asn Leu Thr Glu Leu Asp Gly Ser Pro Tyr His Ala Phe Glu Ser Pro
305                 310                 315                 320

Ala Pro Ile Gly Phe Pro Asp Leu Gly Glu Cys Asp Trp His Met Glu
                325                 330                 335

Ala Ser Pro Thr Thr Gln Phe Asn Thr Gly Asp Val Ile Lys Gln Ile
            340                 345                 350

Asn Val Lys Gln Glu Ser Ala Phe Ala Pro His Leu Gly Thr Ile Gln
        355                 360                 365

Ala Asp Gly Leu Ser Asp Val Ser Val Asn Thr Asn Met Ile Ala Lys
    370                 375                 380

Leu Gly Trp Val Ser Pro Val Ser Asp Gly His Lys Gly Asp Val Asp
```

-continued

```
385                 390                 395                 400

Pro Trp Val Ile Pro Arg Tyr Gly Ser Thr Leu Thr Glu Ala Ala Gln
                405                 410                 415

Leu Ala Pro Pro Ile Tyr Pro Pro Gly Phe Gly Glu Ala Ile Val Phe
            420                 425                 430

Phe Met Ser Asp Phe Pro Ile Ala His Gly Thr Asn Gly Leu Ser Val
        435                 440                 445

Pro Cys Thr Ile Pro Gln Glu Phe Val Thr His Phe Val Asn Glu Gln
    450                 455                 460

Ala Pro Thr Arg Gly Glu Ala Ala Leu Leu His Tyr Leu Asp Pro Asp
465                 470                 475                 480

Thr His Arg Asn Leu Gly Glu Phe Lys Leu Tyr Pro Asp Gly Phe Met
                485                 490                 495

Thr Cys Val Pro Asn Ser Ser Gly Thr Gly Pro Gln Thr Leu Pro Ile
            500                 505                 510

Asn Gly Val Phe Val Phe Val Ser Trp Val Ser Arg Phe Tyr Gln Leu
        515                 520                 525

Lys Pro Val Gly Thr Ala Gly Pro Ala Arg Arg Leu Gly Ile Arg Arg
    530                 535                 540

Ser
545


<210> SEQ ID NO 10
<211> LENGTH: 545
<212> TYPE: PRT
<213> ORGANISM: Norovirus

<400> SEQUENCE: 10

Met Met Met Ala Ser Lys Asp Ala Pro Thr Asn Met Asp Gly Thr Ser
1               5                   10                  15

Gly Ala Gly Gln Leu Val Pro Glu Ala Asn Thr Ala Glu Pro Ile Ser
            20                  25                  30

Met Glu Pro Val Ala Gly Ala Ala Thr Ala Ala Ala Thr Ala Gly Gln
        35                  40                  45

Val Asn Met Ile Asp Pro Trp Ile Met Asn Asn Tyr Val Gln Ala Pro
    50                  55                  60

Gln Gly Glu Phe Thr Ile Ser Pro Asn Asn Thr Pro Gly Asp Ile Leu
65                  70                  75                  80

Phe Asp Leu Gln Leu Gly Pro His Leu Asn Pro Phe Leu Ser His Leu
                85                  90                  95

Ala Gln Met Tyr Asn Gly Trp Val Gly Asn Met Lys Val Lys Val Leu
            100                 105                 110

Leu Ala Gly Asn Ala Phe Thr Ala Gly Lys Ile Ile Ile Ser Cys Ile
        115                 120                 125

Pro Pro Gly Phe Ala Ala Gln Asn Ile Ser Ile Ala Gln Ala Thr Met
    130                 135                 140

Phe Pro His Val Ile Ala Asp Val Arg Val Leu Glu Pro Ile Glu Val
145                 150                 155                 160

Pro Leu Glu Asp Val Arg Asn Val Leu Phe His Asn Asn Asp Asn Thr
                165                 170                 175

Pro Thr Met Arg Leu Val Cys Met Leu Tyr Thr Pro Leu Arg Ala Ser
            180                 185                 190

Gly Ser Ser Ser Gly Thr Asp Pro Phe Val Ile Ala Gly Arg Val Leu
        195                 200                 205
```

Thr Cys Pro Ser Pro Asp Phe Ser Phe Leu Phe Leu Val Pro Pro Asn
210 215 220

Val Glu Gln Lys Thr Lys Pro Phe Ser Val Pro Asn Leu Pro Leu Asn
225 230 235 240

Thr Leu Ser Asn Ser Arg Val Pro Ser Leu Ile Lys Ser Met Met Val
245 250 255

Ser Arg Asp His Gly Gln Met Val Gln Phe Gln Asn Gly Arg Val Thr
260 265 270

Leu Asp Gly Gln Leu Gln Gly Thr Thr Pro Thr Ser Ala Ser Gln Leu
275 280 285

Cys Lys Ile Arg Gly Ser Val Phe His Ala Asn Gly Gly Asn Gly Tyr
290 295 300

Asn Leu Thr Glu Leu Asp Gly Ser Pro Tyr His Ala Phe Glu Ser Pro
305 310 315 320

Ala Pro Ile Gly Phe Pro Asp Leu Gly Glu Cys Asp Trp His Met Glu
325 330 335

Ala Ser Pro Thr Thr Gln Phe Asn Thr Gly Asp Val Ile Lys Gln Ile
340 345 350

Asn Val Lys Gln Glu Ser Ala Phe Ala Pro His Leu Gly Thr Ile Gln
355 360 365

Ala Asp Gly Leu Ser Asp Val Ser Val Asn Thr Asn Met Ile Ala Lys
370 375 380

Leu Gly Trp Val Ser Pro Val Ser Asp Gly His Lys Arg Asp Val Asp
385 390 395 400

Pro Trp Val Ile Pro Arg Tyr Gly Ser Thr Leu Thr Glu Ala Ala Gln
405 410 415

Leu Ala Pro Pro Ile Tyr Pro Pro Gly Phe Gly Glu Ala Ile Val Phe
420 425 430

Phe Met Ser Asp Phe Pro Ile Ala His Gly Thr Asn Gly Leu Ser Val
435 440 445

Pro Cys Thr Ile Pro Gln Glu Phe Val Thr His Phe Val Asn Glu Gln
450 455 460

Ala Pro Thr Arg Gly Glu Ala Ala Leu Leu His Tyr Leu Asp Pro Asp
465 470 475 480

Thr His Arg Asn Leu Gly Glu Phe Lys Leu Tyr Pro Asp Gly Phe Met
485 490 495

Thr Cys Val Pro Asn Ser Ser Gly Thr Gly Pro Gln Thr Leu Pro Ile
500 505 510

Asn Gly Val Phe Val Phe Val Ser Trp Val Ser Arg Phe Tyr Gln Leu
515 520 525

Lys Pro Val Gly Thr Ala Gly Pro Ala Arg Arg Leu Gly Ile Arg Arg
530 535 540

Ser
545

<210> SEQ ID NO 11
<211> LENGTH: 544
<212> TYPE: PRT
<213> ORGANISM: Norovirus

<400> SEQUENCE: 11

Met Met Met Ala Ser Lys Asp Ala Pro Thr Asn Met Asp Gly Thr Ser
1 5 10 15

Gly Ala Gly Gln Leu Val Pro Glu Ala Asn Thr Ala Glu Pro Ile Ser
20 25 30

```
Met Glu Pro Val Ala Gly Ala Ala Thr Ala Ala Ala Thr Ala Gly Gln
        35                  40                  45

Val Asn Met Ile Asp Pro Trp Ile Met Asn Asn Tyr Val Gln Ala Pro
    50                  55                  60

Gln Gly Glu Phe Thr Ile Ser Pro Asn Asn Thr Pro Gly Asp Ile Leu
65                  70                  75                  80

Phe Asp Leu Gln Leu Gly Pro His Leu Asn Pro Phe Leu Ser His Leu
                85                  90                  95

Ala Gln Met Tyr Asn Gly Trp Val Gly Asn Met Lys Val Lys Val Leu
            100                 105                 110

Leu Ala Gly Asn Ala Phe Thr Ala Gly Lys Ile Ile Ile Ser Cys Ile
        115                 120                 125

Pro Pro Gly Phe Ala Ser Gln Asn Ile Ser Ile Ala Gln Ala Thr Met
    130                 135                 140

Phe Pro His Val Ile Ala Asp Val Arg Val Leu Glu Pro Ile Glu Val
145                 150                 155                 160

Pro Leu Glu Asp Val Arg Asn Val Leu Phe His Asn Asn Asp Asn Thr
                165                 170                 175

Pro Thr Met Arg Leu Val Cys Met Leu Tyr Thr Pro Leu Arg Ala Ser
            180                 185                 190

Gly Ser Ser Ser Gly Thr Asp Pro Phe Val Ile Ala Gly Arg Val Leu
        195                 200                 205

Thr Cys Pro Ser Pro Asp Phe Ser Phe Leu Phe Leu Val Pro Pro Asn
    210                 215                 220

Val Glu Gln Lys Thr Lys Pro Phe Ser Val Pro Asn Leu Pro Leu Asn
225                 230                 235                 240

Val Leu Ser Asn Ser Arg Val Pro Ser Leu Ile Lys Ser Met Met Val
                245                 250                 255

Ser Gln Asp His Gly Gln Met Val Gln Phe Gln Asn Gly Arg Val Thr
            260                 265                 270

Leu Asp Gly Gln Leu Gln Gly Thr Thr Pro Thr Ser Ala Ser Gln Leu
        275                 280                 285

Cys Lys Met Arg Gly Thr Val Tyr His Ala Ser Gly Gly Gln Gly Leu
    290                 295                 300

Asn Leu Thr Glu Ile Asp Gly Thr Pro Tyr His Ala Phe Glu Ser Pro
305                 310                 315                 320

Ala Pro Ile Gly Phe Pro Asp Ile Gly Asp Ser Asp Trp His Ile Asn
                325                 330                 335

Ala Ser Pro Ala Thr Thr Phe Asp Ser Gly Glu Ser Ile Lys Arg Leu
            340                 345                 350

Asp Met Glu Gln Gly Ser Ser Phe Ala Pro His Leu Gly Thr Val His
        355                 360                 365

Tyr Thr Asn Ala Asp Tyr Pro Ala Asn Thr Asp Leu Ile Cys Ser Leu
    370                 375                 380

Glu Trp Leu Ser Pro Pro Ser Gly Gly Thr Pro Asn Lys Val Asn Pro
385                 390                 395                 400

Trp Thr Ile Pro Arg Tyr Gly Ser Thr Leu Thr Glu Ala Ala Gln Leu
                405                 410                 415

Ala Pro Pro Ile Tyr Pro Pro Gly Phe Gly Glu Ala Ile Val Phe Phe
            420                 425                 430

Met Ser Asp Phe Pro Ile Ala Asn Gly Gln Asp Gly Leu Lys Val Pro
        435                 440                 445
```

```
Cys Thr Ile Pro Gln Glu Phe Val Thr His Phe Val Asn Glu Gln Ala
    450                 455                 460

Pro Thr Arg Gly Glu Ala Ala Leu Leu His Tyr Val Asp Pro Asp Thr
465                 470                 475                 480

His Arg Asn Leu Gly Glu Phe Lys Leu Tyr Pro Glu Gly Phe Met Thr
                485                 490                 495

Cys Val Pro Asn Ser Ser Gly Ser Gly Pro Gln Thr Leu Pro Ile Asn
            500                 505                 510

Gly Val Phe Thr Phe Val Ser Trp Val Ser Arg Phe Tyr Gln Leu Lys
        515                 520                 525

Pro Val Gly Thr Thr Gly Pro Val Arg Arg Leu Gly Ile Arg Arg Ser
    530                 535                 540


<210> SEQ ID NO 12
<211> LENGTH: 544
<212> TYPE: PRT
<213> ORGANISM: Norovirus

<400> SEQUENCE: 12

Met Met Met Ala Ser Lys Asp Ala Pro Thr Asn Met Asp Gly Thr Ser
1               5                   10                  15

Gly Ala Gly Gln Leu Val Pro Glu Ala Asn Thr Ala Glu Pro Ile Ser
            20                  25                  30

Met Glu Pro Val Ala Gly Ala Ala Thr Ala Ala Ala Thr Ala Gly Gln
        35                  40                  45

Val Asn Met Ile Asp Pro Trp Ile Met Asn Asn Tyr Val Gln Ala Pro
    50                  55                  60

Gln Gly Glu Phe Thr Ile Ser Pro Asn Asn Thr Pro Gly Asp Ile Leu
65                  70                  75                  80

Phe Asp Leu Gln Leu Gly Pro His Leu Asn Pro Phe Leu Ser His Leu
                85                  90                  95

Ala Gln Met Tyr Asn Gly Trp Val Gly Asn Met Lys Val Lys Val Leu
            100                 105                 110

Leu Ala Gly Asn Ala Phe Thr Ala Gly Lys Ile Ile Ile Ser Cys Ile
        115                 120                 125

Pro Pro Gly Phe Ala Ser Gln Asn Ile Ser Ile Ala Gln Ala Thr Met
    130                 135                 140

Phe Pro His Val Ile Ala Asp Val Arg Val Leu Glu Pro Ile Glu Val
145                 150                 155                 160

Pro Leu Glu Asp Val Arg Asn Val Leu Phe His Asn Asn Asp Asn Ser
                165                 170                 175

Pro Thr Met Arg Leu Val Cys Met Leu Tyr Thr Pro Leu Arg Ala Ser
            180                 185                 190

Gly Ser Ser Ser Gly Thr Asp Pro Phe Val Ile Ala Gly Arg Val Leu
        195                 200                 205

Thr Cys Pro Ser Pro Asp Phe Ser Phe Leu Phe Leu Val Pro Pro Asn
    210                 215                 220

Val Glu Gln Lys Thr Lys Pro Phe Ser Val Pro Asn Leu Pro Leu Asn
225                 230                 235                 240

Thr Leu Ser Asn Ser Arg Val Pro Ser Leu Ile Asn Ala Met Met Ile
                245                 250                 255

Ser Arg Asp His Gly Gln Met Val Gln Phe Gln Asn Gly Arg Val Thr
            260                 265                 270

Leu Asp Gly Gln Leu Gln Gly Thr Thr Pro Thr Ser Leu Ser Gln Leu
        275                 280                 285
```

```
Cys Lys Ile Arg Gly Lys Val Phe Leu Ala Ser Gly Gly Asn Gly Leu
    290                 295                 300

Asn Leu Thr Glu Leu Asp Gly Ser Ala Tyr His Ala Phe Glu Ser Pro
305                 310                 315                 320

Ala Pro Ile Gly Phe Pro Asp Ile Gly Asp Cys Asp Trp His Met Asn
                325                 330                 335

Ala Thr Ala Thr Ser Asn Phe Thr Gly Ser Asn Asp Glu His Gln Ile
            340                 345                 350

Leu Val Lys Gln Glu Ser Thr Phe Ala Pro His Leu Gly His Val Gln
        355                 360                 365

Ala Asp His Leu Pro Glu Val Ala Asn Thr Asp Leu Met Val Ser Leu
    370                 375                 380

Ser Trp Ile Ser Pro Val Ser Asp Gln His Arg Arg Asp Val Asp Pro
385                 390                 395                 400

Trp Val Ile Pro Arg Tyr Gly Ser Thr Leu Thr Glu Ala Ala Gln Leu
                405                 410                 415

Ala Pro Pro Ile Tyr Pro Pro Gly Phe Gly Glu Ala Ile Val Phe Phe
            420                 425                 430

Met Ser Asp Phe Pro Val Val Ser Gly Val Asn Gly Met Arg Ile Pro
        435                 440                 445

Cys Thr Leu Pro Gln Glu Tyr Val Ala His Phe Val Asn Glu Gln Ala
    450                 455                 460

Pro Thr Arg Gly Glu Ala Ala Leu Leu His Tyr Val Asp Pro Asp Thr
465                 470                 475                 480

His Arg Asn Leu Gly Glu Phe Lys Ile Tyr Pro Glu Gly Phe Met Thr
                485                 490                 495

Cys Val Pro Asn Ser Ser Gly Thr Gly Pro Gln Thr Leu Pro Ile Asn
            500                 505                 510

Gly Val Phe Thr Phe Val Ser Trp Val Ser Arg Phe Tyr Gln Leu Lys
        515                 520                 525

Pro Val Gly Thr Ala Gly Pro Ala Arg Arg Leu Gly Ile Arg Arg Ser
    530                 535                 540
```

<210> SEQ ID NO 13
<211> LENGTH: 544
<212> TYPE: PRT
<213> ORGANISM: Norovirus

<400> SEQUENCE: 13

```
Met Met Met Ala Ser Lys Asp Ala Thr Pro Ser Ala Asp Gly Ala Thr
1               5                   10                  15

Gly Ala Gly Gln Leu Val Pro Glu Val Asn Thr Ala Asp Pro Ile Pro
            20                  25                  30

Ile Asp Pro Val Ala Gly Ser Ser Thr Ala Leu Ala Thr Ala Gly Gln
        35                  40                  45

Val Asn Leu Ile Asp Pro Trp Ile Ile Asn Asn Phe Val Gln Ala Pro
    50                  55                  60

Gln Gly Glu Phe Thr Ile Ser Pro Asn Asn Thr Pro Gly Asp Val Leu
65                  70                  75                  80

Phe Asp Leu Gln Leu Gly Pro His Leu Asn Pro Phe Leu Ser His Leu
                85                  90                  95

Ser Gln Met Tyr Asn Gly Trp Val Gly Asn Met Arg Val Arg Val Val
            100                 105                 110

Leu Ala Gly Asn Ala Phe Thr Ala Gly Lys Val Ile Ile Cys Cys Val
```

```
        115                 120                 125

Pro Pro Gly Phe Gln Ser Arg Thr Leu Ser Ile Ala Gln Ala Thr Leu
    130                 135                 140

Phe Pro His Val Ile Ala Asp Val Arg Thr Leu Asp Pro Val Glu Val
145                 150                 155                 160

Pro Leu Glu Asp Val Arg Asn Val Leu Tyr His Asn Asn Asp Thr Gln
                165                 170                 175

Pro Thr Met Arg Leu Leu Cys Met Leu Tyr Thr Pro Leu Arg Thr Gly
            180                 185                 190

Gly Ala Ser Gly Gly Thr Asp Ser Phe Val Val Ala Gly Arg Val Leu
        195                 200                 205

Thr Cys Pro Gly Pro Asp Phe Asn Phe Leu Phe Leu Val Pro Pro Thr
    210                 215                 220

Val Glu Gln Lys Thr Arg Pro Phe Thr Val Pro Asn Ile Pro Leu Lys
225                 230                 235                 240

Tyr Leu Ser Asn Ser Arg Ile Pro Asn Pro Ile Glu Gly Met Ser Leu
                245                 250                 255

Ser Pro Asp Gln Thr Gln Asn Val Gln Phe Gln Asn Gly Arg Cys Thr
            260                 265                 270

Ile Asp Gly Gln Pro Leu Gly Thr Thr Pro Val Ser Val Ser Gln Leu
        275                 280                 285

Cys Lys Phe Arg Gly Arg Ile Thr Ser Gly Gln Arg Val Leu Asn Leu
    290                 295                 300

Thr Glu Leu Asp Gly Ser Pro Phe Met Gly Phe Gly Ala Pro Ala Pro
305                 310                 315                 320

Ala Gly Phe Pro Asp Leu Gly Ser Cys Asp Trp His Ile Glu Met Ser
                325                 330                 335

Lys Ile Pro Asn Ser Ser Thr Gln Asn Asn Pro Ile Val Thr Asn Ser
            340                 345                 350

Val Lys Pro Asn Ser Gln Gln Phe Val Pro His Leu Ser Ser Ile Thr
        355                 360                 365

Leu Asp Glu Asn Val Ser Ser Gly Gly Asp Tyr Ile Gly Thr Ile Gln
    370                 375                 380

Trp Thr Ser Pro Pro Ser Asp Ser Gly Gly Ala Asn Thr Asn Phe Trp
385                 390                 395                 400

Lys Ile Pro Asp Tyr Gly Ser Ser Leu Ala Glu Ala Ser Gln Leu Ala
                405                 410                 415

Pro Ala Val Tyr Pro Pro Gly Phe Asn Glu Val Ile Val Tyr Phe Met
            420                 425                 430

Ala Ser Ile Pro Gly Pro Asn Gln Ser Gly Ser Pro Asn Leu Val Pro
        435                 440                 445

Cys Leu Leu Pro Gln Glu Tyr Ile Thr His Phe Ile Ser Glu Gln Ala
    450                 455                 460

Pro Ile Gln Gly Glu Ala Ala Leu Leu His Tyr Val Asp Pro Asp Thr
465                 470                 475                 480

Asn Arg Asn Leu Gly Glu Phe Lys Leu Tyr Pro Gly Gly Tyr Leu Thr
                485                 490                 495

Cys Val Pro Asn Ser Ser Ser Thr Gly Pro Gln Gln Leu Pro Leu Asp
            500                 505                 510

Gly Val Phe Val Phe Ala Ser Trp Val Ser Arg Phe Tyr Gln Leu Lys
        515                 520                 525

Pro Val Gly Thr Ala Gly Pro Ala Arg Gly Arg Leu Gly Val Arg Arg
    530                 535                 540
```

<210> SEQ ID NO 14
<211> LENGTH: 533
<212> TYPE: PRT
<213> ORGANISM: Norovirus

<400> SEQUENCE: 14

```
Met Met Met Ala Ser Lys Asp Ala Thr Pro Ser Ala Asp Gly Ala Thr
1               5                   10                  15

Gly Ala Gly Gln Leu Val Pro Glu Val Asn Thr Ala Asp Pro Ile Pro
            20                  25                  30

Ile Asp Pro Val Ala Gly Ser Ser Thr Ala Leu Ala Thr Ala Gly Gln
        35                  40                  45

Val Asn Leu Ile Asp Pro Trp Ile Ile Asn Asn Phe Val Gln Ala Pro
    50                  55                  60

Gln Gly Glu Phe Thr Ile Ser Pro Asn Asn Thr Pro Gly Asp Val Leu
65                  70                  75                  80

Phe Asp Leu Gln Leu Gly Pro His Leu Asn Pro Phe Leu Ser His Leu
                85                  90                  95

Ser Gln Met Tyr Asn Gly Trp Val Gly Asn Met Arg Val Arg Val Val
            100                 105                 110

Leu Ala Gly Asn Ala Phe Thr Ala Gly Lys Val Ile Ile Cys Cys Val
        115                 120                 125

Pro Pro Gly Phe Gln Ser Arg Thr Leu Ser Ile Ala Gln Ala Thr Leu
    130                 135                 140

Phe Pro His Val Ile Ala Asp Val Arg Thr Leu Asp Pro Val Glu Val
145                 150                 155                 160

Pro Leu Glu Asp Val Arg Asn Val Leu Tyr His Asn Asn Asp Thr Gln
                165                 170                 175

Pro Thr Met Arg Leu Leu Cys Met Leu Tyr Thr Pro Leu Arg Thr Gly
            180                 185                 190

Gly Ala Ser Gly Gly Thr Asp Ser Phe Val Val Ala Gly Arg Val Leu
        195                 200                 205

Thr Cys Pro Gly Pro Asp Phe Asn Phe Leu Phe Leu Val Pro Pro Thr
    210                 215                 220

Val Glu Gln Lys Thr Arg Pro Phe Thr Val Pro Asn Ile Pro Leu Lys
225                 230                 235                 240

Tyr Leu Ser Asn Ser Arg Ile Pro Asn Pro Ile Glu Gly Met Ser Leu
                245                 250                 255

Ser Pro Asp Gln Thr Gln Asn Val Gln Phe Gln Asn Gly Arg Cys Thr
            260                 265                 270

Ile Asp Gly Gln Pro Leu Gly Thr Thr Pro Val Ser Val Ser Gln Leu
        275                 280                 285

Cys Lys Phe Arg Gly Arg Ile Thr Ser Gly Gln Arg Val Leu Asn Leu
    290                 295                 300

Thr Glu Leu Asp Gly Ser Pro Phe Met Ala Phe Ala Ala Pro Ala Pro
305                 310                 315                 320

Ala Gly Phe Pro Asp Leu Gly Ser Cys Asp Trp His Ile Glu Met Ser
                325                 330                 335

Lys Ile Pro Asn Ser Ser Thr Gln Asn Asn Pro Ile Val Val Asn Ser
            340                 345                 350

Val Lys Pro Asn Ser Gln Gln Phe Val Pro His Leu Ser Ser Ile Thr
        355                 360                 365

Leu Asp Asp Asn Val Ser Ser Gly Gly Asp Tyr Ile Gly Thr Ile Gln
```

```
    370                 375                 380

Trp Thr Ser Pro Pro Ser Asp Ser Gly Gly Ala Asn Thr Asn Phe Trp
385                 390                 395                 400

Lys Ile Pro Asp Tyr Gly Ser Ser Leu Ala Glu Ala Ser Gln Leu Ala
                405                 410                 415

Pro Ala Val Tyr Pro Pro Gly Phe Asn Glu Val Ile Val Tyr Phe Met
            420                 425                 430

Ala Ser Ile Pro Gly Pro Asn Gln Ser Gly Ser Pro Asn Leu Val Pro
        435                 440                 445

Cys Leu Leu Pro Gln Glu Tyr Ile Thr His Phe Ile Ser Glu Gln Ala
    450                 455                 460

Pro Ile Gln Gly Glu Ala Ala Leu Leu His Tyr Val Asp Pro Asp Thr
465                 470                 475                 480

Asn Arg Asn Leu Gly Glu Phe Lys Leu Tyr Pro Gly Gly Tyr Leu Thr
                485                 490                 495

Cys Val Pro Asn Ser Ser Ser Thr Gly Pro Gln Gln Leu Pro Leu Asp
            500                 505                 510

Gly Val Phe Val Phe Ala Ser Trp Val Ser Arg Phe Tyr Gln Leu Lys
        515                 520                 525

Pro Val Gly Thr Ala
    530


<210> SEQ ID NO 15
<211> LENGTH: 543
<212> TYPE: PRT
<213> ORGANISM: Norovirus

<400> SEQUENCE: 15

Met Met Met Ala Ser Lys Asp Ala Thr Pro Ser Ala Asp Gly Ala Asn
1               5                   10                  15

Gly Ala Gly Gln Leu Val Pro Glu Val Asn Asn Ala Glu Pro Leu Pro
            20                  25                  30

Leu Asp Pro Val Ala Gly Ala Ser Thr Ala Leu Ala Thr Ala Gly Gln
        35                  40                  45

Val Asn Met Ile Asp Pro Trp Ile Phe Asn Asn Phe Val Gln Ala Pro
    50                  55                  60

Gln Gly Glu Phe Thr Ile Ser Pro Asn Asn Thr Pro Gly Asp Ile Leu
65                  70                  75                  80

Phe Asp Leu Gln Leu Gly Pro His Leu Asn Pro Phe Leu Ala His Leu
                85                  90                  95

Ser Gln Met Tyr Asn Gly Trp Val Gly Asn Met Arg Val Arg Val Ile
            100                 105                 110

Leu Ala Gly Asn Ala Phe Thr Ala Gly Lys Val Ile Ile Cys Cys Val
        115                 120                 125

Pro Pro Gly Phe Gln Ser Arg Thr Leu Ser Ile Ala Gln Ala Thr Leu
    130                 135                 140

Phe Pro His Ile Ile Ala Asp Val Arg Thr Leu Glu Pro Ile Glu Ile
145                 150                 155                 160

Pro Leu Glu Asp Val Arg Asn Thr Leu Tyr His Thr Asn Asp Asn Gln
                165                 170                 175

Pro Thr Met Arg Leu Leu Cys Met Leu Tyr Thr Pro Leu Arg Thr Gly
            180                 185                 190

Gly Gly Ser Gly Gly Thr Asp Ala Phe Val Val Ala Gly Arg Val Leu
        195                 200                 205
```

```
Thr Ser Pro Ser Pro Asp Phe Asn Phe Leu Phe Leu Val Pro Pro Thr
    210                 215                 220

Val Glu Gln Lys Thr Arg Pro Phe Ser Val Pro Asn Ile Pro Leu Gln
225                 230                 235                 240

Leu Leu Ser Asn Ser Arg Val Pro Asn Leu Ile Gln Ser Met Val Pro
                245                 250                 255

Ser Pro Asp Gln Ala Gln Asn Val Gln Phe Gln Asn Gly Arg Cys Thr
            260                 265                 270

Thr Asp Gly Gln Leu Leu Gly Thr Thr Pro Val Ser Val Ser Gln Ile
        275                 280                 285

Leu Lys Phe Arg Gly Lys Val Ser Ala Gly Ser Lys Val Ile Asn Leu
    290                 295                 300

Thr Glu Leu Asp Gly Ser Pro Phe Leu Ala Phe Glu Ala Pro Ala Pro
305                 310                 315                 320

Thr Gly Phe Pro Asp Leu Gly Thr Ser Asp Trp His Ile Glu Met Ser
                325                 330                 335

Leu Asn Ser Asn Ser Gln Ser Ser Gly Asn Pro Ile Leu Leu Arg Asp
            340                 345                 350

Ile Gln Pro Asn Ser Ser Asp Phe Val Pro His Leu Gly Ser Val Ala
        355                 360                 365

Val Thr Thr Ala Ile Asp Thr Ala Gly Asp Tyr Thr Gly Thr Ile Gln
    370                 375                 380

Trp Thr Ser Gln Pro Ser Asn Val Thr Pro Val Pro Asp Val Asn Phe
385                 390                 395                 400

Trp Thr Ile Pro Gln Tyr Gly Ser Asn Leu Ala Glu Ala Ser Gln Leu
                405                 410                 415

Ala Pro Val Val Tyr Pro Pro Gly Phe Gly Glu Ala Ile Val Tyr Phe
            420                 425                 430

Met Ser Pro Ile Pro Gly Pro Asn Thr Ala His Lys Pro Asn Leu Val
        435                 440                 445

Pro Cys Leu Leu Pro Gln Glu Phe Val Thr His Phe Val Ser Glu Gln
    450                 455                 460

Ala Pro Ser Met Gly Glu Ala Ala Leu Val His Tyr Val Asp Pro Asp
465                 470                 475                 480

Thr Asn Arg Asn Leu Gly Glu Phe Lys Leu Tyr Pro Glu Gly Phe Ile
                485                 490                 495

Thr Cys Val Pro Asn Gly Thr Gly Pro Gln Gln Leu Pro Leu Asn Gly
            500                 505                 510

Val Phe Val Phe Ala Ser Trp Val Ser Arg Phe Tyr Gln Leu Lys Pro
        515                 520                 525

Val Gly Thr Ala Asn Ser Ala Arg Gly Arg Leu Gly Val Arg Arg
    530                 535                 540


<210> SEQ ID NO 16
<211> LENGTH: 541
<212> TYPE: PRT
<213> ORGANISM: Norovirus

<400> SEQUENCE: 16

Met Met Met Ala Ser Lys Asp Ala Thr Pro Ser Ala Asp Gly Ala Asn
1               5                   10                  15

Gly Ala Gly Gln Leu Val Pro Glu Val Asn Asn Ala Glu Pro Leu Pro
            20                  25                  30

Leu Asp Pro Val Ala Gly Ala Ser Thr Ala Leu Ala Thr Ala Gly Gln
        35                  40                  45
```

```
Val Asn Met Ile Asp Pro Trp Ile Phe Asn Asn Phe Val Gln Ala Pro
    50                  55                  60

Gln Gly Glu Phe Thr Ile Ser Pro Asn Asn Thr Pro Gly Asp Ile Leu
65                  70                  75                  80

Phe Asp Leu Gln Leu Gly Pro His Leu Asn Pro Phe Leu Ala His Leu
                85                  90                  95

Ser Gln Met Tyr Asn Gly Trp Val Gly Asn Met Arg Val Arg Val Ile
            100                 105                 110

Leu Ala Gly Asn Ala Phe Thr Ala Gly Lys Val Ile Ile Cys Cys Val
        115                 120                 125

Pro Pro Gly Phe Gln Ser Arg Thr Leu Ser Ile Ala Gln Ala Thr Leu
    130                 135                 140

Phe Pro His Val Ile Ala Asp Val Arg Thr Leu Glu Pro Leu Glu Ile
145                 150                 155                 160

Pro Leu Glu Asp Val Arg Asn Thr Leu Tyr His Asn Asn Asp Ser Gln
                165                 170                 175

Pro Thr Met Arg Leu Leu Cys Met Leu Tyr Thr Pro Leu Arg Thr Gly
            180                 185                 190

Gly Gly Ser Gly Gly Thr Asp Ala Phe Val Val Ala Gly Arg Val Leu
        195                 200                 205

Thr Cys Pro Ser Pro Asp Phe Asn Phe Leu Phe Leu Val Pro Pro Thr
    210                 215                 220

Val Glu Gln Lys Thr Arg Pro Phe Ser Val Pro Asn Ile Pro Leu Gln
225                 230                 235                 240

Asn Leu Ser Asn Ser Arg Val Pro Ser Leu Ile Gln Ser Met Val Leu
                245                 250                 255

Ser Ser Asp His Ala Gln Thr Val Gln Phe Gln Asn Gly Arg Cys Thr
            260                 265                 270

Thr Asp Gly His Leu Leu Gly Thr Thr Pro Val Ser Ser Gly Gln Leu
        275                 280                 285

Met Lys Phe Arg Gly Lys Val Thr Pro Gly Ser Lys Val Leu Asn Leu
    290                 295                 300

Thr Glu Leu Asp Gly Ser Pro Phe Leu Ala Phe Glu Pro Pro Ala Pro
305                 310                 315                 320

Ala Gly Phe Pro Asp Leu Gly Lys Cys Asp Trp His Ile Glu Met Ser
                325                 330                 335

Leu Tyr Gln Val Asn Asn Gln Asp Asn Pro Ile Val Leu Arg Ala Ile
            340                 345                 350

Glu Pro Asn Ser Ser Ser Phe Val Pro His Leu Gly Ser Val Ser Phe
        355                 360                 365

Asn Gln Asn Val Asp Ala Ala Gly Asp Tyr Val Cys Thr Ile Gln Tyr
    370                 375                 380

Thr Ser Pro Pro Ser Asn Ser His Asp Ala Asp Val Asp Phe Trp Ser
385                 390                 395                 400

Ile Pro Asp Tyr Gly Ser Asn Leu Ala Glu Ala Ser Gln Leu Ala Pro
                405                 410                 415

Val Val Tyr Pro Pro Gly Phe Gly Glu Ala Ile Val Tyr Phe Met Ser
            420                 425                 430

Arg Val Pro Gly Trp Asn Arg Thr Asn Arg Leu Asn Leu Val Pro Cys
        435                 440                 445

Leu Leu Pro Gln Glu Phe Ile Gly His Phe Val Ser Glu Gln Ala Pro
    450                 455                 460
```

-continued

```
Ala Ile Gly Glu Ala Ala Leu Leu His Tyr Val Asp Pro Asp Thr Asn
465                 470                 475                 480

Arg Asn Leu Gly Glu Phe Lys Leu Tyr Pro Glu Gly Phe Ile Thr Cys
                485                 490                 495

Val Pro Asn Gly Thr Gly Pro Gln Gln Leu Pro Leu Asn Gly Val Phe
            500                 505                 510

Val Phe Ser Ser Trp Val Ser Arg Phe Tyr Gln Leu Lys Pro Val Gly
        515                 520                 525

Thr Ala Ser Ser Ala Arg Gly Arg Leu Gly Ile Arg Arg
    530                 535                 540


<210> SEQ ID NO 17
<211> LENGTH: 539
<212> TYPE: PRT
<213> ORGANISM: Norovirus

<400> SEQUENCE: 17

Met Met Met Ala Ser Lys Asp Ala Pro Thr Ser Pro Asp Gly Ala Ser
1               5                   10                  15

Gly Ala Gly Gln Leu Val Pro Glu Ala Asn Thr Ala Glu Gln Ile Ser
            20                  25                  30

Met Asp Pro Val Ala Gly Ala Ser Thr Ala Val Ala Thr Ala Gly Gln
        35                  40                  45

Val Asn Met Ile Asp Pro Trp Ile Phe Asn Asn Phe Val Gln Ala Pro
    50                  55                  60

Gln Gly Glu Phe Thr Ile Ser Pro Asn Asn Thr Pro Gly Asp Ile Leu
65                  70                  75                  80

Phe Asp Leu Gln Leu Gly Pro His Leu Asn Pro Phe Leu Ala His Leu
                85                  90                  95

Ser Gln Met Tyr Asn Gly Trp Val Gly Asn Met Arg Val Arg Ile Leu
            100                 105                 110

Leu Ala Gly Asn Ala Phe Thr Ala Gly Lys Ile Ile Ile Cys Cys Val
        115                 120                 125

Pro Pro Gly Phe Asp Ala Arg Ile Leu Thr Ile Ala Gln Ala Thr Leu
    130                 135                 140

Phe Pro His Leu Ile Ala Asp Val Arg Thr Leu Glu Pro Val Glu Leu
145                 150                 155                 160

Pro Leu Glu Asp Val Arg Asn Val Leu Tyr His Asn Ser Ser Gln Pro
                165                 170                 175

Gln Pro Thr Met Arg Leu Val Ala Met Leu Tyr Thr Pro Leu Arg Thr
            180                 185                 190

Gly Gly Gly Ser Gly Gly Thr Asp Ala Phe Val Val Ala Gly Arg Val
        195                 200                 205

Leu Thr Cys Pro Ala Pro Asp Phe Ser Phe Leu Phe Leu Val Pro Pro
    210                 215                 220

Ser Val Glu Gln Lys Thr Arg Val Phe Ser Val Pro Asn Ile Pro Leu
225                 230                 235                 240

Lys Asp Leu Ser Asn Ser Arg Val Pro Val Pro Ile Gln Gly Met Phe
                245                 250                 255

Met Ser Pro Asp Val Asn Gln Ser Val Gln Phe Gln Asn Gly Arg Cys
            260                 265                 270

Gln Ile Asp Gly Gln Leu Gln Gly Thr Thr Pro Val Ser Leu Ser Gln
        275                 280                 285

Leu Cys Lys Ile Arg Gly Lys Thr Ser Ser Asn Ala Arg Val Leu Asn
    290                 295                 300
```

Leu Ser Glu Val Asp Gly Thr Pro Phe Ile Pro Leu Glu Ser Pro Ala
305 310 315 320

Pro Val Gly Phe Pro Asp Leu Gly Gly Cys Asp Trp His Val Asn Phe
325 330 335

Thr Phe Gln Ala Gln Asn Gln Asp Pro Ser Gln Ser Val Thr Phe Ala
340 345 350

Thr Asn Asp Ala Ser Phe Val Pro Tyr Leu Gly Ser Ile Ser Pro His
355 360 365

Asn Gly Gly Asp Phe His Ala Gly Asp Ile Ile Gly Ser Leu Gly Trp
370 375 380

Ile Ser Ala Pro Ser Asp Asn Thr Gln Leu Asn Val Trp Thr Ile Pro
385 390 395 400

Lys Tyr Gly Ser Ser Leu Gln Met Ser Leu Thr Leu His Leu Leu Cys
405 410 415

Ser Pro Arg Leu Trp Glu Val Ile Leu Tyr Phe Tyr Ser Thr Phe Pro
420 425 430

Gly Ser Gly Gln Pro Ser Gln Leu Gln Val Pro Cys Leu Leu Pro Gln
435 440 445

Glu Phe Ile Thr His Phe Cys Asn Glu Gln Ala Pro Ile Ala Gly Glu
450 455 460

Ala Ala Leu Leu His Tyr Val Asp Pro Asp Thr Gly Arg Asn Leu Gly
465 470 475 480

Glu Phe Lys Leu Tyr Pro Asp Gly Phe Met Thr Cys Val Pro Asn Ser
485 490 495

Val Ser Ser Gly Pro Gln Thr Leu Pro Ile Asn Gly Val Phe Val Phe
500 505 510

Val Ser Trp Val Ser Arg Phe Tyr Gln Leu Lys Pro Val Gly Thr Ala
515 520 525

Ser Ala Ala Arg Arg Leu Gly Leu Arg Arg Ile
530 535

<210> SEQ ID NO 18
<211> LENGTH: 540
<212> TYPE: PRT
<213> ORGANISM: Norovirus

<400> SEQUENCE: 18

Met Met Met Ala Ser Lys Asp Val Pro Thr Ser Pro Asp Gly Ala Ser
1 5 10 15

Gly Ala Gly Gln Leu Val Pro Glu Val Asn Thr Ala Asp Gln Ile Ser
20 25 30

Met Asp Pro Val Ala Gly Ala Ser Thr Ala Val Ala Thr Ala Gly Gln
35 40 45

Val Asn Met Ile Asp Pro Trp Ile Phe Asn Asn Phe Val Gln Ala Pro
50 55 60

Gln Gly Glu Phe Thr Ile Ser Pro Asn Asn Thr Pro Gly Asp Ile Leu
65 70 75 80

Phe Asp Leu Gln Leu Gly Pro His Leu Asn Pro Phe Leu Ala His Leu
85 90 95

Ser Gln Met Tyr Asn Gly Trp Val Gly Asn Met Arg Val Arg Ile Leu
100 105 110

Leu Ala Gly Asn Ala Phe Thr Ala Gly Lys Ile Ile Ile Cys Cys Val
115 120 125

Pro Pro Gly Phe Asp Ala Arg Ile Leu Thr Ile Ala Gln Ala Thr Leu

```
    130                 135                 140

Phe Pro His Leu Ile Ala Asp Val Arg Thr Leu Glu Pro Val Glu Leu
145                 150                 155                 160

Pro Leu Glu Asp Val Arg Asn Val Leu Tyr His Asn Ser Ser Gln Pro
                165                 170                 175

Gln Pro Thr Met Arg Leu Val Ala Met Leu Tyr Thr Pro Leu Arg Thr
            180                 185                 190

Gly Gly Gly Ser Gly Gly Thr Asp Ala Phe Val Val Ala Gly Arg Val
        195                 200                 205

Leu Thr Cys Pro Ala Pro Asp Phe Ser Phe Leu Phe Leu Val Pro Pro
    210                 215                 220

Ser Val Glu Gln Lys Thr Arg Val Phe Ser Val Pro Asn Ile Pro Leu
225                 230                 235                 240

Lys Asp Leu Ser Asn Ser Arg Val Pro Thr Leu Ile Gln Gly Met Phe
                245                 250                 255

Val Ser Pro Asp Val Asn Gln Ser Val Gln Phe Gln Asn Gly Arg Cys
            260                 265                 270

Gln Ile Asp Gly Gln Leu Gln Gly Thr Thr Pro Val Ser Leu Ser Gln
        275                 280                 285

Leu Cys Lys Ile Arg Gly Lys Thr Ser Ser Asn Thr Arg Val Leu Asn
    290                 295                 300

Leu Ser Glu Val Asp Gly Thr Pro Phe Val Pro Leu Glu Ser Pro Ala
305                 310                 315                 320

Pro Val Gly Phe Pro Asp Ile Gly Gly Cys Asp Trp His Val Gly Phe
                325                 330                 335

Thr Phe Glu Ala Arg Asp Gln Gly Pro Ser Gln Asn Val Thr Phe Ala
            340                 345                 350

Thr Asn Asp Ser Ser Phe Val Pro Tyr Leu Gly Ser Ile Ser Pro His
        355                 360                 365

Asn Gly Asp Gly Phe His Ser Gly Asp Ile Ile Gly Ser Leu Asp Trp
    370                 375                 380

Ile Ser Ala Pro Ser Asp Gly Ser Ala Leu Asp Val Trp Ser Ile Pro
385                 390                 395                 400

Lys Tyr Gly Ser Ser Leu Pro Asp Val Thr His Leu Ala Pro Ala Val
                405                 410                 415

Phe Pro Pro Gly Phe Gly Glu Val Ile Leu Tyr Phe His Ser Lys Phe
            420                 425                 430

Pro Gly Ser Gly Pro Thr Asp Lys Leu Arg Val Pro Cys Leu Met Pro
        435                 440                 445

Gln Glu Phe Ile Thr His Phe Cys Asp Glu Gln Ala Pro Ile Ala Gly
    450                 455                 460

Glu Ala Ala Leu Leu His Tyr Val Asp Pro Asp Ala Gly Arg Asn Leu
465                 470                 475                 480

Gly Glu Phe Lys Leu Tyr Pro Asp Gly Phe Met Thr Cys Val Pro Asn
                485                 490                 495

Ser Ile Ser Ser Gly Pro Gln Thr Leu Pro Ile Asn Gly Val Phe Val
            500                 505                 510

Phe Val Ser Trp Val Ser Arg Phe Tyr Gln Leu Lys Pro Val Gly Thr
        515                 520                 525

Ala Ser Met Ala Arg Arg Leu Gly Leu Arg Arg Ile
    530                 535                 540
```

<210> SEQ ID NO 19

<211> LENGTH: 539
<212> TYPE: PRT
<213> ORGANISM: Norovirus

<400> SEQUENCE: 19

```
Met Met Met Ala Ser Lys Asp Ala Pro Ser Asn Met Asp Gly Thr Ser
1               5                   10                  15

Gly Ala Gly Gln Leu Val Pro Glu Val Asn Ala Ala Glu Pro Leu Pro
            20                  25                  30

Leu Glu Pro Val Val Gly Ala Ala Thr Ala Ala Ala Thr Ala Gly Gln
        35                  40                  45

Val Asn Leu Ile Asp Pro Trp Ile Met Asn Asn Phe Val Gln Ala Pro
    50                  55                  60

Glu Gly Glu Phe Thr Ile Ser Pro Asn Asn Thr Pro Gly Asp Ile Leu
65                  70                  75                  80

Phe Asp Leu His Leu Gly Pro His Leu Asn Pro Phe Leu Gln His Leu
                85                  90                  95

Ser Gln Met Tyr Asn Gly Trp Val Gly Asn Met Arg Val Arg Val Met
            100                 105                 110

Leu Ala Gly Asn Ala Phe Thr Ala Gly Lys Ile Ile Ile Cys Cys Val
        115                 120                 125

Pro Pro Gly Phe Ala Ser Gln Asn Ile Ser Ile Gly Gln Ala Thr Met
    130                 135                 140

Phe Pro His Val Ile Ala Asp Val Arg Val Leu Glu Pro Ile Glu Ile
145                 150                 155                 160

Pro Leu Asp Asp Val Arg Asn Val Leu Phe His Thr Asn Glu Asn Arg
                165                 170                 175

Pro Thr Met Arg Leu Leu Cys Met Leu Tyr Thr Pro Leu Arg Ala Gly
            180                 185                 190

Gly Ala Ser Ser Gly Thr Asp Pro Phe Val Ile Ala Gly Arg Val Leu
        195                 200                 205

Thr Cys Pro Ser Pro Asp Phe Asn Phe Leu Phe Leu Val Pro Pro Ser
    210                 215                 220

Val Glu Gln Lys Thr Arg Gln Leu Thr Val Pro Asn Ile Pro Leu Asn
225                 230                 235                 240

Asn Leu Ala Asn Ser Arg Val Pro Ala Met Ile Asn Lys Met Thr Val
                245                 250                 255

Ser Thr Asp Gln Asn Gln Val Val Gln Phe Gln Asn Gly Arg Cys Thr
            260                 265                 270

Leu Glu Gly Gln Leu Leu Gly Thr Thr Pro Val Ser Ala Ser Gln Val
        275                 280                 285

Ala Arg Ile Arg Gly Lys Val Phe Ser Thr Ala Ser Gly Lys Gly Leu
    290                 295                 300

Asn Leu Thr Glu Leu Asp Gly Thr Pro Tyr His Ala Phe Glu Ser Pro
305                 310                 315                 320

Ala Pro Leu Gly Phe Pro Asp Ile Gly Ala Cys Asp Trp His Val Ser
                325                 330                 335

Thr Phe Lys Val Asp Gln Asn Leu Ser Gly Asp Pro Met Ser Arg Leu
            340                 345                 350

Asp Val Lys Gln Asn Ala Pro Phe Ala Pro His Leu Gly Ser Ile Glu
        355                 360                 365

Phe Thr Ser Asp Gln Asp Pro Thr Gly Asp Gln Leu Gly Thr Leu Ala
    370                 375                 380

Trp Val Ser Pro Ser Thr Ser Gly Ala Arg Val Asp Pro Trp Lys Ile
```

```
385                 390                 395                 400

Pro Ser Tyr Gly Ser Thr Val Thr Glu Ser Thr His Leu Ala Pro Pro
                405                 410                 415

Ile Phe Pro Pro Gly Phe Gly Glu Ala Ile Val Tyr Phe Met Ser Asp
            420                 425                 430

Phe Pro Ile Val Ser Gly Asn Thr Ala Gln Val Pro Cys Thr Leu Pro
        435                 440                 445

Gln Glu Phe Val Ser His Phe Val Glu Gln Gln Ala Pro Val Arg Gly
    450                 455                 460

Glu Ala Ala Leu Leu His Tyr Val Asp Pro Asp Thr His Arg Asn Leu
465                 470                 475                 480

Gly Glu Phe Lys Leu Tyr Pro Asp Gly Phe Ile Thr Cys Val Pro Asn
                485                 490                 495

Thr Gly Gly Gly Pro Gln Asn Leu Pro Thr Asn Gly Val Phe Val Phe
            500                 505                 510

Ser Ser Trp Val Ser Arg Tyr Tyr Gln Leu Lys Pro Val Gly Thr Ala
        515                 520                 525

Gly Pro Ala Arg Arg Leu Gly Val Arg Arg Val
    530                 535


<210> SEQ ID NO 20
<211> LENGTH: 539
<212> TYPE: PRT
<213> ORGANISM: Norovirus

<400> SEQUENCE: 20

Met Met Met Ala Ser Lys Asp Ala Pro Ser Asn Met Asp Gly Thr Ser
1               5                   10                  15

Gly Ala Gly Gln Leu Val Pro Glu Val Asn Ala Ala Glu Pro Leu Pro
            20                  25                  30

Leu Glu Pro Val Val Gly Ala Ala Thr Ala Val Ala Thr Ala Gly Gln
        35                  40                  45

Val Asn Leu Ile Asp Pro Trp Ile Met Asn Asn Phe Val Gln Ala Pro
    50                  55                  60

Glu Gly Glu Phe Thr Ile Ser Pro Asn Asn Thr Pro Gly Asp Ile Leu
65                  70                  75                  80

Phe Asp Leu Gln Leu Gly Pro His Leu Asn Pro Phe Leu Gln His Leu
                85                  90                  95

Ser Gln Met Tyr Asn Gly Trp Val Gly Asn Met Arg Val Arg Val Met
            100                 105                 110

Leu Ala Gly Asn Ala Phe Thr Ala Gly Lys Ile Ile Ile Cys Cys Val
        115                 120                 125

Pro Pro Gly Phe Ala Ser Gln Asn Ile Ser Ile Gly Gln Ala Thr Met
    130                 135                 140

Phe Pro His Val Ile Ala Asp Val Arg Val Leu Glu Pro Ile Glu Ile
145                 150                 155                 160

Pro Leu Asp Asp Val Arg Asn Val Leu Phe His Thr Asn Glu Ser Arg
                165                 170                 175

Pro Thr Met Arg Leu Leu Cys Met Leu Tyr Thr Pro Leu Arg Ala Gly
            180                 185                 190

Gly Ala Ser Ser Gly Thr Asp Pro Phe Val Ile Ala Gly Arg Val Leu
        195                 200                 205

Thr Cys Pro Ser Pro Asp Phe Asn Phe Leu Phe Leu Val Pro Pro Ser
    210                 215                 220
```

-continued

Val Glu Gln Lys Thr Arg Gln Leu Thr Val Pro Asn Ile Pro Leu Asn
225 230 235 240

Asn Leu Ala Asn Ser Arg Val Pro Ala Met Ile Asn Lys Met Thr Val
245 250 255

Ser Thr Asp Gln Ser Gln Val Val Gln Phe Gln Asn Gly Arg Cys Thr
260 265 270

Leu Glu Gly Gln Leu Leu Gly Thr Thr Pro Val Ser Ala Ser Gln Val
275 280 285

Ala Arg Ile Arg Gly Lys Val Phe Ser Thr Ala Ser Gly Lys Gly Leu
290 295 300

Asn Leu Thr Glu Leu Asp Gly Thr Pro Tyr His Ala Phe Glu Ser Pro
305 310 315 320

Ala Pro Leu Gly Phe Pro Asp Ile Gly Ala Cys Asp Trp His Val Ser
325 330 335

Thr Phe Lys Val Asp Gln Asn Leu Ser Gly Asp Pro Met Ser Arg Leu
340 345 350

Asp Ile Lys Gln Asn Ala Pro Phe Ala Pro His Leu Gly Ser Ile Glu
355 360 365

Phe Thr Ser Asp Gln Glu Pro Thr Gly Asp Gln Leu Gly Thr Leu Ala
370 375 380

Trp Val Ser Pro Ser Thr Ser Gly Ala Arg Val Asp Pro Trp Lys Ile
385 390 395 400

Pro Ser Tyr Gly Ser Thr Val Thr Glu Ser Thr His Leu Ala Pro Pro
405 410 415

Ile Phe Pro Pro Gly Phe Gly Glu Ala Ile Val Tyr Phe Met Ser Asp
420 425 430

Phe Pro Ile Val Ser Gly Asn Thr Ala Gln Val Pro Cys Thr Leu Pro
435 440 445

Gln Glu Phe Val Ser His Phe Val Glu Gln Gln Ala Pro Ile Arg Gly
450 455 460

Glu Ala Ala Leu Leu His Tyr Val Asp Pro Asp Thr His Arg Asn Leu
465 470 475 480

Gly Glu Phe Lys Leu Tyr Pro Asp Gly Phe Ile Thr Cys Val Pro Asn
485 490 495

Thr Gly Gly Gly Pro Gln Asn Leu Pro Ile Asn Gly Val Phe Val Phe
500 505 510

Ser Ser Trp Val Ser Arg Tyr Tyr Gln Leu Lys Pro Val Gly Thr Ala
515 520 525

Gly Pro Ala Arg Arg Leu Gly Val Arg Arg Val
530 535

<210> SEQ ID NO 21
<211> LENGTH: 543
<212> TYPE: PRT
<213> ORGANISM: Norovirus

<400> SEQUENCE: 21

Met Met Met Ala Ser Lys Asp Ala Pro Thr Asn Met Asp Gly Thr Ser
1 5 10 15

Gly Ala Gly Gln Leu Val Pro Glu Ala Asn Thr Ala Glu Pro Leu Pro
20 25 30

Ile Lys Pro Val Ala Gly Ala Ala Thr Ala Val Ala Thr Ala Gly Gln
35 40 45

Val Asn Met Ile Asp Pro Trp Ile Met Asn Asn Phe Val Gln Ala Pro
50 55 60

```
Gln Gly Glu Phe Thr Ile Ser Pro Asn Asn Thr Pro Gly Asp Ile Leu
65                  70                  75                  80

Phe Asp Leu Gln Leu Gly Pro His Leu Asn Pro Phe Leu Ala His Leu
                85                  90                  95

Ser Arg Met Tyr Asn Gly Trp Val Gly Asn Met Gln Val Arg Ile Met
            100                 105                 110

Leu Ala Gly Asn Ala Phe Ser Ala Gly Lys Ile Ile Val Cys Cys Ile
        115                 120                 125

Pro Pro Gly Phe Ser Ser Gln Ser Ile Ser Ile Ala Gln Ala Thr Met
    130                 135                 140

Phe Pro His Val Ile Ala Asp Val Arg Val Leu Glu Pro Ile Asp Val
145                 150                 155                 160

Pro Leu Asp Asp Val Arg Asn Val Leu Phe His Asn Asn Asp Asn Pro
                165                 170                 175

Gln Thr Met Arg Leu Leu Cys Met Leu Tyr Thr Pro Leu Arg Ser Gly
            180                 185                 190

Gly Thr Ser Ser Gly Thr Asp Pro Phe Val Ile Ala Gly Arg Val Leu
        195                 200                 205

Thr Cys Pro Thr Pro Asp Phe Ser Phe Leu Phe Leu Val Pro Pro Asp
    210                 215                 220

Ile Glu Gln Arg Thr Lys Pro Phe Ser Val Pro Asn Ile Pro Met Asn
225                 230                 235                 240

Leu Met Ser Asn Ser Arg Val Ser Met Leu Ile Asp Gly Met Met Val
                245                 250                 255

Ser Asn Asp Gln Asn Gln Val Pro Gln Phe Gln Asn Gly Arg Val Thr
            260                 265                 270

Leu Asp Gly Gln Leu Gln Gly Thr Thr Thr Val Ser Ala Ala Cys Val
        275                 280                 285

Ala Arg Met Arg Gly Arg Ile Phe Asn Asn Asn Gly Asn Tyr Gly Val
    290                 295                 300

Asn Leu Thr Glu Leu Asp Gly Asn Pro Tyr His Ala Phe Asp Ser Pro
305                 310                 315                 320

Ala Pro Leu Gly Phe Pro Asp Phe Gly Asn Cys Asp Leu His Met Thr
                325                 330                 335

Phe Val Lys Ile Asn Pro Asn Glu Leu Ser Ser Gly Asp Pro Ser Gly
            340                 345                 350

Lys Val Val Ile Arg Ser Tyr Asp Ala Thr Phe Ala Pro His Leu Gly
        355                 360                 365

Thr Val Lys Leu Glu Asn Asp Asp Glu Leu Ala Arg Phe Val Gly Lys
    370                 375                 380

Glu Val Val Leu Glu Leu Thr Trp Val Ser Asn Arg Glu Gly Ala Thr
385                 390                 395                 400

Leu Asn Leu Trp Ala Val Pro Asn Tyr Gly Ser Ser Leu Thr Gln Ala
                405                 410                 415

Ser Gln Leu Ala Pro Pro Ile Tyr Pro Pro Gly Phe Gly Glu Ala Ile
            420                 425                 430

Val Tyr Phe Thr Ser Thr Phe Pro Thr Val Ser Asn Pro Lys Val Pro
        435                 440                 445

Cys Thr Leu Pro Gln Glu Phe Val Ser His Phe Val Asn Glu Gln Ala
    450                 455                 460

Pro Thr Arg Gly Asp Ala Ala Leu Leu His Tyr Val Asp Pro Asp Thr
465                 470                 475                 480
```

-continued

```
His Arg Asn Leu Gly Glu Phe Lys Met Tyr Pro Glu Gly Tyr Met Thr
                485                 490                 495

Cys Val Pro Asn Ala Gly Gly Gly Pro Gln Thr Leu Pro Ile Asn Gly
            500                 505                 510

Val Phe Val Phe Ile Ser Trp Val Ser Arg Tyr Tyr Gln Leu Lys Pro
        515                 520                 525

Val Gly Thr Ala Gly Ala Ala Arg Arg Leu Gly Leu Arg Arg Ser
    530                 535                 540


<210> SEQ ID NO 22
<211> LENGTH: 550
<212> TYPE: PRT
<213> ORGANISM: Norovirus

<400> SEQUENCE: 22

Met Met Met Ala Ser Lys Asp Ala Thr Ser Asn Met Asp Gly Thr Ser
1               5                   10                  15

Gly Ala Gly Gln Leu Val Pro Glu Asn Asn Asn Thr Ser Glu Pro Ile
            20                  25                  30

Asn Met Glu Pro Val Ala Gly Ala Val Thr Ala Ala Ala Thr Ala Gly
        35                  40                  45

Gln Val Asn Met Ile Asp Pro Trp Ile Met Asn Asn Tyr Val Gln Ala
    50                  55                  60

Pro Gln Gly Glu Phe Thr Ile Ser Pro Asn Asn Thr Pro Gly Asp Ile
65                  70                  75                  80

Leu Phe Asp Leu Gln Leu Gly Pro His Leu Asn Pro Phe Leu Ala His
                85                  90                  95

Leu Ser Gln Met Tyr Asn Gly Trp Val Gly Asn Met Lys Val Arg Val
            100                 105                 110

Val Leu Ala Gly Asn Ala Phe Ser Ala Gly Lys Ile Ile Val Cys Cys
        115                 120                 125

Ile Pro Pro Gly Phe Ser Ala Pro Asn Ile Ser Ile Ala Gln Ala Thr
    130                 135                 140

Met Phe Pro His Val Ile Ala Asp Val Arg Val Leu Glu Pro Ile Asp
145                 150                 155                 160

Ile Pro Leu Asp Asp Val Arg Asn Val Leu Phe His Asn Asn Asp Asn
                165                 170                 175

Gly Asn Gln Thr Met Arg Leu Leu Cys Met Leu Tyr Thr Pro Leu Arg
            180                 185                 190

Ser Gly Gly Thr Ser Ser Gly Thr Asp Pro Phe Val Ile Ala Gly Arg
        195                 200                 205

Val Leu Thr Cys Pro Thr Pro Asp Phe Asn Phe Leu Phe Leu Val Pro
    210                 215                 220

Pro Thr Val Glu Gln Lys Thr Lys Gln Phe Ser Val Pro Asn Leu Pro
225                 230                 235                 240

Leu Asn Val Met Ser Asn Ser Arg Val Pro Ser Leu Leu Asn Ala Met
                245                 250                 255

Val Val Ser Pro Asp Gln Ala Gln Val Val Gln Phe Gln Asn Gly Arg
            260                 265                 270

Cys Thr Leu Asp Gly Gln Met Leu Gly Thr Thr Thr Val Ser Ala Ser
        275                 280                 285

Cys Val Ala Arg Phe Arg Gly Lys Thr Phe Gln Ala Pro Asp Asn Arg
    290                 295                 300

Leu Gly Ile Asn Leu Ala Glu Ile Ser Gly Glu Pro Tyr His Ala Phe
305                 310                 315                 320
```

```
Glu Ser Pro Ala Pro Leu Gly Phe Pro Asp Phe Gly Asp Gly Asp Trp
            325                 330                 335

His Val Thr Ala Thr Lys Val Thr Pro Ser Gln Leu Glu Ala Asn Asp
            340                 345                 350

Pro Val Val Met Gly Asn Val Gln Pro Tyr Asn Pro Gln Phe Ala Pro
        355                 360                 365

His Leu Gly Thr Leu Val Val Glu Asn Pro Thr Pro Asp Asn Val Thr
    370                 375                 380

Thr Gly Thr Asp Leu Leu Phe Asn Ile Thr Trp Leu Ser Asn Arg Ala
385                 390                 395                 400

Asn Asn Arg Phe Asn Pro Trp Val Ile Pro Asn Tyr Gly Ser Thr Leu
            405                 410                 415

Thr Glu Ala Ala Gln Leu Ala Pro Ser Ile Phe Pro Pro Gly Phe Gly
            420                 425                 430

Glu Thr Ile Val Tyr Phe Asn Ser Thr Phe Pro Ala Val Gly Ala Thr
        435                 440                 445

Thr His Ala Ala Ile Pro Cys Leu Leu Pro Gln Glu Phe Val Ala His
    450                 455                 460

Phe Val Asn Glu Gln Ala Pro Ile Arg Gly Glu Ala Ala Leu Leu His
465                 470                 475                 480

Tyr Ile Asp Pro Asp Thr His Arg Asn Leu Gly Glu Phe Lys Ile Tyr
            485                 490                 495

Pro Glu Gly Phe Val Thr Cys Val Pro Asn Val Gly Gly Thr Gly Pro
            500                 505                 510

Gln Ser Leu Pro Thr Asn Gly Ile Phe Val Phe Val Ser Trp Val Ser
        515                 520                 525

Arg Tyr Tyr Gln Leu Lys Pro Val Gly Thr Ala Gly Gln Ala Arg Arg
    530                 535                 540

Leu Gly Phe Arg Arg Val
545                 550
```

<210> SEQ ID NO 23
<211> LENGTH: 543
<212> TYPE: PRT
<213> ORGANISM: Norovirus

<400> SEQUENCE: 23

```
Met Lys Met Ala Ser Asn Asp Ala Ala Pro Ser Asn Asp Gly Ala Ala
1               5                   10                  15

Gly Leu Val Pro Glu Ile Asn Asn Glu Thr Met Ala Leu Glu Pro Val
            20                  25                  30

Ala Gly Gly Ala Ile Ala Ala Pro Leu Thr Gly Gln Thr Asn Phe Ile
        35                  40                  45

Asp Pro Trp Ile Arg Asn Asn Tyr Val Gln Ala Pro Asn Gly Glu Phe
    50                  55                  60

Thr Val Ser Pro Arg Asn Ser Pro Gly Glu Ile Leu Leu Asn Leu Glu
65                  70                  75                  80

Leu Gly Pro Glu Leu Asn Pro Phe Leu Ala His Leu Ser Arg Met Tyr
                85                  90                  95

Asn Gly Tyr Ala Gly Gly Ile Asp Val Gln Val Ile Met Ala Gly Asn
            100                 105                 110

Ala Phe Thr Ala Gly Lys Ile Ile Phe Ala Ala Val Pro Pro His Phe
        115                 120                 125

Pro Ile Asp Asn Ile Ser Pro Pro Gln Ile Thr Met Phe Pro His Ile
```

```
    130                 135                 140

Ile Ile Asp Val Arg Thr Leu Glu Pro Val Asn Ile Pro Leu Pro Asp
145                 150                 155                 160

Val Arg Asn Ser Phe Phe His Tyr Ser Gln Asn Asn Glu Pro Arg Met
                165                 170                 175

Arg Leu Leu Ala Met Leu Tyr Thr Pro Leu Arg Ser Asn Gly Ser Ala
            180                 185                 190

Asp Asp Val Phe Thr Val Ser Cys Arg Val Leu Thr Lys Pro Ser Ala
        195                 200                 205

Asp Phe Glu Phe Asn Tyr Leu Val Pro Pro Thr Val Glu Ser Arg Thr
    210                 215                 220

Lys Pro Phe Thr Ile Pro Ile Leu Thr Ile Gly Glu Met Thr Asn Ser
225                 230                 235                 240

Arg Phe Pro Val Ala Ile Asp Met Leu His Thr Ser Pro Thr Asp Asn
                245                 250                 255

Phe Ile Val Gln Pro Gln Asn Gly Arg Cys Thr Leu Asp Gly Glu Leu
            260                 265                 270

Gln Gly Thr Thr Gln Leu Val Thr Ser Asn Ile Cys Ala Phe Arg Gly
        275                 280                 285

Ser Ile Ser Gly His Glu Asn Asn Gly Asp Gln His Gln Trp His Phe
    290                 295                 300

Ser Ile Thr Asn Pro Asn Gly Thr Pro Phe Asp Pro Thr Glu Asp Val
305                 310                 315                 320

Pro Ala Pro Leu Gly Thr Pro Asp Phe Lys Gly Gln Leu Tyr Gly Val
                325                 330                 335

Ile Ser Gln Arg Asn Arg Glu Gly Ser Pro Gly Asn Gly Asn Gln Lys
            340                 345                 350

Ala Asn Arg Ser His Glu Gly Val Ile Ser Thr Val Ala Pro Arg Phe
        355                 360                 365

Thr Pro Lys Leu Gly Ser Val Met Ile Gly Thr Trp Thr Thr Asp Asp
    370                 375                 380

Ile Gln Asp Gln Pro Ser Arg Phe Thr Pro Val Gly Leu Asn Asp Asp
385                 390                 395                 400

Asp Asn Tyr Lys Gln Trp Glu Leu Pro Asn Tyr Ser Gly Ala Leu Thr
                405                 410                 415

Leu Asn Met Gly Leu Ala Pro Ser Val Phe Pro Thr Tyr Pro Gly Glu
            420                 425                 430

Gln Leu Leu Phe Phe Arg Ser Tyr Ile Pro Met Lys Gly Gly Tyr Gly
        435                 440                 445

Ser Pro Tyr Ile Asp Cys Leu Ile Pro Gln Glu Trp Ile Ser His Phe
    450                 455                 460

Tyr Gln Glu Ser Ala Pro Ser Gln Thr Asp Val Ala Leu Ile Arg Tyr
465                 470                 475                 480

Val Asn Pro Asp Thr Gly Arg Val Leu Phe Glu Ala Lys Leu His Arg
                485                 490                 495

Gln Gly Tyr Ile Thr Val Ala Lys Thr Gly Asp Ser Pro Ile Asn Val
            500                 505                 510

Pro Ala Asn Gly Tyr Phe Arg Phe Asp Ser Trp Val Ser Gln Phe Tyr
        515                 520                 525

Ser Leu Ala Pro Met Gly Thr Gly Asn Gly Arg Arg Arg Ile Gln
    530                 535                 540
```

<210> SEQ ID NO 24

<211> LENGTH: 555
<212> TYPE: PRT
<213> ORGANISM: Norovirus

<400> SEQUENCE: 24

Met Arg Met Ala Ser Ser Asp Ala Pro Val Ser Gly Thr Asp Gly Ala
1 5 10 15

Ala Gly Leu Val Pro Glu Ser Gln Gln Glu Val Leu Pro Leu Glu Pro
20 25 30

Val Ala Gly Val Gln Leu Ala Ala Pro Val Ala Gly Gln Ser Asn Ile
35 40 45

Ile Asp Pro Trp Ile Arg Met Asn Phe Val Gln Ala Pro Ala Gly Glu
50 55 60

Phe Thr Val Ser Pro Arg Asn Ala Pro Gly Glu Val Leu Ile Asp Leu
65 70 75 80

Glu Leu Gly Pro Glu Leu Asn Pro Tyr Leu Asn His Leu Ala Arg Met
85 90 95

Tyr Asn Gly Tyr Val Gly Gly Met Glu Val Glu Val Val Leu Ala Gly
100 105 110

Asn Ala Phe Thr Ala Gly Lys Ile Leu Phe Ala Ala Val Pro Pro Ser
115 120 125

Phe Pro Thr His Gly Ile Ser Ala Ala Gln Ala Thr Met Leu Pro His
130 135 140

Val Ile Val Asp Val Arg Gln Leu Glu Pro Val Arg Leu Pro Leu Pro
145 150 155 160

Asp Val Arg Asn Val Met Phe His Phe Cys Gln Glu Asn Lys Glu Pro
165 170 175

Arg Met Arg Ile Val Ala Ile Leu Tyr Thr Pro Leu Arg Ala Asn Gly
180 185 190

Ala Gly Asp Asp Val Phe Thr Val Ser Cys Arg Val Leu Thr Arg Pro
195 200 205

Ser Pro Asp Phe Asp Phe Ile Phe Leu Val Pro Pro Ser Val Glu Ser
210 215 220

Lys Leu Lys Gln Phe Thr Leu Pro Asn Leu Gln Pro Asn Glu Met Thr
225 230 235 240

Asn Ser Arg Phe Pro Thr Gly Ile Thr Gln Leu Tyr Thr Ser Pro Asn
245 250 255

Thr Asn Leu Val Val Gln Phe Gln Asn Gly Arg Cys Leu Leu Asp Gly
260 265 270

Thr Leu Leu Gly Thr Thr Pro Val Arg Ala Ala Asp Ile Cys Ser Phe
275 280 285

Arg Gly Val Thr Ser Thr Glu Val Asp Ala Thr Asp Ser Pro Arg Val
290 295 300

Ala Gly Ser His Arg Ile Met Val Gln Leu Lys Glu Pro Asp Gly Glu
305 310 315 320

Glu Phe Ser Pro Thr Gly Pro Asn Pro Ala Pro Val Gly Thr Pro Asp
325 330 335

Phe Gln Ala Ala Ile Phe Gly Thr Leu Ser Gln Arg Asn Thr Gly Gly
340 345 350

Thr Gly Gln Asn Ser Asn Arg Ala His Phe Ala Tyr Phe Tyr Thr Arg
355 360 365

Asn Pro Thr Phe Ala Pro Gly Ile Gly Thr Val Val Phe Ser Phe Asp
370 375 380

Thr Thr Asp Phe Gln Asn Arg Gln Pro Thr Lys Phe Ser Pro Ser Gly

-continued

```
385                 390                 395                 400

Val Phe Asp Asp Asp Ser Ser Glu Pro Phe Asn Gln Phe Ser Leu Pro
                405                 410                 415

Tyr Tyr Asn Gly Ser Leu Gly Ala Val Asp Ala Gly Lys Leu Ala Pro
            420                 425                 430

Pro Val Ala Pro Asn Tyr Pro Gly Glu Gln Ile Leu Tyr Phe Arg Gly
        435                 440                 445

Asn Ile Pro Phe Lys Gly Gly Tyr Gly Glu Gly Glu Ile Asp Ser Leu
    450                 455                 460

Leu Pro Gln Glu Trp Ile Thr His Phe Tyr Ala Glu Gln Ala Pro Thr
465                 470                 475                 480

Gln Gly Asp Ala Ala Leu Leu Arg Tyr Tyr Asn Pro Asp Thr Gly Arg
                485                 490                 495

Val Leu Phe Glu Cys Lys Leu His Arg Glu Gly Phe Ile Thr Ile Asn
            500                 505                 510

Tyr Thr Gly Ser Asn Ala Leu Ala Val Pro Val Asn Gly Val Phe Arg
        515                 520                 525

Phe Glu Gly Trp Val Asn Lys Phe Tyr Thr Leu Thr Pro Met Gly Asn
    530                 535                 540

Gly Asn Gly Arg Arg Gly Arg Arg Arg Glu Leu
545                 550                 555
```

<210> SEQ ID NO 25
<211> LENGTH: 555
<212> TYPE: PRT
<213> ORGANISM: Norovirus

<400> SEQUENCE: 25

```
Met Lys Met Ala Ser Lys Asp Ala Ser Pro Ser Thr Asp Gly Thr Ala
1               5                   10                  15

Asn Leu Val Pro Glu Ser Gln Gln Glu Val Leu Ala Leu Gln Pro Val
            20                  25                  30

Ala Gly Ala Gln Ile Ala Ala Pro Val Ala Gly Gln Phe Asn Val Ile
        35                  40                  45

Asp Pro Trp Ile Tyr Gln Asn Phe Val Gln Ala Pro Glu Gly Glu Phe
    50                  55                  60

Thr Val Ser Pro Arg Asn Ser Thr Gly Glu Ile Leu Met Asn Leu Glu
65                  70                  75                  80

Leu Gly Pro Gln Leu Asn Pro Tyr Leu Ala His Leu Ala Arg Met Tyr
                85                  90                  95

Asn Ala Tyr Ala Gly Gly Phe Glu Val Gln Val Leu Leu Ala Gly Asn
            100                 105                 110

Ala Phe Thr Ala Gly Lys Ile Ile Val Cys Ala Val Pro Pro Asn Phe
        115                 120                 125

Pro Leu Gln Asn Ile Ser Ala Ala Gln Ala Thr Gln Leu Pro His Val
    130                 135                 140

Val Val Asp Val Arg Gln Leu Glu Pro Val Val Leu Pro Leu Pro Asp
145                 150                 155                 160

Val Arg Ala Gly Phe Tyr His Tyr Asn Gln Val Glu Glu Ser Arg Met
                165                 170                 175

Arg Leu Val Ala Ile Leu Tyr Thr Pro Leu Arg Thr Asn Ser Ala Gly
            180                 185                 190

Asp Asp Ala Phe Thr Val Ser Cys Arg Ile Leu Thr Arg Pro Ala Pro
        195                 200                 205
```

Asp Phe Ser Phe Phe Phe Leu Ile Pro Pro Thr Ile Glu Ser Lys Thr
    210                 215                 220

Thr Pro Phe Thr Leu Pro Arg Leu Pro Ile Ser Glu Met Thr Asn Ser
225                 230                 235                 240

Arg Phe Pro Leu Val Ile Lys Gly Met Val Val Asp Pro Asn Leu Pro
                245                 250                 255

Leu Gln Ala Asn Phe Gln Asn Gly Arg Ile Thr Leu Asp Gly Glu Leu
            260                 265                 270

Gln Gly Thr Thr Leu Pro Thr Ser Thr Ser Ile Gly Arg Ile Ser Gly
        275                 280                 285

Thr His Met Ser Ser Thr Pro Ser Arg Ile Ile Gln His Glu Asp Ser
    290                 295                 300

Gly Asp Ser Thr Gln Pro Arg Val Phe Asn Pro Val Trp Met Asp Leu
305                 310                 315                 320

Thr Glu Asn Asn Trp Thr Glu Phe Gln Pro Phe Asn Asp Gln Pro Ala
                325                 330                 335

Pro Leu Gly Cys Pro Asp Phe Lys Ala Lys Ile Leu Gly Thr Leu Ile
            340                 345                 350

Arg Gln Pro Asn Asn Gly Ser Tyr Tyr Phe Asp Ala Tyr Leu Asp Thr
        355                 360                 365

Arg Gln His Gly Thr Phe Ala Pro Tyr Thr Gly His Ala Ala Val His
    370                 375                 380

Ser Asp Gln Gln Ala Gly His Leu Ala Gln Gly Tyr Lys Ile Gln Phe
385                 390                 395                 400

Ser Pro Thr Gly Ile Glu Ser Asp Gln Asn Thr Asp Leu Asn Gln Leu
                405                 410                 415

Pro Asp Tyr Gly Gly Ala Met Thr Val Ser Lys Gly Leu Ala Pro Ala
            420                 425                 430

Ala Ala Pro Asp Phe Pro Gly Glu Met Ile Leu Tyr Phe Val Ser Asp
        435                 440                 445

Met Pro Val Arg Asn Pro Asn Gly Glu Arg Arg Asp Thr Glu Ile Leu
    450                 455                 460

Cys Leu Leu Pro Gln Glu Met Val Thr His Phe Tyr Glu Gln Gln Ala
465                 470                 475                 480

Pro Ser Gln Gly Asp Val Ala Leu Val Arg Tyr Ile Asn Ala Glu Thr
                485                 490                 495

Gly Arg Val Met Phe Glu Gly Lys Leu His Arg Asn Gly Phe Phe Thr
            500                 505                 510

Val Ser Ala Thr Ala Arg Thr Leu Ile Val Pro Asp Gly Tyr Phe Arg
        515                 520                 525

Phe Asp Ser Trp Val Asn Arg Phe Tyr Thr Leu Ser Pro Met Gly Thr
    530                 535                 540

Gly Asn Gly Arg Arg Arg Ala Arg Met Leu Glu
545                 550                 555

<210> SEQ ID NO 26
<211> LENGTH: 535
<212> TYPE: PRT
<213> ORGANISM: Norovirus

<400> SEQUENCE: 26

Met Lys Met Ala Ser Asn Asp Ala Asn Pro Ser Ser Asp Gly Ser Ala
1               5                   10                  15

Asn Leu Val Pro Glu Ile Ser Asn Glu Val Met Ala Leu Glu Pro Val
            20                  25                  30

-continued

```
Ala Gly Ala Ala Ile Ala Ala Pro Val Ala Gly Gln Gln Asn Ile Ile
        35                  40                  45

Asp Pro Trp Ile Arg Asn Asn Phe Val Gln Ala Pro Gly Gly Glu Phe
    50                  55                  60

Thr Val Ser Pro Arg Asn Ala Pro Gly Glu Val Leu Leu Asn Leu Pro
65                  70                  75                  80

Leu Ser Pro Asp Ile Asn Pro Tyr Leu Ala His Leu Ser Arg Met Tyr
                85                  90                  95

Asn Gly Tyr Ala Gly Gly Val Glu Val Glu Val Val Leu Ala Gly Asn
            100                 105                 110

Ala Phe Thr Ala Gly Lys Ile Ile Phe Ala Ala Val Pro Pro Asn Phe
        115                 120                 125

Pro Pro Glu Asn Leu Ser Pro Ser Gln Ile Thr Met Leu Pro His Ile
    130                 135                 140

Ile Val Asp Val Arg Gln Leu Glu Pro Val Arg Ile Pro Leu Pro Asp
145                 150                 155                 160

Val Arg Asn Asn Phe Tyr His Tyr Ser Arg Glu Asn Asp Ser Thr Leu
                165                 170                 175

Arg Leu Ile Ala Met Leu Tyr Thr Pro Leu Arg Ala Asn Asn Ala Gly
            180                 185                 190

Asp Asp Val Phe Thr Val Ser Cys Arg Val Leu Thr Arg Pro Ser Pro
        195                 200                 205

Asp Phe Asp Phe Ile Phe Leu Val Pro Pro Thr Val Glu Ser Lys Ser
    210                 215                 220

Lys Pro Phe Thr Ile Pro Met Leu Thr Ile Glu Glu Met Thr Asn Ser
225                 230                 235                 240

Arg Phe Pro Ala Pro Leu Glu Leu Met Thr Thr Gly Pro Ser His Asp
                245                 250                 255

Ile Val Val Gln Pro Gln Asn Gly Arg Cys Thr Ile Asp Gly Val Leu
            260                 265                 270

Leu Gly Thr Thr Gln Leu Ser Pro Val Asn Ile Cys Ser Leu Arg Gly
        275                 280                 285

Val Pro Thr Lys Arg Thr Asn Gly Asn Asp Asn Cys Phe Val Gln Leu
    290                 295                 300

Glu Asn Pro Asn Gly Ser Ala Tyr Asp Pro Thr Glu Asp Ile Pro Ala
305                 310                 315                 320

Val Leu Gly Ser Pro Asp Phe Val Gly Glu Leu Tyr Gly Thr Ile Thr
                325                 330                 335

Gln Arg Ser Ser Asp Asn Ser Thr Arg Ala His Pro Phe Thr Leu Asn
            340                 345                 350

Thr Gly Ser Pro Arg Tyr Thr Pro Lys Ile Gly Ser Val Asp Ile Arg
        355                 360                 365

Val Thr Asp Val Ser Asp Leu Gln Asp His Asp Pro Val Lys Leu Thr
    370                 375                 380

Pro Val Gly Leu Ser Gly Asp Arg Gly Ser Ile His Gln Trp Gln Leu
385                 390                 395                 400

Pro Asn Tyr Ser Gly Val Ala Thr His Asn Met His Leu Ala Pro Ser
                405                 410                 415

Val Ala Pro Leu Phe Pro Gly Glu Gln Ile Leu Phe Phe Arg Ser Thr
            420                 425                 430

Val Pro Gly Cys Gly Gly Tyr Pro Asn Ser Asn Ile Asp Cys Leu Ile
        435                 440                 445
```

```
Pro Gln Glu Trp Val Gln His Phe Tyr Gln Glu Gly Ala Pro Ala Arg
    450                 455                 460

Thr Asp Val Ala Leu Leu Arg Phe Ile Asn Pro Asp Thr Gly Arg Val
465                 470                 475                 480

Leu Phe Glu Cys Lys Leu His Lys His Gly Phe Ile Thr Val Ala Tyr
                485                 490                 495

Ser Gly Asn His Asp Leu Val Met Pro Pro Asn Gly Tyr Phe Arg Phe
            500                 505                 510

Glu Ser Trp Val Asn Gln Phe His Thr Leu Ala Pro Met Gly Thr Gly
        515                 520                 525

Ser Gly Arg Arg Arg Ile Gln
    530                 535


<210> SEQ ID NO 27
<211> LENGTH: 542
<212> TYPE: PRT
<213> ORGANISM: Norovirus

<400> SEQUENCE: 27

Met Lys Met Ala Ser Asn Asp Ala Ala Pro Ser Asn Asp Gly Ala Ala
1               5                   10                  15

Gly Leu Val Pro Glu Ile Asn Asn Glu Thr Met Ala Leu Glu Pro Val
            20                  25                  30

Ala Gly Gly Ala Ile Ala Ala Pro Leu Thr Gly Gln Thr Asn Phe Ile
        35                  40                  45

Asp Pro Trp Ile Arg Gly Asn Tyr Val Gln Ala Pro Asn Gly Glu Phe
    50                  55                  60

Thr Val Ser Pro Arg Asn Ser Pro Gly Glu Ile Leu Leu Asn Leu Glu
65                  70                  75                  80

Leu Gly Pro Glu Leu Asn Pro Phe Leu Ala His Leu Ser Arg Met Tyr
                85                  90                  95

Asn Gly Tyr Ala Gly Gly Ile Asp Val Gln Val Ile Met Ala Gly Asn
            100                 105                 110

Ala Phe Thr Ala Gly Lys Ile Ile Phe Ala Ala Val Pro Pro His Phe
        115                 120                 125

Pro Val Glu Asn Ile Ser Pro Pro Gln Ile Thr Met Phe Pro His Ile
    130                 135                 140

Ile Val Asp Val Arg Thr Leu Glu Pro Ile Asn Ile Pro Val Pro Asp
145                 150                 155                 160

Val Arg Asn Asn Phe Phe His Tyr Asn Gln Asp Arg Asp Ser Arg Met
                165                 170                 175

Arg Leu Val Ala Met Leu Tyr Thr Pro Leu Arg Ser Asn Gly Ser Thr
            180                 185                 190

Asp Asp Val Phe Thr Val Ser Cys Arg Val Leu Thr Lys Pro Ser Ala
        195                 200                 205

Asp Phe Glu Phe Asn Tyr Leu Val Pro Pro Thr Val Glu Ser Arg Thr
    210                 215                 220

Lys Pro Phe Ser Ile Pro Ile Leu Thr Ile Gly Glu Met Thr Asn Ser
225                 230                 235                 240

Arg Phe Pro Leu Pro Ile Asp Met Leu Tyr Thr Ser Pro Thr Glu Asn
                245                 250                 255

Leu Val Val Gln Pro Gln Asn Gly Arg Cys Thr Thr Glu Gly Glu Leu
            260                 265                 270

Leu Gly Thr Thr Gln Leu Val Thr Pro Ser Ile Cys Ser Leu Arg Gly
        275                 280                 285
```

```
Ala Ile Thr Gly His Glu Gly Asn Asp Asp Asp His Lys Trp His Met
    290                 295                 300

Thr Val Thr Ser Pro Asn Gly Ala Ala Phe Asp Pro Thr Glu Asp Val
305                 310                 315                 320

Pro Ala Pro Leu Gly Thr Pro Asp Phe Thr Gly Asp Ile Tyr Gly Val
                325                 330                 335

Leu Ser Gln Arg Asp Arg Asn Ile Asn Pro Gly Gln Thr Ala Pro Ala
            340                 345                 350

Asn Arg Ala His Glu Ala Val Val Ser Thr Arg Ser Asn Lys Phe Thr
        355                 360                 365

Pro Lys Leu Gly Ser Val Met Ile Ala Thr Trp Glu Thr Thr Asp Val
    370                 375                 380

Leu Gln Gln Pro Thr Lys Phe Thr Pro Val Gly Leu Glu Ser Pro Asn
385                 390                 395                 400

His Tyr Asn Gln Trp Gln Leu Pro Asn Tyr Ser Gly Ala Leu Thr Leu
                405                 410                 415

Asn Met Gly Leu Ala Pro Ser Val Phe Pro Thr Tyr Pro Gly Glu Gln
            420                 425                 430

Ile Leu Phe Phe Arg Ser Phe Ile Pro Leu Lys Gly Gly Tyr Gly Asn
        435                 440                 445

Ser Ala Ile Asp Cys Leu Val Pro Gln Glu Trp Ile Gln His Phe Tyr
    450                 455                 460

Gln Glu Ser Ala Pro Ser Gln Thr Asp Val Ala Leu Ile Arg Tyr Val
465                 470                 475                 480

Asn Pro Glu Thr Gly Arg Val Leu Phe Glu Ala Lys Leu His Arg Gln
                485                 490                 495

Gly Phe Ile Thr Val Ala Lys Thr Gly Asp Ser Pro Ile Asn Val Pro
            500                 505                 510

Ala Asn Gly Tyr Phe Arg Phe Asp Ser Trp Val Asn Pro Phe Tyr Ser
        515                 520                 525

Leu Ala Pro Met Gly Thr Gly Asn Gly Arg Arg Arg Asn Gln
    530                 535                 540


<210> SEQ ID NO 28
<211> LENGTH: 538
<212> TYPE: PRT
<213> ORGANISM: Norovirus

<400> SEQUENCE: 28

Met Lys Met Ala Ser Asn Asp Ala Asn Pro Ser Asp Gly Ser Ala Ala
1               5                   10                  15

Asn Leu Val Pro Glu Val Asn Asn Glu Val Met Ala Leu Glu Pro Val
            20                  25                  30

Val Gly Ala Ala Ile Ala Ala Pro Val Ala Gly Gln Gln Asn Val Ile
        35                  40                  45

Asp Pro Trp Ile Arg Asn Asn Phe Val Gln Ala Pro Gly Gly Glu Phe
    50                  55                  60

Thr Val Ser Pro Arg Asn Ala Pro Gly Glu Ile Leu Trp Ser Met Pro
65                  70                  75                  80

Leu Ser Pro Glu Leu Asn Pro Tyr Leu Ser His Leu Ser Arg Met Tyr
                85                  90                  95

Asn Gly Tyr Ala Gly Gly Phe Glu Val Gln Val Ile Leu Ala Gly Asn
            100                 105                 110

Ala Phe Thr Ala Gly Lys Ile Ile Phe Ala Ala Ile Pro Pro Asn Phe
```

-continued

```
        115                 120                 125

Pro Thr Asp Gly Leu Ser Pro Ser Gln Val Thr Met Phe Pro His Ile
    130                 135                 140

Ile Val Asp Val Arg Gln Leu Glu Pro Val Leu Ile Pro Leu Pro Asp
145                 150                 155                 160

Val Arg Asn Asn Phe Tyr His Tyr Asn Gln Ala Asn Asp Ser Thr Leu
                165                 170                 175

Lys Leu Ile Ala Met Leu Tyr Thr Pro Leu Arg Ala Asn Asn Ala Gly
            180                 185                 190

Asp Asp Val Phe Thr Val Ser Cys Arg Val Leu Thr Arg Pro Ser Pro
        195                 200                 205

Asp Phe Asp Phe Ile Phe Leu Val Pro Pro Thr Val Glu Ser Arg Thr
    210                 215                 220

Lys Pro Phe Thr Val Pro Ile Leu Thr Val Asp Glu Met Thr Asn Ser
225                 230                 235                 240

Arg Phe Pro Thr Pro Leu Glu Lys Leu His Thr Gly Pro Asn Asn Ser
                245                 250                 255

Ile Val Val Gln Pro Gln Asn Gly Arg Cys Thr Ile Asp Gly Val Leu
            260                 265                 270

Leu Gly Thr Thr Gln Leu Ser Thr Val Asn Ile Cys Asn Phe Arg Gly
        275                 280                 285

Ser Thr Thr Arg Ala Gly Gln Ser His Ala Tyr Thr Met Asn Leu Val
    290                 295                 300

Ser Gln Asn Trp Asn Asn Tyr Asp Pro Thr Glu Glu Ile Pro Ala Pro
305                 310                 315                 320

Leu Gly Thr Pro Asp Phe Val Gly Lys Ile Val Gly Met Leu Ser Gln
                325                 330                 335

Thr Thr Arg Glu Asn Ser Ser Thr Arg Ala His Lys Ala Thr Val Ser
            340                 345                 350

Thr Gly Asp Ala His Phe Thr Pro Lys Ser Gly Ser Val Leu Phe Thr
        355                 360                 365

Thr Asp Thr Asp Asp Leu Gln Asn Gly Gln Asn Thr Arg Phe Thr Pro
    370                 375                 380

Val Gly Val Ala Gln Asp Gly Glu Pro His Gln Asn Glu Pro Gln Gln
385                 390                 395                 400

Trp Arg Leu Pro Asn Tyr Ser Gly Thr Pro Gly His Asn Val His Leu
                405                 410                 415

Ala Pro Pro Val Ala Pro Thr Phe Pro Gly Glu Gln Leu Leu Phe Phe
            420                 425                 430

Arg Ser Thr Met Pro Gly Cys Gly Gly Tyr Pro Asn Met Asp Leu Asp
        435                 440                 445

Cys Leu Leu Pro Gln Glu Trp Val Arg His Phe Tyr Gln Glu Ala Ala
    450                 455                 460

Pro Ala Gln Ser Asp Val Ala Leu Leu Arg Phe Val Asn Pro Asp Thr
465                 470                 475                 480

Gly Arg Val Leu Phe Glu Cys Lys Leu His Lys Ala Gly Tyr Ile Thr
                485                 490                 495

Val Ser His Thr Gly Pro Tyr Asp Leu Val Ile Pro Pro Asn Gly Tyr
            500                 505                 510

Phe Arg Phe Asp Ser Trp Val Asn Gln Phe Tyr Ala Leu Ala Pro Met
        515                 520                 525

Gly Thr Gly Thr Gly Arg Arg Arg Ala Leu
    530                 535
```

<210> SEQ ID NO 29
<211> LENGTH: 535
<212> TYPE: PRT
<213> ORGANISM: Norovirus

<400> SEQUENCE: 29

```
Met Lys Met Ala Ser Asn Asp Ala Ala Pro Ser Asn Asp Gly Ala Ala
1               5                   10                  15

Gly Leu Val Pro Glu Val Asn Asn Glu Met Met Ala Leu Glu Pro Val
            20                  25                  30

Ala Gly Ala Ser Ile Ala Ala Pro Leu Thr Gly Gln Asn Asn Val Ile
        35                  40                  45

Asp Pro Trp Ile Arg Met Asn Phe Val Gln Ala Pro Asn Gly Glu Phe
    50                  55                  60

Thr Val Ser Pro Arg Asn Ser Pro Gly Glu Ile Leu Leu Asn Leu Glu
65                  70                  75                  80

Leu Gly Pro Glu Leu Asn Pro Phe Leu Ala His Leu Ser Arg Met Tyr
                85                  90                  95

Asn Gly Tyr Ala Gly Gly Val Glu Val Gln Val Leu Leu Ala Gly Asn
            100                 105                 110

Ala Phe Thr Ala Gly Lys Leu Val Phe Ala Ala Ile Pro Pro Arg Phe
        115                 120                 125

Pro Ile Glu Asn Leu Ser Pro Gly Gln Ile Thr Met Phe Pro His Val
    130                 135                 140

Ile Ile Asp Val Arg Thr Leu Glu Pro Val Leu Leu Pro Leu Pro Asp
145                 150                 155                 160

Val Arg Asn Asn Phe Phe His Tyr Asn Gln Glu Pro Glu Pro Arg Met
                165                 170                 175

Arg Leu Val Ala Met Leu Tyr Thr Pro Leu Arg Ser Asn Gly Ser Gly
            180                 185                 190

Asp Asp Val Phe Thr Val Ser Cys Arg Val Leu Thr Arg Pro Ser Pro
        195                 200                 205

Asp Phe Asp Phe Asn Tyr Leu Val Pro Pro Thr Val Glu Ser Lys Thr
    210                 215                 220

Lys Pro Phe Thr Leu Pro Ile Leu Thr Ile Gly Glu Leu Ser Asn Ser
225                 230                 235                 240

Arg Phe Pro Ala Pro Ile Asp Glu Leu Tyr Thr Ser Pro Asn Glu Gly
                245                 250                 255

Leu Val Val Gln Pro Gln Asn Gly Arg Ser Thr Leu Asp Gly Glu Leu
            260                 265                 270

Leu Gly Thr Thr Gln Leu Val Pro Ser Asn Ile Cys Ser Leu Arg Gly
        275                 280                 285

Arg Ile Asn Ala His Leu Pro Asp Asn Gln His Arg Trp Asn Met Gln
    290                 295                 300

Val Thr Asn Ala Asn Gly Thr Pro Phe Asp Pro Thr Glu Asp Val Pro
305                 310                 315                 320

Ala Pro Leu Gly Thr Pro Asp Phe Leu Ala Asn Ile Tyr Gly Val Thr
                325                 330                 335

Ser Gln Arg Asn Pro Asp Asn Thr Cys Arg Ala His Asp Gly Ile Leu
            340                 345                 350

Ala Thr Trp Ser Pro Lys Phe Thr Pro Lys Leu Gly Ser Val Val Leu
        355                 360                 365

Gly Thr Trp Glu Asp Arg Asp Phe Asp Ile Asn Gln Pro Thr Arg Phe
```

370 375 380

Thr Pro Val Gly Leu Tyr Asp Thr Asp His Phe Asn Gln Trp Ala Leu
385 390 395 400

Pro Asn Tyr Ser Gly Ala Leu Thr Leu Asn Met Asn Leu Ala Pro Ser
405 410 415

Val Ala Pro Leu Phe Pro Gly Glu Gln Leu Leu Phe Phe Arg Ser His
420 425 430

Ile Pro Leu Lys Gly Gly Thr Ser Asn Gly Ala Ile Asp Cys Leu Leu
435 440 445

Pro Gln Glu Trp Val Gln His Phe Tyr Gln Glu Ser Ala Pro Ser Ser
450 455 460

Thr Asp Val Ala Leu Ile Arg Tyr Thr Asn Pro Asp Thr Gly Arg Val
465 470 475 480

Leu Phe Glu Ala Lys Leu His Arg Gln Gly Phe Ile Thr Val Ala Asn
485 490 495

Ser Gly Ser Arg Pro Ile Val Val Pro Pro Asn Gly Tyr Phe Arg Phe
500 505 510

Asp Ser Trp Val Asn Gln Phe Tyr Ser Leu Ala Pro Met Gly Thr Gly
515 520 525

Asn Gly Arg Arg Arg Val Gln
530 535

<210> SEQ ID NO 30
<211> LENGTH: 535
<212> TYPE: PRT
<213> ORGANISM: Norovirus

<400> SEQUENCE: 30

Met Lys Met Ala Ser Asn Asp Val Ala Pro Ser Asn Asp Gly Ala Ala
1 5 10 15

Gly Leu Val Pro Glu Val Ser Asn Glu Thr Met Ala Leu Glu Pro Val
20 25 30

Ala Gly Ala Ser Ile Ala Ala Pro Leu Thr Gly Gln Asn Asn Val Ile
35 40 45

Asp Pro Trp Ile Arg Met Asn Phe Val Gln Ala Pro Asn Gly Glu Phe
50 55 60

Thr Val Ser Pro Arg Asn Ser Pro Gly Glu Val Leu Leu Asn Leu Glu
65 70 75 80

Leu Gly Pro Glu Leu Asn Pro Phe Leu Ala His Leu Ala Arg Met Tyr
85 90 95

Asn Gly Tyr Ala Gly Gly Val Glu Val Gln Val Leu Leu Ala Gly Asn
100 105 110

Ala Phe Thr Ala Gly Lys Leu Val Phe Ala Ala Ile Pro Pro His Phe
115 120 125

Pro Leu Glu Asn Leu Ser Pro Gly Gln Ile Thr Met Phe Pro His Val
130 135 140

Ile Ile Asp Val Arg Thr Leu Glu Pro Val Leu Leu Pro Leu Pro Asp
145 150 155 160

Val Arg Asn Asn Phe Phe His Tyr Asn Gln Gln Pro Glu Pro Arg Met
165 170 175

Arg Leu Val Ala Met Leu Tyr Thr Pro Leu Arg Ser Asn Gly Ser Gly
180 185 190

Asp Asp Val Phe Thr Val Ser Cys Arg Val Leu Thr Arg Pro Ser Pro
195 200 205

```
Asp Phe Asp Phe Asn Tyr Leu Val Pro Pro Thr Val Glu Ser Lys Thr
    210                 215                 220

Lys Pro Phe Thr Leu Pro Ile Leu Thr Ile Gly Glu Leu Ser Asn Ser
225                 230                 235                 240

Arg Phe Pro Val Pro Ile Asp Glu Leu Tyr Thr Ser Pro Asn Glu Gly
                245                 250                 255

Val Val Val Gln Pro Gln Asn Gly Arg Ser Thr Leu Asp Gly Glu Leu
            260                 265                 270

Leu Gly Thr Thr Gln Leu Val Pro Ser Asn Ile Cys Ala Leu Arg Gly
        275                 280                 285

Arg Ile Asn Ala Gln Val Pro Asp Asp His His Gln Trp Asn Leu Gln
    290                 295                 300

Val Thr Asn Ala Asn Gly Thr Ser Phe Asp Pro Thr Glu Asp Val Pro
305                 310                 315                 320

Ala Pro Leu Gly Thr Pro Asp Phe Leu Ala Asn Ile Tyr Gly Val Thr
                325                 330                 335

Ser Gln Arg Asn Pro Asp Asn Thr Cys Arg Ala His Asp Gly Val Leu
            340                 345                 350

Ala Thr Trp Ser Pro Lys Phe Thr Pro Lys Leu Gly Ser Val Val Leu
        355                 360                 365

Gly Thr Trp Glu Glu Ser Asp Leu Asp Leu Asn Gln Pro Thr Arg Phe
    370                 375                 380

Thr Pro Val Gly Leu Tyr Asp Thr Asn His Phe Asp Gln Trp Ile Leu
385                 390                 395                 400

Pro Asn Tyr Ser Gly Arg Leu Thr Leu Asn Met Asn Leu Ala Pro Ser
                405                 410                 415

Val Ala Pro Leu Phe Pro Gly Glu Gln Ile Leu Phe Phe Arg Ser His
            420                 425                 430

Ile Pro Leu Lys Gly Gly Thr Ser Asn Gly Ala Ile Asp Cys Leu Leu
        435                 440                 445

Pro Gln Glu Trp Ile Gln His Phe Tyr Gln Glu Ser Ala Pro Ser Pro
    450                 455                 460

Thr Asp Val Ala Leu Ile Arg Tyr Thr Asn Pro Asp Thr Gly Arg Val
465                 470                 475                 480

Leu Phe Glu Ala Lys Leu His Arg Gln Gly Phe Ile Thr Val Ala Asn
                485                 490                 495

Ser Gly Ser Arg Pro Ile Val Val Pro Pro Asn Gly Tyr Phe Arg Phe
            500                 505                 510

Asp Ser Trp Val Asn Gln Phe Tyr Ser Leu Ala Pro Met Gly Thr Gly
        515                 520                 525

Asn Gly Arg Arg Arg Val Gln
    530                 535
```

<210> SEQ ID NO 31
<211> LENGTH: 542
<212> TYPE: PRT
<213> ORGANISM: Norovirus

<400> SEQUENCE: 31

```
Met Lys Met Ala Ser Asn Asp Ala Ala Pro Ser Thr Asp Gly Ala Ala
1               5                   10                  15

Gly Leu Val Pro Glu Ser Asn Asn Glu Val Met Ala Leu Glu Pro Val
            20                  25                  30

Ala Gly Ala Ala Leu Ala Ala Pro Val Thr Gly Gln Thr Asn Ile Ile
        35                  40                  45
```

```
Asp Pro Trp Ile Arg Ala Asn Phe Val Gln Ala Pro Asn Gly Glu Phe
    50                  55                  60

Thr Val Ser Pro Arg Asn Ala Pro Gly Glu Val Leu Leu Asn Leu Glu
65                  70                  75                  80

Leu Gly Pro Glu Leu Asn Pro Tyr Leu Ala His Leu Ala Arg Met Tyr
                85                  90                  95

Asn Gly Tyr Ala Gly Gly Met Glu Val Gln Val Met Leu Ala Gly Asn
            100                 105                 110

Ala Phe Thr Ala Gly Lys Leu Val Phe Ala Ala Val Pro Pro His Phe
        115                 120                 125

Pro Val Glu Asn Leu Ser Pro Gln Gln Ile Thr Met Phe Pro His Val
    130                 135                 140

Ile Ile Asp Val Arg Thr Leu Glu Pro Val Leu Leu Pro Leu Pro Asp
145                 150                 155                 160

Val Arg Asn Asn Phe Phe His Tyr Asn Gln Lys Asp Asp Pro Lys Met
                165                 170                 175

Arg Ile Val Ala Met Leu Tyr Thr Pro Leu Arg Ser Asn Gly Ser Gly
            180                 185                 190

Asp Asp Val Phe Thr Val Ser Cys Arg Val Leu Thr Arg Pro Ser Pro
        195                 200                 205

Asp Phe Asp Phe Thr Tyr Leu Val Pro Pro Thr Val Glu Ser Lys Thr
    210                 215                 220

Lys Pro Phe Thr Leu Pro Ile Leu Thr Leu Gly Glu Leu Ser Asn Ser
225                 230                 235                 240

Arg Phe Pro Val Ser Ile Asp Gln Met Tyr Thr Ser Pro Asn Glu Val
                245                 250                 255

Ile Ser Val Gln Cys Gln Asn Gly Arg Cys Thr Leu Asp Gly Glu Leu
            260                 265                 270

Gln Gly Thr Thr Gln Leu Gln Val Ser Gly Ile Cys Ala Phe Lys Gly
        275                 280                 285

Glu Val Thr Ala His Leu His Asp Asn Asp His Leu Tyr Asn Val Thr
    290                 295                 300

Ile Thr Asn Leu Asn Gly Ser Pro Phe Asp Pro Ser Glu Asp Ile Pro
305                 310                 315                 320

Ala Pro Leu Gly Val Pro Asp Phe Gln Gly Arg Val Phe Gly Val Ile
                325                 330                 335

Ser Gln Arg Asp Lys His Asn Ser Pro Gly His Asn Glu Pro Ala Asn
            340                 345                 350

Arg Gly His Asp Ala Val Val Pro Thr Tyr Thr Ser Gln Tyr Thr Pro
        355                 360                 365

Lys Leu Gly Gln Ile Gln Ile Gly Thr Trp Gln Thr Asp Asp Leu Thr
    370                 375                 380

Val Asn Gln Pro Val Lys Phe Thr Pro Val Gly Leu Asn Asp Thr Glu
385                 390                 395                 400

His Phe Asn Gln Trp Val Val Pro Arg Tyr Ala Gly Ala Leu Asn Leu
                405                 410                 415

Asn Thr Asn Leu Ala Pro Ser Val Ala Pro Val Phe Pro Gly Glu Arg
            420                 425                 430

Leu Leu Phe Phe Arg Ser Tyr Ile Pro Leu Lys Gly Gly Tyr Gly Asn
        435                 440                 445

Pro Ala Ile Asp Cys Leu Leu Pro Gln Glu Trp Val Gln His Phe Tyr
    450                 455                 460
```

```
Gln Glu Ala Ala Pro Ser Met Ser Glu Val Ala Leu Val Arg Tyr Ile
465                 470                 475                 480

Asn Pro Asp Thr Gly Arg Ala Leu Phe Glu Ala Lys Leu His Arg Ala
                485                 490                 495

Gly Phe Met Thr Val Ser Ser Asn Thr Ser Ala Pro Val Val Val Pro
            500                 505                 510

Ala Asn Gly Tyr Phe Arg Phe Asp Ser Trp Val Asn Gln Phe Tyr Ser
        515                 520                 525

Leu Ala Pro Met Gly Thr Gly Asn Gly Arg Arg Arg Val Gln
    530                 535                 540


<210> SEQ ID NO 32
<211> LENGTH: 542
<212> TYPE: PRT
<213> ORGANISM: Norovirus

<400> SEQUENCE: 32

Met Lys Met Ala Ser Asn Asp Ala Ala Pro Ser Thr Asp Gly Ala Ala
1               5                   10                  15

Gly Leu Val Pro Glu Ser Asn Asn Glu Val Met Ala Leu Glu Pro Val
            20                  25                  30

Ala Gly Ala Ala Leu Ala Ala Pro Val Thr Gly Gln Thr Asn Ile Ile
        35                  40                  45

Asp Pro Trp Ile Arg Ala Asn Phe Val Gln Ala Pro Asn Gly Glu Phe
    50                  55                  60

Thr Val Ser Pro Arg Asn Ala Pro Gly Glu Val Leu Leu Ser Leu Glu
65                  70                  75                  80

Leu Gly Pro Glu Leu Asn Pro Tyr Leu Ala His Leu Ala Arg Met Tyr
                85                  90                  95

Asn Gly Tyr Ala Gly Gly Met Glu Val Gln Val Met Leu Ala Gly Asn
            100                 105                 110

Ala Phe Thr Ala Gly Lys Leu Val Phe Ala Ala Val Pro Pro His Phe
        115                 120                 125

Pro Val Glu Asn Leu Ser Pro Gln Gln Ile Thr Met Phe Pro His Val
    130                 135                 140

Ile Ile Asp Val Arg Thr Leu Glu Pro Val Leu Leu Pro Leu Pro Asp
145                 150                 155                 160

Val Arg Asn Asn Phe Phe His Tyr Asn Gln Lys Asp Asp Pro Lys Met
                165                 170                 175

Arg Ile Val Ala Met Leu Tyr Thr Pro Leu Arg Ser Asn Gly Ser Gly
            180                 185                 190

Asp Asp Val Phe Thr Val Ser Cys Arg Val Leu Thr Arg Pro Ser Pro
        195                 200                 205

Asp Phe Asp Phe Thr Tyr Leu Val Pro Pro Thr Val Glu Ser Lys Thr
    210                 215                 220

Lys Pro Phe Thr Leu Pro Ile Leu Thr Leu Gly Glu Leu Ser Asn Ser
225                 230                 235                 240

Arg Phe Pro Val Ser Ile Asp Gln Met Tyr Thr Ser Pro Asn Glu Val
                245                 250                 255

Ile Ser Val Gln Cys Gln Asn Gly Arg Cys Thr Leu Asp Gly Glu Leu
            260                 265                 270

Gln Gly Thr Thr Gln Leu Gln Val Ser Gly Ile Cys Ala Phe Lys Gly
        275                 280                 285

Glu Val Thr Ala His Leu His Asp Asn Asp His Leu Tyr Asn Val Thr
    290                 295                 300
```

Ile Thr Asn Leu Asn Gly Pro Pro Phe Asp Pro Ser Glu Asp Ile Pro
305 310 315 320

Ala Pro Leu Gly Val Pro Asp Phe Gln Gly Arg Val Phe Gly Val Ile
325 330 335

Ser Gln Arg Asp Lys Gln Asn Ala Ala Gly His Ser Glu Pro Ala Asn
340 345 350

Arg Gly His Asp Ala Val Val Pro Thr Tyr Thr Ala Gln Tyr Thr Pro
355 360 365

Lys Leu Gly Gln Val Gln Ile Gly Thr Trp Gln Thr Asp Asp Leu Gln
370 375 380

Val Asn Gln Pro Val Lys Phe Thr Pro Val Gly Leu Asn Asp Thr Glu
385 390 395 400

His Phe Asn Gln Trp Val Val Pro Arg Tyr Ala Gly Ala Leu Asn Leu
405 410 415

Asn Thr Asn Leu Ala Pro Ser Val Ala Pro Val Phe Pro Gly Glu Arg
420 425 430

Leu Leu Phe Phe Arg Ser Tyr Ile Pro Leu Lys Gly Gly Tyr Gly Asn
435 440 445

Pro Ala Ile Asp Cys Leu Leu Pro Gln Glu Trp Val Gln His Phe Tyr
450 455 460

Gln Glu Ala Ala Pro Ser Met Ser Glu Val Ala Leu Val Arg Tyr Ile
465 470 475 480

Asn Pro Asp Thr Gly Arg Ala Leu Phe Glu Ala Lys Leu His Arg Ala
485 490 495

Gly Phe Val Thr Val Ser Ser Asn Thr Ser Ala Pro Val Val Val Pro
500 505 510

Ala Asn Gly Tyr Phe Arg Phe Asp Ser Trp Val Asn Gln Phe Tyr Ser
515 520 525

Leu Ala Pro Met Gly Ala Gly Asn Gly Arg Arg Arg Val Gln
530 535 540

<210> SEQ ID NO 33
<211> LENGTH: 542
<212> TYPE: PRT
<213> ORGANISM: Norovirus

<400> SEQUENCE: 33

Met Lys Met Ala Ser Asn Asp Ala Val Pro Ser Thr Asp Gly Ala Ala
1 5 10 15

Gly Leu Val Pro Glu Ser Asn Asn Glu Val Met Ala Leu Glu Pro Val
20 25 30

Ala Gly Ala Ala Leu Ala Ala Pro Val Thr Gly Gln Thr Asn Ile Ile
35 40 45

Asp Pro Trp Ile Arg Ala Asn Phe Val Gln Ala Pro Asn Gly Glu Phe
50 55 60

Thr Val Ser Pro Arg Asn Ser Pro Gly Glu Val Leu Leu Asn Leu Glu
65 70 75 80

Leu Gly Pro Glu Leu Asn Pro Tyr Leu Ala His Leu Ala Arg Met Tyr
85 90 95

Asn Gly Tyr Ala Gly Gly Met Glu Val Gln Val Met Leu Ala Gly Asn
100 105 110

Ala Phe Thr Ala Gly Lys Leu Val Phe Ala Ala Val Pro Pro His Phe
115 120 125

Pro Val Glu Asn Leu Ser Pro Gln Gln Ile Thr Met Phe Pro His Val

```
    130                 135                 140

Ile Ile Asp Val Arg Thr Leu Glu Pro Val Leu Leu Pro Leu Pro Asp
145                 150                 155                 160

Val Arg Asn Asn Phe Phe His Tyr Asn Gln Lys Asp Asp Pro Lys Met
                165                 170                 175

Arg Ile Val Ala Met Leu Tyr Thr Pro Leu Arg Ser Asn Gly Ser Gly
            180                 185                 190

Asp Asp Val Phe Thr Val Ser Cys Arg Val Leu Thr Arg Pro Ser Pro
        195                 200                 205

Asp Phe Asp Phe Thr Tyr Leu Val Pro Pro Thr Val Glu Ser Lys Thr
    210                 215                 220

Lys Pro Phe Thr Leu Pro Ile Leu Thr Leu Gly Glu Leu Ser Asn Ser
225                 230                 235                 240

Arg Phe Pro Val Ser Ile Asp Gln Met Tyr Thr Ser Pro Asn Glu Val
                245                 250                 255

Ile Ser Val Gln Cys Gln Asn Gly Arg Cys Thr Leu Asp Gly Glu Leu
            260                 265                 270

Gln Gly Thr Thr Gln Leu Gln Val Ser Gly Ile Cys Ala Phe Lys Gly
        275                 280                 285

Glu Val Thr Ala His Leu His Asp Asn Glu His Leu Tyr Asn Val Thr
    290                 295                 300

Ile Thr Asn Leu Asn Gly Ser Pro Phe Asp Pro Ser Glu Asp Ile Pro
305                 310                 315                 320

Ala Pro Leu Gly Val Pro Asp Phe Gln Gly Arg Val Phe Gly Val Ile
                325                 330                 335

Ser Gln Arg Asp Lys His Asn Thr Pro Gly His Asn Glu Pro Ala Asn
            340                 345                 350

Arg Ala His Asp Ala Val Val Pro Thr Tyr Thr Ala Gln Tyr Thr Pro
        355                 360                 365

Lys Leu Gly Gln Val Gln Ile Gly Thr Trp Gln Thr Asp Asp Leu Thr
    370                 375                 380

Asp Asn Gln Pro Val Lys Phe Thr Pro Val Gly Leu Asn Asp Thr Glu
385                 390                 395                 400

His Phe Asn Gln Trp Val Val Pro Arg Tyr Ala Gly Ala Leu Asn Leu
                405                 410                 415

Asn Thr Asn Leu Ala Pro Ser Val Ala Pro Val Phe Pro Gly Glu Arg
            420                 425                 430

Leu Leu Phe Phe Arg Ser Tyr Ile Pro Leu Lys Gly Gly Tyr Gly Thr
        435                 440                 445

Pro Ala Ile Asp Cys Leu Leu Pro Gln Glu Trp Val Gln His Phe Tyr
    450                 455                 460

Gln Glu Ala Ala Pro Ser Met Ser Glu Val Ala Leu Val Arg Tyr Ile
465                 470                 475                 480

Asn Pro Asp Thr Gly Arg Ala Leu Phe Glu Ala Lys Leu His Arg Ala
                485                 490                 495

Gly Phe Met Thr Val Ser Ser Asn Thr Ser Ala Pro Val Val Val Pro
            500                 505                 510

Ala Asn Gly Tyr Phe Arg Phe Asp Ser Trp Val Asn Gln Phe Tyr Ser
        515                 520                 525

Leu Ala Pro Met Gly Thr Gly Asn Gly Arg Arg Arg Ile Gln
    530                 535                 540
```

<210> SEQ ID NO 34

```
<211> LENGTH: 542
<212> TYPE: PRT
<213> ORGANISM: Norovirus

<400> SEQUENCE: 34

Met Lys Met Ala Ser Ile Asp Ala Ala Pro Ser Thr Asp Gly Ala Ala
1               5                   10                  15

Gly Leu Val Pro Glu Ser Asn Asn Glu Val Met Ala Leu Glu Pro Val
            20                  25                  30

Ala Gly Ala Ala Leu Ala Ala Pro Val Thr Gly Gln Thr Asn Ile Ile
        35                  40                  45

Asp Pro Trp Ile Arg Ala Asn Phe Val Gln Ala Pro Asn Gly Glu Phe
    50                  55                  60

Thr Val Ser Pro Arg Asn Ala Pro Gly Glu Val Leu Leu Asn Leu Glu
65                  70                  75                  80

Leu Gly Pro Glu Leu Asn Pro Tyr Leu Ala His Leu Ala Arg Met Tyr
                85                  90                  95

Asn Gly Tyr Ala Gly Gly Met Glu Val Gln Val Met Leu Ala Gly Asn
            100                 105                 110

Ala Phe Thr Ala Gly Lys Leu Val Phe Ala Ala Val Pro Pro His Phe
        115                 120                 125

Pro Val Glu Asn Leu Ser Pro Gln Gln Ile Thr Met Phe Pro His Val
    130                 135                 140

Ile Ile Asp Val Arg Thr Leu Glu Pro Val Leu Leu Pro Leu Pro Asp
145                 150                 155                 160

Val Arg Asn Asn Phe Phe His Tyr Asn Gln Lys Asp Asp Pro Lys Met
                165                 170                 175

Arg Ile Val Ala Met Leu Tyr Thr Pro Leu Arg Ser Asn Gly Ser Gly
            180                 185                 190

Asp Asp Val Phe Thr Val Ser Cys Arg Val Leu Thr Arg Pro Ser Pro
        195                 200                 205

Asp Phe Asp Phe Thr Tyr Leu Val Pro Pro Thr Val Glu Ser Lys Thr
    210                 215                 220

Lys Pro Phe Thr Leu Pro Ile Leu Thr Leu Gly Glu Leu Ser Asn Ser
225                 230                 235                 240

Arg Phe Pro Val Ser Ile Asp Gln Met Tyr Thr Ser Pro Asn Glu Val
                245                 250                 255

Ile Ser Val Gln Cys Gln Asn Gly Arg Cys Thr Leu Asp Gly Glu Leu
            260                 265                 270

Gln Gly Thr Thr Gln Leu Gln Val Ser Gly Ile Cys Ala Phe Lys Gly
        275                 280                 285

Glu Val Thr Ala His Leu His Asp Asn Asp His Leu Tyr Asn Val Thr
    290                 295                 300

Ile Thr Asn Leu Asn Gly Ser Pro Phe Asp Pro Ser Glu Asp Ile Pro
305                 310                 315                 320

Ala Pro Leu Gly Val Pro Asp Phe Gln Gly Arg Val Phe Gly Val Ile
                325                 330                 335

Ser Gln Arg Asp Lys His Asn Ser Pro Gly His Asn Glu Pro Ala Asn
            340                 345                 350

Arg Gly His Asp Ala Val Val Pro Thr Tyr Thr Ser Gln Tyr Thr Pro
        355                 360                 365

Lys Leu Gly Gln Ile Gln Ile Gly Thr Trp Gln Thr Asp Asp Leu Thr
    370                 375                 380

Val Asn Gln Pro Val Lys Phe Thr Pro Val Gly Leu Asn Asp Thr Glu
```

385 390 395 400

His Phe Asn Gln Trp Val Val Pro Arg Tyr Ala Gly Ala Leu Asn Leu
405 410 415

Asn Thr Asn Leu Ala Pro Ser Val Ala Pro Val Phe Pro Gly Glu Arg
420 425 430

Leu Leu Phe Phe Arg Ser Tyr Ile Pro Leu Lys Gly Gly Tyr Gly Asn
435 440 445

Pro Ala Ile Asp Cys Leu Leu Pro Gln Glu Trp Val Gln His Phe Tyr
450 455 460

Gln Glu Ala Ala Pro Ser Met Ser Glu Val Ala Leu Val Arg Tyr Ile
465 470 475 480

Asn Pro Asp Thr Gly Arg Ala Leu Phe Glu Ala Lys Leu His Arg Ala
485 490 495

Gly Phe Met Thr Val Ser Ser Asn Thr Ser Ala Pro Val Val Val Pro
500 505 510

Ala Asn Gly Tyr Phe Arg Phe Asp Ser Trp Val Asn Gln Phe Tyr Ser
515 520 525

Leu Ala Pro Met Gly Thr Gly Asn Gly Arg Arg Arg Val Gln
530 535 540

<210> SEQ ID NO 35
<211> LENGTH: 548
<212> TYPE: PRT
<213> ORGANISM: Norovirus

<400> SEQUENCE: 35

Met Lys Met Ala Ser Asn Asp Ala Ala Pro Ser Asn Asp Gly Ala Ala
1 5 10 15

Gly Leu Val Pro Glu Ile Asn Asn Glu Ala Met Ala Leu Glu Pro Val
20 25 30

Ala Gly Ala Ala Ile Ala Ala Pro Leu Thr Gly Gln Gln Asn Ile Ile
35 40 45

Asp Pro Trp Ile Met Asn Asn Phe Val Gln Ala Pro Gly Gly Glu Phe
50 55 60

Thr Val Ser Pro Arg Asn Ser Pro Gly Glu Val Leu Leu Asn Leu Glu
65 70 75 80

Leu Gly Pro Glu Ile Asn Pro Tyr Leu Ala His Leu Ala Arg Met Tyr
85 90 95

Asn Gly Tyr Ala Gly Gly Phe Glu Val Gln Val Val Leu Ala Gly Asn
100 105 110

Ala Phe Thr Ala Gly Lys Val Ile Phe Ala Ala Ile Pro Pro Asn Phe
115 120 125

Pro Ile Asp Asn Leu Ser Ala Ala Gln Ile Thr Met Cys Pro His Val
130 135 140

Ile Val Asp Val Arg Gln Leu Glu Pro Ile Asn Leu Pro Met Pro Asp
145 150 155 160

Val Arg Asn Asn Phe Phe His Tyr Asn Gln Gly Ser Asp Ser Arg Leu
165 170 175

Arg Leu Ile Ala Met Leu Tyr Thr Pro Leu Arg Ala Asn Asn Ser Gly
180 185 190

Asp Asp Val Phe Thr Val Ser Cys Arg Val Leu Thr Arg Pro Ser Pro
195 200 205

Asp Phe Ser Phe Asn Phe Leu Val Pro Pro Thr Val Glu Ser Lys Thr
210 215 220

-continued

Lys Leu Phe Thr Leu Pro Ile Leu Thr Ile Ser Glu Met Ser Asn Ser
225 230 235 240

Arg Phe Pro Val Pro Ile Asp Ser Leu His Thr Ser Pro Thr Glu Asn
245 250 255

Ile Val Val Gln Cys Gln Asn Gly Arg Val Thr Leu Asp Gly Glu Leu
260 265 270

Met Gly Thr Thr Gln Leu Leu Pro Ser Gln Ile Cys Ala Phe Arg Gly
275 280 285

Thr Leu Thr Arg Ser Thr Ser Arg Ala Ser Asp Gln Ala Asp Thr Pro
290 295 300

Thr Pro Arg Leu Phe Asn His Arg Trp His Ile Gln Leu Asp Asn Leu
305 310 315 320

Asn Gly Thr Pro Tyr Asp Pro Ala Glu Asp Ile Pro Ala Pro Leu Gly
325 330 335

Thr Pro Asp Phe Arg Gly Lys Val Phe Gly Val Ala Ser Gln Arg Asn
340 345 350

Pro Asp Ser Thr Thr Arg Ala His Glu Ala Lys Val Asp Thr Thr Ser
355 360 365

Gly Arg Phe Thr Pro Lys Leu Gly Ser Leu Glu Ile Thr Thr Glu Ser
370 375 380

Asp Asp Phe Asp Thr Asn Gln Ser Thr Lys Phe Thr Pro Val Gly Ile
385 390 395 400

Gly Val Asp Asn Glu Ala Glu Phe Gln Gln Trp Ser Leu Pro Asn Tyr
405 410 415

Ser Gly Gln Phe Thr His Asn Met Asn Leu Ala Pro Ala Val Ala Pro
420 425 430

Asn Phe Pro Gly Glu Gln Leu Leu Phe Phe Arg Ser Gln Leu Pro Ser
435 440 445

Ser Gly Gly Arg Ser Asn Gly Val Leu Asp Cys Leu Val Pro Gln Glu
450 455 460

Trp Val Gln His Phe Tyr Gln Glu Ser Ala Pro Ala Gln Thr Gln Val
465 470 475 480

Ala Leu Val Arg Tyr Val Asn Pro Asp Thr Gly Arg Val Leu Phe Glu
485 490 495

Ala Lys Leu His Lys Leu Gly Phe Met Thr Ile Ala Lys Asn Gly Asp
500 505 510

Ser Pro Ile Thr Val Pro Pro Asn Gly Tyr Phe Arg Phe Glu Ser Trp
515 520 525

Val Asn Pro Phe Tyr Thr Leu Ala Pro Met Gly Thr Gly Asn Gly Arg
530 535 540

Arg Arg Ile Gln
545

<210> SEQ ID NO 36
<211> LENGTH: 548
<212> TYPE: PRT
<213> ORGANISM: Norovirus

<400> SEQUENCE: 36

Met Lys Met Ala Ser Asn Asp Ala Thr Pro Ser Asn Asp Gly Ala Ala
1 5 10 15

Gly Leu Val Pro Glu Ile Asn Asn Glu Ala Met Ala Leu Asp Pro Val
20 25 30

Ala Gly Ala Ala Ile Ala Ala Pro Leu Thr Gly Gln Gln Asn Ile Ile
35 40 45

-continued

```
Asp Pro Trp Ile Met Asn Asn Phe Val Gln Ala Pro Gly Gly Glu Phe
    50                  55                  60

Thr Val Ser Pro Arg Asn Ser Pro Gly Glu Val Leu Leu Asn Leu Glu
65                  70                  75                  80

Leu Gly Pro Glu Ile Asn Pro Tyr Leu Ala His Leu Ala Arg Met Tyr
                85                  90                  95

Asn Gly Tyr Ala Gly Gly Phe Glu Val Gln Val Val Leu Ala Gly Asn
            100                 105                 110

Ala Phe Thr Ala Gly Lys Ile Ile Phe Ala Ala Ile Pro Pro Asn Phe
        115                 120                 125

Pro Ile Asp Asn Leu Ser Ala Arg Gln Ile Thr Met Cys Pro His Val
    130                 135                 140

Ile Val Asp Val Arg Gln Leu Glu Pro Val Asn Leu Pro Met Pro Asp
145                 150                 155                 160

Val Arg Asn Asn Phe Phe His Tyr Asn Gln Gly Ser Asp Ser Arg Leu
                165                 170                 175

Arg Leu Ile Ala Met Leu Tyr Thr Pro Leu Arg Ala Asn Asn Ser Gly
            180                 185                 190

Asp Asp Val Phe Thr Val Ser Cys Arg Val Leu Thr Arg Pro Ser Pro
        195                 200                 205

Asp Phe Ser Phe Asn Phe Leu Val Pro Pro Thr Val Glu Ser Lys Thr
    210                 215                 220

Lys Pro Phe Thr Leu Pro Ile Leu Thr Ile Ser Glu Met Ser Asn Ser
225                 230                 235                 240

Arg Phe Pro Val Pro Ile Asp Ser Leu His Thr Ser Pro Thr Glu Asn
                245                 250                 255

Ile Val Val Gln Cys Gln Asn Gly Arg Val Thr Leu Asp Gly Glu Leu
            260                 265                 270

Met Gly Thr Thr Gln Leu Leu Pro Ser Gln Ile Cys Ala Phe Met Gly
        275                 280                 285

Val Leu Thr Arg Ser Thr Ser Arg Ala Ser Asp Gln Ala Asp Thr Ala
    290                 295                 300

Thr Pro Arg Leu Phe Asn Tyr Tyr Trp His Ile Gln Leu Asp Asn Pro
305                 310                 315                 320

Asn Gly Thr Pro Tyr Asp Pro Ala Glu Asp Ile Pro Gly Pro Leu Gly
                325                 330                 335

Thr Pro Asp Phe Arg Gly Lys Val Phe Gly Val Ala Ser Gln Arg Asn
            340                 345                 350

Pro Asp Ser Thr Thr Arg Ala His Glu Ala Lys Val Asp Thr Thr Ala
        355                 360                 365

Gly Arg Phe Thr Pro Lys Leu Gly Ser Leu Glu Ile Ser Thr Glu Ser
    370                 375                 380

Asp Asp Phe His Gln Asn Gln Pro Thr Arg Phe Thr Pro Val Gly Ile
385                 390                 395                 400

Gly Val Asp Asn Glu Ala Asp Phe Gln Gln Trp Ser Leu Pro Asp Tyr
                405                 410                 415

Ser Gly Gln Phe Thr His Asn Met Asn Leu Ala Pro Ala Val Ala Pro
            420                 425                 430

Asn Phe Pro Gly Glu Gln Leu Leu Phe Phe Arg Ser Gln Leu Pro Ser
        435                 440                 445

Ser Gly Gly Arg Ser Asn Gly Ile Leu Asp Cys Leu Val Pro Gln Glu
    450                 455                 460
```

```
Trp Val Gln His Phe Tyr Gln Glu Ser Ala Pro Ser Gln Thr Gln Val
465                 470                 475                 480

Ala Leu Val Arg Tyr Val Asn Pro Asp Thr Gly Arg Val Leu Phe Glu
                485                 490                 495

Ala Lys Leu His Lys Leu Gly Phe Met Thr Ile Ala Lys Asn Gly Asp
            500                 505                 510

Ser Pro Ile Thr Val Pro Pro Asn Gly Tyr Phe Arg Phe Glu Ser Trp
        515                 520                 525

Val Asn Pro Phe Tyr Thr Leu Ala Pro Met Gly Thr Gly Asn Gly Arg
    530                 535                 540

Arg Arg Ile Gln
545


<210> SEQ ID NO 37
<211> LENGTH: 548
<212> TYPE: PRT
<213> ORGANISM: Norovirus

<400> SEQUENCE: 37

Met Lys Met Ala Ser Asn Asp Ala Ala Pro Ser Asn Asp Gly Ala Ala
1               5                   10                  15

Gly Leu Val Pro Glu Ile Asn Asn Glu Ala Met Ala Leu Asp Pro Val
            20                  25                  30

Ala Gly Ala Ala Ile Ala Ala Pro Leu Thr Gly Gln Gln Asn Ile Ile
        35                  40                  45

Asp Pro Trp Ile Met Asn Asn Phe Val Gln Ala Pro Gly Gly Glu Phe
    50                  55                  60

Thr Val Ser Pro Arg Asn Ser Pro Gly Glu Val Leu Leu Asn Leu Glu
65                  70                  75                  80

Leu Gly Pro Glu Ile Asn Pro Tyr Leu Ala His Leu Ala Arg Met Tyr
                85                  90                  95

Asn Gly Tyr Ala Gly Gly Phe Glu Val Gln Val Val Leu Ala Gly Asn
            100                 105                 110

Ala Phe Thr Ala Gly Lys Val Ile Phe Ala Ala Ile Pro Pro Asn Phe
        115                 120                 125

Pro Ile Asp Asn Leu Ser Ala Ala Gln Ile Thr Met Cys Pro His Val
    130                 135                 140

Ile Val Asp Val Arg Gln Leu Glu Pro Ile Asn Leu Pro Met Pro Asp
145                 150                 155                 160

Val Arg Asn Asn Phe Phe His Tyr Asn Gln Gly Ser Asp Ser Arg Leu
                165                 170                 175

Arg Leu Ile Ala Met Leu Tyr Thr Pro Leu Arg Ala Asn Asn Ser Gly
            180                 185                 190

Asp Asp Val Phe Thr Val Ser Cys Arg Val Leu Thr Arg Pro Ser Pro
        195                 200                 205

Asp Phe Ser Phe Asn Phe Leu Val Pro Pro Thr Val Glu Ser Lys Thr
    210                 215                 220

Lys Pro Phe Thr Leu Pro Ile Leu Thr Ile Ser Glu Met Ser Asn Ser
225                 230                 235                 240

Arg Phe Pro Val Pro Ile Asp Ser Leu His Thr Ser Pro Thr Glu Ser
                245                 250                 255

Val Val Val Gln Cys Gln Asn Gly Arg Val Thr Leu Asp Gly Glu Leu
            260                 265                 270

Met Gly Thr Thr Gln Leu Leu Pro Ser Gln Ile Cys Ala Phe Arg Gly
        275                 280                 285
```

```
Thr Leu Thr Arg Pro Thr Asn Arg Ala Ser Asp Gln Ala Asp Thr Ala
    290                 295                 300

Thr Pro Arg Leu Phe Asn His Gln Trp His Ile Gln Leu Asp Asn Leu
305                 310                 315                 320

Asn Gly Thr Pro Tyr Asp Pro Ala Glu Asp Ile Pro Ala Pro Leu Gly
                325                 330                 335

Thr Pro Asp Phe Arg Gly Lys Val Phe Gly Val Ala Ser Gln Arg Asp
            340                 345                 350

Pro Asp Gly Thr Thr Arg Ala His Glu Ala Lys Val Asp Thr Thr Ser
        355                 360                 365

Gly Arg Phe Thr Pro Lys Leu Gly Ser Leu Glu Ile Thr Thr Glu Ser
    370                 375                 380

Asp Asp Phe Asn Gln Asn Lys Pro Thr Arg Phe Thr Pro Val Gly Ile
385                 390                 395                 400

Gly Val Asp Asn Glu Ala Asp Phe Gln Gln Trp Ile Leu Pro Asp Tyr
                405                 410                 415

Ser Gly Gln Phe Thr His Asn Met Asn Leu Ala Pro Ala Val Ala Pro
            420                 425                 430

Asn Phe Pro Gly Glu Gln Leu Leu Phe Phe Arg Ser Gln Leu Pro Ser
        435                 440                 445

Ser Gly Gly Arg Ser Asn Gly Ile Leu Asp Cys Leu Val Pro Gln Glu
    450                 455                 460

Trp Val Gln His Phe Tyr Gln Glu Ser Ala Pro Ala Gln Thr Gln Val
465                 470                 475                 480

Ala Leu Val Arg Tyr Val Asn Pro Asp Thr Gly Arg Val Leu Phe Glu
                485                 490                 495

Ala Lys Leu His Lys Met Gly Phe Met Thr Ile Ala Lys Asn Gly Asp
            500                 505                 510

Ser Pro Ile Thr Val Pro Pro Asn Gly Tyr Phe Arg Phe Glu Ser Trp
        515                 520                 525

Val Asn Pro Phe Tyr Thr Leu Ala Pro Met Gly Thr Gly Lys Gly Arg
    530                 535                 540

Arg Arg Ile Gln
545
```

<210> SEQ ID NO 38
<211> LENGTH: 548
<212> TYPE: PRT
<213> ORGANISM: Norovirus

<400> SEQUENCE: 38

```
Met Lys Met Ala Ser Asn Asp Ala Thr Pro Ser Asn Asp Gly Ala Ala
1               5                   10                  15

Gly Leu Val Pro Glu Ile Asn Asn Glu Ala Met Ala Leu Asp Pro Val
            20                  25                  30

Ala Gly Ala Ala Ile Ala Ala Pro Leu Thr Gly Gln Gln Asn Ile Ile
        35                  40                  45

Asp Pro Trp Ile Met Asn Asn Phe Val Gln Ala Pro Gly Gly Glu Phe
    50                  55                  60

Thr Val Ser Pro Arg Asn Ser Pro Gly Glu Val Leu Leu Asn Leu Glu
65                  70                  75                  80

Leu Gly Pro Glu Ile Asn Pro Tyr Leu Ala His Leu Ala Arg Met Tyr
                85                  90                  95

Asn Gly Tyr Ala Gly Gly Phe Glu Val Gln Val Val Leu Ala Gly Asn
```

-continued

```
            100                 105                 110

Ala Phe Thr Ala Gly Lys Ile Ile Phe Ala Ala Ile Pro Pro Asn Phe
        115                 120                 125

Pro Ile Asp Asn Leu Ser Ala Ala Gln Ile Thr Met Cys Pro His Val
    130                 135                 140

Ile Val Asp Val Arg Gln Leu Glu Pro Val Asn Leu Pro Met Pro Asp
145                 150                 155                 160

Val Arg Asn Asn Phe Phe His Tyr Asn Gln Gly Ser Asp Ser Arg Leu
                165                 170                 175

Arg Leu Val Ala Met Leu Tyr Thr Pro Leu Arg Ala Asn Asn Ser Gly
            180                 185                 190

Asp Asp Val Phe Thr Val Ser Cys Arg Val Leu Thr Arg Pro Ser Pro
        195                 200                 205

Glu Phe Ser Phe Asn Phe Leu Val Pro Pro Thr Val Glu Ser Lys Thr
    210                 215                 220

Lys Pro Phe Thr Leu Pro Ile Leu Thr Ile Ser Glu Met Ser Asn Ser
225                 230                 235                 240

Arg Phe Pro Val Pro Ile Asp Ser Leu His Thr Ser Pro Thr Glu Asn
                245                 250                 255

Ile Val Val Gln Cys Gln Asn Gly Arg Val Thr Leu Asp Gly Glu Leu
            260                 265                 270

Met Gly Thr Thr Gln Leu Leu Pro Ser Gln Ile Cys Ala Phe Arg Gly
        275                 280                 285

Val Leu Thr Arg Ser Thr Ser Arg Thr Ser Asp Gln Ala Asp Thr Ala
    290                 295                 300

Thr Pro Arg Leu Phe Asn Tyr Tyr Trp His Ile Gln Leu Asp Asn Leu
305                 310                 315                 320

Asn Gly Thr Pro Tyr Asp Pro Ala Glu Asp Ile Pro Gly Pro Leu Gly
                325                 330                 335

Thr Pro Asp Phe Arg Gly Lys Val Phe Gly Val Ala Ser Gln Arg Asn
            340                 345                 350

Pro Asp Ser Thr Thr Arg Ala His Glu Ala Lys Val Asp Thr Thr Ala
        355                 360                 365

Gly Arg Phe Thr Pro Lys Leu Gly Ser Leu Glu Ile Ser Thr Glu Ser
    370                 375                 380

Gly Asp Phe Asp Gln Asn Gln Pro Thr Arg Phe Thr Pro Val Gly Ile
385                 390                 395                 400

Gly Val Asp His Glu Ala Asp Phe Gln Gln Trp Ser Leu Pro Asp Tyr
                405                 410                 415

Ser Gly Gln Phe Thr His Asn Met Asn Leu Ala Pro Ala Val Ala Pro
            420                 425                 430

Asn Phe Pro Gly Glu Gln Leu Leu Phe Phe Arg Ser Gln Leu Pro Ser
        435                 440                 445

Ser Gly Gly Arg Ser Asn Gly Ile Leu Asp Cys Leu Val Pro Gln Glu
    450                 455                 460

Trp Val Gln His Phe Tyr Gln Glu Ser Ala Pro Ala Gln Thr Gln Val
465                 470                 475                 480

Ala Leu Val Arg Tyr Val Asn Pro Asp Thr Gly Arg Val Leu Phe Glu
                485                 490                 495

Ala Lys Leu His Lys Leu Gly Phe Met Thr Ile Ala Lys Asn Gly Asp
            500                 505                 510

Ser Pro Ile Thr Val Pro Pro Asn Gly Tyr Phe Arg Phe Glu Ser Trp
        515                 520                 525
```

```
Val Asn Pro Phe Tyr Thr Leu Ala Pro Met Gly Thr Gly Asn Gly Arg
    530                 535                 540

Arg Arg Val Gln
545


<210> SEQ ID NO 39
<211> LENGTH: 548
<212> TYPE: PRT
<213> ORGANISM: Norovirus

<400> SEQUENCE: 39

Met Lys Met Ala Ser Asn Asp Ala Ala Pro Ser Asn Asp Gly Ala Ala
1               5                   10                  15

Gly Leu Val Pro Glu Ile Asn Asn Glu Ala Met Ala Leu Glu Pro Val
            20                  25                  30

Ala Gly Ala Ala Ile Ala Ala Pro Leu Thr Gly Gln Gln Asn Ile Ile
        35                  40                  45

Asp Pro Trp Ile Met Asn Asn Phe Val Gln Ala Pro Gly Gly Glu Phe
    50                  55                  60

Thr Val Ser Pro Arg Asn Ser Pro Gly Glu Val Leu Leu Asn Leu Glu
65                  70                  75                  80

Leu Gly Pro Glu Ile Asn Pro Tyr Leu Ala His Leu Ala Arg Met Tyr
                85                  90                  95

Asn Gly Tyr Ala Gly Gly Phe Glu Val Gln Val Val Leu Ala Gly Asn
            100                 105                 110

Ala Phe Thr Ala Gly Lys Ile Ile Phe Ala Ala Ile Pro Pro Asn Phe
        115                 120                 125

Pro Ile Asp Asn Leu Ser Ala Ala Gln Ile Thr Met Cys Pro His Val
    130                 135                 140

Ile Val Asp Val Arg Gln Leu Glu Pro Val Asn Leu Pro Met Pro Asp
145                 150                 155                 160

Val Arg Asn Asn Phe Phe His Tyr Asn Gln Gly Ser Asp Ser Arg Leu
                165                 170                 175

Arg Leu Val Ala Met Leu Tyr Thr Pro Leu Arg Ala Asn Asn Ser Gly
            180                 185                 190

Asp Asp Val Phe Thr Val Ser Cys Arg Val Leu Thr Arg Pro Ser Pro
        195                 200                 205

Asp Phe Ser Phe Asn Phe Leu Val Pro Pro Thr Val Glu Ser Lys Thr
    210                 215                 220

Lys Pro Phe Thr Leu Pro Ile Leu Thr Ile Ser Glu Met Ser Asn Ser
225                 230                 235                 240

Arg Phe Pro Val Pro Ile Asp Ser Leu His Thr Ser Pro Thr Glu Asn
                245                 250                 255

Ile Val Val Gln Cys Gln Asn Gly Arg Val Thr Leu Asp Gly Glu Leu
            260                 265                 270

Met Gly Thr Thr Gln Leu Leu Pro Ser Gln Ile Cys Ala Phe Arg Gly
        275                 280                 285

Val Leu Thr Arg Ser Thr Ser Arg Ala Ser Asp Gln Ala Asp Thr Ala
    290                 295                 300

Thr Pro Arg Leu Phe Asn Tyr Tyr Trp His Ile Gln Leu Ala Asn Leu
305                 310                 315                 320

Asn Gly Thr Pro Tyr Asp Pro Ala Glu Asp Ile Pro Gly Pro Leu Gly
                325                 330                 335

Thr Pro Asp Phe Arg Gly Lys Val Phe Gly Val Ala Cys Gln Arg Asn
```

340 345 350

Pro Asp Cys Thr Thr Arg Ala His Glu Ala Lys Val Asp Thr Thr Ala
355 360 365

Gly Arg Phe Thr Pro Lys Leu Gly Ser Leu Glu Ile Ser Thr Glu Ser
370 375 380

Gly Asp Phe Asp Gln Asn Gln Pro Thr Arg Phe Thr Pro Val Gly Ile
385 390 395 400

Gly Val Asp His Glu Ala Asp Phe Gln Gln Trp Ser Leu Pro Asp Tyr
405 410 415

Ser Gly Gln Phe Thr His Asn Met Asn Leu Ala Pro Ala Val Ala Pro
420 425 430

Asn Phe Pro Gly Glu Gln Leu Leu Phe Phe Arg Ser Gln Leu Pro Ser
435 440 445

Ser Gly Gly Arg Ser Asn Gly Ile Leu Asp Cys Leu Val Pro Gln Glu
450 455 460

Trp Val Gln His Phe Tyr Gln Glu Ser Ala Pro Ala Gln Thr Gln Val
465 470 475 480

Ala Leu Val Arg Tyr Val Asn Pro Asp Thr Gly Arg Val Leu Phe Glu
485 490 495

Ala Lys Leu His Lys Leu Gly Phe Met Thr Ile Ala Lys Asn Gly Asp
500 505 510

Ser Pro Ile Thr Val Pro Pro Asn Gly Tyr Phe Arg Phe Glu Ser Trp
515 520 525

Val Asn Pro Phe Tyr Thr Leu Ala Pro Met Gly Thr Gly Asn Gly Arg
530 535 540

Arg Arg Ile Gln
545

<210> SEQ ID NO 40
<211> LENGTH: 540
<212> TYPE: PRT
<213> ORGANISM: Norovirus

<400> SEQUENCE: 40

Met Lys Met Ala Ser Ser Asp Ala Asn Pro Ser Asp Gly Ser Thr Ala
1 5 10 15

Asn Leu Val Pro Glu Val Asn Asn Glu Val Met Ala Leu Glu Pro Val
20 25 30

Val Gly Ala Ala Ile Ala Ala Pro Val Ala Gly Gln Gln Asn Val Ile
35 40 45

Asp Pro Trp Ile Arg Asn Asn Phe Val Gln Ala Pro Gly Gly Glu Phe
50 55 60

Thr Val Ser Pro Arg Asn Ala Pro Gly Glu Ile Leu Trp Ser Ala Pro
65 70 75 80

Leu Gly Pro Asp Leu Asn Pro Tyr Leu Ser His Leu Ala Arg Met Tyr
85 90 95

Asn Ser Tyr Ala Gly Gly Phe Glu Val Gln Val Ile Leu Ala Gly Asn
100 105 110

Ala Phe Thr Ala Gly Lys Ile Ile Phe Ala Ala Val Pro Pro Asn Phe
115 120 125

Pro Thr Glu Gly Leu Ser Pro Ser Gln Val Thr Met Phe Pro His Ile
130 135 140

Ile Val Asp Val Arg Gln Leu Glu Pro Val Leu Ile Pro Leu Pro Asp
145 150 155 160

-continued

```
Val Arg Asn Asn Phe Tyr His Tyr Asn Gln Ser Asn Asp Pro Thr Ile
                165                 170                 175

Lys Leu Ile Ala Met Leu Tyr Thr Pro Leu Arg Ala Asn Asn Ala Gly
            180                 185                 190

Asp Asp Val Phe Thr Val Ser Cys Arg Val Leu Thr Arg Pro Ser Pro
        195                 200                 205

Asp Phe Asp Phe Ile Phe Leu Val Pro Pro Thr Val Glu Ser Arg Thr
    210                 215                 220

Lys Pro Phe Ser Val Pro Ile Leu Thr Val Glu Glu Met Thr Asn Ser
225                 230                 235                 240

Arg Phe Pro Ile Pro Leu Glu Lys Leu Phe Thr Gly Pro Ser Ser Ala
                245                 250                 255

Phe Val Val Gln Pro Gln Asn Gly Arg Cys Thr Thr Asp Gly Val Leu
            260                 265                 270

Leu Gly Thr Thr Gln Leu Ser Pro Val Asn Ile Cys Thr Phe Arg Gly
        275                 280                 285

Asp Val Thr His Ile Ala Gly Thr Gln Glu Tyr Thr Met Asn Leu Ala
    290                 295                 300

Ser Gln Asn Trp Asn Asn Tyr Asp Pro Thr Glu Glu Ile Pro Ala Pro
305                 310                 315                 320

Leu Gly Thr Pro Asp Phe Val Gly Lys Ile Gln Gly Val Leu Thr Gln
                325                 330                 335

Thr Thr Arg Arg Asp Gly Ser Thr Arg Gly His Lys Ala Thr Val Ser
            340                 345                 350

Thr Gly Ser Val His Phe Thr Pro Lys Leu Gly Arg Ile Gln Phe Ser
        355                 360                 365

Thr Asp Thr Ser Asn Asp Phe Glu Thr Gly Gln Asn Thr Arg Phe Thr
    370                 375                 380

Pro Val Gly Val Val Gln Asp Gly Ser Thr Thr His Gln Asn Glu Pro
385                 390                 395                 400

Gln Gln Trp Val Leu Pro Asn Tyr Ser Gly Arg Asp Ser His Asn Val
                405                 410                 415

His Leu Ala Pro Ala Val Ala Pro Ser Phe Pro Gly Glu Gln Leu Leu
            420                 425                 430

Phe Phe Arg Ser Thr Met Pro Gly Cys Ser Gly Tyr Pro Asn Met Asn
        435                 440                 445

Leu Asp Cys Leu Leu Pro Gln Glu Trp Val Gln His Phe Tyr Gln Glu
    450                 455                 460

Ala Ala Pro Ala Gln Ser Asp Val Ala Leu Leu Arg Phe Val Asn Pro
465                 470                 475                 480

Asp Thr Gly Arg Val Leu Phe Glu Cys Lys Leu His Lys Ser Gly Tyr
                485                 490                 495

Val Thr Val Ala His Thr Gly Gln His Asp Leu Val Ile Pro Pro Asn
            500                 505                 510

Gly Tyr Phe Arg Phe Asp Ser Trp Val Asn Gln Phe Tyr Thr Leu Ala
        515                 520                 525

Pro Met Gly Asn Gly Thr Gly Arg Arg Arg Ala Leu
    530                 535                 540
```

<210> SEQ ID NO 41
<211> LENGTH: 540
<212> TYPE: PRT
<213> ORGANISM: Norovirus

<400> SEQUENCE: 41

-continued

```
Met Lys Met Ala Ser Ser Asp Ala Asn Pro Ser Asp Gly Ser Ala Ala
1               5                   10                  15

Asn Leu Val Pro Glu Val Asn Asn Glu Val Met Ala Leu Glu Pro Val
            20                  25                  30

Val Gly Ala Ala Ile Ala Ala Pro Val Ala Gly Gln Gln Asn Val Ile
        35                  40                  45

Asp Pro Trp Ile Arg Asn Asn Phe Val Gln Ala Pro Gly Gly Glu Phe
    50                  55                  60

Thr Val Ser Pro Arg Asn Ala Pro Gly Glu Ile Leu Trp Ser Ala Pro
65                  70                  75                  80

Leu Gly Pro Asp Leu Asn Pro Tyr Leu Ser His Leu Ala Arg Met Tyr
                85                  90                  95

Asn Gly Tyr Ala Gly Gly Phe Glu Val Gln Val Ile Leu Ala Gly Asn
            100                 105                 110

Ala Phe Thr Ala Gly Lys Val Ile Phe Ala Ala Val Pro Pro Asn Phe
        115                 120                 125

Pro Thr Glu Gly Leu Ser Pro Ser Gln Val Thr Met Phe Pro His Ile
    130                 135                 140

Val Val Asp Val Arg Gln Leu Glu Pro Val Leu Ile Pro Leu Pro Asp
145                 150                 155                 160

Val Arg Asn Asn Phe Tyr His Tyr Asn Gln Ser Asn Asp Pro Thr Ile
                165                 170                 175

Lys Leu Ile Ala Met Leu Tyr Thr Pro Leu Arg Ala Asn Asn Ala Gly
            180                 185                 190

Asp Asp Val Phe Thr Val Ser Cys Arg Val Leu Thr Arg Pro Ser Pro
        195                 200                 205

Asp Phe Asp Phe Ile Phe Leu Val Pro Pro Thr Val Glu Ser Arg Thr
    210                 215                 220

Lys Pro Phe Ser Val Pro Val Leu Thr Val Glu Glu Met Thr Asn Ser
225                 230                 235                 240

Arg Phe Pro Ile Pro Leu Glu Lys Leu Phe Thr Gly Pro Ser Ser Ala
                245                 250                 255

Phe Val Val Gln Pro Gln Asn Gly Arg Cys Thr Thr Asp Gly Val Leu
            260                 265                 270

Leu Gly Thr Thr Gln Leu Ser Pro Val Asn Ile Cys Thr Phe Arg Gly
        275                 280                 285

Asp Val Thr His Ile Thr Gly Ser Arg Asn Tyr Thr Met Asn Leu Ala
    290                 295                 300

Ser Gln Asn Trp Asn Asp Tyr Asp Pro Thr Glu Glu Ile Pro Ala Pro
305                 310                 315                 320

Leu Gly Thr Pro Asp Phe Val Gly Lys Ile Gln Gly Val Leu Thr Gln
                325                 330                 335

Thr Thr Arg Thr Asp Gly Ser Thr Arg Gly His Lys Ala Thr Val Tyr
            340                 345                 350

Thr Gly Ser Ala Asp Phe Ala Pro Lys Leu Gly Arg Val Gln Phe Glu
        355                 360                 365

Thr Asp Thr Asp Arg Asp Phe Glu Ala Asn Gln Asn Thr Lys Phe Thr
    370                 375                 380

Pro Val Gly Val Ile Gln Asp Gly Gly Thr Thr His Arg Asn Glu Pro
385                 390                 395                 400

Gln Gln Trp Val Leu Pro Ser Tyr Ser Gly Arg Asn Thr His Asn Val
                405                 410                 415
```

```
His Leu Ala Pro Ala Val Ala Pro Thr Phe Pro Gly Glu Gln Leu Leu
            420                 425                 430

Phe Phe Arg Ser Thr Met Pro Gly Cys Ser Gly Tyr Pro Asn Met Asp
        435                 440                 445

Leu Asp Cys Leu Leu Pro Gln Glu Trp Val Gln Tyr Phe Tyr Gln Glu
    450                 455                 460

Ala Ala Pro Ala Gln Ser Asp Val Ala Leu Leu Arg Phe Val Asn Pro
465                 470                 475                 480

Asp Thr Gly Arg Val Leu Phe Glu Cys Lys Leu His Lys Ser Gly Tyr
                485                 490                 495

Val Thr Val Ala His Thr Gly Gln His Asp Leu Val Ile Pro Pro Asn
            500                 505                 510

Gly Tyr Phe Arg Phe Asp Ser Trp Val Asn Gln Phe Tyr Thr Leu Ala
        515                 520                 525

Pro Met Gly Asn Gly Thr Gly Arg Arg Arg Ala Val
    530                 535                 540


<210> SEQ ID NO 42
<211> LENGTH: 540
<212> TYPE: PRT
<213> ORGANISM: Norovirus

<400> SEQUENCE: 42

Met Lys Met Ala Ser Asn Asp Ala Asn Pro Ser Asp Gly Ser Ala Ala
1               5                   10                  15

Asn Leu Val Pro Glu Val Asn Asn Glu Val Met Ala Leu Glu Pro Val
            20                  25                  30

Val Gly Ala Ala Ile Ala Ala Pro Val Ala Gly Gln Gln Asn Val Ile
        35                  40                  45

Asp Pro Trp Ile Arg Asn Asn Phe Val Gln Ala Pro Gly Gly Glu Phe
    50                  55                  60

Thr Val Ser Pro Arg Asn Ala Pro Gly Glu Ile Leu Trp Ser Ala Pro
65                  70                  75                  80

Leu Gly Pro Asp Leu Asn Pro Tyr Leu Ser His Leu Ala Arg Met Tyr
                85                  90                  95

Asn Gly Tyr Ala Gly Gly Phe Glu Val Gln Val Ile Leu Ala Gly Asn
            100                 105                 110

Ala Phe Thr Ala Gly Lys Ile Ile Phe Ala Ala Val Pro Pro Asn Phe
        115                 120                 125

Pro Thr Glu Gly Leu Ser Pro Ser Gln Val Thr Met Phe Pro His Ile
    130                 135                 140

Ile Val Asp Val Arg Gln Leu Glu Pro Val Leu Ile Pro Leu Pro Asp
145                 150                 155                 160

Val Arg Asn Asn Phe Tyr His Tyr Asn Gln Ser Asn Asp Ser Thr Ile
                165                 170                 175

Lys Leu Ile Ala Met Leu Tyr Thr Pro Leu Arg Ala Asn Asn Ala Gly
            180                 185                 190

Asp Asp Val Phe Thr Val Ser Cys Arg Val Leu Thr Arg Pro Ser Pro
        195                 200                 205

Asp Phe Asp Phe Ile Phe Leu Val Pro Pro Thr Val Glu Ser Arg Thr
    210                 215                 220

Lys Pro Phe Ser Val Pro Ile Leu Thr Val Glu Glu Met Thr Asn Ser
225                 230                 235                 240

Arg Phe Pro Ile Pro Leu Glu Lys Leu Phe Thr Gly Pro Ser Ser Thr
                245                 250                 255
```

-continued

```
Phe Val Val Gln Pro Gln Asn Gly Arg Cys Thr Thr Asp Gly Val Leu
            260                 265                 270

Leu Gly Thr Thr Gln Leu Ser Pro Val Asn Ile Cys Thr Phe Arg Gly
        275                 280                 285

Asp Val Thr His Ile Ala Gly Ser Arg Asn Tyr Thr Met Asn Leu Ala
    290                 295                 300

Ser Gln Asn Trp Asn Ser Tyr Asp Pro Thr Glu Glu Ile Pro Ala Pro
305                 310                 315                 320

Leu Gly Thr Pro Asp Phe Val Gly Lys Ile Gln Gly Val Leu Thr Gln
                325                 330                 335

Thr Thr Arg Thr Asp Gly Ser Thr Arg Gly His Lys Ala Thr Val Tyr
            340                 345                 350

Thr Gly Ser Ala Asp Phe Ser Pro Lys Leu Gly Arg Val Gln Phe Ala
        355                 360                 365

Thr Asp Thr Glu Asn Asp Phe Val Thr Asn Gln Asn Thr Lys Phe Thr
    370                 375                 380

Pro Val Gly Val Ile Gln Asp Gly Gly Thr Thr His Arg Asn Glu Pro
385                 390                 395                 400

Gln Gln Trp Val Leu Pro Ser Tyr Ser Gly Arg Asn Thr His Asn Val
                405                 410                 415

His Leu Ala Pro Ala Val Ala Pro Thr Phe Pro Gly Glu Gln Leu Leu
            420                 425                 430

Phe Phe Arg Ser Thr Met Pro Gly Cys Ser Gly Tyr Pro Asp Met Asp
        435                 440                 445

Leu Asp Cys Leu Leu Pro Gln Glu Trp Ile Gln Tyr Phe Tyr Gln Glu
    450                 455                 460

Ala Ala Pro Ala Gln Ser Asp Val Ala Leu Leu Arg Phe Val Asn Pro
465                 470                 475                 480

Asp Thr Gly Arg Val Leu Phe Glu Cys Lys Leu His Lys Ser Gly Tyr
                485                 490                 495

Val Thr Val Ala His Thr Gly Gln His Asp Leu Val Ile Pro Pro Asn
            500                 505                 510

Gly Tyr Phe Arg Phe Asp Ser Trp Val Asn Gln Phe Tyr Thr Leu Ala
        515                 520                 525

Pro Met Gly Asn Gly Thr Gly Arg Arg Arg Ala Leu
    530                 535                 540


<210> SEQ ID NO 43
<211> LENGTH: 540
<212> TYPE: PRT
<213> ORGANISM: Norovirus

<400> SEQUENCE: 43

Met Lys Met Ala Ser Ser Asp Ala Asn Pro Ser Asp Gly Ser Ala Ala
1               5                   10                  15

Asn Leu Val Pro Glu Val Asn Asn Glu Val Met Ala Leu Glu Pro Val
            20                  25                  30

Val Gly Ala Ala Ile Ala Ala Pro Val Ala Gly Gln Gln Asn Val Ile
        35                  40                  45

Asp Pro Trp Ile Arg Asn Asn Phe Val Gln Ala Pro Gly Gly Glu Phe
    50                  55                  60

Thr Val Ser Pro Arg Asn Ala Pro Gly Glu Ile Leu Trp Ser Ala Pro
65                  70                  75                  80

Leu Gly Pro Asp Leu Asn Pro Tyr Leu Ser His Leu Ala Arg Met Tyr
```

```
                85                  90                  95

Asn Gly Tyr Ala Gly Gly Phe Glu Val Gln Val Ile Leu Ala Gly Asn
            100                 105                 110

Ala Phe Thr Ala Gly Lys Ile Ile Phe Ala Ala Val Pro Pro Asn Phe
        115                 120                 125

Pro Thr Glu Gly Leu Ser Pro Ser Gln Val Thr Met Phe Pro His Ile
    130                 135                 140

Ile Val Asp Val Arg Gln Leu Glu Pro Val Leu Ile Pro Leu Pro Asp
145                 150                 155                 160

Val Arg Asn Asn Phe Tyr His Tyr Asn Gln Ser Asn Asp Ser Thr Ile
                165                 170                 175

Lys Leu Ile Ala Met Leu Tyr Thr Pro Leu Arg Ala Asn Asn Ala Gly
            180                 185                 190

Asp Asp Val Phe Thr Val Ser Cys Arg Val Leu Thr Arg Pro Ser Pro
        195                 200                 205

Asp Phe Asp Phe Ile Phe Leu Val Pro Pro Thr Val Glu Ser Arg Thr
    210                 215                 220

Lys Pro Phe Ser Val Pro Val Leu Thr Val Glu Glu Met Thr Asn Ser
225                 230                 235                 240

Arg Phe Pro Ile Pro Leu Glu Lys Leu Phe Thr Gly Pro Ser Ser Ala
                245                 250                 255

Phe Val Val Gln Pro Gln Asn Gly Arg Cys Thr Thr Asp Gly Val Leu
            260                 265                 270

Leu Gly Thr Thr Gln Leu Ser Pro Val Asn Ile Cys Thr Phe Arg Gly
        275                 280                 285

Asp Val Ser His Ile Thr Gly Ser Arg Asn Tyr Thr Met Asn Leu Ala
    290                 295                 300

Ser Gln Asn Trp Asn Asn Tyr Asp Pro Thr Glu Glu Ile Pro Ala Pro
305                 310                 315                 320

Leu Gly Thr Pro Asp Phe Val Gly Lys Ile Gln Gly Met Leu Thr Gln
                325                 330                 335

Thr Thr Arg Ala Asp Gly Ser Thr Arg Gly His Lys Ala Thr Val Tyr
            340                 345                 350

Thr Gly Ser Ala Asp Phe Ala Pro Lys Leu Gly Arg Val Gln Phe Glu
        355                 360                 365

Thr Asp Thr Asp His Asp Phe Glu Ala Asn Gln Asn Thr Lys Phe Thr
    370                 375                 380

Pro Val Gly Val Ile Gln Asp Gly Ser Thr Thr His Arg Asn Glu Pro
385                 390                 395                 400

Gln Gln Trp Val Leu Pro Ser Tyr Ser Gly Arg Asn Thr His Asn Val
                405                 410                 415

His Leu Ala Pro Ala Val Ala Pro Thr Phe Pro Gly Glu Gln Leu Leu
            420                 425                 430

Phe Phe Arg Ser Thr Met Pro Gly Cys Ser Gly Tyr Pro Asn Met Asp
        435                 440                 445

Leu Asp Cys Leu Leu Pro Gln Glu Trp Val Gln Tyr Phe Tyr Gln Glu
    450                 455                 460

Ala Ala Pro Ala Gln Ser Asp Val Ala Leu Leu Arg Phe Val Asn Pro
465                 470                 475                 480

Asp Thr Gly Arg Val Leu Phe Glu Cys Lys Leu His Lys Ser Gly Tyr
                485                 490                 495

Val Thr Val Ala His Thr Gly Gln His Asp Leu Val Ile Pro Pro Asn
            500                 505                 510
```

Gly Tyr Phe Arg Phe Asp Ser Trp Val Asn Gln Phe Tyr Thr Leu Ala
        515                 520                 525

Pro Met Gly Asn Gly Thr Gly Arg Arg Arg Ala Val
    530                 535                 540

<210> SEQ ID NO 44
<211> LENGTH: 539
<212> TYPE: PRT
<213> ORGANISM: Norovirus

<400> SEQUENCE: 44

Met Lys Met Ala Ser Asn Asp Ala Asn Pro Ser Asp Gly Ser Thr Ala
1               5                   10                  15

Asn Leu Val Pro Glu Val Asn Asn Glu Val Met Ala Leu Glu Pro Val
            20                  25                  30

Val Gly Ala Ala Ile Ala Ala Pro Val Ala Gly Gln Gln Asn Val Ile
        35                  40                  45

Asp Pro Trp Ile Arg Asn Asn Phe Val Gln Ala Pro Gly Gly Glu Phe
    50                  55                  60

Thr Val Ser Pro Arg Asn Ala Pro Gly Glu Ile Leu Trp Ser Ala Pro
65                  70                  75                  80

Leu Gly Pro Asp Leu Asn Pro Tyr Leu Ser His Leu Ala Arg Met Tyr
                85                  90                  95

Asn Gly Tyr Ala Gly Gly Phe Glu Val Gln Val Ile Leu Ala Gly Asn
            100                 105                 110

Ala Phe Thr Ala Gly Lys Ile Ile Phe Ala Ala Val Pro Pro Asn Phe
        115                 120                 125

Pro Thr Glu Gly Leu Ser Pro Ser Gln Val Thr Met Phe Pro His Ile
    130                 135                 140

Ile Val Asp Val Arg Gln Leu Glu Pro Val Leu Ile Pro Leu Pro Asp
145                 150                 155                 160

Val Arg Asn Asn Phe Tyr His Tyr Asn Gln Ser Asn Asp Ser Thr Ile
                165                 170                 175

Lys Leu Ile Ala Met Leu Tyr Thr Pro Leu Arg Ala Asn Asn Ala Gly
            180                 185                 190

Asp Asp Val Phe Thr Val Ser Cys Arg Val Leu Thr Arg Pro Ser Pro
        195                 200                 205

Asp Phe Asp Phe Ile Phe Leu Val Pro Pro Thr Val Glu Ser Arg Thr
    210                 215                 220

Lys Pro Phe Thr Val Pro Ile Leu Thr Val Glu Glu Met Ser Asn Ser
225                 230                 235                 240

Arg Phe Pro Ile Pro Leu Glu Lys Leu Tyr Thr Gly Pro Ser Ser Ala
                245                 250                 255

Phe Val Val Gln Pro Gln Asn Gly Arg Cys Thr Thr Asp Gly Val Leu
            260                 265                 270

Leu Gly Thr Thr Gln Leu Ser Ala Val Asn Ile Cys Thr Phe Arg Gly
        275                 280                 285

Asp Val Thr His Ile Ala Gly Ser His Asp Tyr Thr Met Asn Leu Ala
    290                 295                 300

Ser Gln Asn Trp Asn Asn Tyr Asp Pro Thr Glu Glu Ile Pro Ala Pro
305                 310                 315                 320

Leu Gly Thr Pro Asp Phe Val Gly Lys Ile Gln Gly Leu Leu Thr Gln
                325                 330                 335

Thr Thr Arg Glu Asp Gly Ser Thr Arg Ala His Lys Ala Thr Val Ser

```
            340                 345                 350

Thr Gly Ser Val His Phe Thr Pro Lys Leu Gly Ser Val Gln Tyr Thr
        355                 360                 365

Thr Asp Thr Asn Asn Asp Phe Gln Thr Gly Gln Asn Thr Lys Phe Thr
    370                 375                 380

Pro Val Gly Val Ile Gln Asp Gly Asn Asn His Gln Asn Glu Pro Gln
385                 390                 395                 400

Gln Trp Val Leu Pro Asn Tyr Ser Gly Arg Thr Gly His Asn Val His
                405                 410                 415

Leu Ala Pro Ala Val Ala Pro Thr Phe Pro Gly Glu Gln Leu Leu Phe
            420                 425                 430

Phe Arg Ser Thr Met Pro Gly Cys Ser Gly Tyr Pro Asn Met Asn Leu
        435                 440                 445

Asp Cys Leu Leu Pro Gln Glu Trp Val Gln His Phe Tyr Gln Glu Ala
    450                 455                 460

Ala Pro Ala Gln Ser Asp Val Ala Leu Leu Arg Phe Val Asn Pro Asp
465                 470                 475                 480

Thr Gly Arg Val Leu Phe Glu Cys Lys Leu His Lys Ser Gly Tyr Val
                485                 490                 495

Thr Val Ala His Thr Gly Pro His Asp Leu Val Ile Pro Pro Asn Gly
            500                 505                 510

Tyr Phe Arg Phe Asp Ser Trp Val Asn Gln Phe Tyr Thr Leu Ala Pro
        515                 520                 525

Met Gly Asn Gly Ala Gly Arg Arg Arg Ala Leu
    530                 535


<210> SEQ ID NO 45
<211> LENGTH: 540
<212> TYPE: PRT
<213> ORGANISM: Norovirus

<400> SEQUENCE: 45

Met Lys Met Ala Ser Asn Asp Ala Asn Pro Ser Asp Gly Ser Ala Ala
1               5                   10                  15

Asn Leu Val Pro Glu Val Asn Asn Glu Val Met Ala Leu Glu Pro Val
            20                  25                  30

Ala Gly Ala Ala Leu Ala Ala Pro Val Ala Gly Gln Gln Asn Val Ile
        35                  40                  45

Asp Pro Trp Ile Arg Asn Asn Phe Val Gln Ala Pro Gly Gly Glu Phe
    50                  55                  60

Thr Val Ser Pro Arg Asn Ala Pro Gly Glu Ile Leu Trp Ser Ala Pro
65                  70                  75                  80

Leu Ser Pro Asp Leu Asn Pro Tyr Leu Ser His Leu Ala Arg Met Tyr
                85                  90                  95

Asn Ser Tyr Ala Gly Gly Phe Glu Val Gln Val Ile Leu Ala Gly Asn
            100                 105                 110

Ala Phe Thr Ala Gly Lys Ile Ile Phe Ala Ala Val Pro Pro Asn Phe
        115                 120                 125

Pro Ile Glu Gly Leu Ser Pro Ser Gln Val Thr Met Phe Pro His Ile
    130                 135                 140

Ile Val Asp Val Arg Gln Leu Glu Pro Val Leu Ile Pro Leu Pro Asp
145                 150                 155                 160

Val Arg Asn Asn Phe Tyr His Tyr Asn Gln Thr Asn Glu Pro Thr Ile
                165                 170                 175
```

```
Lys Leu Ile Ala Met Leu Tyr Thr Pro Leu Arg Ala Asn Asn Ala Gly
            180                 185                 190

Glu Asp Val Phe Thr Val Ser Cys Arg Val Leu Thr Arg Pro Ser Pro
        195                 200                 205

Asp Phe Asp Phe Ile Phe Leu Val Pro Pro Thr Val Glu Ser Arg Thr
    210                 215                 220

Lys Pro Phe Thr Val Pro Ile Leu Thr Val Glu Glu Met Thr Asn Ser
225                 230                 235                 240

Arg Phe Pro Ile Pro Leu Glu Lys Leu Phe Thr Gly Pro Ser Ser Ser
                245                 250                 255

Phe Val Val Gln Pro Gln Asn Gly Arg Cys Thr Thr Asp Gly Val Leu
            260                 265                 270

Leu Gly Thr Thr Gln Leu Ser Pro Val Asn Ile Cys Thr Phe Arg Gly
        275                 280                 285

Asp Val Thr His Ile Ala Gly Ser Arg Asn Tyr Thr Met Asn Leu Ala
    290                 295                 300

Ser Ile Asn Trp Asn Asn Tyr Asp Pro Thr Glu Glu Ile Pro Ala Pro
305                 310                 315                 320

Leu Gly Thr Pro Asp Phe Val Gly Lys Ile Gln Gly Met Leu Thr Gln
                325                 330                 335

Thr Thr Arg Gly Glu Gly Ser Thr Arg Ala His Arg Ala Thr Val Tyr
            340                 345                 350

Thr Gly Ser Ala Pro Phe Thr Pro Lys Leu Gly Ser Val Gln Phe Thr
        355                 360                 365

Thr Asp Thr Asp Asn Asp Phe Asp Ala Asn Gln Asn Thr Lys Phe Thr
    370                 375                 380

Pro Val Gly Val Ile Gln Asp Gly Asp Thr Ala His Arg Asn Glu Pro
385                 390                 395                 400

Gln Gln Trp Val Leu Pro Ser Tyr Ser Gly Arg Asn Val Gln Asn Val
                405                 410                 415

His Leu Ala Pro Ala Val Ala Pro Thr Phe Pro Gly Glu Gln Leu Leu
            420                 425                 430

Phe Phe Arg Ser Thr Met Pro Gly Cys Ser Gly Tyr Pro Asn Met Asp
        435                 440                 445

Leu Asp Cys Leu Leu Pro Gln Glu Trp Val Gln His Phe Tyr Gln Glu
    450                 455                 460

Ala Ala Pro Ala Gln Ser Asp Val Ala Leu Leu Arg Phe Val Asn Pro
465                 470                 475                 480

Asp Thr Gly Arg Val Leu Phe Glu Cys Lys Leu His Lys Ser Gly Tyr
                485                 490                 495

Val Thr Val Ala His Thr Gly Gln His Asp Leu Val Ile Pro Pro Asn
            500                 505                 510

Gly Tyr Phe Arg Phe Asp Ser Trp Val Asn Gln Phe Tyr Thr Leu Ala
        515                 520                 525

Pro Met Gly Asn Gly Ala Gly Arg Arg Arg Ala Leu
    530                 535                 540
```

<210> SEQ ID NO 46
<211> LENGTH: 540
<212> TYPE: PRT
<213> ORGANISM: Norovirus

<400> SEQUENCE: 46

```
Met Lys Met Ala Ser Asn Asp Ala Asn Pro Ser Asp Gly Ser Ala Ala
1               5                   10                  15
```

-continued

```
Asn Leu Val Pro Glu Val Asn Asn Glu Val Met Ala Leu Glu Pro Val
            20                  25                  30

Val Gly Ala Ala Ile Ala Ala Pro Val Ala Gly Gln Gln Asn Val Ile
        35                  40                  45

Asp Pro Trp Ile Arg Asn Asn Phe Val Gln Ala Pro Gly Gly Glu Phe
    50                  55                  60

Thr Val Ser Pro Arg Asn Ala Pro Gly Glu Ile Leu Trp Ser Ala Pro
65                  70                  75                  80

Leu Gly Pro Asp Leu Asn Pro Tyr Leu Ser His Leu Ala Arg Met Tyr
                85                  90                  95

Asn Gly Tyr Ala Gly Gly Phe Glu Val Gln Val Ile Leu Ala Gly Asn
            100                 105                 110

Ala Phe Thr Ala Gly Lys Ile Ile Phe Ala Ala Val Pro Pro Asn Phe
        115                 120                 125

Pro Thr Glu Gly Leu Ser Pro Ser Gln Val Thr Met Phe Pro His Ile
    130                 135                 140

Ile Val Asp Val Arg Gln Leu Glu Pro Val Leu Ile Pro Leu Pro Asp
145                 150                 155                 160

Val Arg Asn Asn Phe Tyr His Tyr Asn Gln Ser Asn Asp Ser Thr Ile
                165                 170                 175

Lys Leu Ile Ala Met Leu Tyr Thr Pro Leu Arg Ala Asn Asn Ala Gly
            180                 185                 190

Asp Asp Val Phe Thr Val Ser Cys Arg Val Leu Thr Arg Pro Ser Pro
        195                 200                 205

Asp Phe Asp Phe Ile Phe Leu Val Pro Pro Thr Val Glu Ser Arg Ser
    210                 215                 220

Lys Pro Phe Ser Val Pro Val Leu Thr Val Glu Glu Met Thr Asn Ser
225                 230                 235                 240

Arg Phe Pro Ala Thr Leu Asp Lys Leu Phe Thr Gly Pro Ser Ser Thr
                245                 250                 255

Phe Val Val Gln Pro Gln Asn Gly Arg Cys Met Ile Asp Gly Val Leu
            260                 265                 270

Leu Gly Thr Thr Gln Leu Ser Pro Val Asn Ile Cys Thr Phe Arg Gly
        275                 280                 285

Asp Val Thr His Leu Arg Asp Ser Pro Ile Tyr Thr Met Asn Leu Ala
    290                 295                 300

Ser Pro Asn Trp Asn Asn Tyr Asp Ser Thr Glu Glu Ile Pro Ala Pro
305                 310                 315                 320

Leu Gly Thr Pro Asp Phe Val Gly Lys Ile Gln Gly Val Leu Thr Gln
                325                 330                 335

Thr Thr Lys Gly Glu Gly Ser Thr Arg Gly His Arg Ala Thr Val Tyr
            340                 345                 350

Val Gly Ser Ala Asn Tyr Thr Pro Lys Leu Gly Lys Val Gln Phe Glu
        355                 360                 365

Thr Asn Thr Thr Asn Asp Leu Tyr Ala His Gln Asn Thr Lys Phe Thr
    370                 375                 380

Pro Val Gly Val Val Gln Gly Gly Glu Ser Ala His Arg Ser Glu Pro
385                 390                 395                 400

Gln Gln Trp Val Leu Pro Gly Tyr Ser Gly Arg Asp Thr Pro Asn Val
                405                 410                 415

His Leu Ala Pro Ala Val Ala Pro Thr Phe Pro Gly Glu Gln Leu Leu
            420                 425                 430
```

-continued

```
Phe Phe Arg Ser Thr Ile Pro Gly Cys Gly Gly His Pro Asn Met Asp
        435                 440                 445

Leu Asp Cys Leu Leu Pro Gln Glu Trp Val Gln His Phe Tyr Gln Glu
    450                 455                 460

Ala Ala Pro Ala Gln Ser Asp Val Ala Leu Leu Arg Phe Val Asn Pro
465                 470                 475                 480

Asp Thr Ser Arg Val Leu Phe Glu Cys Lys Leu His Lys Ser Gly Tyr
                485                 490                 495

Val Thr Val Ala His Thr Gly Gln His Asp Leu Val Ile Pro Pro Asn
            500                 505                 510

Gly Tyr Phe Arg Phe Asp Ser Trp Val Asn Gln Phe Tyr Thr Leu Ala
        515                 520                 525

Pro Met Gly Asn Gly Thr Gly Arg Lys Arg Ala Ile
    530                 535                 540


<210> SEQ ID NO 47
<211> LENGTH: 539
<212> TYPE: PRT
<213> ORGANISM: Norovirus

<400> SEQUENCE: 47

Met Lys Met Ala Ser Ser Asp Ala Asn Pro Ser Asp Gly Ser Ala Ala
1               5                   10                  15

Asn Leu Val Pro Glu Val Asn Asn Glu Val Met Ala Leu Glu Pro Val
            20                  25                  30

Val Gly Ala Ala Ile Ala Ala Pro Val Ala Gly Gln Gln Asn Val Ile
        35                  40                  45

Asp Pro Trp Ile Arg Asn Asn Phe Val Gln Ala Pro Gly Gly Glu Phe
    50                  55                  60

Thr Val Ser Pro Arg Asn Ala Pro Gly Glu Ile Leu Trp Ser Ala Pro
65                  70                  75                  80

Leu Gly Pro Asp Leu Asn Pro Tyr Leu Ser His Leu Ala Arg Met Tyr
                85                  90                  95

Asn Gly Tyr Ala Gly Gly Phe Glu Val Gln Val Ile Leu Ala Gly Asn
            100                 105                 110

Ala Phe Thr Ala Gly Lys Ile Ile Phe Ala Ala Val Pro Pro Thr Phe
        115                 120                 125

Pro Thr Glu Gly Leu Ser Pro Ser Gln Val Thr Met Phe Pro His Ile
    130                 135                 140

Ile Val Asp Val Arg Gln Leu Glu Pro Val Leu Ile Pro Leu Pro Asp
145                 150                 155                 160

Val Arg Asn Asn Phe Tyr His Tyr Asn Gln Ser Asn Asp Ser Thr Ile
                165                 170                 175

Lys Leu Ile Ala Met Leu Tyr Thr Pro Leu Arg Ala Asn Asn Pro Gly
            180                 185                 190

Asp Asp Val Phe Thr Val Ser Cys Arg Val Leu Thr Arg Pro Ser Pro
        195                 200                 205

Asp Phe Asp Phe Ile Phe Leu Val Pro Pro Thr Val Glu Ser Arg Thr
    210                 215                 220

Lys Pro Phe Ser Val Pro Ile Leu Thr Val Gly Glu Met Thr Asn Ser
225                 230                 235                 240

Arg Phe Pro Ile Asn Leu Glu Arg Leu Phe Thr Gly Pro Ser Ser Ala
                245                 250                 255

Asn Val Val Gln Pro Gln Asn Gly Arg Cys Thr Ile Asp Gly Glu Leu
            260                 265                 270
```

Leu Gly Thr Thr Gln Leu Ser Ser Val Asn Ile Cys Thr Phe Arg Gly
275 280 285

Asp Val Thr His Ile Gly Ser Thr His His Trp Thr Met Asn Leu Ala
290 295 300

Ser Pro Asn Trp Asn Asn Tyr Asp Pro Thr Glu Glu Thr Pro Ala Pro
305 310 315 320

Leu Gly Thr Pro Asp Phe Val Gly Lys Ile His Gly Met Leu Thr Gln
325 330 335

Thr Thr Gln Gly Asn Gly Ser Thr Arg Gly His Arg Ala Thr Val Tyr
340 345 350

Val Gly Ser Ala Glu Phe Thr Pro Lys Leu Gly Lys Val Gln Phe Lys
355 360 365

Thr Glu Thr Asp His Asp Leu Ala Ile Arg Gln Asn Thr Lys Phe Thr
370 375 380

Pro Val Gly Val Ile Gln Glu Ser Asp His His Arg Asp Glu Pro Gln
385 390 395 400

Gln Trp Arg Leu Pro Asn Tyr Ser Gly Ala Asn Thr Phe Asn Val His
405 410 415

Leu Ala Pro Ala Val Ala Pro Asn Phe Pro Gly Glu Gln Leu Leu Phe
420 425 430

Phe Arg Ser Thr Leu Pro Gly Cys Gly Gly His Pro Asn Met Asp Leu
435 440 445

Asp Cys Leu Leu Pro Gln Glu Trp Val Gln His Phe Tyr Gln Glu Ala
450 455 460

Ala Pro Ala Gln Ser Asp Val Ala Leu Leu Arg Phe Val Asn Pro Asp
465 470 475 480

Thr Ser Arg Val Leu Phe Glu Cys Lys Leu His Lys Ser Gly Tyr Val
485 490 495

Thr Val Ala His Thr Gly Gln Tyr Asp Leu Val Leu Pro Ser Asn Gly
500 505 510

Tyr Phe Arg Phe Asp Ser Trp Val Asn Gln Phe Tyr Thr Leu Ala Pro
515 520 525

Met Gly Asn Gly Thr Gly Arg Arg Arg Ala Leu
530 535

<210> SEQ ID NO 48
<211> LENGTH: 539
<212> TYPE: PRT
<213> ORGANISM: Norovirus

<400> SEQUENCE: 48

Met Lys Met Ala Ser Asn Asp Ala Ser Pro Ser Asp Gly Ser Ala Ala
1 5 10 15

Asn Leu Val Pro Glu Val Asn Asn Glu Val Met Ala Leu Glu Pro Val
20 25 30

Val Gly Ala Ala Ile Ala Ala Pro Val Ala Gly Gln Gln Asn Val Ile
35 40 45

Asp Pro Trp Ile Arg Asn Asn Phe Val Gln Ala Pro Gly Gly Glu Phe
50 55 60

Thr Val Ser Pro Arg Asn Ala Pro Gly Glu Ile Leu Trp Ser Ala Pro
65 70 75 80

Leu Gly Pro Asp Leu Asn Pro Tyr Leu Ser His Leu Ala Arg Met Tyr
85 90 95

Asn Gly Tyr Ala Gly Gly Phe Glu Val Gln Val Ile Leu Ala Gly Asn

-continued

```
            100                 105                 110

Ala Phe Thr Ala Gly Lys Ile Ile Phe Ala Ala Val Pro Pro Asn Phe
        115                 120                 125

Pro Thr Glu Gly Leu Ser Pro Ser Gln Val Thr Met Phe Pro His Ile
    130                 135                 140

Val Val Asp Val Arg Gln Leu Glu Pro Val Leu Ile Pro Leu Pro Asp
145                 150                 155                 160

Val Arg Asn Asn Phe Tyr His Tyr Asn Gln Ser Lys Asp Pro Thr Ile
                165                 170                 175

Lys Leu Ile Ala Met Leu Tyr Thr Pro Leu Arg Ala Asn Asn Ala Gly
            180                 185                 190

Glu Asp Val Phe Thr Val Ser Cys Arg Val Leu Thr Arg Pro Ser Pro
        195                 200                 205

Asp Phe Asp Phe Ile Phe Leu Val Pro Pro Thr Val Glu Ser Arg Ser
    210                 215                 220

Lys Pro Phe Thr Val Pro Ile Leu Thr Val Glu Glu Met Thr Asn Ser
225                 230                 235                 240

Arg Phe Pro Ile Pro Leu Glu Lys Leu Phe Thr Gly Pro Ser Gly Ala
                245                 250                 255

Phe Val Val Gln Pro Gln Asn Gly Arg Cys Thr Thr Asp Gly Val Leu
            260                 265                 270

Leu Gly Thr Thr Gln Leu Ser Pro Val Asn Ile Cys Thr Phe Arg Gly
        275                 280                 285

Asp Leu Thr His Phe Thr Gly Thr Ser Glu Tyr Ala Met Asn Leu Ala
    290                 295                 300

Ser Gln Asn Trp Asp Asn Tyr Asp Pro Thr Glu Glu Ile Pro Ala Pro
305                 310                 315                 320

Leu Gly Ala Pro Asp Phe Val Gly Lys Ile Arg Gly Met Leu Thr Gln
                325                 330                 335

Thr Thr Arg Arg Asp Gly Ser Thr Arg Gly His Arg Ala Thr Leu Ser
            340                 345                 350

Thr Gly Ser Ala His Phe Thr Pro Lys Leu Gly Asn Ile Arg Phe Ser
        355                 360                 365

Thr Asp Thr Asn Asn Asp Phe Glu Ala Gly Gln Asn Thr Lys Phe Thr
    370                 375                 380

Pro Val Gly Val Phe Gln Glu Gly Asp Asn His Gln Asn Glu Pro Gln
385                 390                 395                 400

Gln Trp Val Leu Pro Asn Tyr Ser Gly Ala Thr Ala His Asn Val His
                405                 410                 415

Leu Ala Pro Ala Val Ala Pro Ala Phe Pro Gly Glu Gln Leu Leu Phe
            420                 425                 430

Phe Arg Ser Thr Met Pro Gly Cys Gly Gly Tyr Pro Asn Met Asn Leu
        435                 440                 445

Asp Cys Leu Leu Pro Gln Glu Trp Val Gln His Phe Tyr Gln Glu Ala
    450                 455                 460

Ala Pro Ala Gln Ser Asp Val Ala Leu Leu Arg Phe Val Asn Pro Asp
465                 470                 475                 480

Thr Ser Arg Val Leu Phe Glu Cys Lys Leu His Lys Ser Gly Tyr Val
                485                 490                 495

Thr Val Ala His Thr Gly Gln His Asp Leu Val Ile Pro Pro Asn Gly
            500                 505                 510

Tyr Phe Arg Phe Asp Ser Trp Val Asn Gln Phe Tyr Thr Leu Ala Pro
        515                 520                 525
```

Met Gly Asn Gly Thr Gly Arg Arg Arg Ala Leu
530 535

<210> SEQ ID NO 49
<211> LENGTH: 539
<212> TYPE: PRT
<213> ORGANISM: Norovirus

<400> SEQUENCE: 49

Met Lys Met Ala Ser Ser Asp Ala Asn Pro Ser Asp Gly Ser Thr Ala
1 5 10 15

Asn Leu Val Pro Glu Ala Asn Asn Glu Val Met Ala Leu Glu Pro Val
20 25 30

Val Gly Ala Ala Ile Ala Ala Pro Val Ala Gly Gln Gln Asn Val Ile
35 40 45

Asp Pro Trp Ile Arg Asn Asn Phe Val Gln Ala Pro Gly Gly Glu Phe
50 55 60

Thr Val Ser Pro Arg Asn Ala Pro Gly Glu Ile Leu Trp Ser Ala Pro
65 70 75 80

Leu Gly Pro Asp Leu Asn Pro Tyr Leu Ser His Leu Ser Arg Met Tyr
85 90 95

Asn Gly Tyr Ala Gly Gly Phe Glu Val Gln Val Ile Leu Ala Gly Asn
100 105 110

Ala Phe Ala Ala Gly Lys Ile Ile Phe Ala Ala Val Pro Pro Asn Phe
115 120 125

Pro Thr Glu Gly Leu Ser Pro Ser Gln Val Thr Met Phe Pro His Leu
130 135 140

Ile Val Asp Val Arg Gln Leu Glu Pro Val Met Ile Pro Leu Pro Asp
145 150 155 160

Ile Arg Asn Asn Phe Tyr His Tyr Asn Gln Ser Asn Asp Pro Thr Ile
165 170 175

Lys Leu Ile Ala Met Leu Tyr Thr Pro Leu Arg Ala Asn Asn Val Gly
180 185 190

Asp Asp Val Phe Thr Val Ser Cys Arg Val Leu Thr Arg Pro Ser Pro
195 200 205

Asp Phe Asp Phe Ile Phe Leu Val Pro Pro Thr Val Glu Ser Lys Thr
210 215 220

Asn Pro Phe Ser Val Pro Ile Leu Thr Ile Glu Glu Met Thr Asn Ser
225 230 235 240

Arg Phe Pro Ile Pro Leu Glu Lys Leu Phe Thr Gly Pro Ser Ser Ala
245 250 255

Leu Val Val Gln Pro Gln Asn Gly Arg Cys Thr Thr Asp Gly Val Leu
260 265 270

Leu Gly Thr Thr Gln Leu Ser Pro Val Asn Ile Cys Thr Phe Arg Gly
275 280 285

Asp Val Thr His Thr Thr Lys Thr His Thr Tyr Gln Met Asn Leu Ala
290 295 300

Ala Gln Asn Trp Asn Ser Tyr Asp Pro Thr Glu Glu Ile Pro Ala Pro
305 310 315 320

Leu Gly Thr Pro Asp Phe Val Gly Lys Ile Gln Gly Val Leu Thr Gln
325 330 335

Thr Thr Lys Gly Asn Gly Ser Thr Arg Ala His Lys Ala Thr Val Tyr
340 345 350

Thr Gly Ser Ala Glu Phe Thr Pro Lys Leu Gly Arg Ile Gln Leu Phe

```
        355                 360                 365

Thr Asp Thr Asp Asn Asp Leu Glu Ala Asn Gln Asn Thr Lys Phe Thr
    370                 375                 380

Pro Val Gly Val Ile Gln Asp Gly Asp Thr His Gln Asn Glu Pro Gln
385                 390                 395                 400

Gln Trp Val Leu Pro Ser Tyr Ser Gly Arg Asn Asn His Asn Val His
                405                 410                 415

Leu Ala Pro Ala Val Ala Pro Thr Phe Pro Gly Glu Gln Leu Leu Phe
            420                 425                 430

Phe Arg Ser Thr Met Pro Gly Cys Ser Gly Tyr Pro Asn Met Asn Leu
        435                 440                 445

Asp Cys Leu Leu Pro Gln Glu Trp Val Gln Tyr Phe Tyr Gln Glu Ala
    450                 455                 460

Ala Pro Ala Gln Ser Asp Val Ala Leu Leu Arg Phe Val Asn Pro Asp
465                 470                 475                 480

Thr Gly Arg Val Leu Phe Glu Cys Lys Leu His Lys Ser Gly Tyr Val
                485                 490                 495

Thr Val Ala His Thr Gly His His Asp Leu Phe Ile Pro Pro Asn Gly
            500                 505                 510

Tyr Phe Arg Phe Asp Ser Trp Val Ser Pro Phe Tyr Thr Leu Ala Pro
        515                 520                 525

Met Gly Asn Gly Thr Gly Arg Arg Arg Ala Leu
    530                 535


<210> SEQ ID NO 50
<211> LENGTH: 538
<212> TYPE: PRT
<213> ORGANISM: Norovirus

<400> SEQUENCE: 50

Met Lys Met Ala Ser Ser Asp Ala Asn Pro Ser Asp Gly Ser Ala Ala
1               5                   10                  15

Asn Leu Val Pro Glu Val Asn Asn Glu Val Met Ala Leu Glu Pro Val
            20                  25                  30

Val Gly Ala Ala Ile Ala Ala Pro Val Ala Gly Gln Gln Asn Val Ile
        35                  40                  45

Asp Pro Trp Ile Arg Asn Asn Phe Val Gln Ala Pro Gly Gly Glu Phe
    50                  55                  60

Thr Ile Ser Pro Arg Asn Ala Pro Gly Glu Ile Leu Trp Ser Ala Pro
65                  70                  75                  80

Leu Gly Pro Asp Leu Asn Pro Tyr Leu Ser His Leu Ala Arg Met Tyr
                85                  90                  95

Asn Gly Tyr Ala Gly Gly Phe Glu Val Gln Val Val Leu Ala Gly Asn
            100                 105                 110

Ala Phe Thr Ala Gly Lys Ile Ile Phe Ala Ala Val Pro Pro Asn Phe
        115                 120                 125

Pro Thr Glu Gly Leu Ser Pro Ser Gln Val Thr Met Phe Pro His Ile
    130                 135                 140

Ile Val Asp Val Arg Gln Leu Glu Pro Val Leu Ile Pro Leu Pro Asp
145                 150                 155                 160

Val Arg Asn Asn Phe Tyr His Tyr Asn Gln Ser Lys Asp Ser Thr Ile
                165                 170                 175

Lys Leu Ile Ala Met Leu Tyr Thr Pro Leu Arg Ala Asn Asn Ala Gly
            180                 185                 190
```

```
Asp Asp Val Phe Thr Val Ser Cys Arg Val Leu Thr Arg Pro Ser Pro
        195                 200                 205

Asp Phe Asp Phe Ile Phe Leu Val Pro Pro Thr Val Glu Ser Arg Thr
    210                 215                 220

Lys Pro Phe Ser Val Pro Val Leu Thr Val Glu Glu Met Thr Asn Ser
225                 230                 235                 240

Arg Phe Pro Ile Pro Leu Glu Lys Leu Phe Thr Gly Pro Ser Ser Ala
                245                 250                 255

Phe Val Val Gln Pro Gln Asn Gly Arg Cys Thr Thr Asp Gly Val Leu
            260                 265                 270

Leu Gly Thr Thr Gln Leu Ser Ala Val Asn Ile Cys Thr Phe Arg Gly
        275                 280                 285

Asp Val Thr His Val Ala Gly Asp Thr Phe Ala Met Asn Leu Ala Ser
    290                 295                 300

Leu Asn Trp Asn Asn Tyr Asp Pro Thr Glu Glu Thr Pro Ala Pro Leu
305                 310                 315                 320

Gly Thr Pro Asp Phe Val Gly Arg Ile His Gly Met Leu Thr Gln Thr
                325                 330                 335

Thr Arg Ser Asp Gly Ala Thr Arg Ala His Lys Ala Thr Val Ser Thr
            340                 345                 350

Gly Gly Ala Asp Phe Thr Pro Lys Leu Gly Ser Val Arg Tyr Ser Thr
        355                 360                 365

Asp Thr Ser Ser Asp Leu Glu Val Arg Glu Asn Thr Lys Phe Thr Pro
    370                 375                 380

Ile Gly Val Leu His Ser Ser Gly Gly His Arg Ala Glu Pro Asp Gln
385                 390                 395                 400

Trp Arg Leu Pro Glu Tyr Ser Gly Arg Asn Val His Asn Val His Leu
                405                 410                 415

Ala Pro Ala Val Ala Pro Thr Phe Pro Gly Glu Gln Leu Leu Phe Phe
            420                 425                 430

Arg Ser Thr Met Pro Gly Cys Gly Gly Tyr Pro Asn Met Asp Leu Asp
        435                 440                 445

Cys Leu Leu Pro Gln Glu Trp Val Gln His Phe Tyr Gln Glu Ala Ala
    450                 455                 460

Pro Ala Gln Ser Asp Val Ala Leu Leu Arg Phe Val Asn Pro Asp Thr
465                 470                 475                 480

Gly Arg Val Leu Phe Glu Cys Lys Leu His Lys Ser Gly Tyr Val Thr
                485                 490                 495

Val Ala His Thr Gly Pro His Asp Leu Val Ile Pro Pro Asn Gly Tyr
            500                 505                 510

Phe Arg Phe Asp Ser Trp Val Asn Gln Phe Tyr Thr Leu Ala Pro Met
        515                 520                 525

Gly Asn Gly Thr Gly Arg Arg Arg Ala Leu
    530                 535
```

<210> SEQ ID NO 51
<211> LENGTH: 539
<212> TYPE: PRT
<213> ORGANISM: Norovirus

<400> SEQUENCE: 51

```
Met Lys Met Ala Ser Ser Asp Ala Asn Pro Ser Asp Gly Ser Ala Ala
1               5                   10                  15

Asn Leu Val Pro Glu Val Asn Asn Glu Val Met Ala Leu Glu Pro Val
            20                  25                  30
```

-continued

```
Val Gly Ala Ala Ile Ala Ala Pro Val Ala Gly Gln Gln Asn Ile Ile
        35                  40                  45

Asp Pro Trp Ile Arg Asn Asn Phe Val Gln Ala Pro Gly Gly Glu Phe
    50                  55                  60

Thr Val Ser Pro Arg Asn Ala Pro Gly Glu Ile Leu Trp Ser Ala Pro
65                  70                  75                  80

Leu Gly Pro Asp Leu Asn Pro Tyr Leu Ser His Leu Ser Arg Met Tyr
                85                  90                  95

Asn Gly Tyr Ala Gly Gly Phe Glu Val Gln Val Ile Leu Ala Gly Asn
            100                 105                 110

Ala Phe Thr Ala Gly Lys Val Ile Phe Ala Ala Val Pro Pro Asn Phe
        115                 120                 125

Pro Thr Glu Gly Leu Ser Pro Ser Gln Val Thr Met Phe Pro His Ile
    130                 135                 140

Ile Val Asp Val Arg Gln Leu Glu Pro Val Leu Ile Pro Leu Pro Asp
145                 150                 155                 160

Val Arg Asn Asn Phe Tyr His Tyr Asn Gln Ser His Asp Ser Thr Leu
                165                 170                 175

Lys Leu Ile Ala Val Leu Tyr Thr Pro Leu Arg Thr Asn Asn Ala Gly
            180                 185                 190

Asp Asp Val Phe Thr Val Ser Cys Arg Val Leu Thr Arg Pro Ser Pro
        195                 200                 205

Asp Phe Asp Phe Ile Phe Leu Val Pro Pro Thr Val Glu Ser Arg Thr
    210                 215                 220

Lys Pro Phe Thr Val Pro Ile Leu Thr Val Glu Glu Met Ser Asn Ser
225                 230                 235                 240

Arg Phe Pro Ile Pro Leu Glu Lys Leu Tyr Thr Gly Pro Ser Ser Ala
                245                 250                 255

Phe Val Val Gln Pro Gln Asn Gly Arg Cys Thr Thr Asp Gly Val Leu
            260                 265                 270

Leu Gly Thr Thr Gln Leu Ser Ala Val Asn Ile Cys Asn Phe Arg Gly
        275                 280                 285

Asp Val Thr His Ile Val Gly Ser His Glu Thr Thr Met Asn Leu Ala
    290                 295                 300

Ser Gln Asn Trp Ser Asn Tyr Asp Pro Thr Gln Lys Ile Pro Ala Pro
305                 310                 315                 320

Leu Gly Thr Pro His Phe Val Gly Lys Ile Gln Gly Leu Leu Thr Gln
                325                 330                 335

Thr Thr Arg Ala His Gly Ser Thr Arg Ala His Lys Ala Thr Val Ser
            340                 345                 350

Thr Gly Ser Val His Phe Thr Pro Lys Leu Gly Ser Val Gln Phe Thr
        355                 360                 365

Thr Asp Thr Asn Asn Asp Phe Gln Thr Gly Gln Asn Thr Lys Phe Thr
    370                 375                 380

Pro Val Gly Val Ile Gln Asp Gly Asp His His Gln Asn Glu Pro Gln
385                 390                 395                 400

Gln Trp Val Leu Pro Asn Tyr Ser Gly Arg Thr Gly His Asn Val His
                405                 410                 415

Leu Ala Pro Ala Val Ala Pro Thr Phe Pro Gly Glu Gln Leu Leu Phe
            420                 425                 430

Phe Arg Ser Thr Met Pro Gly Cys Ser Gly Tyr Pro Asn Met Asn Leu
        435                 440                 445
```

-continued

Asp Cys Leu Leu Pro His Glu Trp Val Leu His Phe Tyr Gln Glu Ala
450 455 460

Ala Pro Ala Gln Ser Asp Val Ala Leu Leu Arg Phe Val Asn Pro Asp
465 470 475 480

Thr Gly Arg Val Leu Phe Glu Cys Lys Leu His Lys Ser Gly Tyr Ile
485 490 495

Thr Val Ala His Thr Gly Pro Phe Asp Leu Gly Ile Pro Pro Asn Gly
500 505 510

Tyr Phe Arg Phe Asp Ser Trp Val Asn Gln Phe Tyr Thr Leu Ala Pro
515 520 525

Met Gly Asn Gly Thr Gly Arg Arg Arg Ala Leu
530 535

<210> SEQ ID NO 52
<211> LENGTH: 539
<212> TYPE: PRT
<213> ORGANISM: Norovirus

<400> SEQUENCE: 52

Met Lys Met Ala Ser Asn Asp Ala Ser Pro Ser Asp Gly Ser Thr Ala
1 5 10 15

Asn Leu Val Pro Glu Val Asn Asn Glu Val Met Ala Leu Glu Pro Val
20 25 30

Val Gly Ala Ala Ile Ala Ala Pro Val Ala Gly Gln Gln Asn Val Ile
35 40 45

Asp Pro Trp Ile Arg Asn Ser Ser Val Gln Ala Pro Gly Gly Glu Phe
50 55 60

Thr Val Ser Pro Arg Asp Ala Pro Gly Glu Ile Leu Trp Ser Ala Pro
65 70 75 80

Leu Gly Pro Asp Leu Asn Pro Tyr Leu Ser His Leu Ala Arg Met Tyr
85 90 95

Asn Gly Tyr Ala Gly Gly Phe Glu Val Gln Val Ile Leu Ala Gly Asn
100 105 110

Ala Phe Thr Ala Gly Lys Ile Ile Phe Ala Ala Ala Pro Pro Asn Phe
115 120 125

Pro Thr Glu Gly Leu Ser Pro Ser Gln Val Thr Met Phe Pro His Ile
130 135 140

Ile Val Gly Val Arg Gln Leu Glu Pro Val Leu Ile Pro Leu Pro Asp
145 150 155 160

Val Arg Asn Asn Phe Tyr His Tyr Asn Gln Ser Asn Asp Ser Thr Ile
165 170 175

Lys Leu Ile Ala Met Leu Tyr Thr Pro Leu Arg Ala Asn Asn Ala Gly
180 185 190

Asp Asp Val Phe Thr Val Ser Cys Arg Val Leu Thr Arg Pro Ser Pro
195 200 205

Asp Phe Asp Phe Ile Phe Leu Val Pro Pro Thr Val Glu Ser Arg Thr
210 215 220

Lys Pro Phe Thr Val Pro Ile Leu Thr Val Glu Glu Met Thr Asn Ser
225 230 235 240

Arg Phe Pro Ile Pro Leu Glu Asn Cys Ser Arg Val Pro Ala Val Pro
245 250 255

Leu Ser Ser Asn His Lys Met Gln Cys Thr Thr Asp Gly Val Leu Leu
260 265 270

Gly Thr Thr Gln Leu Ser Pro Val Asn Ile Cys Thr Phe Arg Gly Asp
275 280 285

Val Thr His Ile Pro Gly Thr Arg Thr Tyr Arg Met Asn Leu Ala Ser
290 295 300

Gln Asn Trp Asn Asn Tyr Asp Pro Thr Glu Glu Ile Pro Ala Pro Leu
305 310 315 320

Gly Thr Pro Asp Phe Val Gly Lys Ile Gln Gly Met Leu Thr Gln Thr
325 330 335

Thr Lys Gly Asp Gly Ser Thr Arg Gly His Lys Ala Thr Val Ser Thr
340 345 350

Gly Ser Val Asp Phe Thr Pro Lys Leu Gly Ser Val Gln Phe Ala Thr
355 360 365

Asp Thr Asp Asn Asp Phe Glu Thr Gly Gln Asn Thr Arg Phe Thr Pro
370 375 380

Val Gly Val Ile Gln Asp Gly Ser Ser Thr His Arg Asn Glu Pro Gln
385 390 395 400

Gln Trp Val Leu Pro Asp Tyr Ser Gly Arg Thr Val His Asn Val His
405 410 415

Leu Ala Pro Ala Val Ala Pro Thr Phe Pro Gly Glu Gln Leu Leu Phe
420 425 430

Phe Arg Ser Thr Met Pro Gly Cys Ser Gly Tyr Pro Asn Met Asp Leu
435 440 445

Asp Cys Leu Leu Pro Gln Glu Trp Val Gln His Phe Tyr Gln Glu Ala
450 455 460

Ala Pro Ser Gln Ser Asp Val Ala Leu Leu Arg Phe Val Asn Pro Asp
465 470 475 480

Thr Gly Arg Val Leu Phe Glu Cys Lys Leu His Lys Ala Gly Tyr Val
485 490 495

Thr Val Ala His Thr Gly Gln His Asp Leu Val Ile Pro Pro Asn Gly
500 505 510

Tyr Phe Arg Phe Asp Ser Trp Val Asn Gln Phe Tyr Thr Leu Ala Pro
515 520 525

Met Gly Asn Gly Ala Gly Arg Arg Arg Ala Leu
530 535

<210> SEQ ID NO 53
<211> LENGTH: 539
<212> TYPE: PRT
<213> ORGANISM: Norovirus

<400> SEQUENCE: 53

Met Lys Met Ala Ser Ser Asp Ala Asn Pro Ser Asp Gly Ser Ser Ala
1 5 10 15

Asn Leu Val Pro Glu Val Asn Asn Glu Val Met Ala Leu Glu Pro Val
20 25 30

Val Gly Ala Ala Ile Ala Ala Pro Val Ala Gly Gln Gln Asn Ile Ile
35 40 45

Asp Pro Trp Ile Arg Asn Asn Phe Val Gln Ala Pro Gly Gly Glu Phe
50 55 60

Thr Val Ser Pro Arg Asn Ala Pro Gly Glu Ile Leu Trp Ser Ala Pro
65 70 75 80

Leu Ser Pro Asp Leu Asn Pro Tyr Leu Ser His Leu Ser Arg Met Tyr
85 90 95

Asn Gly Tyr Ala Gly Gly Phe Glu Val Gln Val Ile Leu Ala Gly Asn
100 105 110

Ala Phe Thr Ala Gly Lys Ile Val Phe Ala Ala Val Pro Pro Asn Phe

-continued

```
        115                 120                 125

Pro Thr Glu Gly Leu Ser Pro Ser Gln Val Thr Met Phe Pro His Ile
    130                 135                 140

Ile Val Asp Val Arg Gln Leu Glu Pro Val Leu Ile Pro Leu Pro Asp
145                 150                 155                 160

Val Arg Asn Asn Phe Tyr His Tyr Asn Gln Ala Asn Asp Ser Thr Leu
                165                 170                 175

Lys Leu Ile Ala Met Leu Tyr Thr Pro Leu Arg Ala Asn Asn Ala Gly
            180                 185                 190

Asp Asp Val Phe Thr Val Ser Cys Arg Val Leu Thr Arg Pro Ser Pro
        195                 200                 205

Asp Phe Asp Phe Ile Phe Leu Val Pro Pro Thr Val Glu Ser Arg Thr
    210                 215                 220

Lys Pro Phe Thr Val Pro Val Leu Thr Val Glu Glu Met Thr Asn Ser
225                 230                 235                 240

Arg Phe Pro Ile Pro Leu Glu Arg Leu Phe Thr Gly Pro Ser Thr Ala
                245                 250                 255

Phe Val Val Gln Pro Gln Asn Gly Arg Cys Thr Thr Asp Gly Val Leu
            260                 265                 270

Leu Gly Thr Thr Gln Leu Ser Ala Val Asn Ile Cys Asn Phe Arg Gly
        275                 280                 285

Glu Val Asn His Ile Ala Gly Thr His Asp Tyr Thr Met Arg Leu Thr
    290                 295                 300

Ser Gln Asn Trp Asn Asn Tyr Asp Pro Thr Glu Glu Ile Pro Ala Pro
305                 310                 315                 320

Leu Gly Thr Pro Asp Phe Val Gly Arg Ile Gln Gly Val Leu Thr Gln
                325                 330                 335

Thr Thr Arg Ser Asp Gly Ser Thr Arg Ser His Lys Ala Thr Val Ser
            340                 345                 350

Thr Gly Ser Val His Phe Thr Pro Lys Leu Gly Ser Val Gln Phe Thr
        355                 360                 365

Thr Asp Thr Thr Asn Asp Leu Asn Ala Gly Gln Asn Thr Lys Phe Thr
    370                 375                 380

Pro Val Gly Val Glu Gln Thr Ser Gly Asp His Gln Ser Glu Pro Gln
385                 390                 395                 400

Gln Trp Thr Leu Pro Asn Tyr Ser Gly Thr Pro Asn His Asn Val His
                405                 410                 415

Leu Ala Pro Ala Val Ala Pro Thr Phe Pro Gly Glu Gln Leu Leu Phe
            420                 425                 430

Phe Arg Ser Thr Leu Pro Gly Cys Gly Gly Tyr Pro Asn Met Asn Leu
        435                 440                 445

Asp Cys Leu Leu Pro Gln Glu Trp Val Leu His Phe Tyr Gln Glu Ala
    450                 455                 460

Ala Pro Ala Gln Ser Asp Val Ala Leu Leu Arg Phe Val Asn Pro Asp
465                 470                 475                 480

Thr Gly Arg Val Leu Phe Glu Cys Lys Leu His Arg Ser Gly Phe Ile
                485                 490                 495

Thr Val Ala His Ser Gly Ser His Asp Leu Val Ile Pro Pro Asn Gly
            500                 505                 510

Tyr Phe Arg Phe Asp Ser Trp Val Asn Gln Phe Tyr Thr Leu Ala Pro
        515                 520                 525

Met Gly Asn Gly Ser Gly Arg Arg Arg Val Val
    530                 535
```

<210> SEQ ID NO 54
<211> LENGTH: 537
<212> TYPE: PRT
<213> ORGANISM: Norovirus

<400> SEQUENCE: 54

Met Lys Met Ala Ser Ser Asp Ala Asn Pro Ser Asp Gly Ser Thr Ala
1 5 10 15

Ser Leu Val Pro Glu Val Asn Asn Glu Val Met Ala Leu Glu Pro Val
20 25 30

Val Gly Ala Ala Ile Ala Ala Pro Val Ala Gly Gln Gln Asn Val Ile
35 40 45

Asp Pro Trp Ile Arg Asn Asn Phe Val Gln Ala Pro Gly Gly Glu Phe
50 55 60

Thr Val Ser Pro Arg Asn Ala Pro Gly Glu Ile Leu Trp Ser Ala Pro
65 70 75 80

Leu Gly Pro Asp Leu Asn Pro Tyr Leu Ser His Leu Ala Arg Met Tyr
85 90 95

Asn Gly Tyr Ala Gly Gly Phe Glu Val Gln Val Ile Leu Ala Gly Asn
100 105 110

Ala Phe Thr Ala Gly Lys Ile Ile Phe Ala Ala Val Pro Pro Asn Phe
115 120 125

Pro Thr Glu Gly Leu Ser Pro Ser Gln Val Thr Met Phe Pro His Ile
130 135 140

Ile Val Asp Val Arg Gln Leu Glu Pro Val Leu Ile Pro Leu Pro Asp
145 150 155 160

Val Arg Asn Asn Phe Tyr His Tyr Asn Gln Ser Asn Asp Ser Thr Ile
165 170 175

Lys Leu Ile Ala Met Leu Tyr Thr Pro Leu Arg Ala Asn Asn Ala Gly
180 185 190

Asp Asp Val Phe Thr Val Ser Cys Arg Val Leu Thr Arg Pro Ser Pro
195 200 205

Asp Phe Asp Phe Ile Phe Leu Val Pro Pro Thr Val Glu Ser Arg Thr
210 215 220

Lys Pro Phe Ser Val Pro Ile Leu Thr Val Glu Glu Met Thr Asn Ser
225 230 235 240

Arg Phe Pro Ile Pro Leu Glu Lys Leu Phe Thr Gly Pro Ser Ser Thr
245 250 255

Phe Val Val Gln Pro Gln Asn Gly Arg Cys Thr Thr Asp Gly Val Leu
260 265 270

Leu Gly Thr Thr Gln Leu Ser Pro Val Asn Ile Cys Thr Phe Arg Gly
275 280 285

Gly Ile Thr Arg Ile Gly Gln Ser Glu Ser Tyr Lys Met Asn Leu Ala
290 295 300

Ser Gln Asn Trp Asn Asn Tyr Asp Pro Thr Glu Glu Ile Pro Ala Pro
305 310 315 320

Leu Gly Thr Pro Asp Phe Lys Gly Arg Ile Arg Gly Leu Leu Thr Gln
325 330 335

Thr Thr Lys Gly Ala Gly Ser Thr Arg Gly His Lys Ala Thr Val Leu
340 345 350

Thr Gly Gly Ser Asp Phe Thr Pro Lys Leu Gly Thr Val Arg Phe Asp
355 360 365

Thr Lys Ser Ile Asp Phe Glu Asn Asn Gln Asn Thr Lys Phe Thr Pro 370 375 380

Val Gly Val Val Gln Asp Gly Asn Asn His Asp Glu Pro Thr Gln Trp
385 390 395 400

Val Leu Pro Asn Tyr Ser Gly Pro Asp Thr His Asn Val His Leu Ala
405 410 415

Pro Ala Val Ala Pro Thr Phe Pro Gly Glu Gln Leu Leu Phe Phe Arg
420 425 430

Ser Thr Met Pro Gly Cys Ser Gly Tyr Pro Lys Met Glu Leu Asp Cys
435 440 445

Leu Leu Pro Gln Glu Trp Val Gln His Phe Tyr Gln Glu Ala Ala Pro
450 455 460

Ala Gln Thr Asp Val Ala Leu Leu Arg Phe Val Asn Pro Asp Thr Gly
465 470 475 480

Arg Val Leu Phe Glu Cys Lys Leu His Lys Ser Gly Tyr Val Thr Val
485 490 495

Ala His Thr Gly Asp His Asp Leu Val Ile Pro Pro Asn Gly Tyr Phe
500 505 510

Arg Phe Asp Ser Trp Val Asn Gln Phe Tyr Thr Leu Ala Pro Met Gly
515 520 525

Asn Gly Thr Gly Arg Arg Arg Ala Leu
530 535

<210> SEQ ID NO 55
<211> LENGTH: 540
<212> TYPE: PRT
<213> ORGANISM: Norovirus

<400> SEQUENCE: 55

Met Lys Met Ala Ser Asn Asp Ala Thr Pro Ser Asn Asp Gly Ala Ala
1 5 10 15

Gly Leu Val Pro Glu Ser Asn Asn Glu Ala Met Ala Leu Glu Pro Val
20 25 30

Val Gly Ala Ser Leu Ala Ala Pro Val Thr Gly Gln Thr Asn Ile Ile
35 40 45

Asp Pro Trp Ile Arg Thr Asn Phe Val Gln Ala Pro Asn Gly Glu Phe
50 55 60

Thr Val Ser Pro Arg Asn Ser Pro Gly Glu Ile Leu Val Asn Leu Glu
65 70 75 80

Leu Gly Pro Glu Leu Asn Pro Tyr Leu Ala His Leu Ala Arg Met Tyr
85 90 95

Asn Gly Tyr Ala Gly Gly Met Glu Val Gln Val Met Leu Ala Gly Asn
100 105 110

Ala Phe Thr Ala Gly Lys Ile Ile Phe Ala Ala Val Pro Pro Tyr Phe
115 120 125

Pro Val Glu Asn Leu Ser Pro Ser Gln Ile Thr Met Phe Pro His Val
130 135 140

Ile Ile Asp Val Arg Thr Leu Glu Pro Val Leu Leu Pro Met Pro Asp
145 150 155 160

Val Arg Ser Thr Leu Phe His Phe Asn Gln Lys Asp Glu Pro Lys Met
165 170 175

Arg Leu Val Ala Met Leu Tyr Thr Pro Leu Arg Ser Asn Gly Ser Gly
180 185 190

Asp Asp Val Phe Thr Val Ser Cys Arg Ile Leu Thr Arg Pro Ser Pro
195 200 205

```
Glu Phe Asp Phe Thr Tyr Leu Val Pro Pro Thr Val Glu Ser Lys Thr
    210                 215                 220

Lys Pro Phe Thr Leu Pro Val Leu Thr Leu Gly Glu Leu Ser Asn Ser
225                 230                 235                 240

Arg Phe Pro Leu Ser Ile Asp Glu Met Val Thr Ser Pro Asn Glu Ser
                245                 250                 255

Ile Val Val Gln Pro Gln Asn Gly Arg Val Thr Leu Asp Gly Glu Leu
            260                 265                 270

Leu Gly Thr Thr Gln Leu Gln Ala Cys Asn Ile Cys Ser Ile Arg Gly
        275                 280                 285

Lys Val Thr Gly Gln Val Pro Asn Glu Gln His Met Trp Asn Leu Gln
    290                 295                 300

Ile Thr Asn Leu Asn Gly Thr Gln Phe Asp Pro Thr Asp Asp Val Pro
305                 310                 315                 320

Ala Pro Leu Gly Val Pro Asp Phe Ala Gly Glu Val Phe Gly Val Leu
                325                 330                 335

Ser Gln Arg Asn Arg Gly Glu Ser Asn Pro Ala Asn Arg Ala His Asp
            340                 345                 350

Ala Val Val Ala Thr Tyr Ser Asp Lys Tyr Thr Pro Lys Leu Gly Leu
        355                 360                 365

Val Gln Ile Gly Thr Trp Asn Thr Asn Asp Val Glu Asn Gln Pro Thr
    370                 375                 380

Lys Phe Thr Pro Ile Gly Leu Asn Glu Val Ala Asn Gly His Arg Phe
385                 390                 395                 400

Glu Gln Trp Thr Leu Pro Arg Tyr Ser Gly Ala Leu Thr Leu Asn Met
                405                 410                 415

Asn Leu Ala Pro Ala Val Ala Pro Leu Phe Pro Gly Glu Arg Leu Leu
            420                 425                 430

Phe Phe Arg Ser Tyr Val Pro Leu Lys Gly Gly Phe Gly Asn Pro Ala
        435                 440                 445

Ile Asp Cys Leu Val Pro Gln Glu Trp Val Gln His Phe Tyr Gln Glu
    450                 455                 460

Ser Ala Pro Ser Leu Gly Asp Val Ala Leu Val Arg Tyr Val Asn Pro
465                 470                 475                 480

Asp Thr Gly Arg Val Leu Phe Glu Ala Lys Leu His Lys Gly Gly Phe
                485                 490                 495

Leu Thr Val Ser Ser Thr Ser Thr Gly Pro Val Val Val Pro Ala Asn
            500                 505                 510

Gly Tyr Phe Arg Phe Asp Ser Trp Val Asn Gln Phe Tyr Ser Leu Ala
        515                 520                 525

Pro Met Gly Thr Gly Asn Gly Arg Arg Arg Phe Gln
    530                 535                 540
```

<210> SEQ ID NO 56
<211> LENGTH: 550
<212> TYPE: PRT
<213> ORGANISM: Norovirus

<400> SEQUENCE: 56

```
Met Lys Met Ala Ser Asn Asp Ala Ala Pro Ser Asn Asp Gly Ala Ala
1               5                   10                  15

Asn Leu Val Pro Glu Ala Asn Asp Glu Val Met Ala Leu Glu Pro Val
            20                  25                  30

Val Gly Ala Ser Ile Ala Ala Pro Val Val Gly Gln Gln Asn Ile Ile
        35                  40                  45
```

-continued

```
Asp Pro Trp Ile Arg Glu Asn Phe Val Gln Ala Pro Gln Gly Glu Phe
    50                  55                  60

Thr Val Ser Pro Arg Asn Ser Pro Gly Glu Met Leu Leu Asn Leu Glu
65                  70                  75                  80

Leu Gly Pro Glu Leu Asn Pro Tyr Leu Ser His Leu Ser Arg Met Tyr
                85                  90                  95

Asn Gly Tyr Ala Gly Gly Met Gln Val Gln Val Val Leu Ala Gly Asn
            100                 105                 110

Ala Phe Thr Ala Gly Lys Ile Ile Phe Ala Ala Val Pro Pro His Phe
        115                 120                 125

Pro Val Glu Asn Ile Ser Ala Ala Gln Ile Thr Met Cys Pro His Val
    130                 135                 140

Ile Val Asp Val Arg Gln Leu Glu Pro Val Leu Leu Pro Leu Pro Asp
145                 150                 155                 160

Ile Arg Asn Arg Phe Phe His Tyr Asn Gln Glu Asn Thr Pro Arg Met
                165                 170                 175

Arg Leu Val Ala Met Leu Tyr Thr Pro Leu Arg Ala Asn Ser Gly Glu
            180                 185                 190

Asp Val Phe Thr Val Ser Cys Arg Val Leu Thr Arg Pro Ala Pro Asp
        195                 200                 205

Phe Glu Phe Thr Phe Leu Val Pro Pro Thr Val Glu Ser Lys Thr Lys
    210                 215                 220

Pro Phe Thr Leu Pro Ile Leu Thr Leu Gly Glu Leu Ser Asn Ser Arg
225                 230                 235                 240

Phe Pro Ala Ala Ile Asp Met Leu Tyr Thr Asp Pro Asn Glu Ser Ile
                245                 250                 255

Val Val Gln Pro Gln Asn Gly Arg Cys Thr Leu Asp Gly Thr Leu Gln
            260                 265                 270

Gly Thr Thr Gln Leu Val Pro Thr Gln Ile Cys Ala Phe Arg Gly Thr
        275                 280                 285

Leu Ile Ser Gln Thr Ala Arg Ala Ala Asp Ser Thr Asp Ser Pro Gln
    290                 295                 300

Arg Ala Arg Asn His Pro Leu His Val Gln Val Lys Asn Leu Asp Gly
305                 310                 315                 320

Thr Gln Tyr Asp Pro Thr Asp Asp Ile Pro Ala Val Leu Gly Ala Ile
                325                 330                 335

Asp Phe Lys Gly Thr Val Phe Gly Val Ala Ser Gln Arg Asp Val Ser
            340                 345                 350

Gly Gln Gln Glu Gln Gly His Tyr Ala Thr Arg Ala His Glu Ala His
        355                 360                 365

Ile Asp Thr Thr Asp Pro Lys Tyr Ala Pro Lys Leu Gly Thr Ile Leu
    370                 375                 380

Ile Lys Ser Gly Ser Asp Asp Phe Asn Thr Asn Gln Pro Ile Arg Phe
385                 390                 395                 400

Thr Pro Val Gly Met Gly Asp Asn Asn Trp Arg Gln Trp Glu Leu Pro
                405                 410                 415

Asp Tyr Ser Gly Arg Leu Thr Leu Asn Met Asn Leu Ala Pro Ala Val
            420                 425                 430

Ser Pro Ser Phe Pro Gly Glu Arg Ile Leu Phe Phe Arg Ser Ile Val
        435                 440                 445

Pro Ser Ala Gly Gly Tyr Gly Ser Gly Tyr Ile Asp Cys Leu Ile Pro
    450                 455                 460
```

```
Gln Glu Trp Val Gln His Phe Tyr Gln Glu Ala Ala Pro Ser Gln Ser
465                 470                 475                 480

Ala Val Ala Leu Val Arg Tyr Val Asn Pro Asp Thr Gly Arg Asn Ile
                485                 490                 495

Phe Glu Ala Lys Leu His Arg Glu Gly Phe Leu Thr Val Ala Asn Cys
            500                 505                 510

Gly Asn Asn Pro Ile Val Val Pro Pro Asn Gly Tyr Phe Arg Phe Glu
        515                 520                 525

Ala Trp Gly Asn Gln Phe Tyr Thr Leu Ala Pro Met Gly Ser Gly Gln
    530                 535                 540

Gly Arg Arg Arg Ala Gln
545                 550


<210> SEQ ID NO 57
<211> LENGTH: 550
<212> TYPE: PRT
<213> ORGANISM: Norovirus

<400> SEQUENCE: 57

Met Lys Met Ala Ser Asn Asp Ala Ala Pro Ser Asn Asp Gly Ala Ala
1               5                   10                  15

Asn Leu Val Pro Glu Ala Asn Asn Glu Val Met Ala Leu Glu Pro Val
            20                  25                  30

Val Gly Ala Ser Ile Ala Ala Pro Val Val Gly Gln Gln Asn Ile Ile
        35                  40                  45

Asp Pro Trp Ile Arg Glu Asn Phe Val Gln Ala Pro Gln Gly Glu Phe
    50                  55                  60

Thr Val Ser Pro Arg Asn Ser Pro Gly Glu Met Leu Leu Asn Leu Glu
65                  70                  75                  80

Leu Gly Pro Glu Leu Asn Pro Tyr Leu Ser His Leu Ser Arg Met Tyr
                85                  90                  95

Asn Gly Tyr Ala Gly Gly Met Gln Val Gln Val Val Leu Ala Gly Asn
            100                 105                 110

Ala Phe Thr Ala Gly Lys Ile Ile Phe Ala Ala Val Pro Pro His Phe
        115                 120                 125

Pro Val Asp Asn Ile Ser Ala Ala Gln Ile Thr Met Cys Pro His Val
    130                 135                 140

Ile Val Asp Val Arg Gln Leu Glu Pro Val Leu Leu Pro Leu Pro Asp
145                 150                 155                 160

Ile Arg Asn Arg Phe Phe His Tyr Asn Gln Glu Asn Thr Pro Arg Met
                165                 170                 175

Arg Leu Val Ala Met Leu Tyr Thr Pro Leu Arg Ala Asn Ser Gly Glu
            180                 185                 190

Asp Val Phe Thr Val Ser Cys Arg Val Leu Thr Arg Pro Ala Pro Asp
        195                 200                 205

Phe Glu Phe Thr Phe Leu Val Pro Pro Thr Val Glu Ser Lys Thr Lys
    210                 215                 220

Pro Phe Thr Leu Pro Ile Leu Thr Leu Gly Glu Leu Ser Asn Ser Arg
225                 230                 235                 240

Phe Pro Ala Ala Ile Asp Met Leu Tyr Ala Asp Pro Asn Glu Ser Ile
                245                 250                 255

Val Val Gln Pro Gln Asn Gly Arg Cys Thr Leu Asp Gly Thr Leu Gln
            260                 265                 270

Gly Thr Thr Gln Leu Val Pro Thr Gln Ile Cys Ala Phe Arg Gly Thr
        275                 280                 285
```

Leu Ile Ser Gln Thr Ala Arg Ala Thr Asp Ser Thr Asp Ser Pro Gln
    290                 295                 300

Arg Ala Arg Asp His Pro Leu His Val Gln Val Lys Asn Leu Asp Gly
305                 310                 315                 320

Thr Gln Tyr Asp Pro Thr Asp Asp Ile Pro Ala Val Leu Gly Ala Ile
                325                 330                 335

Asp Phe Lys Gly Thr Val Phe Gly Val Ala Ser Gln Arg Asp Val Ser
            340                 345                 350

Gly Pro Gln Glu Gln Gly His Tyr Ala Thr Arg Ala His Glu Ala His
        355                 360                 365

Ile Asp Thr Thr Asp Pro Lys Tyr Ala Pro Lys Leu Gly Thr Ile Leu
    370                 375                 380

Ile Lys Ser Glu Ser Asn Asp Phe Ile Thr Asn Gln Pro Ile Arg Phe
385                 390                 395                 400

Thr Pro Val Gly Met Gly Asp Asn Asn Trp Arg Gln Trp Glu Leu Pro
                405                 410                 415

Asp Tyr Ser Gly Arg Leu Thr Leu Asn Met Asn Leu Ala Pro Ala Val
            420                 425                 430

Ser Pro Ser Phe Pro Gly Glu Arg Ile Leu Phe Phe Arg Ser Ile Val
        435                 440                 445

Pro Ser Ala Gly Gly Tyr Gly Ser Gly Tyr Ile Asp Cys Leu Ile Pro
    450                 455                 460

Gln Glu Trp Gly Gln His Phe Tyr Gln Glu Ala Ala Pro Ser Gln Ser
465                 470                 475                 480

Ala Val Ala Leu Val Arg Tyr Val Asn Pro Asp Thr Gly Arg Asn Ile
                485                 490                 495

Phe Glu Ala Lys Leu His Arg Glu Gly Phe Leu Thr Val Ala Asn Ser
            500                 505                 510

Gly Asn Asn Pro Ile Val Val Pro Pro Asn Gly Tyr Phe Arg Phe Glu
        515                 520                 525

Ala Trp Val Asn Gln Phe Tyr Thr Leu Ala Pro Met Gly Ser Gly Gln
    530                 535                 540

Gly Arg Arg Arg Ala Gln
545                 550

<210> SEQ ID NO 58
<211> LENGTH: 547
<212> TYPE: PRT
<213> ORGANISM: Norovirus

<400> SEQUENCE: 58

Met Lys Met Ala Ser Asn Asp Ala Ala Pro Ser Asn Asp Gly Ala Ala
1               5                   10                  15

Asn Leu Val Pro Glu Ala Asn Asn Glu Val Met Ala Leu Glu Pro Val
            20                  25                  30

Ala Gly Ala Ser Ile Ala Ala Pro Val Val Gly Gln Gln Asn Ile Ile
        35                  40                  45

Asp Pro Trp Ile Arg Glu Asn Phe Val Gln Ala Pro Gln Gly Glu Phe
    50                  55                  60

Thr Val Ser Pro Arg Asn Ser Pro Gly Glu Met Leu Leu Asn Leu Glu
65                  70                  75                  80

Leu Gly Pro Glu Leu Asn Pro Tyr Leu Ser His Leu Ser Arg Met Tyr
                85                  90                  95

Asn Gly Tyr Ala Gly Gly Met Gln Val Gln Val Val Leu Ala Gly Asn

-continued

```
            100                 105                 110

Ala Phe Thr Ala Gly Lys Ile Ile Phe Ala Ala Val Pro Pro His Phe
        115                 120                 125

Pro Val Lys Asn Ile Ser Ala Ala Gln Ile Thr Met Cys Pro His Val
    130                 135                 140

Ile Val Asp Val Arg Gln Leu Glu Pro Val Leu Leu Pro Leu Pro Asp
145                 150                 155                 160

Ile Arg Asn Arg Phe Phe His Tyr Asn Gln Glu Asn Thr Pro Arg Met
                165                 170                 175

Arg Leu Val Ala Met Leu Tyr Thr Pro Leu Arg Ala Asn Ser Gly Glu
            180                 185                 190

Asp Val Phe Thr Val Ser Cys Arg Val Leu Thr Arg Pro Ala Pro Asp
        195                 200                 205

Phe Glu Phe Thr Phe Leu Val Pro Pro Thr Val Glu Ser Lys Thr Lys
    210                 215                 220

Pro Phe Thr Leu Pro Ile Leu Thr Leu Gly Glu Leu Ser Asn Ser Arg
225                 230                 235                 240

Phe Pro Ala Pro Ile Asp Met Leu Tyr Thr Asp Pro Asn Glu Gly Ile
                245                 250                 255

Val Val Gln Pro Gln Asn Gly Arg Cys Thr Leu Asp Gly Thr Leu Gln
            260                 265                 270

Gly Thr Thr Gln Leu Val Pro Thr Gln Ile Cys Ala Phe Arg Gly Thr
        275                 280                 285

Leu Ile Gly Gln Thr Ser Arg Ser Ser Asp Ser Thr Asp Ser Ala Pro
    290                 295                 300

Arg Arg Arg Asp His Pro Leu His Val Gln Leu Lys Asn Leu Asp Gly
305                 310                 315                 320

Thr Gln Tyr Asp Pro Thr Asp Glu Val Pro Ala Val Leu Gly Ala Ile
                325                 330                 335

Asp Phe Lys Gly Thr Val Phe Gly Val Ala Ser Gln Arg Asp Val Ser
            340                 345                 350

Gly Gln Gln Val Gly Ala Thr Arg Ala His Glu Val His Ile Asn Thr
        355                 360                 365

Thr Asp Pro Arg Tyr Thr Pro Lys Leu Gly Ser Ile Leu Ile His Ser
    370                 375                 380

Glu Ser Asp Asp Phe Val Thr Gly Gln Pro Val Arg Phe Thr Pro Ile
385                 390                 395                 400

Gly Met Gly Asp Asn Asp Trp His Gln Trp Glu Leu Pro Asp Tyr Ser
                405                 410                 415

Gly His Leu Thr Leu Asn Met Asn Leu Ala Pro Ala Val Ala Pro Ala
            420                 425                 430

Phe Pro Gly Glu Arg Ile Leu Phe Phe Arg Ser Met Val Pro Ser Ala
        435                 440                 445

Gly Gly Tyr Gly Ser Gly Gln Ile Asp Cys Leu Ile Pro Gln Glu Trp
    450                 455                 460

Val Gln His Phe Tyr Gln Glu Ala Ala Pro Ser Gln Ser Ala Val Ala
465                 470                 475                 480

Leu Ile Arg Tyr Val Asn Pro Asp Thr Gly Arg Asn Ile Phe Glu Ala
                485                 490                 495

Lys Leu His Arg Glu Gly Phe Ile Thr Val Ala Asn Ser Gly Asn Asn
            500                 505                 510

Pro Ile Val Val Pro His Asn Gly Tyr Phe Arg Phe Glu Ala Trp Val
        515                 520                 525
```

Asn Gln Phe Tyr Thr Leu Thr Pro Met Gly Thr Gly Gln Gly Arg Arg
530 535 540

Arg Asn Gln
545

<210> SEQ ID NO 59
<211> LENGTH: 541
<212> TYPE: PRT
<213> ORGANISM: Norovirus

<400> SEQUENCE: 59

Met Lys Met Ala Ser Asn Asp Ala Ala Pro Ser Ser Asp Gly Ala Ala
1 5 10 15

Gly Leu Val Pro Glu Ile Asn Asn Glu Val Met Pro Leu Glu Pro Val
20 25 30

Ala Gly Ala Ser Leu Ala Thr Pro Val Val Gly Gln Gln Asn Ile Ile
35 40 45

Asp Pro Trp Ile Arg Asn Asn Phe Val Gln Ala Pro Ala Gly Glu Phe
50 55 60

Thr Val Ser Pro Arg Asn Ser Pro Gly Glu Ile Leu Leu Asp Leu Glu
65 70 75 80

Leu Gly Pro Asp Leu Asn Pro Tyr Leu Ala His Leu Ala Arg Met Tyr
85 90 95

Asn Gly His Ala Gly Gly Met Glu Val Gln Ile Val Leu Ala Gly Asn
100 105 110

Ala Phe Thr Ala Gly Lys Ile Ile Phe Ala Ala Ile Pro Pro Gly Phe
115 120 125

Pro Tyr Glu Asn Leu Ser Pro Ser Gln Ile Thr Met Cys Pro His Val
130 135 140

Ile Ile Asp Val Arg Gln Leu Glu Pro Phe Leu Leu Pro Met Pro Asp
145 150 155 160

Ile Trp Asn Asn Phe Phe His Tyr Asn Gln Gly Asn Asp Pro Lys Leu
165 170 175

Arg Leu Val Ala Met Leu Tyr Thr Pro Leu Arg Ala Asn Asn Ser Gly
180 185 190

Asp Asp Val Phe Thr Val Ser Cys Arg Val Leu Thr Lys Pro Ser Pro
195 200 205

Asp Phe Glu Phe Thr Phe Leu Val Pro Pro Thr Val Glu Ser Lys Thr
210 215 220

Lys Gln Phe Ala Leu Pro Ile Leu Lys Ile Ser Glu Met Thr Asn Ser
225 230 235 240

Arg Phe Pro Val Pro Val Asp Val Met Tyr Thr Ala Arg Asn Glu Asn
245 250 255

Gln Val Val Gln Pro Gln Asn Gly Arg Val Thr Leu Asp Gly Glu Leu
260 265 270

Leu Gly Thr Thr Pro Leu Leu Ala Val Asn Ile Cys Lys Phe Lys Gly
275 280 285

Glu Val Ile Ala Lys Asn Gly Asp Val Arg Ser Tyr Arg Met Asp Met
290 295 300

Glu Ile Thr Asn Thr Asp Gly Thr Pro Ile Asp Pro Thr Glu Asp Thr
305 310 315 320

Pro Gly Pro Ile Gly Ser Pro Asp Phe Gln Gly Ile Leu Phe Gly Val
325 330 335

Ala Ser Gln Arg Asn Lys Asn Glu Gln Asn Pro Ala Thr Arg Ala His

```
            340                 345                 350

Glu Ala Ile Ile Asn Thr Gly Gly Asp His Leu Cys Pro Gln Ile Ser
        355                 360                 365

Ser Ser Glu Ile Tyr Leu Thr Ser Pro Asn Ile Leu Arg Cys Thr Asn
    370                 375                 380

Pro Gln Pro Leu Pro Gln Ser Gly Leu Arg Gly Thr Ile Leu Ile Arg
385                 390                 395                 400

Ser Asp Asn Gly His Cys His Asp Met Val Gly Thr Ser Pro Thr Thr
                405                 410                 415

Pro Thr Trp Pro Gln Gln Trp Arg Arg Cys Ser Arg Gly Ser Asn Cys
            420                 425                 430

Cys Ser Ser Gly His Arg Tyr Pro Val Pro Val Val Met Asn Arg Val
        435                 440                 445

Thr Trp Ile Val Leu Ser His Lys Ser Gly Phe Ser Thr Ser Thr Arg
    450                 455                 460

Lys Leu Pro Gln Leu Asn Leu Arg Trp Pro Leu Ile Arg Phe Ile Asn
465                 470                 475                 480

Pro Asp Thr Gly Arg Val Leu Phe Glu Ala Arg Leu His Lys Gln Gly
                485                 490                 495

Phe Ile Thr Val Ala His Thr Gly Asp Asn Pro Ile Val Met Pro Pro
            500                 505                 510

Asn Gly Tyr Phe Arg Phe Glu Ala Trp Val Asn Gln Phe Tyr Ser Leu
        515                 520                 525

Ala Pro Val Gly Thr Gly Lys Gly Arg Arg Arg Val Gln
    530                 535                 540


<210> SEQ ID NO 60
<211> LENGTH: 540
<212> TYPE: PRT
<213> ORGANISM: Norovirus

<400> SEQUENCE: 60

Met Lys Met Ala Ser Asn Asp Ala Ala Pro Ser Asn Asp Gly Ala Ala
1               5                   10                  15

Gly Leu Val Pro Glu Ile Asn Asn Glu Val Met Pro Leu Glu Pro Val
            20                  25                  30

Ala Gly Ala Ser Leu Ala Thr Pro Val Val Gly Gln Gln Asn Ile Ile
        35                  40                  45

Asp Pro Trp Ile Arg Asn Asn Phe Val Gln Ala Pro Ala Gly Glu Phe
    50                  55                  60

Thr Val Ser Pro Arg Asn Ser Pro Gly Glu Ile Leu Leu Asp Leu Glu
65                  70                  75                  80

Leu Gly Pro Glu Leu Asn Pro Tyr Leu Ala His Leu Ala Arg Met Tyr
                85                  90                  95

Asn Gly His Ala Gly Gly Met Glu Val Gln Ile Val Leu Ala Gly Asn
            100                 105                 110

Ala Phe Thr Ala Gly Lys Ile Ile Phe Ala Ala Ile Pro Pro Gly Phe
        115                 120                 125

Pro Tyr Glu Asn Leu Ser Pro Ser Gln Ile Thr Met Cys Pro His Val
    130                 135                 140

Ile Ile Asp Val Arg Gln Leu Glu Pro Val Leu Leu Pro Met Pro Asp
145                 150                 155                 160

Ile Arg Asn Asn Phe Phe His Tyr Asn Gln Gly Asn Asp Pro Lys Leu
                165                 170                 175
```

-continued

```
Arg Leu Ile Ala Met Leu Tyr Thr Pro Leu Arg Ala Asn Asn Ser Gly
            180                 185                 190

Asp Asp Val Phe Thr Val Ser Cys Arg Val Leu Thr Lys Pro Ser Pro
        195                 200                 205

Asp Phe Glu Phe Thr Phe Leu Val Pro Pro Thr Val Glu Ser Lys Thr
    210                 215                 220

Lys Gln Phe Thr Leu Pro Ile Leu Lys Ile Ser Glu Met Thr Asn Ser
225                 230                 235                 240

Arg Phe Pro Val Pro Val Glu Met Met Tyr Thr Ala Arg Asn Glu Asn
                245                 250                 255

Gln Val Val Gln Pro Gln Asn Gly Arg Val Thr Leu Asp Gly Glu Leu
            260                 265                 270

Leu Gly Thr Thr Pro Leu Leu Ala Val Asn Ile Cys Lys Phe Lys Gly
        275                 280                 285

Glu Val Ile Ala Lys Asn Gly Asp Val Arg Ser Tyr Arg Met Asp Met
    290                 295                 300

Glu Ile Thr Asn Thr Asp Gly Thr Pro Ile Asp Pro Thr Glu Asp Thr
305                 310                 315                 320

Pro Gly Pro Ile Gly Ser Pro Asp Phe Gln Gly Ile Leu Phe Gly Val
                325                 330                 335

Ala Ser Gln Arg Asn Lys Asn Glu Gln Asn Pro Ala Thr Arg Ala His
            340                 345                 350

Glu Ala Asn Ile Asn Thr Gly Gly Asp Gln Tyr Ala Pro Lys Leu Ala
        355                 360                 365

Gln Val Lys Phe Phe Ser Glu Ser Gln Asp Phe Glu Val His Gln Pro
    370                 375                 380

Thr Val Phe Thr Pro Val Gly Val Ala Gly Asp Thr Ser His Pro Phe
385                 390                 395                 400

Arg Gln Trp Val Leu Pro Arg Tyr Gly Gly His Leu Thr Asn Asn Thr
                405                 410                 415

His Leu Ala Pro Ala Val Ala Pro Leu Phe Pro Gly Glu Gln Ile Leu
            420                 425                 430

Phe Phe Arg Ser Gln Ile Pro Ser Ser Gly Gly His Glu Leu Gly Tyr
        435                 440                 445

Met Asp Cys Leu Val Pro Gln Glu Trp Val Gln His Phe Tyr Gln Glu
    450                 455                 460

Ala Ala Thr Ala Gln Ser Glu Val Ala Leu Ile Arg Phe Ile Asn Pro
465                 470                 475                 480

Asp Thr Gly Arg Val Leu Phe Glu Ala Lys Leu His Lys Gln Gly Phe
                485                 490                 495

Ile Thr Val Ala His Thr Gly Asp Asn Pro Ile Val Met Pro Pro Asn
            500                 505                 510

Gly Tyr Phe Arg Phe Glu Ala Trp Val Asn Gln Phe Tyr Ser Leu Ala
        515                 520                 525

Pro Val Gly Thr Gly Asn Gly Arg Arg Arg Ile Gln
    530                 535                 540
```

<210> SEQ ID NO 61
<211> LENGTH: 537
<212> TYPE: PRT
<213> ORGANISM: Norovirus

<400> SEQUENCE: 61

```
Met Lys Met Ala Ser Asn Asp Ala Ala Pro Ser Asn Asp Gly Ala Ala
1               5                   10                  15
```

```
Gly Leu Val Pro Glu Ile Asn His Glu Val Met Ala Ile Glu Pro Val
            20                  25                  30

Ala Gly Ala Ser Leu Ala Ala Pro Val Val Gly Gln Leu Asn Ile Ile
        35                  40                  45

Asp Pro Trp Ile Arg Asn Asn Phe Val Gln Ala Pro Ala Gly Glu Phe
    50                  55                  60

Thr Val Ser Pro Arg Asn Ala Pro Gly Glu Phe Leu Leu Asp Leu Glu
65                  70                  75                  80

Leu Gly Pro Glu Leu Asn Pro Tyr Leu Ala His Leu Ala Arg Met Tyr
                85                  90                  95

Asn Gly His Ala Gly Gly Met Glu Val Gln Ile Val Leu Ala Gly Asn
            100                 105                 110

Ala Phe Thr Ala Gly Lys Ile Leu Phe Ala Val Ile Pro Pro Gly Phe
        115                 120                 125

Pro Tyr Glu Asn Leu Ser Pro Ala Gln Leu Thr Met Cys Pro His Val
    130                 135                 140

Val Val Asp Val Arg Gln Leu Glu Pro Ile Leu Leu Pro Met Pro Asp
145                 150                 155                 160

Ile Arg Asn Thr Phe Phe His Tyr Asn Gln Ser Asn Gly Pro Lys Leu
                165                 170                 175

Arg Leu Val Ala Met Leu Tyr Thr Pro Leu Arg Ala Asn Asn Ala Gly
            180                 185                 190

Asp Asp Val Phe Thr Val Ser Cys Arg Val Leu Thr Arg Pro Ser Pro
        195                 200                 205

Asp Phe Glu Phe Asn Phe Leu Val Pro Pro Ser Val Glu Ser Lys Thr
    210                 215                 220

Lys Ala Phe Thr Leu Pro Ile Leu Lys Ile Ser Glu Met Thr Asn Ser
225                 230                 235                 240

Arg Phe Pro Ile Pro Val Asp Gln Met Tyr Thr Ser Arg Asn Glu Asn
                245                 250                 255

Val Val Val Gln Pro Gln Asn Gly Arg Val Thr Leu Asp Gly Glu Leu
            260                 265                 270

Gln Gly Thr Thr Thr Leu Gln Pro Val Ser Ile Cys Gly Phe Arg Gly
        275                 280                 285

Thr Leu Gln Thr Arg Leu Ala Asp Gln Pro Asn Tyr Thr Tyr Gln Val
    290                 295                 300

His Leu Glu Asn Leu Asp Gly Ser Pro Val Asp Pro Thr Asp Glu Val
305                 310                 315                 320

Pro Ala Pro Leu Gly Thr Pro Asp Phe Gln Ala Gln Leu Phe Gly Val
                325                 330                 335

Val Ser Gln Arg Ser Ser Asp Asn Ala Thr Arg Ala His Glu Ala Arg
            340                 345                 350

Val Asn Thr Asn Asp Pro Thr Phe Ala Pro Gln Ile Ala Gln Val Arg
        355                 360                 365

Phe Lys Ser Pro Ser His Asp Phe Phe Asp Asn Glu Pro Ile Lys Phe
    370                 375                 380

Thr Pro Val Gly Ile Ser Val Asp Ser Glu Asn Ser Tyr Asn Gln Trp
385                 390                 395                 400

Leu Leu Pro Arg Tyr Gly Gly His Leu Thr Asn Asn Thr His Leu Ala
                405                 410                 415

Pro Ser Val Ser Pro Met Phe Pro Gly Glu Gln Ile Leu Phe Phe Arg
            420                 425                 430
```

```
Ser Phe Met Pro Gly Ala Ser Gly His Thr Asp Gly Ala Ile Asp Cys
        435                 440                 445

Leu Leu Pro Gln Glu Trp Val Ala His Phe Tyr Gln Glu Ala Ala Thr
    450                 455                 460

Ala Gln Thr Asp Val Ala Leu Ile Arg Phe Val Asn Pro Asp Thr Gly
465                 470                 475                 480

Arg Val Leu Phe Glu Gly Lys Leu His Lys Gln Gly Phe Ile Thr Ile
                485                 490                 495

Ser Asn Ser Gly Asp His Pro Ile Val Met Pro Ala Asn Gly Tyr Phe
            500                 505                 510

Arg Phe Glu Ala Trp Val Asn Gln Phe Tyr Ser Leu Ala Pro Val Gly
        515                 520                 525

Thr Gly Ser Gly Arg Arg Arg Ile Gln
    530                 535


<210> SEQ ID NO 62
<211> LENGTH: 535
<212> TYPE: PRT
<213> ORGANISM: Norovirus

<400> SEQUENCE: 62

Met Lys Met Ala Ser Asn Asp Ala Ala Pro Ser Asn Asp Gly Ala Ala
1               5                   10                  15

Gly Leu Val Pro Glu Val Asn Asn Glu Thr Met Ala Leu Glu Pro Val
            20                  25                  30

Ala Gly Ala Ser Ile Ala Ala Pro Leu Thr Gly Gln Asn Asn Val Ile
        35                  40                  45

Asp Pro Trp Ile Arg Leu Asn Phe Val Gln Ala Pro Asn Gly Glu Phe
    50                  55                  60

Thr Val Ser Pro Arg Asn Ser Pro Gly Glu Val Leu Leu Asn Leu Glu
65                  70                  75                  80

Leu Gly Pro Glu Leu Asn Pro Tyr Leu Ala His Leu Ser Arg Met Tyr
                85                  90                  95

Asn Gly Tyr Ala Gly Gly Val Glu Val Gln Val Leu Leu Ala Gly Asn
            100                 105                 110

Ala Phe Thr Ala Gly Lys Leu Val Phe Ala Ala Val Pro Pro His Phe
        115                 120                 125

Pro Leu Glu Asn Ile Ser Pro Gly Gln Ile Thr Met Phe Pro His Val
    130                 135                 140

Ile Ile Asp Val Arg Thr Leu Glu Pro Val Leu Leu Pro Leu Pro Asp
145                 150                 155                 160

Val Arg Asn Asn Phe Phe His Tyr Asn Gln Gln Asn Glu Pro Arg Met
                165                 170                 175

Arg Leu Val Ala Met Leu Tyr Thr Pro Leu Arg Ser Asn Gly Ser Gly
            180                 185                 190

Asp Asp Val Phe Thr Val Ser Cys Arg Val Leu Thr Arg Pro Ser Pro
        195                 200                 205

Asp Phe Asp Phe Asn Tyr Leu Val Pro Pro Thr Val Glu Ser Lys Thr
    210                 215                 220

Lys Pro Phe Thr Leu Pro Ile Leu Thr Ile Gly Glu Leu Thr Asn Ser
225                 230                 235                 240

Arg Phe Pro Val Pro Ile Asp Glu Leu Tyr Thr Ser Pro Asn Glu Ser
                245                 250                 255

Leu Val Val Gln Pro Gln Asn Gly Arg Cys Ala Leu Asp Gly Glu Leu
            260                 265                 270
```

Gln Gly Thr Thr Gln Leu Leu Pro Thr Ala Ile Cys Ser Phe Arg Gly
275 280 285

Arg Ile Asn Gln Lys Val Ser Gly Glu Asn His Val Trp Asn Met Gln
290 295 300

Ile Thr Asn Ile Asn Gly Thr Pro Phe Asp Pro Thr Glu Asp Val Pro
305 310 315 320

Ala Pro Leu Gly Thr Pro Asp Phe Ser Gly Lys Leu Phe Gly Val Leu
325 330 335

Ser Gln Arg Asp His Asp Asn Ala Cys Arg Ser His Asp Ala Val Ile
340 345 350

Ala Thr Asn Ser Ala Lys Phe Thr Pro Lys Leu Gly Ala Ile Gln Ile
355 360 365

Gly Thr Trp Glu Gln Asp Asp Val His Ile Asn Gln Pro Thr Lys Phe
370 375 380

Thr Pro Val Gly Leu Phe Glu Ser Glu Gly Phe Asn Gln Trp Thr Leu
385 390 395 400

Pro Asn Tyr Ser Gly Ala Leu Thr Leu Asn Met Gly Leu Ala Pro Pro
405 410 415

Val Ala Pro Thr Phe Pro Gly Glu Gln Ile Leu Phe Phe Arg Ser His
420 425 430

Ile Pro Leu Lys Gly Gly Val Ala Asp Pro Val Ile Asp Cys Leu Leu
435 440 445

Pro Gln Glu Trp Ile Gln His Leu Tyr Gln Glu Ser Ala Pro Ser Gln
450 455 460

Thr Asp Val Ala Leu Ile Arg Phe Thr Asn Pro Asp Thr Gly Arg Val
465 470 475 480

Leu Phe Glu Ala Lys Leu His Arg Ser Gly Tyr Ile Thr Val Ala Asn
485 490 495

Thr Gly Ser Arg Pro Ile Val Val Pro Ala Asn Gly Tyr Phe Arg Phe
500 505 510

Asp Ser Trp Val Asn Gln Phe Tyr Ser Leu Ala Pro Met Gly Thr Gly
515 520 525

Asn Gly Arg Arg Arg Val Gln
530 535

<210> SEQ ID NO 63
<211> LENGTH: 542
<212> TYPE: PRT
<213> ORGANISM: Norovirus

<400> SEQUENCE: 63

Met Lys Met Ala Ser Asn Asp Ala Ala Pro Ser Asn Asp Gly Ala Ala
1 5 10 15

Ser Leu Val Pro Glu Gly Ile Asn Glu Thr Met Pro Leu Glu Pro Val
20 25 30

Ala Gly Ala Ser Ile Ala Ala Pro Val Ala Gly Gln Thr Asn Ile Ile
35 40 45

Asp Pro Trp Ile Arg Thr Asn Phe Val Gln Ala Pro Asn Gly Glu Phe
50 55 60

Thr Val Ser Pro Arg Asn Ser Pro Gly Glu Ile Leu Leu Asn Leu Glu
65 70 75 80

Leu Gly Pro Asp Leu Asn Pro Tyr Leu Ala His Leu Ser Arg Met Tyr
85 90 95

Asn Gly Tyr Ala Gly Gly Val Glu Val Gln Val Leu Leu Ala Gly Asn

```
            100                 105                 110

Ala Phe Thr Ala Gly Lys Ile Leu Phe Ala Ala Ile Pro Pro Asn Phe
        115                 120                 125

Leu Val Asp Met Ile Ser Pro Ala Gln Ile Thr Met Leu Pro His Leu
    130                 135                 140

Ile Val Asp Val Arg Thr Leu Glu Pro Ile Met Thr Pro Leu Pro Asp
145                 150                 155                 160

Val Arg Asn Val Phe Tyr His Phe Asn Asn Gln Pro Gln Pro Arg Met
                165                 170                 175

Arg Leu Val Ala Met Leu Tyr Thr Pro Leu Arg Ser Asn Gly Ser Gly
            180                 185                 190

Asp Asp Val Phe Thr Val Ser Cys Arg Val Leu Thr Arg Pro Thr Pro
        195                 200                 205

Asp Phe Glu Phe Ile Tyr Leu Val Pro Pro Ser Val Glu Ser Lys Thr
    210                 215                 220

Lys Pro Phe Thr Leu Pro Ile Leu Thr Ile Ser Glu Leu Thr Asn Ser
225                 230                 235                 240

Arg Phe Pro Ile Pro Ile Glu Gln Leu Tyr Thr Ala Pro Asn Glu Thr
                245                 250                 255

Asn Val Val Gln Cys Gln Asn Gly Arg Cys Thr Leu Asp Gly Glu Leu
            260                 265                 270

Gln Gly Thr Thr Gln Leu Leu Ser Ser Ala Val Cys Phe Leu Gln Gly
        275                 280                 285

Arg Thr Val Ala Asp Asn Gly Asp Asn Trp Asp Gln Asn Leu Leu Gln
    290                 295                 300

Leu Thr Tyr Pro Asn Gly Ala Ser Tyr Asp Pro Thr Asp Glu Val Pro
305                 310                 315                 320

Ala Pro Leu Gly Thr Gln Asp Phe Ser Gly Met Leu Tyr Gly Val Leu
                325                 330                 335

Thr Gln Asp Asn Val Asn Val Ser Thr Gly Glu Ala Lys Asn Ala Lys
            340                 345                 350

Gly Ile Tyr Ile Ser Thr Thr Ser Gly Lys Phe Thr Pro Lys Ile Gly
        355                 360                 365

Ser Ile Gly Leu His Ser Ile Thr Glu His Val His Pro Asn Gln Gln
    370                 375                 380

Ser Arg Phe Thr Pro Val Gly Val Ala Val Asp Glu Asn Thr Pro Phe
385                 390                 395                 400

Gln Gln Trp Val Leu Pro His Tyr Ala Gly Ser Leu Ala Leu Asn Thr
                405                 410                 415

Asn Leu Ala Pro Ala Val Ala Pro Thr Phe Pro Gly Glu Gln Leu Leu
            420                 425                 430

Phe Phe Arg Ser Arg Val Pro Cys Val Gln Gly Leu Gln Gly Gln Asp
        435                 440                 445

Ala Phe Ile Asp Cys Leu Leu Pro Gln Glu Trp Val Asn His Phe Tyr
    450                 455                 460

Gln Glu Ala Ala Pro Ser Gln Ala Asp Val Ala Leu Ile Arg Tyr Val
465                 470                 475                 480

Asn Pro Asp Thr Gly Arg Thr Leu Phe Glu Ala Lys Leu His Arg Ser
                485                 490                 495

Gly Phe Ile Thr Val Ser His Thr Gly Ala Tyr Pro Leu Val Val Pro
            500                 505                 510

Pro Asn Gly His Phe Arg Phe Asp Ser Trp Val Asn Gln Phe Tyr Ser
        515                 520                 525
```

```
Leu Ala Pro Met Gly Thr Gly Asn Gly Arg Arg Arg Ile Gln
    530                 535                 540


<210> SEQ ID NO 64
<211> LENGTH: 528
<212> TYPE: PRT
<213> ORGANISM: Norovirus

<400> SEQUENCE: 64

Met Lys Met Ala Ser Asn Asp Ala Ala Pro Ser Asn Asp Gly Ala Ala
1               5                   10                  15

Ser Leu Val Pro Glu Ala Ile Asn Glu Thr Met Pro Leu Glu Pro Val
            20                  25                  30

Ala Gly Ala Ser Ile Ala Ala Pro Val Ala Gly Gln Thr Asn Ile Ile
        35                  40                  45

Asp Pro Trp Ile Arg Thr Asn Phe Val Gln Ala Pro Asn Gly Glu Phe
    50                  55                  60

Thr Val Ser Pro Arg Asn Ser Pro Gly Glu Ile Leu Leu Asn Leu Glu
65                  70                  75                  80

Leu Gly Pro Asp Leu Asn Pro Tyr Leu Ala His Leu Ser Arg Met Tyr
                85                  90                  95

Asn Gly Tyr Ala Gly Gly Val Glu Val Gln Val Leu Leu Ala Gly Asn
            100                 105                 110

Ala Phe Thr Ala Gly Lys Ile Leu Phe Ala Ala Ile Pro Pro Asn Phe
        115                 120                 125

Pro Val Asp Met Ile Ser Pro Ala Gln Ile Thr Met Leu Pro His Leu
    130                 135                 140

Ile Val Asp Val Arg Thr Leu Glu Pro Ile Met Ile Pro Leu Pro Asp
145                 150                 155                 160

Val Arg Asn Val Phe Tyr His Phe Asn Asn Gln Pro Gln Pro Arg Met
                165                 170                 175

Arg Leu Val Ala Met Leu Tyr Thr Pro Leu Arg Ser Asn Gly Ser Gly
            180                 185                 190

Asp Asp Val Phe Thr Val Ser Cys Arg Val Leu Thr Arg Pro Thr Pro
        195                 200                 205

Asp Phe Glu Phe Ile Tyr Leu Val Pro Pro Ser Val Glu Ser Lys Thr
    210                 215                 220

Lys Pro Phe Thr Leu Pro Ile Leu Thr Ile Ser Glu Leu Thr Asn Ser
225                 230                 235                 240

Arg Phe Pro Ile Pro Ile Glu Gln Leu Tyr Thr Ala Pro Asn Glu Asn
                245                 250                 255

Asn Val Val Gln Cys Gln Asn Gly Arg Cys Thr Leu Asp Gly Glu Leu
            260                 265                 270

Gln Gly Thr Thr Gln Leu Leu Ser Ser Ala Val Cys Ser Tyr Arg Gly
        275                 280                 285

Arg Thr Val Ala Asn Arg Gly Asp Asn Trp Asp Gln Asn Leu Leu Gln
    290                 295                 300

Leu Thr Tyr Pro Ser Gly Ala Ser Tyr Asp Pro Thr Asp Glu Val Pro
305                 310                 315                 320

Ala Pro Leu Gly Thr Gln Asp Phe Ser Gly Ile Leu Tyr Gly Val Leu
                325                 330                 335

Thr Gln Asp Asn Val Ser Glu Gly Thr Gly Glu Ala Lys Asn Ala Lys
            340                 345                 350

Gly Val Tyr Ile Ser Thr Thr Ser Gly Lys Phe Thr Pro Lys Ile Gly
```

```
        355                 360                 365

Ser Ile Gly Leu His Ser Ile Thr Glu Asn Val His Pro Asn Gln Gln
    370                 375                 380

Ser Arg Phe Thr Pro Val Gly Val Ala Gln Asn Glu Asn Thr Pro Phe
385                 390                 395                 400

Gln Gln Trp Val Leu Pro His Tyr Ala Gly Ala Leu Ala Leu Asn Thr
                405                 410                 415

Asn Leu Ala Pro Ala Val Ala Pro Thr Phe Pro Gly Glu Gln Leu Leu
            420                 425                 430

Phe Phe Arg Ser Arg Val Pro Cys Val Gln Gly Leu Arg Gly Gln Asp
        435                 440                 445

Ala Phe Ile Asp Cys Leu Leu Pro Gln Glu Trp Val Asn His Phe Tyr
    450                 455                 460

Gln Glu Ala Ala Pro Ser Gln Ala Asp Val Ala Leu Ile Arg Tyr Val
465                 470                 475                 480

Asn Pro Asp Thr Gly Arg Thr Leu Phe Glu Ala Lys Leu His Arg Ser
                485                 490                 495

Gly Phe Ile Thr Val Ser His Thr Gly Ala Tyr Pro Leu Val Val Pro
            500                 505                 510

Pro Asn Gly His Phe Arg Phe Asp Ser Trp Val Asn Gln Phe Tyr Ser
        515                 520                 525


<210> SEQ ID NO 65
<211> LENGTH: 536
<212> TYPE: PRT
<213> ORGANISM: Norovirus

<400> SEQUENCE: 65

Met Lys Met Ala Ser Asn Asp Ala Thr Pro Ser Asp Asp Gly Ala Ala
1               5                   10                  15

Gly Leu Val Pro Glu Ile Asn Ser Glu Val Met Ala Leu Glu Pro Val
            20                  25                  30

Ala Gly Ala Ser Ile Ala Ala Pro Val Val Gly Gln Gln Asn Ile Ile
        35                  40                  45

Asp Pro Trp Ile Arg Asn Asn Phe Val Gln Ala Pro Ala Gly Glu Phe
    50                  55                  60

Thr Val Ser Pro Arg Asn Ser Pro Gly Glu Leu Leu Leu Asp Leu Glu
65                  70                  75                  80

Leu Gly Pro Glu Leu Asn Pro Tyr Leu Ala His Leu Ala Arg Met Tyr
                85                  90                  95

Asn Gly His Ala Gly Gly Met Glu Val Gln Ile Val Leu Ala Gly Asn
            100                 105                 110

Ala Phe Thr Ala Gly Lys Ile Leu Phe Ala Ala Ile Pro Pro Ser Phe
        115                 120                 125

Pro Tyr Glu Asn Leu Ser Pro Ala Gln Leu Thr Met Cys Pro His Val
    130                 135                 140

Ile Val Asp Val Arg Gln Leu Glu Pro Val Leu Leu Pro Met Pro Asp
145                 150                 155                 160

Ile Arg Asn Val Phe Tyr His Tyr Asn Gln Asn Asn Ser Pro Lys Leu
                165                 170                 175

Arg Leu Val Ala Met Leu Tyr Thr Pro Leu Arg Ala Asn Asn Ser Gly
            180                 185                 190

Asp Asp Val Phe Thr Val Ser Cys Arg Val Leu Thr Arg Pro Ser Pro
        195                 200                 205
```

Asp Phe Gln Phe Thr Phe Leu Val Pro Pro Thr Val Glu Ser Lys Thr
    210                 215                 220

Lys Asn Phe Thr Leu Pro Val Leu Arg Val Ser Glu Met Thr Asn Ser
225                 230                 235                 240

Arg Phe Pro Val Val Leu Asp Gln Met Tyr Thr Ser Arg Asn Glu Asn
                245                 250                 255

Thr Ile Val Gln Pro Gln Asn Gly Arg Cys Thr Thr Asp Gly Glu Leu
            260                 265                 270

Leu Gly Thr Thr Ile Leu Gln Ser Val Ser Ile Cys Asn Phe Lys Gly
        275                 280                 285

Thr Met Gln Ala Lys Leu Asn Glu Glu Pro Arg Tyr Gln Leu Gln Leu
    290                 295                 300

Thr Asn Leu Asp Gly Ser Pro Ile Asp Pro Thr Asp Asp Met Pro Ala
305                 310                 315                 320

Pro Leu Gly Thr Pro Asp Phe Gln Ala Val Leu Tyr Gly Val Ala Ser
                325                 330                 335

Gln Arg Ser Ser Arg Asp Asn Ala Thr Arg Ala His Asp Ala Gln Ile
            340                 345                 350

Asp Thr Ala Gly Asp Thr Phe Ala Pro Lys Ile Gly Gln Val Arg Phe
        355                 360                 365

Lys Ser Ser Ser Asn Asp Phe Asp Leu His Asp Pro Thr Lys Phe Thr
    370                 375                 380

Pro Ile Gly Val Asn Val Asp Asp Gln His Pro Phe Arg Gln Trp Ser
385                 390                 395                 400

Leu Pro Asn Tyr Gly Gly His Leu Ala Leu Asn Asn His Leu Ala Pro
                405                 410                 415

Ala Val Thr Pro Leu Phe Pro Gly Glu Gln Ile Leu Phe Phe Arg Ser
            420                 425                 430

Tyr Ile Pro Ser Ala Gly Gly His Thr Asp Gly Ala Met Asp Cys Leu
        435                 440                 445

Leu Pro Gln Glu Trp Val Glu His Phe Tyr Gln Glu Ala Ala Pro Ser
    450                 455                 460

Gln Ser Asp Ile Ala Leu Val Arg Phe Ile Asn Pro Asp Thr Gly Arg
465                 470                 475                 480

Val Leu Phe Glu Ala Lys Leu His Lys Gln Gly Phe Leu Thr Ile Ala
                485                 490                 495

Ala Ser Gly Asp His Pro Ile Val Met Pro Thr Asn Gly Tyr Phe Arg
            500                 505                 510

Phe Glu Ala Trp Val Asn Pro Phe Tyr Thr Leu Ala Pro Val Gly Thr
        515                 520                 525

Gly Ser Gly Arg Arg Arg Ile Gln
    530                 535

<210> SEQ ID NO 66
<211> LENGTH: 536
<212> TYPE: PRT
<213> ORGANISM: Norovirus

<400> SEQUENCE: 66

Met Lys Met Ala Ser Asn Asp Ala Thr Pro Ser Asp Asp Gly Ala Ala
1               5                   10                  15

Gly Leu Val Pro Glu Ile Asn Asn Glu Val Met Ala Leu Glu Pro Val
            20                  25                  30

Ala Gly Ala Ser Ile Ala Ala Pro Val Val Gly Gln Gln Asn Ile Ile
        35                  40                  45

```
Asp Pro Trp Ile Arg Asn Asn Phe Val Gln Ala Pro Ala Gly Glu Phe
    50                  55                  60

Thr Val Ser Pro Arg Asn Ser Pro Gly Glu Leu Leu Leu Asp Leu Glu
65                  70                  75                  80

Leu Gly Pro Glu Leu Asn Pro Tyr Leu Ala His Leu Ala Arg Met Tyr
                85                  90                  95

Asn Gly His Ala Gly Gly Met Glu Val Gln Ile Val Leu Ala Gly Asn
            100                 105                 110

Ala Phe Thr Ala Gly Lys Ile Leu Phe Ala Ala Ile Pro Pro Ser Phe
        115                 120                 125

Pro Tyr Glu Asn Leu Ser Pro Ala Gln Leu Thr Met Cys Pro His Val
    130                 135                 140

Ile Val Asp Val Arg Gln Leu Glu Pro Val Leu Leu Pro Met Pro Asp
145                 150                 155                 160

Ile Arg Asn Val Phe Tyr His Tyr Asn Gln Asn Asn Ser Pro Lys Leu
                165                 170                 175

Arg Leu Val Ala Met Leu Tyr Thr Pro Leu Arg Ala Asn Asn Ser Gly
            180                 185                 190

Asp Asp Val Phe Thr Val Ser Cys Arg Val Leu Thr Arg Pro Ser Pro
        195                 200                 205

Asp Phe Gln Phe Thr Phe Leu Val Pro Pro Thr Val Glu Ser Lys Thr
    210                 215                 220

Lys Asn Phe Thr Leu Pro Val Leu Arg Val Ser Glu Met Thr Asn Ser
225                 230                 235                 240

Arg Phe Pro Val Val Leu Asp Gln Met Tyr Thr Ser Arg Asn Glu Asn
                245                 250                 255

Ile Ile Val Gln Pro Gln Asn Gly Arg Cys Thr Thr Asp Gly Glu Leu
            260                 265                 270

Leu Gly Thr Thr Thr Leu Gln Ser Val Ser Ile Cys Asn Phe Arg Gly
        275                 280                 285

Thr Met Gln Ala Lys Leu Asn Glu Gln Pro Arg Tyr Gln Leu Gln Leu
    290                 295                 300

Thr Asn Leu Asp Gly Ser Pro Ile Asp Pro Thr Asp Asp Met Pro Ala
305                 310                 315                 320

Pro Leu Gly Thr Pro Asp Phe Gln Ala Met Leu Tyr Gly Val Ala Ser
                325                 330                 335

Gln Arg Ser Ser Arg Asp Asn Ala Thr Arg Ala His Asp Ala Gln Ile
            340                 345                 350

Asp Thr Ala Gly Asp Thr Phe Ala Pro Lys Ile Gly Gln Val Arg Phe
        355                 360                 365

Lys Ser Ser Ser Asp Asp Phe Asp Leu His Asp Pro Thr Lys Phe Thr
    370                 375                 380

Pro Ile Gly Val Asn Val Asp Asp Gln His Pro Phe Arg Gln Trp Ser
385                 390                 395                 400

Leu Pro Asn Tyr Gly Gly His Leu Ala Leu Asn Asn His Leu Ala Pro
                405                 410                 415

Ala Val Thr Pro Leu Phe Pro Gly Glu Gln Ile Leu Phe Phe Arg Ser
            420                 425                 430

His Ile Pro Ser Ala Gly Gly His Thr Asp Gly Ala Ile Asp Cys Leu
        435                 440                 445

Leu Pro Gln Glu Trp Ile Glu His Phe Tyr Gln Glu Ala Ala Pro Ser
    450                 455                 460
```

```
Gln Ser Asp Ile Ala Leu Val Arg Phe Ile Asn Pro Asp Thr Gly Arg
465                 470                 475                 480

Val Leu Leu Glu Ala Lys Leu His Lys Gln Gly Phe Leu Thr Val Ala
                485                 490                 495

Ala Ser Gly Asp His Pro Ile Val Met Pro Thr Asn Gly Tyr Phe Arg
            500                 505                 510

Phe Glu Ala Trp Val Asn Pro Phe Tyr Thr Leu Ala Pro Val Gly Thr
        515                 520                 525

Gly Ser Gly Arg Arg Arg Ile Gln
    530                 535


<210> SEQ ID NO 67
<211> LENGTH: 540
<212> TYPE: PRT
<213> ORGANISM: Norovirus

<400> SEQUENCE: 67

Met Met Met Ala Ser Asn Asp Ala Ala Pro Ser Asn Asp Gly Ala Thr
1               5                   10                  15

Gly Leu Val Pro Glu Ile Asn His Glu Thr Leu Pro Leu Glu Pro Val
            20                  25                  30

Ala Gly Ala Ala Ile Ala Ala Pro Val Thr Gly Gln Asn Asn Ile Ile
        35                  40                  45

Asp Pro Trp Ile Arg Thr Asn Phe Val Gln Ala Pro Asn Gly Glu Phe
    50                  55                  60

Thr Val Ser Pro Arg Asn Ser Pro Gly Glu Ile Leu Leu Asn Leu Glu
65                  70                  75                  80

Leu Gly Pro Asp Leu Asn Pro Tyr Leu Ala His Leu Ser Arg Met Tyr
                85                  90                  95

Asn Gly Tyr Ala Gly Gly Val Glu Val Gln Val Leu Leu Ala Gly Asn
            100                 105                 110

Ala Phe Thr Ala Gly Lys Ile Leu Phe Ala Ala Val Pro Pro Asn Phe
        115                 120                 125

Pro Val Glu Phe Leu Ser Pro Ala Gln Ile Thr Met Leu Pro His Leu
    130                 135                 140

Ile Val Asp Val Arg Thr Leu Glu Pro Ile Met Ile Pro Leu Pro Asp
145                 150                 155                 160

Val Arg Asn Thr Phe Phe His Tyr Asn Asn Gln Pro Ala Asn Arg Met
                165                 170                 175

Arg Leu Val Ala Met Leu Tyr Thr Pro Leu Arg Ser Asn Gly Ser Gly
            180                 185                 190

Asp Asp Val Phe Thr Val Ser Cys Arg Val Leu Thr Arg Pro Thr Pro
        195                 200                 205

Asp Phe Glu Phe Thr Tyr Leu Val Pro Pro Ser Val Glu Ser Lys Thr
    210                 215                 220

Lys Pro Phe Ser Leu Pro Ile Leu Thr Ile Ser Glu Leu Thr Asn Ser
225                 230                 235                 240

Arg Phe Pro Ala Pro Ile Asp Ser Leu Tyr Thr Ala Gln Asn Asn Asn
                245                 250                 255

Leu Asn Val Gln Cys Gln Asn Gly Arg Cys Thr Leu Asp Gly Glu Leu
            260                 265                 270

Gln Gly Thr Thr Gln Leu Leu Pro Ser Gly Ile Cys Ala Phe Arg Gly
        275                 280                 285

Lys Leu Thr Ala Asp Val His Gln Ser His Asp Asp Arg Trp His Met
    290                 295                 300
```

Gln Leu Thr Asn Leu Asn Gly Thr Pro Phe Asp Pro Thr Glu Asp Val
305 310 315 320

Pro Ala Pro Leu Gly Thr Pro Asp Phe Thr Gly Leu Leu Phe Gly Val
325 330 335

Ala Ser Gln Arg Asn Val Val Ser Asn Pro Asn Thr Thr Arg Ala His
340 345 350

Glu Ala Val Ile Ser Thr Thr Ser Ser Gln Phe Val Pro Lys Leu Gly
355 360 365

Ser Ile Asn Phe Gly Ser Thr Ser Asp Asp Phe Gln Leu Gln Gln Pro
370 375 380

Thr Lys Phe Thr Pro Val Gly Ile Lys Val Glu Ser Gly His Asp Phe
385 390 395 400

Asp Gln Trp Ala Leu Pro Arg Tyr Ser Gly His Leu Thr Leu Asn Met
405 410 415

Asn Leu Ala Pro Pro Val Ala Pro Asn Phe Pro Gly Glu Gln Leu Leu
420 425 430

Phe Phe Arg Ser Asn Val Pro Cys Ala Gly Gly Val Ser Asp Gly Val
435 440 445

Ile Asp Cys Leu Leu Pro Gln Glu Trp Ile Gln Tyr Phe Tyr Gln Glu
450 455 460

Ser Ala Pro Ser Gln Ser Asp Val Ala Leu Ile Arg Tyr Val Asn Pro
465 470 475 480

Asp Thr Gly Arg Thr Leu Phe Glu Ala Lys Leu His Arg Thr Gly Tyr
485 490 495

Ile Thr Val Ala His Ser Gly Asp Tyr Pro Leu Val Val Pro Ser Asn
500 505 510

Gly Tyr Phe Arg Phe Asp Ser Trp Val Asn Gln Phe Tyr Ser Leu Ala
515 520 525

Pro Met Gly Thr Gly Asn Gly Arg Arg Arg Val Gln
530 535 540

<210> SEQ ID NO 68
<211> LENGTH: 538
<212> TYPE: PRT
<213> ORGANISM: Norovirus

<400> SEQUENCE: 68

Met Lys Met Ala Ser Asn Asp Ala Ala Pro Ser Asn Asp Gly Ala Ala
1 5 10 15

Gly Leu Val Pro Glu Gly Asn Asn Glu Thr Leu Pro Leu Glu Pro Val
20 25 30

Ala Gly Ala Ala Ile Ala Ala Pro Val Thr Gly Gln Asn Asn Ile Ile
35 40 45

Asp Pro Trp Ile Arg Thr Asn Phe Val Gln Ala Pro Asn Gly Glu Phe
50 55 60

Thr Val Ser Pro Arg Asn Ser Pro Gly Glu Ile Leu Leu Asn Leu Glu
65 70 75 80

Leu Gly Pro Asp Leu Asn Pro Tyr Leu Ala His Leu Ser Arg Met Tyr
85 90 95

Asn Gly Tyr Ala Gly Gly Val Glu Val Gln Val Leu Leu Ala Gly Asn
100 105 110

Ala Phe Thr Ala Gly Lys Ile Leu Phe Ala Ala Val Pro Pro Asn Phe
115 120 125

Pro Val Glu Phe Leu Ser Pro Ala Gln Ile Thr Met Leu Pro His Leu

```
    130                 135                 140

Ile Val Asp Val Arg Thr Leu Glu Pro Ile Met Ile Pro Leu Pro Asp
145                 150                 155                 160

Val Arg Asn Thr Phe Phe His Tyr Asn Asn Gln Pro Asn Ser Arg Met
                165                 170                 175

Arg Leu Val Ala Met Leu Tyr Thr Pro Leu Arg Ser Asn Gly Ser Gly
            180                 185                 190

Asp Asp Val Phe Thr Val Ser Cys Arg Val Leu Thr Arg Pro Thr Pro
        195                 200                 205

Asp Phe Glu Phe Thr Tyr Leu Val Pro Pro Ser Val Glu Ser Lys Thr
    210                 215                 220

Lys Pro Phe Ser Leu Pro Ile Leu Thr Leu Ser Glu Leu Thr Asn Ser
225                 230                 235                 240

Arg Phe Pro Val Pro Ile Asp Ser Leu Phe Thr Ala Gln Asn Asn Val
                245                 250                 255

Leu Gln Val Gln Cys Gln Asn Gly Arg Cys Thr Leu Asp Gly Glu Leu
            260                 265                 270

Gln Gly Thr Thr Gln Leu Leu Pro Ser Gly Ile Cys Ala Phe Arg Gly
        275                 280                 285

Arg Val Thr Ala Glu Thr Asp His Arg Asp Lys Trp His Met Gln Leu
    290                 295                 300

Gln Asn Leu Asn Gly Thr Thr Tyr Asp Pro Thr Asp Asp Val Pro Ala
305                 310                 315                 320

Pro Leu Gly Thr Pro Asp Phe Lys Gly Val Val Phe Gly Val Ala Ser
                325                 330                 335

Gln Arg Asn Val Gly Asn Asp Ala Pro Gly Ser Thr Arg Ala His Glu
            340                 345                 350

Ala Val Ile Ser Thr Tyr Ser Pro Gln Phe Val Pro Lys Leu Gly Ser
        355                 360                 365

Val Asn Phe Arg Ser Asn Asp Asn Asp Phe Gln Leu Gln Pro Thr Lys
    370                 375                 380

Phe Thr Pro Val Gly Ile Asn Asp Asp Gly Asp His Pro Phe Arg Gln
385                 390                 395                 400

Trp Glu Leu Pro Asp Tyr Ser Gly Leu Leu Thr Leu Asn Met Asn Leu
                405                 410                 415

Ala Pro Pro Val Ala Pro Asn Phe Pro Gly Glu Gln Leu Leu Phe Phe
            420                 425                 430

Arg Ser Phe Val Pro Cys Ser Gly Gly Tyr Asn Gln Gly Ile Val Asp
        435                 440                 445

Cys Leu Ile Pro Gln Glu Trp Ile Gln His Phe Tyr Gln Glu Ser Ala
    450                 455                 460

Pro Ser Gln Ser Asp Val Ala Leu Ile Arg Tyr Val Asn Pro Asp Thr
465                 470                 475                 480

Gly Arg Thr Leu Phe Glu Ala Lys Leu His Arg Ser Gly Tyr Ile Thr
                485                 490                 495

Val Ala His Ser Gly Asp Tyr Pro Leu Val Val Pro Ala Asn Gly Tyr
            500                 505                 510

Phe Arg Phe Asp Ser Trp Val Asn Gln Phe Tyr Ser Leu Ala Pro Met
        515                 520                 525

Gly Thr Gly Asn Gly Arg Arg Arg Ala Gln
    530                 535
```

<210> SEQ ID NO 69

<211> LENGTH: 540
<212> TYPE: PRT
<213> ORGANISM: Norovirus

<400> SEQUENCE: 69

```
Met Lys Met Ala Ser Asn Asp Ala Ala Pro Ser Asn Asp Gly Ala Ala
1               5                   10                  15

Gly Leu Val Pro Glu Gly Asn Asn Glu Thr Leu Pro Leu Glu Pro Val
            20                  25                  30

Ala Gly Ala Ala Ile Ala Ala Pro Val Thr Gly Gln Asn Asn Ile Ile
        35                  40                  45

Asp Pro Trp Ile Arg Thr Asn Phe Val Gln Ala Pro Asn Gly Glu Phe
    50                  55                  60

Thr Val Ser Pro Arg Asn Ser Pro Gly Glu Ile Leu Leu Asn Leu Glu
65                  70                  75                  80

Leu Gly Pro Asp Leu Asn Pro Tyr Leu Ala His Leu Ser Arg Met Tyr
                85                  90                  95

Asn Gly Tyr Ala Gly Gly Val Glu Val Gln Val Leu Leu Ala Gly Asn
            100                 105                 110

Ala Phe Thr Ala Gly Lys Ile Leu Phe Ala Ala Val Pro Pro Asn Phe
        115                 120                 125

Pro Val Glu Phe Leu Ser Pro Ala Gln Ile Thr Met Leu Pro His Leu
    130                 135                 140

Ile Val Asp Val Arg Thr Leu Glu Pro Ile Met Ile Pro Leu Pro Asp
145                 150                 155                 160

Val Arg Asn Thr Phe Phe His Tyr Ser Asn Gln Pro Asn Ser Arg Met
                165                 170                 175

Arg Leu Val Ala Met Leu Tyr Thr Pro Leu Arg Ser Asn Gly Ser Gly
            180                 185                 190

Asp Asp Val Phe Thr Val Ser Cys Arg Val Leu Thr Arg Pro Thr Pro
        195                 200                 205

Asp Phe Glu Phe Thr Tyr Leu Val Pro Pro Ser Val Glu Ser Lys Thr
    210                 215                 220

Lys Pro Phe Ser Leu Pro Ile Leu Thr Leu Ser Glu Leu Thr Asn Ser
225                 230                 235                 240

Arg Phe Pro Val Pro Ile Asp Ser Leu Phe Thr Ala Gln Asn Asn Val
                245                 250                 255

Leu Gln Val Gln Cys Gln Asn Gly Arg Cys Thr Leu Asp Gly Glu Leu
            260                 265                 270

Gln Gly Thr Thr Gln Leu Leu Pro Thr Gly Ile Cys Ala Phe Arg Gly
        275                 280                 285

Arg Val Thr Ala Gln Ile Asn Gln Arg Asp Arg Trp His Met Gln Leu
    290                 295                 300

Gln Asn Leu Asn Gly Thr Thr Tyr Asp Pro Thr Asp Asp Val Pro Ala
305                 310                 315                 320

Pro Leu Gly Thr Pro Asp Phe Lys Gly Val Val Phe Gly Met Val Ser
                325                 330                 335

Gln Arg Asn Val Gly Asn Asp Ala Pro Gly Ser Thr Arg Ala Gln Gln
            340                 345                 350

Ala Trp Val Ser Thr Tyr Ser Pro Gln Phe Val Pro Lys Leu Gly Ser
        355                 360                 365

Val Asn Leu Arg Ile Ser Asp Asn Asp Asp Phe Gln Phe Gln Pro Thr
    370                 375                 380

Lys Phe Thr Pro Val Gly Val Asn Asp Asp Asp Asp Gly His Pro Phe
```

```
385                 390                 395                 400

Arg Gln Trp Glu Leu Pro Asn Tyr Ser Gly Glu Leu Thr Leu Asn Met
                405                 410                 415

Asn Leu Ala Pro Pro Val Ala Pro Asn Phe Pro Gly Glu Gln Leu Leu
            420                 425                 430

Phe Phe Arg Ser Phe Val Pro Cys Ser Gly Gly Tyr Asn Gln Gly Ile
        435                 440                 445

Ile Asp Cys Leu Ile Pro Gln Glu Trp Ile Gln His Phe Tyr Gln Glu
    450                 455                 460

Ser Ala Pro Ser Gln Ser Asp Val Ala Leu Ile Arg Tyr Val Asn Pro
465                 470                 475                 480

Asp Thr Gly Arg Thr Leu Phe Glu Ala Lys Leu His Arg Ser Gly Tyr
                485                 490                 495

Ile Thr Val Ala His Ser Gly Asp Tyr Pro Leu Val Val Pro Ala Asn
            500                 505                 510

Gly His Phe Arg Phe Asp Ser Trp Val Asn Gln Phe Tyr Ser Leu Ala
        515                 520                 525

Pro Met Gly Thr Gly Asn Gly Arg Arg Arg Ala Gln
    530                 535                 540


<210> SEQ ID NO 70
<211> LENGTH: 540
<212> TYPE: PRT
<213> ORGANISM: Norovirus

<400> SEQUENCE: 70

Met Lys Met Ala Ser Asn Asp Ala Ala Pro Ser Asn Asp Gly Ala Thr
1               5                   10                  15

Gly Leu Val Pro Glu Ile Asn Asn Glu Thr Leu Pro Leu Glu Pro Val
            20                  25                  30

Ala Gly Ala Ala Ile Ala Ala Pro Val Thr Gly Gln Asn Asn Ile Ile
        35                  40                  45

Asp Pro Trp Ile Arg Thr Asn Phe Val Gln Ala Pro Asn Gly Glu Phe
    50                  55                  60

Thr Val Ser Pro Arg Asn Ser Pro Gly Glu Ile Leu Leu Asn Leu Glu
65                  70                  75                  80

Leu Gly Pro Asp Leu Asn Pro Tyr Leu Ala His Leu Ser Arg Met Tyr
                85                  90                  95

Asn Gly Tyr Ala Gly Gly Val Glu Val Gln Val Leu Leu Ala Gly Asn
            100                 105                 110

Ala Phe Thr Ala Gly Lys Ile Leu Phe Ala Ala Val Pro Pro Asn Phe
        115                 120                 125

Pro Val Glu Phe Leu Ser Pro Ala Gln Ile Thr Met Leu Pro His Leu
    130                 135                 140

Ile Val Asp Val Arg Thr Leu Glu Pro Ile Met Ile Pro Leu Pro Asp
145                 150                 155                 160

Val Arg Asn Thr Phe Phe His Tyr Asn Asn Gln Pro Ala Asn Arg Met
                165                 170                 175

Arg Leu Val Ala Met Leu Tyr Thr Pro Leu Arg Ser Asn Gly Ser Gly
            180                 185                 190

Asp Asp Val Phe Thr Val Ser Cys Arg Val Leu Thr Arg Pro Thr Pro
        195                 200                 205

Asp Phe Glu Phe Thr Tyr Leu Val Pro Pro Ser Val Glu Ser Lys Thr
    210                 215                 220
```

Lys Pro Phe Ser Leu Pro Ile Leu Thr Ile Ser Glu Leu Thr Asn Ser
225 230 235 240

Arg Phe Pro Ala Pro Ile Asp Ser Leu Phe Thr Ala Gln Asn Asn Asn
245 250 255

Leu Asn Val Gln Cys Gln Asn Gly Arg Cys Thr Leu Asp Gly Glu Leu
260 265 270

Gln Gly Thr Thr Gln Leu Leu Pro Ser Gly Ile Cys Ala Phe Arg Gly
275 280 285

Arg Leu Thr Ala Asp Val Asp Gly Ser His Asp Asp Arg Trp His Met
290 295 300

Gln Leu Thr Asn Leu Asn Gly Thr Pro Phe Asp Pro Thr Glu Asp Val
305 310 315 320

Pro Ala Pro Leu Gly Thr Pro Asp Phe Thr Gly Leu Leu Phe Gly Val
325 330 335

Ala Ser Gln Arg Asn Val Gly Ser Asn Pro Asn Thr Thr Arg Ala His
340 345 350

Glu Ala Val Ile Ser Thr Thr Ser Ser Gln Phe Val Pro Lys Leu Gly
355 360 365

Ser Val Asn Phe Gly Ser Thr Ser Thr Asp Phe Gln Leu Gln Gln Pro
370 375 380

Thr Lys Phe Thr Pro Val Gly Ile Lys Ile Glu Ser Gly His Glu Phe
385 390 395 400

Asp Gln Trp Ala Leu Pro Arg Tyr Ser Gly His Leu Thr Leu Asn Met
405 410 415

Asn Leu Ala Pro Pro Ile Ala Pro Asn Phe Pro Gly Glu Gln Leu Leu
420 425 430

Phe Phe Arg Ser Asn Val Pro Cys Ala Gly Gly Val Ser Asp Gly Val
435 440 445

Ile Asp Cys Leu Leu Pro Gln Glu Trp Ile Gln His Phe Tyr Gln Glu
450 455 460

Ser Ala Pro Ser Gln Ser Asp Val Ala Leu Ile Arg Tyr Val Asn Pro
465 470 475 480

Asp Thr Gly Arg Thr Leu Phe Glu Ala Lys Leu His Arg Thr Gly Tyr
485 490 495

Ile Thr Val Ala His Ser Gly Asp Tyr Pro Leu Val Val Pro Ser Asn
500 505 510

Gly Tyr Phe Arg Phe Asp Ser Trp Val Asn Gln Phe Tyr Ser Leu Ala
515 520 525

Pro Met Gly Thr Gly Asn Gly Arg Arg Arg Val Gln
530 535 540

<210> SEQ ID NO 71
<211> LENGTH: 538
<212> TYPE: PRT
<213> ORGANISM: Norovirus

<400> SEQUENCE: 71

Met Lys Met Ala Ser Asn Asp Ala Ala Pro Ser Asn Asp Gly Ala Ala
1 5 10 15

Gly Leu Val Pro Glu Gly Asn Asn Glu Thr Leu Pro Leu Glu Pro Val
20 25 30

Ala Gly Ala Ala Ile Ala Ala Pro Val Thr Gly Gln Asn Asn Ile Ile
35 40 45

Asp Pro Trp Ile Arg Thr Asn Phe Val Gln Ala Pro Asn Gly Glu Phe
50 55 60

```
Thr Val Ser Pro Arg Asn Ser Pro Gly Glu Ile Leu Leu Asn Leu Glu
65                  70                  75                  80

Leu Gly Pro Asp Leu Asn Pro Tyr Leu Ala His Leu Ser Arg Met Tyr
                85                  90                  95

Asn Gly Tyr Ala Gly Gly Val Glu Val Gln Val Leu Leu Ala Gly Asn
            100                 105                 110

Ala Phe Thr Ala Gly Lys Ile Leu Phe Ala Ala Val Pro Pro Asn Phe
        115                 120                 125

Pro Val Glu Phe Leu Ser Pro Ala Gln Ile Thr Met Leu Pro His Ile
    130                 135                 140

Ile Val Asp Val Arg Thr Leu Glu Pro Ile Met Ile Pro Leu Pro Asp
145                 150                 155                 160

Val Arg Asn Thr Phe Phe His Tyr Asn Asn Gln Pro Asn Ser Arg Met
                165                 170                 175

Arg Leu Val Ala Met Leu Tyr Thr Pro Leu Arg Ser Asn Gly Ser Gly
            180                 185                 190

Asp Asp Val Phe Thr Val Ser Cys Arg Val Leu Thr Arg Pro Thr Pro
        195                 200                 205

Asp Phe Glu Phe Thr Tyr Leu Val Pro Pro Ser Val Glu Ser Lys Thr
    210                 215                 220

Lys Pro Phe Ser Leu Pro Ile Leu Thr Leu Ser Glu Leu Thr Asn Ser
225                 230                 235                 240

Arg Phe Pro Val Pro Ile Asp Ser Leu Phe Thr Ala Gln Asn Asn Val
                245                 250                 255

Leu Gln Val Gln Cys Gln Asn Gly Arg Cys Thr Leu Asp Gly Glu Leu
            260                 265                 270

Gln Gly Thr Thr Gln Leu Leu Pro Ser Gly Ile Cys Ala Phe Arg Gly
        275                 280                 285

Arg Val Thr Ala Glu Thr Asp Asn Pro Asp Lys Trp His Met Gln Leu
    290                 295                 300

Gln Asn Leu Asn Gly Thr Thr Tyr Asp Pro Thr Asp Asp Val Pro Ala
305                 310                 315                 320

Pro Leu Gly Thr Pro Asp Phe Lys Gly Val Val Phe Gly Val Ala Ser
                325                 330                 335

Gln Arg Asn Val Gly Asn Asp Ala Pro Gly Ser Thr Arg Ala His Glu
            340                 345                 350

Ala Val Ile Ser Thr Tyr Ser Pro Lys Phe Val Pro Lys Leu Gly Ser
        355                 360                 365

Val Asn Phe Arg Ser Asn Asp Asp Asp Phe Gln Leu Gln Pro Thr Arg
    370                 375                 380

Phe Thr Pro Val Gly Ile Asn Asp Asp Gly Asn His Pro Phe Arg Gln
385                 390                 395                 400

Trp Glu Leu Pro Asp Tyr Ser Gly Val Leu Thr Leu Asn Met Asn Leu
                405                 410                 415

Ala Pro Pro Val Ala Pro Asn Phe Pro Gly Glu Gln Leu Leu Leu Phe
            420                 425                 430

Arg Ser Phe Val Pro Cys Ser Gly Gly Tyr Asn Gln Gly Ile Ile Asp
        435                 440                 445

Cys Leu Ile Pro Gln Glu Trp Ile Gln His Phe Tyr Gln Glu Ser Ala
    450                 455                 460

Pro Ser Gln Ser Asp Val Ala Leu Ile Arg Tyr Val Asn Pro Asp Thr
465                 470                 475                 480
```

```
Gly Arg Thr Leu Phe Glu Ala Lys Leu His Arg Ser Gly Tyr Ile Thr
                485                 490                 495

Val Ala His Ser Gly Asp Tyr Pro Leu Val Val Pro Ala Asn Gly Tyr
            500                 505                 510

Phe Arg Phe Asp Ser Trp Val Asn Gln Phe Tyr Ser Leu Ala Pro Met
        515                 520                 525

Gly Thr Gly Asn Gly Arg Arg Arg Ala Gln
    530                 535


<210> SEQ ID NO 72
<211> LENGTH: 540
<212> TYPE: PRT
<213> ORGANISM: Norovirus

<400> SEQUENCE: 72

Met Lys Met Ala Ser Asn Asp Ala Ala Pro Ser Asn Asp Gly Ala Ala
1               5                   10                  15

Gly Leu Val Pro Glu Ile Asn Thr Glu Thr Leu Pro Leu Glu Pro Val
            20                  25                  30

Ala Gly Ala Ala Ile Ala Ala Pro Val Thr Gly Gln Asn Asn Ile Ile
        35                  40                  45

Asp Pro Trp Ile Arg Asn Asn Phe Val Gln Ala Pro Asn Gly Glu Phe
    50                  55                  60

Thr Val Ser Pro Arg Asn Ser Pro Gly Glu Ile Leu Met Asn Leu Glu
65                  70                  75                  80

Leu Gly Pro Asp Leu Asn Pro Tyr Leu Ala His Leu Ser Arg Met Tyr
                85                  90                  95

Asn Gly Tyr Ala Gly Gly Val Glu Val Gln Val Leu Leu Ala Gly Asn
            100                 105                 110

Ala Phe Thr Ala Gly Lys Ile Leu Phe Ala Ala Val Pro Pro Asn Phe
        115                 120                 125

Pro Val Asp Met Leu Ser Pro Ala Gln Ile Thr Met Leu Pro His Leu
    130                 135                 140

Ile Val Asp Val Arg Thr Leu Glu Pro Ile Met Ile Pro Leu Pro Asp
145                 150                 155                 160

Val Arg Asn Val Phe Tyr His Phe Asn Asn Gln Pro Ala Pro Arg Met
                165                 170                 175

Arg Leu Val Ala Met Leu Tyr Thr Pro Leu Arg Ser Asn Gly Ser Gly
            180                 185                 190

Asp Asp Val Phe Thr Val Ser Cys Arg Val Leu Thr Arg Pro Thr Pro
        195                 200                 205

Asp Phe Glu Phe Thr Tyr Leu Val Pro Pro Ser Val Glu Ser Lys Thr
    210                 215                 220

Lys Pro Phe Thr Leu Pro Ile Leu Thr Ile Gly Glu Leu Thr Asn Ser
225                 230                 235                 240

Arg Phe Pro Ala Pro Ile Asp Gln Leu Tyr Thr Ser Pro Asn Ala Asp
                245                 250                 255

Val Val Val Gln Pro Gln Asn Gly Arg Cys Thr Leu Asp Gly Glu Leu
            260                 265                 270

Gln Gly Thr Thr Gln Leu Leu Thr Thr Ala Ile Cys Ser Tyr Arg Gly
        275                 280                 285

Thr Thr Ser Asn Pro Thr Ser Asp Tyr Trp Asp Asp His Leu Leu His
    290                 295                 300

Leu Val His Pro Asn Gly Ala Thr Tyr Asp Pro Thr Glu Asp Val Pro
305                 310                 315                 320
```

Ala Pro Phe Gly Thr Gln Asp Phe Arg Gly Ile Leu Tyr Gly Val Leu
325 330 335

Thr Gln Asn Thr Gln Asn Pro Arg Asp Glu Val Ser Asn Ser Arg Gly
340 345 350

Ile Tyr Ile Ser Ser Thr Ser Asp Lys Phe Thr Pro Lys Leu Gly Thr
355 360 365

Ile Gly Leu His Gln Val Gln Gly Asp Thr Ala Ser Asn Gln Gln Ser
370 375 380

Lys Phe Thr Pro Val Gly Ile Ala Val Asn Gln Asn Thr Pro Phe Lys
385 390 395 400

Gln Trp Glu Leu Pro Asn Tyr Ser Gly Ala Leu Thr Leu Asn Thr Asn
405 410 415

Leu Ala Pro Ala Val Gly Pro Asn Phe Pro Gly Glu Gln Ile Leu Phe
420 425 430

Phe Arg Ser Asn Val Pro Ser Val Gln Gly Asn His Pro Thr Gln Glu
435 440 445

Ile Asp Cys Leu Ile Pro Gln Glu Trp Ile Ser His Phe Tyr Gln Glu
450 455 460

Ser Ala Pro Ser Gln Ser Asp Val Ala Leu Val Arg Tyr Val Asn Pro
465 470 475 480

Asp Thr Gly Arg Thr Ile Phe Glu Ala Lys Leu His Arg Gln Gly Phe
485 490 495

Ile Thr Ile Ala Ala Thr Gly Ser Asn Pro Val Val Val Pro Pro Asn
500 505 510

Gly Tyr Phe Arg Phe Asp Ser Trp Val Asn Gln Phe Tyr Ala Leu Ala
515 520 525

Pro Met Gly Thr Gly Asn Gly Arg Arg Arg Ala Gln
530 535 540

<210> SEQ ID NO 73
<211> LENGTH: 541
<212> TYPE: PRT
<213> ORGANISM: Norovirus

<400> SEQUENCE: 73

Met Lys Met Ala Ser Asn Asp Ala Ala Pro Ser Asn Asp Gly Ala Ala
1 5 10 15

Gly Leu Val Pro Glu Ile Asn Thr Glu Val Met Ala Leu Glu Pro Val
20 25 30

Ala Gly Gly Ala Ile Ala Ala Pro Leu Thr Gly Gln Thr Asn Ile Ile
35 40 45

Asp Pro Trp Ile Arg Asn Asn Phe Val Gln Ala Pro Asn Gly Glu Phe
50 55 60

Thr Ile Ser Pro Arg Asn Ser Pro Gly Glu Ile Leu Leu Asn Met Glu
65 70 75 80

Leu Gly Pro Glu Leu Asn Pro Phe Leu Ala His Leu Ser Arg Met Tyr
85 90 95

Asn Gly Phe Ala Gly Gly Met Glu Val Gln Val Leu Met Ala Gly Asn
100 105 110

Ala Phe Thr Ala Gly Lys Val Ile Phe Ala Ala Ile Pro Pro His Phe
115 120 125

Pro Val Glu Asn Leu Ser Pro Pro Gln Ile Thr Met Phe Pro His Ile
130 135 140

Ile Ile Asp Val Arg Thr Leu Glu Pro Val Leu Leu Pro Met Pro Asp

```
145                 150                 155                 160

Val Arg Asn Gln Phe Phe His Tyr Asn Gln Val Asn Glu Pro Arg Met
                165                 170                 175

Arg Leu Val Ala Met Leu Tyr Thr Pro Leu Arg Ser Asn Gly Ser Thr
            180                 185                 190

Glu Asp Val Phe Thr Val Ser Cys Arg Val Leu Thr Arg Pro Ser Pro
        195                 200                 205

Asp Phe Glu Phe Asn Tyr Leu Val Pro Pro Thr Val Glu Ser Arg Thr
    210                 215                 220

Lys Pro Phe Thr Leu Pro Ile Leu Thr Ile Gly Glu Met Thr Asn Ser
225                 230                 235                 240

Arg Phe Pro Ala Pro Ile Asp Met Leu Tyr Thr Ser Pro Asn Asp Asn
                245                 250                 255

Val Val Val Gln Pro Gln Asn Gly Arg Cys Thr Leu Asp Gly Glu Leu
            260                 265                 270

Gln Gly Ser Thr Gln Leu Val Pro Ala Asn Val Cys Ala Phe Lys Gly
        275                 280                 285

Lys Ile Thr Ala Arg Ile Val Asp Gln Ala Ala His Gln Trp His Met
    290                 295                 300

Gln Ile Asp Asn Pro Asn Gly Thr Leu Phe Asp Pro Thr Glu Asp Val
305                 310                 315                 320

Pro Ala Pro Leu Gly Thr Pro Asp Phe Lys Ala Lys Ile Phe Gly Val
                325                 330                 335

Ile Ser Gln Arg Asn Asp Tyr Asn Asp Gly Ser Gln Gly Pro Ala Asn
            340                 345                 350

Arg Ala His Asp Ala Val Val Pro Thr Thr Ser Ala Lys Phe Thr Pro
        355                 360                 365

Lys Leu Gly Ser Ile Leu Val Gly Thr Trp Glu Asn Asn Asp Ile Glu
    370                 375                 380

Thr Gln Pro Ser Lys Phe Thr Pro Val Gly Leu Leu Glu Met Asn Asp
385                 390                 395                 400

Phe Asn Gln Trp Ser Leu Pro Asn Tyr Ser Gly Ala Leu Thr Leu Asn
                405                 410                 415

Met Gly Leu Ala Pro Ala Val Phe Pro Thr Phe Pro Gly Glu Gln Ile
            420                 425                 430

Leu Phe Phe Arg Ser Phe Ile Pro Leu Lys Gly Gly His Gly Asn Pro
        435                 440                 445

Ala Ile Asp Cys Leu Leu Pro Gln Glu Trp Ile Gln His Phe Tyr Gln
    450                 455                 460

Glu Ser Ala Pro Ser Gln Thr Ser Val Ala Leu Ile Arg Tyr Val Asn
465                 470                 475                 480

Pro Asp Thr Gly Arg Val Leu Phe Glu Gly Lys Leu His Arg Gln Gly
                485                 490                 495

Phe Ile Thr Ile Ala Lys Ser Gly Asp Gly Pro Ile Val Val Pro Pro
            500                 505                 510

Asn Gly Tyr Phe Arg Phe Asp Ser Trp Val Asn Gln Phe Tyr Ser Leu
        515                 520                 525

Ala Pro Met Gly Asn Gly Asn Gly Arg Arg Arg Ile Gln
    530                 535                 540
```

<210> SEQ ID NO 74
<211> LENGTH: 542
<212> TYPE: PRT
<213> ORGANISM: Norovirus

<400> SEQUENCE: 74

Met Lys Met Ala Ser Asn Asp Ala Ala Pro Ser Asn Asp Gly Ala Ala
1               5                   10                  15

Asn Leu Val Pro Glu Ala Asn Lys Glu Val Met Ala Leu Glu Pro Val
            20                  25                  30

Ala Gly Gly Ala Ile Ala Ala Pro Leu Thr Gly Gln Thr Asn Ile Ile
        35                  40                  45

Asp Pro Trp Ile Met Asn Asn Phe Val Gln Ala Pro Asn Gly Glu Phe
    50                  55                  60

Thr Ile Ser Pro Arg Asn Ser Pro Gly Glu Val Leu Leu Asn Leu Glu
65                  70                  75                  80

Leu Gly Pro Asp Leu Asn Pro Phe Leu Ala His Leu Ser Arg Met Tyr
                85                  90                  95

Asn Gly Tyr Ala Gly Gly Val Glu Val Gln Val Ile Met Ala Gly Asn
            100                 105                 110

Ala Phe Thr Ala Gly Lys Val Ile Phe Ala Ala Val Pro Pro His Phe
        115                 120                 125

Pro Val Asp Asn Leu Ser Pro Pro Gln Val Thr Met Phe Pro His Val
    130                 135                 140

Ile Val Asp Val Arg Thr Phe Glu Pro Ile Leu Leu Pro Leu Pro Asp
145                 150                 155                 160

Val Arg Asn Ser Phe Tyr His Tyr Asn Gln Val Asn Asp Ser Arg Met
                165                 170                 175

Arg Leu Ile Ala Met Leu Tyr Thr Pro Leu Arg Ser Asn Gly Ser Ser
            180                 185                 190

Asp Asp Val Phe Thr Val Ser Cys Arg Val Leu Thr Arg Pro Thr Pro
        195                 200                 205

Asp Phe Glu Phe Asn Tyr Leu Val Pro Pro Thr Val Glu Ser Arg Thr
    210                 215                 220

Lys Pro Phe Ser Val Pro Ile Leu Thr Ile Gly Glu Met Thr Asn Ser
225                 230                 235                 240

Arg Phe Pro Leu Pro Ile Asp Met Leu Tyr Thr Ser Pro Thr Glu Asn
                245                 250                 255

Ile Val Val Gln Pro Gln Asn Gly Arg Cys Thr Leu Glu Gly Glu Leu
            260                 265                 270

Leu Gly Thr Thr Gln Leu Val Thr Pro Asn Ile Cys Ala Leu Arg Gly
        275                 280                 285

Glu Ile Arg Gly His Glu Gly Ser Gly Asp Asn His Lys Trp His Phe
    290                 295                 300

Met Val Arg Ser Pro Asn Gly Ala Ala Phe Asp Pro Thr Glu Asp Val
305                 310                 315                 320

Pro Ala Pro Leu Gly Thr Pro Asp Phe Ile Gly Asp Val Phe Gly Val
                325                 330                 335

Leu Ser Gln Arg Asn Arg Asn Thr Asp Ser Gly Gln Ser Gly Pro Ala
            340                 345                 350

Asn Arg Ser His Asp Ala Val Val Ser Thr Arg Asp Ser Arg Phe Thr
        355                 360                 365

Pro Lys Leu Gly Ser Val Met Ile Ala Thr Trp Glu Thr Ser Asp Ile
    370                 375                 380

Gln Asp Gln Pro Thr Arg Phe Thr Pro Val Gly Leu Glu Asn Pro Asp
385                 390                 395                 400

His Tyr Asn Gln Trp Gln Leu Pro Asn Tyr Ser Gly Ala Leu Thr Leu

```
                405                 410                 415

Asn Met Gly Leu Ala Pro Ser Val Phe Pro Thr Tyr Pro Gly Glu Gln
            420                 425                 430

Ile Leu Phe Phe Arg Ser Tyr Ile Pro Leu Lys Gly Gly Tyr Gly Asp
        435                 440                 445

Ser His Ile Asp Cys Leu Val Pro Gln Glu Trp Ile Gln His Phe Tyr
    450                 455                 460

Gln Glu Ser Ala Pro Ser Gln Thr Asp Val Ala Leu Ile Arg Tyr Val
465                 470                 475                 480

Asn Pro Glu Thr Gly Arg Val Leu Phe Glu Ala Lys Leu His Arg Gln
                485                 490                 495

Gly Tyr Ile Thr Val Ala Arg Ser Gly Ser Ser Pro Ile Asn Val Pro
            500                 505                 510

Ala Asn Gly Tyr Phe Arg Phe Asp Ser Trp Val Asn Gln Phe Tyr Ser
        515                 520                 525

Leu Ala Pro Met Gly Thr Gly Asn Gly Arg Arg Arg Ile Gln
    530                 535                 540


<210> SEQ ID NO 75
<211> LENGTH: 541
<212> TYPE: PRT
<213> ORGANISM: Norovirus

<400> SEQUENCE: 75

Met Lys Met Ala Ser Asn Asp Ala Ala Pro Ser Asn Asp Gly Ala Ala
1               5                   10                  15

Gly Leu Val Pro Glu Ile Asn Asn Glu Val Met Ala Leu Glu Pro Val
            20                  25                  30

Ala Gly Gly Ala Ile Ala Ala Pro Leu Thr Gly Gln Thr Asn Val Ile
        35                  40                  45

Asp Pro Trp Ile Arg Thr Asn Phe Val Gln Ala Pro Asn Gly Glu Phe
    50                  55                  60

Thr Ile Ser Pro Arg Asn Ser Pro Gly Glu Val Leu Leu Asn Met Glu
65                  70                  75                  80

Leu Gly Pro Glu Leu Asn Pro Phe Leu Gly His Leu Ser Arg Met Tyr
                85                  90                  95

Asn Gly Tyr Ala Gly Gly Ile Glu Val Gln Val Leu Met Ala Gly Asn
            100                 105                 110

Ala Phe Thr Ala Gly Lys Val Ile Phe Ala Ala Val Pro Pro His Phe
        115                 120                 125

Pro Val Glu Asn Leu Ser Pro Pro Gln Val Thr Met Phe Pro His Ile
    130                 135                 140

Ile Val Asp Val Arg Thr Leu Glu Pro Ile Leu Leu Pro Leu Pro Asp
145                 150                 155                 160

Val Arg Asn Gln Phe Phe His Tyr Ser Gln Val Asp Glu Pro Lys Met
                165                 170                 175

Arg Leu Val Ala Met Leu Tyr Thr Pro Leu Arg Ser Asn Gly Ser Ala
            180                 185                 190

Glu Asp Val Phe Thr Val Ser Cys Arg Val Leu Thr Arg Pro Ser Pro
        195                 200                 205

Asp Phe Glu Phe Asn Tyr Leu Val Pro Pro Thr Val Glu Ser Arg Thr
    210                 215                 220

Lys Pro Phe Thr Val Pro Ile Leu Thr Ile Gly Glu Met Ser Asn Ser
225                 230                 235                 240
```

Arg Phe Pro Ala Pro Ile Asp Met Leu Tyr Thr Ser Pro Asn Asp Asn
245 250 255

Gln Asn Val Gln Pro Gln Asn Gly Arg Cys Thr Leu Asp Gly Glu Leu
260 265 270

Gln Gly Thr Thr Gln Leu Val Pro Ser Gly Val Cys Ala Phe Arg Gly
275 280 285

Arg Ile Thr Gly His Glu Gly Ser Glu Gln Asn Gln Trp His Met Gln
290 295 300

Leu Thr Asn Leu Asn Gly Thr Pro Phe Asp Pro Thr Glu Asp Ile Pro
305 310 315 320

Ala Pro Leu Gly Thr Pro Asp Phe Lys Gly Glu Ile Phe Gly Phe Ile
325 330 335

Ser Gln Arg Asn Ala Gln Asn Asp Pro Gly Gln Ser Gln Pro Ala Asn
340 345 350

Arg Ala His Asp Ala Val Val Ser Thr Arg Ala Pro Lys Phe Thr Pro
355 360 365

Lys Leu Gly Ser Val Met Ile Gly Thr Trp Val Asn Ser Asp Ile Glu
370 375 380

Asn Gln Pro Ser Lys Phe Thr Pro Val Gly Leu Asn Ser Asn Glu Asn
385 390 395 400

Phe Arg Gln Trp Glu Leu Pro Asp Tyr Ser Gly Val Leu Thr Leu Asn
405 410 415

Met Gly Leu Ala Pro Val Val His Pro Thr Tyr Pro Gly Glu Gln Ile
420 425 430

Leu Phe Phe Arg Ser Tyr Ile Pro Leu Lys Gly Gly His Gly Asn Pro
435 440 445

Ala Ile Asp Cys Leu Leu Pro Gln Glu Trp Ile Gln His Phe Tyr Gln
450 455 460

Glu Ser Ala Pro Ser Gln Thr Asp Val Ala Leu Leu Arg Tyr Val Asn
465 470 475 480

Pro Asp Thr Gly Arg Val Leu Phe Glu Ala Lys Leu His Arg Gln Gly
485 490 495

Tyr Ile Thr Ile Ala Lys Ser Gly Asp Gly Pro Ile Val Val Pro Pro
500 505 510

Asn Gly Tyr Phe Arg Phe Asp Ser Trp Val Asn Gln Phe Tyr Ser Leu
515 520 525

Ala Pro Met Gly Asn Gly Asn Gly Arg Arg Arg Val Gln
530 535 540

<210> SEQ ID NO 76
<211> LENGTH: 556
<212> TYPE: PRT
<213> ORGANISM: Norovirus

<400> SEQUENCE: 76

Met Lys Met Ala Ser Ser Asp Ala Ala Pro Ser Ala Asp Gly Ala Gly
1 5 10 15

Asn Leu Val Pro Glu Ser Gln Gln Glu Val Leu Pro Leu Ala Pro Val
20 25 30

Ala Gly Ala Ala Leu Ala Ala Pro Val Val Gly Gln Thr Asn Ile Ile
35 40 45

Asp Pro Trp Ile Lys Glu Asn Phe Val Gln Ala Pro Gln Gly Glu Phe
50 55 60

Thr Val Ser Pro Lys Asn Ser Pro Gly Glu Ile Leu Val Asn Leu Glu
65 70 75 80

```
Leu Gly Pro Lys Leu Asn Pro Tyr Leu Asp His Leu Ser Arg Met Tyr
                85                  90                  95

Asn Ser Tyr Ala Gly Gly Ile Asp Val Met Val Val Leu Ala Gly Asn
            100                 105                 110

Ala Phe Thr Ala Gly Lys Val Leu Ile Ala Ala Ile Pro Pro Asn Phe
        115                 120                 125

Pro Val Glu Gly Val Ser Ala Ser Gln Ala Thr Gln Phe Pro His Val
    130                 135                 140

Ile Ile Asp Val Arg Thr Leu Asp Pro Val Arg Leu Pro Leu Pro Asp
145                 150                 155                 160

Val Arg Ser Thr Phe Phe His Tyr Thr Asn Asp Thr Glu Pro Lys Met
                165                 170                 175

Arg Leu Val Ile Trp Leu Tyr Thr Pro Leu Arg Thr Asn Gly Ser Gly
            180                 185                 190

Asp Asp Ser Phe Thr Val Ser Gly Arg Ile Leu Thr Arg Pro Ser Gln
        195                 200                 205

Asp Phe Glu Phe Ala Phe Leu Ile Pro Pro Thr Val Glu Thr Lys Thr
    210                 215                 220

Thr Pro Phe Ser Val Pro Gly Phe Ser Val Gln Glu Met Ser Asn Ser
225                 230                 235                 240

Arg Trp Pro Ala Ala Ile Ser Ala Met Val Val Arg Gly Asn Glu Pro
                245                 250                 255

Gln Val Val Gln Phe Gln Asn Gly Arg Ala His Leu Asp Gly Met Leu
            260                 265                 270

Leu Gly Thr Thr Pro Val Ser Pro Asn Tyr Ile Ala Ser Tyr Arg Gly
        275                 280                 285

Ile Ser Thr Gly Asn Ser Arg Ser Ala Ser Ser Glu Ala Asp Glu Arg
    290                 295                 300

Ala Val Gly Ser Phe Asp Val Trp Ile Arg Leu Gln Glu Pro Asp Gly
305                 310                 315                 320

Gln Pro Tyr Asp Ile Phe Gly Lys Gln Pro Ala Pro Ile Gly Thr Pro
                325                 330                 335

Asp Phe Lys Ala Val Ile Val Gly Phe Ala Ala Arg Pro Leu Thr Ser
            340                 345                 350

Gly Ser Tyr Ala Asn Glu Ala Tyr Val Asn Thr Thr Ala Ser Asp Tyr
        355                 360                 365

Ala Pro Ala Thr Gly Asn Met Arg Phe Thr Val Arg Asn Gly Gly Thr
    370                 375                 380

Gly His Ile Ser Ala Asn Lys Tyr Trp Glu Phe Arg Ser Phe Gly Val
385                 390                 395                 400

Glu Gly Glu Arg His Thr Asp Val Gln Tyr Gln Glu Tyr Glu Leu Pro
                405                 410                 415

Asp Tyr Ser Gly Gln Val Ala Ser Asn His Asn Leu Ala Pro Pro Val
            420                 425                 430

Ala Pro Arg Met Pro Gly Glu Ser Leu Leu Leu Phe Gln Ser Asn Met
        435                 440                 445

Pro Val Trp Asp Asp Gly Arg Gly Glu Ser Thr Pro Lys Lys Ile His
    450                 455                 460

Cys Leu Leu Pro Gln Glu Phe Ile Gly His Phe Phe Asp Lys Gln Ala
465                 470                 475                 480

Pro Ser Leu Gly Asp Ala Ala Leu Leu Arg Tyr Val Asn Gln Glu Thr
                485                 490                 495
```

Asn Arg Val Leu Phe Glu Cys Lys Leu Tyr Arg Asp Gly Tyr Ile Thr
500 505 510

Val Ala Ala Ala Ser Gly Leu Leu Asp Phe Pro Leu Asp Gly Phe Phe
515 520 525

Arg Phe Asp Ser Trp Val Ser Ser Phe Tyr Ile Leu Ser Pro Val Gly
530 535 540

Ser Gly Gln Gly Arg Arg Gly Arg Val Arg Phe Gln
545 550 555

<210> SEQ ID NO 77
<211> LENGTH: 556
<212> TYPE: PRT
<213> ORGANISM: Norovirus

<400> SEQUENCE: 77

Met Lys Met Ala Ser Ser Asp Ala Ala Pro Ser Thr Asp Gly Ala Gly
1 5 10 15

Asn Leu Val Pro Glu Ser Gln Gln Glu Val Leu Pro Leu Ala Pro Val
20 25 30

Ala Gly Ala Ala Leu Ala Ala Pro Val Val Gly Gln Thr Asn Ile Ile
35 40 45

Asp Pro Trp Ile Lys Glu Asn Phe Val Gln Ala Pro Gln Gly Glu Phe
50 55 60

Thr Val Ser Pro Lys Asn Ser Pro Gly Glu Ile Leu Val Asn Leu Glu
65 70 75 80

Leu Gly Pro Lys Leu Asn Pro Tyr Leu Asp His Leu Ser Arg Met Tyr
85 90 95

Asn Ser Tyr Ala Gly Gly Ile Asp Val Met Val Val Leu Ala Gly Asn
100 105 110

Ala Phe Thr Ala Gly Lys Val Leu Ile Ala Ala Ile Pro Pro Asn Phe
115 120 125

Pro Val Glu Gly Val Ser Ala Ser Gln Ala Thr Gln Phe Pro His Val
130 135 140

Ile Ile Asp Val Arg Thr Leu Asp Pro Val Arg Leu Pro Leu Pro Asp
145 150 155 160

Val Arg Ser Thr Phe Phe His Tyr Thr Asn Asp Thr Glu Pro Lys Met
165 170 175

Arg Leu Val Ile Trp Leu Tyr Thr Pro Leu Arg Thr Asn Gly Ser Gly
180 185 190

Asp Asp Ser Phe Thr Val Ser Gly Arg Ile Leu Thr Arg Pro Ser Gln
195 200 205

Asp Phe Glu Phe Ala Phe Leu Ile Pro Pro Thr Val Glu Thr Lys Thr
210 215 220

Thr Pro Phe Ser Val Pro Gly Phe Ser Val Gln Glu Met Ser Asn Ser
225 230 235 240

Arg Trp Pro Ala Ala Ile Ser Ala Met Val Val Arg Gly Asn Glu Pro
245 250 255

Gln Val Val Gln Phe Gln Asn Gly Arg Ala His Leu Asp Gly Met Leu
260 265 270

Leu Gly Thr Thr Pro Val Ser Pro Asn Tyr Ile Ala Ser Tyr Arg Gly
275 280 285

Ile Ser Thr Gly Asn Ser Arg Ser Ala Ser Ser Glu Ala Asp Glu Arg
290 295 300

Ala Val Gly Ser Phe Asp Val Trp Val Arg Leu Gln Glu Pro Asp Gly
305 310 315 320

Gln Pro Tyr Asp Ile Phe Gly Lys Gln Pro Ala Pro Ile Gly Thr Pro
325 330 335

Asp Phe Lys Ala Val Ile Val Gly Phe Ala Ala Arg Pro Leu Thr Ser
340 345 350

Gly Ser Tyr Ala Asn Glu Ala Tyr Val Asn Thr Thr Ala Ser Asp Tyr
355 360 365

Ala Pro Ala Thr Gly Asn Met Arg Phe Thr Val Arg Asn Gly Gly Thr
370 375 380

Gly His Ile Ser Ala Asn Lys Tyr Trp Glu Phe Lys Ser Phe Gly Val
385 390 395 400

Glu Gly Glu Arg His Thr Asp Ile Gln Tyr Gln Glu Tyr Glu Leu Pro
405 410 415

Asp Tyr Ser Gly Gln Val Ala Ser Asn His Asn Leu Ala Pro Pro Val
420 425 430

Ala Pro Arg Met Pro Gly Glu Ser Leu Leu Leu Phe Gln Ser Asn Met
435 440 445

Pro Val Trp Asp Asp Gly His Gly Glu Ser Thr Pro Lys Lys Ile His
450 455 460

Cys Leu Leu Pro Gln Glu Phe Ile Gly His Phe Phe Asp Arg Gln Ala
465 470 475 480

Pro Ser Leu Gly Asp Ala Ala Leu Leu Arg Tyr Val Asn Gln Glu Thr
485 490 495

Asn Arg Val Leu Phe Glu Cys Lys Leu Tyr Arg Asp Gly Tyr Ile Thr
500 505 510

Val Ala Ala Ser Ser Gly Leu Leu Asp Phe Pro Leu Asp Gly Phe Phe
515 520 525

Arg Phe Asp Ser Trp Val Ser Ser Phe Tyr Ile Leu Ser Pro Val Gly
530 535 540

Ser Gly Gln Gly Arg Arg Gly Arg Val Arg Phe Gln
545 550 555

<210> SEQ ID NO 78
<211> LENGTH: 554
<212> TYPE: PRT
<213> ORGANISM: Norovirus

<400> SEQUENCE: 78

Met Lys Met Ala Ser Asn Asp Ala Pro Pro Ser Ser Asp Gly Ala Gly
1 5 10 15

Asn Leu Val Pro Glu Ser His Gln Glu Val Leu Pro Leu Ala Pro Val
20 25 30

Ala Gly Ala Glu Leu Ala Ala Pro Val Val Gly Gln Thr Asn Ile Ile
35 40 45

Asp Pro Trp Ile Lys Glu Asn Phe Val Gln Ala Pro Gln Gly Glu Phe
50 55 60

Thr Val Ser Pro Lys Asn Ala Pro Gly Glu Ile Leu Val Asn Leu Glu
65 70 75 80

Leu Gly Pro Asn Leu Asn Pro Tyr Leu Glu His Leu Ser Arg Met Tyr
85 90 95

Asn Ala Tyr Ala Gly Gly Ile Glu Val Glu Ile Ile Leu Ala Gly Asn
100 105 110

Ala Phe Thr Ala Gly Lys Ile Leu Ile Ala Ala Val Pro Pro Asn Phe
115 120 125

Pro Val Glu Ser Val Ser Ala Ser Gln Ala Thr Gln Phe Pro His Ala

```
    130                 135                 140

Ile Val Asp Val Arg Thr Leu Glu Pro Val Arg Leu Pro Leu Pro Asp
145                 150                 155                 160

Val Arg Ser Asn Phe Phe His Tyr Thr Thr Lys Asp Glu Pro Lys Met
                165                 170                 175

Arg Leu Val Ile Trp Leu Tyr Thr Pro Leu Arg Thr Asn Gly Ser Gly
            180                 185                 190

Asp Asp Ser Phe Thr Val Ser Gly Arg Leu Leu Thr Arg Pro Ser Met
        195                 200                 205

Asp Phe Gln Phe Ser Phe Leu Val Pro Pro Thr Val Glu Thr Lys Thr
    210                 215                 220

Val Leu Phe Thr Val Pro Gly Leu Thr Pro Gln Glu Met Ser Asn Ser
225                 230                 235                 240

Arg Trp Pro Ala Gln Ile Ser Gly Met Val Val Arg Gly Asn Glu Pro
                245                 250                 255

Gln Val Val Gln Phe Gln Asn Gly Arg Cys His Thr Asp Gly Thr Leu
            260                 265                 270

Leu Gly Thr Thr Thr Val Ser Glu Gln Cys Ile Ala Gly Phe Val Gly
        275                 280                 285

Thr Ser Thr Asn Thr Arg Ser Ala Thr Gly Ser Thr Thr Glu Thr Arg
    290                 295                 300

Thr Gly Asp Thr Asp Leu Trp Leu Arg Leu Glu Glu Pro Asn Gly Gln
305                 310                 315                 320

Pro Tyr Asp Ile Phe Gly Asp Gln Pro Ala Pro Leu Gly Thr Pro Asp
                325                 330                 335

Phe Arg Ala Val Ile Val Gly Phe Ala Ser Arg Pro Gln Thr Gln Gly
            340                 345                 350

Ser Tyr Met Asn Glu Ala Tyr Val Asn Thr Val Asp Ser His Phe Ala
        355                 360                 365

Pro Ala Thr Gly Asn Thr Lys Ile Ile Leu Arg Arg Gly Gly Thr Gly
    370                 375                 380

His Val Gly Gly Gly His Leu Trp Lys Phe Arg Pro Phe Gly Val Glu
385                 390                 395                 400

Gly Gly Glu Gly Arg Val Ser Tyr Gln Glu Tyr Val Leu Pro Asn Tyr
                405                 410                 415

Ser Gly Ala Thr Ala Ser Asn His Asn Leu Ala Pro Pro Val Ala Pro
            420                 425                 430

Arg Met Pro Gly Glu Leu Leu Leu Leu Phe Glu Ser Asp Met Pro Val
        435                 440                 445

Trp Asp Asp Gly His Gly Ala Ala Pro Ala Gln Lys Ile His Cys Leu
    450                 455                 460

Leu Pro Gln Gln Phe Ile Thr His Phe Phe Asp Ser Gln Ala Pro Ala
465                 470                 475                 480

Leu Ala Glu Ala Ala Leu Leu Arg Tyr Val His Pro Asp Ser Ser Arg
                485                 490                 495

Val Leu Phe Glu Thr Lys Leu Tyr Arg Glu Gly Phe Met Val Val Ser
            500                 505                 510

Ala Pro Thr Gly Arg Phe Asp Phe Pro Leu Asp Gly Tyr Phe Arg Phe
        515                 520                 525

Asp Ser Trp Val Asn Ser Phe Tyr Val Leu Ser Pro Val Gly Ser Gly
    530                 535                 540

Gln Gly Arg Arg Gly Arg Ser Lys Val Val
545                 550
```

<210> SEQ ID NO 79
<211> LENGTH: 103
<212> TYPE: PRT
<213> ORGANISM: Vibrio cholerae

<400> SEQUENCE: 79

```
Thr Pro Gln Asn Ile Thr Asp Leu Cys Ala Glu Tyr His Asn Thr Gln
1               5                   10                  15

Ile His Thr Leu Asn Asp Lys Ile Phe Ser Tyr Thr Glu Ser Leu Ala
            20                  25                  30

Gly Lys Arg Glu Met Ala Ile Ile Thr Phe Lys Asn Gly Ala Thr Phe
        35                  40                  45

Gln Val Glu Val Pro Gly Ser Gln His Ile Asp Ser Gln Lys Lys Ala
    50                  55                  60

Ile Glu Arg Met Lys Asp Thr Leu Arg Ile Ala Tyr Leu Thr Glu Ala
65                  70                  75                  80

Lys Val Glu Lys Leu Cys Val Trp Asn Asn Lys Thr Pro His Ala Ile
                85                  90                  95

Ala Ala Ile Ser Met Ala Asn
            100
```

<210> SEQ ID NO 80
<211> LENGTH: 103
<212> TYPE: PRT
<213> ORGANISM: Vibrio cholerae

<400> SEQUENCE: 80

```
Cys Pro Gln Asn Ile Thr Asp Leu Cys Ala Glu Tyr His Asn Thr Gln
1               5                   10                  15

Ile His Thr Leu Asn Asp Lys Ile Phe Ser Tyr Thr Glu Ser Leu Ala
            20                  25                  30

Gly Lys Arg Glu Met Ala Ile Ile Thr Phe Lys Asn Gly Ala Thr Phe
        35                  40                  45

Gln Val Glu Val Pro Gly Ser Gln His Ile Asp Ser Gln Lys Lys Ala
    50                  55                  60

Ile Glu Arg Met Lys Asp Thr Leu Arg Ile Ala Tyr Leu Thr Glu Ala
65                  70                  75                  80

Lys Val Glu Lys Leu Cys Val Trp Asn Asn Lys Cys Pro His Ala Ile
                85                  90                  95

Ala Ala Ile Ser Met Ala Asn
            100
```

<210> SEQ ID NO 81
<211> LENGTH: 103
<212> TYPE: PRT
<213> ORGANISM: Vibrio cholerae

<400> SEQUENCE: 81

```
Thr Pro Gln Asn Ile Thr Asp Leu Cys Ala Glu Tyr His Asn Thr Gln
1               5                   10                  15

Ile His Thr Leu Asn Asp Lys Ile Phe Ser Tyr Thr Glu Ser Leu Ala
            20                  25                  30

Gly Lys Arg Glu Met Ala Ile Ile Thr Phe Lys Asn Gly Ala Thr Phe
        35                  40                  45

Gln Val Glu Val Pro Gly Ser Gln His Ile Asp Ser Gln Lys Lys Ala
    50                  55                  60
```

```
Ile Glu Arg Met Lys Asp Thr Leu Arg Ile Ala Tyr Leu Thr Glu Ala
65                  70                  75                  80

Lys Val Glu Lys Leu Cys Val Trp Asn Asn Lys Thr Pro His Ala Ile
                85                  90                  95

Ala Ala Ile Thr Met Ala Asn
            100


<210> SEQ ID NO 82
<211> LENGTH: 103
<212> TYPE: PRT
<213> ORGANISM: Vibrio cholerae

<400> SEQUENCE: 82

Cys Pro Gln Asn Ile Thr Asp Leu Cys Ala Glu Tyr His Asn Thr Gln
1               5                   10                  15

Ile His Thr Leu Asn Asp Lys Ile Phe Ser Tyr Thr Glu Ser Leu Ala
            20                  25                  30

Gly Lys Arg Glu Met Ala Ile Ile Thr Phe Lys Asn Gly Ala Thr Phe
        35                  40                  45

Gln Val Glu Val Pro Gly Ser Gln His Ile Asp Ser Gln Lys Lys Ala
    50                  55                  60

Ile Glu Arg Met Lys Asp Thr Leu Arg Ile Ala Tyr Leu Thr Glu Ala
65                  70                  75                  80

Lys Val Glu Lys Leu Cys Val Trp Asn Asn Lys Cys Pro His Ala Ile
                85                  90                  95

Ala Ala Ile Thr Met Ala Asn
            100


<210> SEQ ID NO 83
<211> LENGTH: 141
<212> TYPE: PRT
<213> ORGANISM: Vibrio cholerae

<400> SEQUENCE: 83

Met Gly Ser Ser His His His His His His Ser Ser Gly Leu Val Pro
1               5                   10                  15

Arg Gly Ser His Met Ala Ser Met Thr Gly Gly Gln Gln Met Gly Arg
            20                  25                  30

Gly Ser Glu Phe Arg Thr Thr Pro Gln Asn Ile Thr Asp Leu Cys Ala
        35                  40                  45

Glu Tyr His Asn Thr Gln Ile His Thr Leu Asn Asp Lys Ile Phe Ser
    50                  55                  60

Tyr Thr Glu Ser Leu Ala Gly Lys Arg Glu Met Ala Ile Ile Thr Phe
65                  70                  75                  80

Lys Asn Gly Ala Thr Phe Gln Val Glu Val Pro Gly Ser Gln His Ile
                85                  90                  95

Asp Ser Gln Lys Lys Ala Ile Glu Arg Met Lys Asp Thr Leu Arg Ile
            100                 105                 110

Ala Tyr Leu Thr Glu Ala Lys Val Glu Lys Leu Cys Val Trp Asn Asn
        115                 120                 125

Lys Thr Pro His Ala Ile Ala Ala Ile Ser Met Ala Asn
    130                 135                 140


<210> SEQ ID NO 84
<211> LENGTH: 119
<212> TYPE: PRT
<213> ORGANISM: Vibrio cholerae
```

<400> SEQUENCE: 84

Met His His His His His His Ser Ser Gly Asp Asp Asp Asp Lys Gly
1               5                   10                  15

Thr Pro Gln Asn Ile Thr Asp Leu Cys Ala Glu Tyr His Asn Thr Gln
            20                  25                  30

Ile His Thr Leu Asn Asp Lys Ile Phe Ser Tyr Thr Glu Ser Leu Ala
        35                  40                  45

Gly Lys Arg Glu Met Ala Ile Ile Thr Phe Lys Asn Gly Ala Thr Phe
    50                  55                  60

Gln Val Glu Val Pro Gly Ser Gln His Ile Asp Ser Gln Lys Lys Ala
65                  70                  75                  80

Ile Glu Arg Met Lys Asp Thr Leu Arg Ile Ala Tyr Leu Thr Glu Ala
                85                  90                  95

Lys Val Glu Lys Leu Cys Val Trp Asn Asn Lys Thr Pro His Ala Ile
            100                 105                 110

Ala Ala Ile Ser Met Ala Asn
        115

<210> SEQ ID NO 85
<211> LENGTH: 103
<212> TYPE: PRT
<213> ORGANISM: Vibrio cholerae

<400> SEQUENCE: 85

Thr Pro Gln Ser Ile Thr Asp Leu Cys Ala Glu Tyr His Asn Thr Gln
1               5                   10                  15

Ile His Thr Leu Asn Asp Lys Ile Phe Ser Tyr Thr Glu Ser Leu Ala
            20                  25                  30

Gly Lys Arg Glu Met Ala Ile Ile Thr Phe Lys Asn Gly Ala Thr Phe
        35                  40                  45

Gln Val Glu Val Pro Gly Ser Gln His Ile Asp Ser Gln Lys Lys Ala
    50                  55                  60

Ile Glu Arg Met Lys Asp Thr Leu Arg Ile Ala Tyr Leu Thr Glu Ala
65                  70                  75                  80

Lys Val Glu Lys Leu Cys Val Trp Asn Asn Lys Thr Pro His Ala Ile
                85                  90                  95

Ala Ala Ile Ser Met Ala Asn
            100

<210> SEQ ID NO 86
<211> LENGTH: 109
<212> TYPE: PRT
<213> ORGANISM: Vibrio cholerae

<400> SEQUENCE: 86

Thr Pro Gln Ser Ile Thr Asp Leu Cys Ala Glu Tyr His Asn Thr Gln
1               5                   10                  15

Ile His Thr Leu Asn Asp Lys Ile Phe Ser Tyr Thr Glu Ser Leu Ala
            20                  25                  30

Gly Lys Arg Glu Met Ala Ile Ile Thr Phe Lys Asn Gly Ala Thr Phe
        35                  40                  45

Gln Val Glu Val Pro Gly Ser Gln His Ile Asp Ser Gln Lys Lys Ala
    50                  55                  60

Ile Glu Arg Met Lys Asp Thr Leu Arg Ile Ala Tyr Leu Thr Glu Ala
65                  70                  75                  80

Lys Val Glu Lys Leu Cys Val Trp Asn Asn Lys Thr Pro His Ala Ile

```
                85                  90                  95

Ala Ala Ile Ser Met Ala Asn Ser Glu Lys Asp Glu Leu
            100                 105


<210> SEQ ID NO 87
<211> LENGTH: 109
<212> TYPE: PRT
<213> ORGANISM: Vibrio cholerae

<400> SEQUENCE: 87

Thr Pro Gln Asn Ile Thr Asp Leu Cys Ala Glu Tyr His Asn Thr Gln
1               5                   10                  15

Ile His Thr Leu Asn Asp Lys Ile Phe Ser Tyr Thr Glu Ser Leu Ala
            20                  25                  30

Gly Lys Arg Glu Met Ala Ile Ile Thr Phe Lys Asn Gly Ala Thr Phe
        35                  40                  45

Gln Val Glu Val Pro Gly Ser Gln His Ile Asp Ser Gln Lys Lys Ala
    50                  55                  60

Ile Glu Arg Met Lys Asp Thr Leu Arg Ile Ala Tyr Leu Thr Glu Ala
65                  70                  75                  80

Lys Val Glu Lys Leu Cys Val Trp Asn Asn Lys Thr Pro His Ala Ile
                85                  90                  95

Ala Ala Ile Ser Met Ala Asn Ser Glu Lys Asp Glu Leu
            100                 105


<210> SEQ ID NO 88
<211> LENGTH: 103
<212> TYPE: PRT
<213> ORGANISM: Vibrio cholerae

<400> SEQUENCE: 88

Cys Pro Gln Ser Ile Thr Asp Leu Cys Ala Glu Tyr His Asn Thr Gln
1               5                   10                  15

Ile His Thr Leu Asn Asp Lys Ile Phe Ser Tyr Thr Glu Ser Leu Ala
            20                  25                  30

Gly Lys Arg Glu Met Ala Ile Ile Thr Phe Lys Asn Gly Ala Thr Phe
        35                  40                  45

Gln Val Glu Val Pro Gly Ser Gln His Ile Asp Ser Gln Lys Lys Ala
    50                  55                  60

Ile Glu Arg Met Lys Asp Thr Leu Arg Ile Ala Tyr Leu Thr Glu Ala
65                  70                  75                  80

Lys Val Glu Lys Leu Cys Val Trp Asn Asn Lys Cys Pro His Ala Ile
                85                  90                  95

Ala Ala Ile Ser Met Ala Asn
            100


<210> SEQ ID NO 89
<211> LENGTH: 103
<212> TYPE: PRT
<213> ORGANISM: Vibrio cholerae

<400> SEQUENCE: 89

Thr Pro Gln Ser Ile Thr Asp Leu Cys Ala Glu Tyr His Asn Thr Gln
1               5                   10                  15

Ile His Thr Leu Asn Asp Lys Ile Phe Ser Tyr Thr Glu Ser Leu Ala
            20                  25                  30

Gly Lys Arg Glu Met Ala Ile Ile Thr Phe Lys Asn Gly Ala Thr Phe
        35                  40                  45
```

```
Gln Val Glu Val Pro Gly Ser Gln His Ile Asp Ser Gln Lys Lys Ala
    50                  55                  60

Ile Glu Arg Met Lys Asp Thr Leu Arg Ile Ala Tyr Leu Thr Glu Ala
65                  70                  75                  80

Lys Val Glu Lys Leu Cys Val Trp Asn Asn Lys Thr Pro His Ala Ile
                85                  90                  95

Ala Ala Ile Thr Met Ala Asn
            100
```

<210> SEQ ID NO 90
<211> LENGTH: 103
<212> TYPE: PRT
<213> ORGANISM: Vibrio cholerae

<400> SEQUENCE: 90

```
Cys Pro Gln Ser Ile Thr Asp Leu Cys Ala Glu Tyr His Asn Thr Gln
1               5                   10                  15

Ile His Thr Leu Asn Asp Lys Ile Phe Ser Tyr Thr Glu Ser Leu Ala
            20                  25                  30

Gly Lys Arg Glu Met Ala Ile Ile Thr Phe Lys Asn Gly Ala Thr Phe
        35                  40                  45

Gln Val Glu Val Pro Gly Ser Gln His Ile Asp Ser Gln Lys Lys Ala
    50                  55                  60

Ile Glu Arg Met Lys Asp Thr Leu Arg Ile Ala Tyr Leu Thr Glu Ala
65                  70                  75                  80

Lys Val Glu Lys Leu Cys Val Trp Asn Asn Lys Cys Pro His Ala Ile
                85                  90                  95

Ala Ala Ile Thr Met Ala Asn
            100
```

<210> SEQ ID NO 91
<211> LENGTH: 109
<212> TYPE: PRT
<213> ORGANISM: Vibrio cholerae

<400> SEQUENCE: 91

```
Cys Pro Gln Asn Ile Thr Asp Leu Cys Ala Glu Tyr His Asn Thr Gln
1               5                   10                  15

Ile His Thr Leu Asn Asp Lys Ile Phe Ser Tyr Thr Glu Ser Leu Ala
            20                  25                  30

Gly Lys Arg Glu Met Ala Ile Ile Thr Phe Lys Asn Gly Ala Thr Phe
        35                  40                  45

Gln Val Glu Val Pro Gly Ser Gln His Ile Asp Ser Gln Lys Lys Ala
    50                  55                  60

Ile Glu Arg Met Lys Asp Thr Leu Arg Ile Ala Tyr Leu Thr Glu Ala
65                  70                  75                  80

Lys Val Glu Lys Leu Cys Val Trp Asn Asn Lys Cys Pro His Ala Ile
                85                  90                  95

Ala Ala Ile Ser Met Ala Asn Ser Glu Lys Asp Glu Leu
            100                 105
```

<210> SEQ ID NO 92
<211> LENGTH: 109
<212> TYPE: PRT
<213> ORGANISM: Vibrio cholerae

<400> SEQUENCE: 92

Thr Pro Gln Asn Ile Thr Asp Leu Cys Ala Glu Tyr His Asn Thr Gln
1 5 10 15

Ile His Thr Leu Asn Asp Lys Ile Phe Ser Tyr Thr Glu Ser Leu Ala
20 25 30

Gly Lys Arg Glu Met Ala Ile Ile Thr Phe Lys Asn Gly Ala Thr Phe
35 40 45

Gln Val Glu Val Pro Gly Ser Gln His Ile Asp Ser Gln Lys Lys Ala
50 55 60

Ile Glu Arg Met Lys Asp Thr Leu Arg Ile Ala Tyr Leu Thr Glu Ala
65 70 75 80

Lys Val Glu Lys Leu Cys Val Trp Asn Asn Lys Thr Pro His Ala Ile
85 90 95

Ala Ala Ile Thr Met Ala Asn Ser Glu Lys Asp Glu Leu
100 105

<210> SEQ ID NO 93
<211> LENGTH: 109
<212> TYPE: PRT
<213> ORGANISM: Vibrio cholerae

<400> SEQUENCE: 93

Cys Pro Gln Asn Ile Thr Asp Leu Cys Ala Glu Tyr His Asn Thr Gln
1 5 10 15

Ile His Thr Leu Asn Asp Lys Ile Phe Ser Tyr Thr Glu Ser Leu Ala
20 25 30

Gly Lys Arg Glu Met Ala Ile Ile Thr Phe Lys Asn Gly Ala Thr Phe
35 40 45

Gln Val Glu Val Pro Gly Ser Gln His Ile Asp Ser Gln Lys Lys Ala
50 55 60

Ile Glu Arg Met Lys Asp Thr Leu Arg Ile Ala Tyr Leu Thr Glu Ala
65 70 75 80

Lys Val Glu Lys Leu Cys Val Trp Asn Asn Lys Cys Pro His Ala Ile
85 90 95

Ala Ala Ile Thr Met Ala Asn Ser Glu Lys Asp Glu Leu
100 105

<210> SEQ ID NO 94
<211> LENGTH: 109
<212> TYPE: PRT
<213> ORGANISM: Vibrio cholerae

<400> SEQUENCE: 94

Cys Pro Gln Ser Ile Thr Asp Leu Cys Ala Glu Tyr His Asn Thr Gln
1 5 10 15

Ile His Thr Leu Asn Asp Lys Ile Phe Ser Tyr Thr Glu Ser Leu Ala
20 25 30

Gly Lys Arg Glu Met Ala Ile Ile Thr Phe Lys Asn Gly Ala Thr Phe
35 40 45

Gln Val Glu Val Pro Gly Ser Gln His Ile Asp Ser Gln Lys Lys Ala
50 55 60

Ile Glu Arg Met Lys Asp Thr Leu Arg Ile Ala Tyr Leu Thr Glu Ala
65 70 75 80

Lys Val Glu Lys Leu Cys Val Trp Asn Asn Lys Cys Pro His Ala Ile
85 90 95

Ala Ala Ile Ser Met Ala Asn Ser Glu Lys Asp Glu Leu
100 105

<210> SEQ ID NO 95
<211> LENGTH: 109
<212> TYPE: PRT
<213> ORGANISM: Vibrio cholerae

<400> SEQUENCE: 95

```
Thr Pro Gln Ser Ile Thr Asp Leu Cys Ala Glu Tyr His Asn Thr Gln
1               5                   10                  15

Ile His Thr Leu Asn Asp Lys Ile Phe Ser Tyr Thr Glu Ser Leu Ala
            20                  25                  30

Gly Lys Arg Glu Met Ala Ile Ile Thr Phe Lys Asn Gly Ala Thr Phe
        35                  40                  45

Gln Val Glu Val Pro Gly Ser Gln His Ile Asp Ser Gln Lys Lys Ala
    50                  55                  60

Ile Glu Arg Met Lys Asp Thr Leu Arg Ile Ala Tyr Leu Thr Glu Ala
65                  70                  75                  80

Lys Val Glu Lys Leu Cys Val Trp Asn Asn Lys Thr Pro His Ala Ile
                85                  90                  95

Ala Ala Ile Thr Met Ala Asn Ser Glu Lys Asp Glu Leu
            100                 105
```

<210> SEQ ID NO 96
<211> LENGTH: 109
<212> TYPE: PRT
<213> ORGANISM: Vibrio cholerae

<400> SEQUENCE: 96

```
Cys Pro Gln Ser Ile Thr Asp Leu Cys Ala Glu Tyr His Asn Thr Gln
1               5                   10                  15

Ile His Thr Leu Asn Asp Lys Ile Phe Ser Tyr Thr Glu Ser Leu Ala
            20                  25                  30

Gly Lys Arg Glu Met Ala Ile Ile Thr Phe Lys Asn Gly Ala Thr Phe
        35                  40                  45

Gln Val Glu Val Pro Gly Ser Gln His Ile Asp Ser Gln Lys Lys Ala
    50                  55                  60

Ile Glu Arg Met Lys Asp Thr Leu Arg Ile Ala Tyr Leu Thr Glu Ala
65                  70                  75                  80

Lys Val Glu Lys Leu Cys Val Trp Asn Asn Lys Cys Pro His Ala Ile
                85                  90                  95

Ala Ala Ile Thr Met Ala Asn Ser Glu Lys Asp Glu Leu
            100                 105
```

<210> SEQ ID NO 97
<211> LENGTH: 103
<212> TYPE: PRT
<213> ORGANISM: Escherichia coli

<400> SEQUENCE: 97

```
Ala Pro Gln Thr Ile Thr Glu Leu Cys Ser Glu Tyr Arg Asn Thr Gln
1               5                   10                  15

Ile Tyr Thr Ile Asn Asp Lys Ile Leu Ser Tyr Thr Glu Ser Met Ala
            20                  25                  30

Gly Lys Arg Glu Met Val Ile Ile Thr Phe Lys Ser Gly Glu Thr Phe
        35                  40                  45

Gln Val Glu Val Pro Gly Ser Gln His Ile Asp Ser Gln Lys Lys Ala
    50                  55                  60

Ile Glu Arg Met Lys Asp Thr Leu Arg Ile Thr Tyr Leu Thr Glu Thr
```

```
65                  70                  75                  80

Lys Ile Asp Lys Leu Cys Val Trp Asn Asn Lys Thr Pro Asn Ser Ile
                85                  90                  95

Ala Ala Ile Ser Met Lys Asn
            100


<210> SEQ ID NO 98
<211> LENGTH: 103
<212> TYPE: PRT
<213> ORGANISM: Escherichia coli

<400> SEQUENCE: 98

Ala Pro Gln Ser Ile Thr Glu Leu Cys Ser Glu Tyr Arg Asn Thr Gln
1               5                   10                  15

Ile Tyr Thr Ile Asn Asp Lys Ile Leu Ser Tyr Thr Glu Ser Met Ala
            20                  25                  30

Gly Lys Arg Glu Met Val Ile Ile Thr Phe Lys Ser Gly Ala Thr Phe
        35                  40                  45

Gln Val Glu Val Pro Gly Ser Gln His Ile Asp Ser Gln Lys Lys Ala
    50                  55                  60

Ile Glu Arg Met Lys Asp Thr Leu Arg Ile Thr Tyr Leu Thr Glu Thr
65                  70                  75                  80

Lys Ile Asp Lys Leu Cys Val Trp Asn Asn Lys Thr Pro Asn Ser Ile
                85                  90                  95

Ala Ala Ile Ser Met Glu Asn
            100


<210> SEQ ID NO 99
<211> LENGTH: 109
<212> TYPE: PRT
<213> ORGANISM: Escherichia coli

<400> SEQUENCE: 99

Ala Pro Gln Ser Ile Thr Glu Leu Cys Ser Glu Tyr Arg Asn Thr Gln
1               5                   10                  15

Ile Tyr Thr Ile Asn Asp Lys Ile Leu Ser Tyr Thr Glu Ser Met Ala
            20                  25                  30

Gly Lys Arg Glu Met Val Ile Ile Thr Phe Lys Ser Gly Ala Thr Phe
        35                  40                  45

Gln Val Glu Val Pro Gly Ser Gln His Ile Asp Ser Gln Lys Lys Ala
    50                  55                  60

Ile Glu Arg Met Lys Asp Thr Leu Arg Ile Thr Tyr Leu Thr Glu Thr
65                  70                  75                  80

Lys Ile Asp Lys Leu Cys Val Trp Asn Asn Lys Thr Pro Asn Ser Ile
                85                  90                  95

Ala Ala Ile Ser Met Glu Asn Ser Glu Lys Asp Glu Leu
            100                 105


<210> SEQ ID NO 100
<211> LENGTH: 103
<212> TYPE: PRT
<213> ORGANISM: Escherichia coli

<400> SEQUENCE: 100

Ala Pro Gln Ser Ile Thr Glu Leu Cys Ser Glu Tyr His Asn Thr Gln
1               5                   10                  15

Ile Tyr Thr Ile Asn Asp Lys Ile Leu Ser Tyr Thr Glu Ser Met Ala
            20                  25                  30
```

-continued

```
Gly Lys Arg Glu Met Val Ile Ile Thr Phe Lys Ser Gly Ala Thr Phe
        35                  40                  45

Gln Val Glu Val Pro Gly Ser Gln His Ile Asp Ser Gln Lys Lys Ala
    50                  55                  60

Ile Glu Arg Met Lys Asp Thr Leu Arg Ile Thr Tyr Leu Thr Glu Thr
65                  70                  75                  80

Lys Ile Asp Lys Leu Cys Val Trp Asn Asn Lys Thr Pro Asn Ser Ile
                85                  90                  95

Ala Ala Ile Ser Met Glu Asn
            100
```